(12) United States Patent
Marriott et al.

(10) Patent No.: US 11,903,700 B2
(45) Date of Patent: Feb. 20, 2024

(54) VITAL SIGNS MONITORING SYSTEMS AND METHODS

(71) Applicant: RDS, Strasbourg (FR)

(72) Inventors: Mark P. Marriott, Palo Alto, CA (US); George Stefan Golda, El Granada, CA (US); Steve Hurwitz, Emerald Hills, CA (US); Sam Eletr, Paris (FR); Jeffrey C. Marshall, Belmont, CA (US); George E. Smith, Sunnyvale, CA (US); Clifton J. Shak, Sunnyvale, CA (US); Bruce O'Neil, Greenbrae, CA (US)

(73) Assignee: RDS, Strasbourg (FR)

( * ) Notice: Subject to any disclaimer, the term of this patent is extended or adjusted under 35 U.S.C. 154(b) by 239 days.

(21) Appl. No.: 17/006,658

(22) Filed: Aug. 28, 2020

(65) Prior Publication Data

US 2021/0059586 A1    Mar. 4, 2021

Related U.S. Application Data

(60) Provisional application No. 62/893,173, filed on Aug. 28, 2019.

(51) Int. Cl.
*A61B 5/1455* (2006.01)
*A61B 5/00* (2006.01)
(Continued)

(52) U.S. Cl.
CPC .......... *A61B 5/14552* (2013.01); *A61B 5/352* (2021.01); *A61B 5/6833* (2013.01);
(Continued)

(58) Field of Classification Search
CPC ... A61B 5/14552; A61B 5/352; A61B 5/6833; A61B 5/721; A61B 5/7225;
(Continued)

(56) References Cited

U.S. PATENT DOCUMENTS 3,830,970 A    8/1974    Hurley et al.
3,911,906 A    10/1975   Reinhold, Jr.
(Continued)

FOREIGN PATENT DOCUMENTS

CN    2785556 Y    6/2006
CN    101822533 A  9/2010
(Continued)

OTHER PUBLICATIONS

Kadota, Hiroshi, Japanese Patent Office, Japanese Office Action dated/transmitted Nov. 30, 2021 for Japanese Application No. 2020-218861, original 3 pages, and translation 3 pages; Japanese Patent Office.

(Continued)

*Primary Examiner* — Eric F Winakur
*Assistant Examiner* — Abid A Mustansir
(74) *Attorney, Agent, or Firm* — EIP US LLP; Jared A. Barnard

(57) ABSTRACT

Systems, methods and devices for reducing noise in health monitoring including monitoring systems, methods and/or devices receiving a health signal and/or having at least one sensor for health monitoring.

15 Claims, 71 Drawing Sheets

(51) Int. Cl.
*H05B 45/10* (2020.01)
*A61B 5/352* (2021.01)

(52) U.S. Cl.
CPC ............ *A61B 5/721* (2013.01); *A61B 5/7225* (2013.01); *H05B 45/10* (2020.01); *A61B 2560/0209* (2013.01); *A61B 2560/0214* (2013.01)

(58) Field of Classification Search
CPC .... A61B 2560/0209; A61B 2560/0214; A61B 5/01; A61B 5/0205; A61B 5/08; A61B 5/11; A61B 5/4818; A61B 5/7203; H05B 45/10; H05B 45/20
See application file for complete search history.

(56) References Cited

U.S. PATENT DOCUMENTS

| | | |
|---|---|---|
| 4,141,366 A | 2/1979 | Cross, Jr. et al. |
| 4,164,215 A | 8/1979 | Finlayson et al. |
| 4,221,223 A | 9/1980 | Linden |
| 4,224,948 A | 9/1980 | Cramer |
| 4,230,127 A | 10/1980 | Larson |
| 4,295,472 A | 10/1981 | Adams |
| 4,360,030 A | 11/1982 | Citron et al. |
| 4,412,546 A | 11/1983 | Barthels |
| 4,494,550 A | 1/1985 | Blazek et al. |
| 4,580,339 A | 4/1986 | Ioffe |
| 4,583,190 A | 4/1986 | Salb |
| 4,583,549 A | 4/1986 | Manoli |
| 4,674,511 A | 6/1987 | Cartmell |
| 4,803,992 A | 2/1989 | Lemelson |
| 4,859,057 A | 8/1989 | Taylor et al. |
| 4,869,254 A | 9/1989 | Stone et al. |
| 4,880,304 A | 11/1989 | Jaeb et al. |
| 4,890,622 A | 1/1990 | Ferrari |
| 4,902,886 A | 2/1990 | Smisko |
| 4,934,372 A | 6/1990 | Corenman et al. |
| 4,938,228 A | 7/1990 | Righter et al. |
| 4,967,264 A | 10/1990 | Parulski et al. |
| 5,025,791 A | 6/1991 | Niwa |
| 5,184,620 A | 2/1993 | Cudahy et al. |
| 5,203,329 A | 4/1993 | Takatani et al. |
| 5,215,087 A | 6/1993 | Anderson |
| 5,224,486 A | 7/1993 | Lerman et al. |
| 5,261,401 A | 11/1993 | Baker et al. |
| 5,265,579 A | 11/1993 | Ferrari |
| 5,307,818 A | 5/1994 | Segalowitz |
| 5,372,125 A | 12/1994 | Lyons |
| 5,419,321 A | 5/1995 | Evans |
| 5,427,093 A | 6/1995 | Ogawa et al. |
| 5,448,991 A | 9/1995 | Polson |
| 5,465,715 A | 11/1995 | Lyons |
| 5,465,727 A | 11/1995 | Reinhold |
| 5,511,553 A | 4/1996 | Segalowitz |
| 5,549,116 A | 8/1996 | Mauer |
| 5,632,272 A | 5/1997 | Diab et al. |
| 5,673,692 A | 10/1997 | Schulze et al. |
| 5,730,143 A | 3/1998 | Schwarzberg |
| 5,779,631 A | 7/1998 | Chance |
| 5,817,008 A | 10/1998 | Rafert et al. |
| 5,912,703 A | 6/1999 | Tamayama |
| 5,931,791 A | 8/1999 | Saltzstein et al. |
| 5,938,597 A | 8/1999 | Stratbucker |
| 5,971,930 A | 10/1999 | Elghazzawi |
| 6,032,060 A | 2/2000 | Carim et al. |
| 6,041,247 A | 3/2000 | Weckstrom |
| 6,088,607 A | 7/2000 | Diab et al. |
| 6,122,535 A | 9/2000 | Kaestle et al. |
| 6,134,460 A | 10/2000 | Chance |
| 6,263,222 B1 | 7/2001 | Diab et al. |
| 6,327,487 B1 | 12/2001 | Stratbucker |
| 6,385,473 B1 | 5/2002 | Haines et al. |
| 6,453,186 B1 | 9/2002 | Lovejoy et al. |
| 6,525,386 B1 | 2/2003 | Mills |
| 6,526,300 B1 | 2/2003 | Kiani et al. |
| 6,569,095 B2 | 5/2003 | Eggers |
| 6,647,287 B1 | 11/2003 | Peel et al. |
| 6,661,161 B1 | 12/2003 | Lanzo |
| 6,662,033 B2 | 12/2003 | Casciani et al. |
| 6,665,385 B2 | 12/2003 | Rogers et al. |
| 6,694,177 B2 | 2/2004 | Eggers et al. |
| 6,699,194 B1 | 3/2004 | Diab et al. |
| 6,725,074 B1 | 4/2004 | Kaestle |
| 6,745,061 B1 | 6/2004 | Hicks et al. |
| 6,830,711 B2 | 6/2004 | Mills et al. |
| 6,801,137 B2 | 10/2004 | Eggers |
| 6,934,570 B2 | 8/2005 | Kiani et al. |
| 6,940,403 B2 | 9/2005 | Kail, IV |
| 7,018,338 B2 | 3/2006 | Vetter et al. |
| 7,027,858 B2 | 4/2006 | Cao et al. |
| 7,067,893 B2 | 6/2006 | Mills et al. |
| 7,099,715 B2 | 8/2006 | Korzinov et al. |
| 7,130,396 B2 | 10/2006 | Rogers et al. |
| 7,194,300 B2 | 3/2007 | Korzinov |
| 7,212,850 B2 | 5/2007 | Prystowsky |
| 7,215,984 B2 | 5/2007 | Diab et al. |
| 7,257,438 B2 | 8/2007 | Kinast |
| 7,332,784 B2 | 2/2008 | Mills et al. |
| 7,341,559 B2 | 3/2008 | Schulz et al. |
| 7,412,282 B2 | 8/2008 | Houben |
| 7,502,643 B2 | 3/2009 | Farringdon et al. |
| 7,553,166 B2 | 6/2009 | Gobron |
| 7,587,237 B2 | 9/2009 | Korzinov et al. |
| 7,668,588 B2 | 2/2010 | Kovacs |
| 7,729,753 B2 | 6/2010 | Kremliovsky et al. |
| 7,831,301 B2 | 11/2010 | Webb et al. |
| 7,881,765 B2 | 2/2011 | Mertz et al. |
| D634,431 S | 3/2011 | Severe et al. |
| 7,904,133 B2 | 3/2011 | Gehman et al. |
| 7,907,996 B2 | 3/2011 | Prystowsky et al. |
| 7,941,207 B2 | 5/2011 | Korzinov |
| 7,962,202 B2 | 6/2011 | Bhunia |
| 7,988,638 B2 | 8/2011 | Novae |
| 8,116,841 B2 | 2/2012 | Bly et al. |
| 8,145,287 B2 | 3/2012 | Diab et al. |
| 8,150,502 B2 | 4/2012 | Kumar et al. |
| 8,160,682 B2 | 4/2012 | Kumar et al. |
| D659,836 S | 5/2012 | Bensch et al. |
| 8,172,761 B1 | 5/2012 | Rulkov et al. |
| 8,200,319 B2 | 6/2012 | Pu et al. |
| 8,200,320 B2 | 6/2012 | Kovacs |
| 8,203,704 B2 | 6/2012 | Merritt et al. |
| 8,219,198 B2 | 7/2012 | Gollasch et al. |
| 8,249,686 B2 | 8/2012 | Libbus et al. |
| 8,271,072 B2 | 9/2012 | Houben et al. |
| RE43,767 E | 10/2012 | Eggers et al. |
| 8,285,356 B2 | 10/2012 | Bly et al. |
| 8,290,129 B2 | 10/2012 | Rogers et al. |
| 8,290,574 B2 | 10/2012 | Field et al. |
| 8,301,236 B2 | 10/2012 | Baumann et al. |
| 8,374,686 B2 | 2/2013 | Ghanem |
| 8,428,682 B1 | 4/2013 | Rood et al. |
| 8,452,364 B2 | 5/2013 | Hannula et al. |
| 8,460,189 B2 | 6/2013 | Libbus et al. |
| 8,473,039 B2 | 6/2013 | Michelson et al. |
| 8,473,047 B2 | 6/2013 | Chakravarthy et al. |
| 8,538,503 B2 | 9/2013 | Kumar et al. |
| 8,554,311 B2 | 10/2013 | Warmer et al. |
| 8,560,046 B2 | 10/2013 | Kumar et al. |
| 8,577,431 B2 | 11/2013 | Lamego et al. |
| 8,585,605 B2 | 11/2013 | Sola I Caros et al. |
| 8,591,430 B2 | 11/2013 | Amurthur et al. |
| D701,964 S | 4/2014 | Yoneta et al. |
| 8,688,190 B2 | 4/2014 | Libbus et al. |
| 8,718,752 B2 | 5/2014 | Libbus et al. |
| 8,731,649 B2 | 5/2014 | Lisogurski |
| 8,743,258 B2 | 6/2014 | Park et al. |
| 8,821,397 B2 | 9/2014 | Al-Ali et al. |
| 8,989,830 B2 | 3/2015 | LeBoeuf et al. |
| D738,757 S | 9/2015 | Cross et al. |
| D744,109 S | 11/2015 | Yoneta et al. |
| D744,110 S | 11/2015 | Kubo et al. |
| 9,186,112 B2 | 11/2015 | Bechtel et al. |

(56) References Cited

U.S. PATENT DOCUMENTS

| | | |
|---|---|---|
| 9,241,643 B2 | 1/2016 | Lisogurski |
| 9,277,864 B2 | 3/2016 | Yang et al. |
| 9,289,175 B2 | 3/2016 | LeBoeuf et al. |
| D760,903 S | 7/2016 | Lin et al. |
| 9,392,946 B1 | 7/2016 | Sarantos |
| 9,398,870 B2 | 7/2016 | Bechtel et al. |
| 9,506,802 B2 | 11/2016 | Chu et al. |
| D787,066 S | 5/2017 | Kim et al. |
| 9,636,057 B2 | 5/2017 | Scheuing et al. |
| 9,642,565 B2 | 5/2017 | Gonopolskiy et al. |
| 9,664,556 B2 | 5/2017 | Chu et al. |
| 9,696,199 B2 | 7/2017 | Chu et al. |
| 9,717,425 B2 | 8/2017 | Kiani et al. |
| 9,752,925 B2 | 9/2017 | Chu et al. |
| D800,313 S | 10/2017 | Chang |
| 9,775,548 B2 | 10/2017 | Sarantos et al. |
| 9,782,132 B2 | 10/2017 | Golda et al. |
| 9,801,547 B2 | 10/2017 | Yuen et al. |
| D810,944 S | 2/2018 | Goolkasian |
| 9,888,872 B2 | 2/2018 | Bechtel et al. |
| D812,229 S | 3/2018 | Al-Siddiq |
| 10,045,722 B2 | 8/2018 | Kintz et al. |
| 10,080,527 B2 | 9/2018 | Golda et al. |
| 10,088,356 B2 | 10/2018 | Chu et al. |
| 10,244,949 B2 | 4/2019 | Moyer et al. |
| D850,626 S | 6/2019 | Gardner et al. |
| D851,253 S | 6/2019 | Goolkasian |
| 10,413,251 B2 | 9/2019 | Golda et al. |
| D868,974 S | 12/2019 | Albert et al. |
| D868,977 S | 12/2019 | Vardi |
| D880,703 S | 4/2020 | Emery et al. |
| 10,610,159 B2 | 4/2020 | Eletr et al. |
| 10,824,391 B2 | 11/2020 | Moyer et al. |
| 10,863,947 B2 | 12/2020 | Golda et al. |
| 10,959,678 B2 | 3/2021 | Golda et al. |
| 10,980,486 B2 | 4/2021 | Van Zandt Moyer et al. |
| D931,467 S | 9/2021 | Golda et al. |
| 11,185,291 B2 | 11/2021 | Eletr et al. |
| 2002/0026127 A1 | 2/2002 | Balbierz et al. |
| 2002/0038082 A1 | 3/2002 | Chin |
| 2002/0072685 A1 | 6/2002 | Rymut et al. |
| 2002/0180605 A1 | 12/2002 | Ozguz et al. |
| 2003/0055478 A1 | 3/2003 | Lyster |
| 2003/0065269 A1 | 4/2003 | Vetter et al. |
| 2003/0073916 A1 | 4/2003 | Yonce |
| 2003/0139654 A1 | 7/2003 | Kim et al. |
| 2003/0176795 A1 | 9/2003 | Harris et al. |
| 2003/0225322 A1 | 12/2003 | Uchiyama et al. |
| 2003/0225323 A1 | 12/2003 | Kani et al. |
| 2004/0010201 A1 | 1/2004 | Korzinov et al. |
| 2004/0015091 A1 | 1/2004 | Greenwald et al. |
| 2004/0039419 A1 | 2/2004 | Stickney et al. |
| 2004/0039420 A1 | 2/2004 | Jayne et al. |
| 2004/0042581 A1 | 3/2004 | Okerlund |
| 2004/0054273 A1 | 3/2004 | Finneran et al. |
| 2004/0082842 A1 | 4/2004 | Lumba et al. |
| 2004/0082862 A1 | 4/2004 | Chance |
| 2004/0146149 A1 | 7/2004 | Rogers et al. |
| 2004/0260189 A1 | 12/2004 | Eggers et al. |
| 2005/0096557 A1 | 5/2005 | Vosburgh |
| 2005/0187446 A1 | 8/2005 | Nordstrom |
| 2005/0197549 A1 | 9/2005 | Baker, Jr. |
| 2005/0261559 A1 | 11/2005 | Mumford |
| 2005/0277841 A1 | 12/2005 | Shennib |
| 2005/0288726 A1 | 12/2005 | Gollasch |
| 2006/0056487 A1 | 3/2006 | Kuroda et al. |
| 2006/0167515 A1 | 7/2006 | Stickney et al. |
| 2006/0170649 A1 | 8/2006 | Kosugi et al. |
| 2006/0224072 A1 | 10/2006 | Shennib |
| 2007/0070800 A1 | 3/2007 | Virag et al. |
| 2007/0093705 A1 | 4/2007 | Shin et al. |
| 2007/0103296 A1 | 5/2007 | Paessel et al. |
| 2007/0106136 A1 | 5/2007 | Sterling et al. |
| 2007/0129642 A1 | 6/2007 | Korzinov |
| 2007/0130657 A1 | 6/2007 | Rogers et al. |
| 2007/0142715 A1 | 6/2007 | Banet et al. |
| 2007/0156054 A1 | 7/2007 | Korzinov et al. |
| 2007/0167850 A1 | 7/2007 | Russell et al. |
| 2007/0191723 A1 | 8/2007 | Prystowsky et al. |
| 2007/0191728 A1 | 8/2007 | Shennib |
| 2007/0206655 A1 | 9/2007 | Haslett et al. |
| 2007/0208542 A1 | 9/2007 | Vock et al. |
| 2007/0255156 A1 | 11/2007 | Mertz et al. |
| 2007/0255184 A1 | 11/2007 | Shennnib |
| 2007/0282212 A1 | 12/2007 | Sierra et al. |
| 2007/0293776 A1 | 12/2007 | Korzinov et al. |
| 2008/0013747 A1 | 1/2008 | Tran |
| 2008/0061846 A1 | 3/2008 | Kase et al. |
| 2008/0091090 A1 | 4/2008 | Guillory et al. |
| 2008/0101064 A1* | 5/2008 | Draganov ............ F21K 9/00 362/231 |
| 2008/0139953 A1 | 6/2008 | Baker et al. |
| 2008/0288026 A1 | 11/2008 | Cross |
| 2008/0294126 A1 | 11/2008 | Reuben |
| 2008/0300641 A1 | 12/2008 | Brunekreeft et al. |
| 2009/0054742 A1 | 2/2009 | Kaminska |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0105602 A1 | 4/2009 | Gehman et al. |
| 2009/0171177 A1 | 7/2009 | Hannula et al. |
| 2009/0234410 A1 | 9/2009 | Libbus et al. |
| 2009/0290279 A1 | 11/2009 | Rodgriguez et al. |
| 2009/0306536 A1 | 12/2009 | Ranganathan et al. |
| 2010/0004518 A1 | 1/2010 | Vo et al. |
| 2010/0026995 A1 | 2/2010 | Merritt et al. |
| 2010/0030039 A1 | 2/2010 | Lamego |
| 2010/0054138 A1 | 3/2010 | Gips et al. |
| 2010/0134241 A1 | 6/2010 | Gips et al. |
| 2010/0160794 A1 | 6/2010 | Banet et al. |
| 2010/0179391 A1 | 7/2010 | Quintanar et al. |
| 2010/0191509 A1 | 7/2010 | Li et al. |
| 2010/0198044 A1 | 8/2010 | Gehman et al. |
| 2010/0204586 A1 | 8/2010 | Pu et al. |
| 2010/0204599 A1 | 8/2010 | Pu et al. |
| 2010/0249541 A1 | 9/2010 | Geva et al. |
| 2010/0262430 A1 | 10/2010 | Gips et al. |
| 2010/0268103 A1 | 10/2010 | Mcnamara et al. |
| 2010/0324387 A1 | 10/2010 | Moon et al. |
| 2010/0286495 A1 | 11/2010 | McGonigle et al. |
| 2010/0286532 A1 | 11/2010 | Farringdon et al. |
| 2010/0298655 A1 | 11/2010 | McCombie |
| 2010/0298656 A1 | 11/2010 | McCombie |
| 2010/0312188 A1 | 12/2010 | Robertson |
| 2010/0317937 A1 | 12/2010 | Kuhn et al. |
| 2010/0317942 A1 | 12/2010 | Cinbis et al. |
| 2010/0317947 A1 | 12/2010 | Cinbis et al. |
| 2010/0317958 A1 | 12/2010 | Beck et al. |
| 2010/0318146 A1 | 12/2010 | Cinbis et al. |
| 2010/0324389 A1 | 12/2010 | Moon et al. |
| 2011/0004106 A1 | 1/2011 | Iwamiya et al. |
| 2011/0021897 A1 | 1/2011 | Webb et al. |
| 2011/0066039 A1 | 3/2011 | Banet et al. |
| 2011/0066049 A1 | 3/2011 | Matsumoto |
| 2011/0066062 A1 | 3/2011 | Banet et al. |
| 2011/0098933 A1 | 4/2011 | Ochs |
| 2011/0105860 A1 | 5/2011 | Houben et al. |
| 2011/0105926 A1 | 5/2011 | Kornet |
| 2011/0124979 A1 | 5/2011 | Heneghan |
| 2011/0125040 A1 | 5/2011 | Crawford et al. |
| 2011/0144470 A1 | 6/2011 | Mazar et al. |
| 2011/0158284 A1 | 6/2011 | Goto |
| 2011/0160604 A1 | 6/2011 | Istvan et al. |

(56) References Cited

U.S. PATENT DOCUMENTS

| | | |
|---|---|---|
| 2011/0166434 A1 | 7/2011 | Gargiulo |
| 2011/0166468 A1 | 7/2011 | Prystowsky et al. |
| 2011/0190598 A1 | 8/2011 | Shusterman |
| 2011/0194007 A1 | 8/2011 | Kim et al. |
| 2011/0208076 A1 | 8/2011 | Fong et al. |
| 2011/0208078 A1 | 8/2011 | Cho et al. |
| 2011/0263994 A1 | 10/2011 | Burns |
| 2011/0270049 A1 | 11/2011 | Katra et al. |
| 2011/0270112 A1 | 11/2011 | Manera et al. |
| 2011/0279963 A1 | 11/2011 | Kumar |
| 2011/0301445 A9 | 12/2011 | Webb et al. |
| 2011/0301493 A1 | 12/2011 | Husheer |
| 2012/0016245 A1 | 1/2012 | Niwa et al. |
| 2012/0029306 A1 | 2/2012 | Paquet |
| 2012/0029320 A1 | 2/2012 | Watson et al. |
| 2012/0035490 A1 | 2/2012 | Shen et al. |
| 2012/0035494 A1 | 2/2012 | Chakravarthy et al. |
| 2012/0061695 A1 | 3/2012 | Kim |
| 2012/0071744 A1 | 3/2012 | Euliano et al. |
| 2012/0083673 A1 | 4/2012 | Al-Ali et al. |
| 2012/0101396 A1 | 4/2012 | Solosko et al. |
| 2012/0108917 A1 | 5/2012 | Libbus et al. |
| 2012/0108920 A1 | 5/2012 | Bly et al. |
| 2012/0109572 A1 | 5/2012 | Shimizu |
| 2012/0110226 A1 | 5/2012 | Vlach et al. |
| 2012/0110228 A1 | 5/2012 | Vlach et al. |
| 2012/0136226 A1 | 5/2012 | Wilke |
| 2012/0143079 A1 | 6/2012 | Lia et al. |
| 2012/0176599 A1 | 7/2012 | Leung |
| 2012/0197150 A1 | 8/2012 | Cao et al. |
| 2012/0203077 A1 | 8/2012 | He et al. |
| 2012/0204068 A1 | 8/2012 | Ye et al. |
| 2012/0226129 A1 | 9/2012 | Callahan et al. |
| 2012/0232369 A1 | 9/2012 | Kim et al. |
| 2012/0245951 A1 | 9/2012 | Gips et al. |
| 2012/0277549 A1 | 11/2012 | Libbus et al. |
| 2012/0284003 A1 | 11/2012 | Gosh |
| 2012/0289839 A1 | 11/2012 | Takenoshita |
| 2012/0330126 A1 | 12/2012 | Hoppe |
| 2012/0330151 A1 | 12/2012 | Weinstein et al. |
| 2013/0012938 A1 | 1/2013 | Asirvatham |
| 2013/0030257 A1 | 1/2013 | Nakata |
| 2013/0030259 A1 | 1/2013 | Thomsen et al. |
| 2013/0085347 A1 | 4/2013 | Manicka et al. |
| 2013/0085708 A1 | 4/2013 | Sattler |
| 2013/0096395 A1 | 4/2013 | Katra et al. |
| 2013/0116520 A1 | 5/2013 | Roham |
| 2013/0116534 A1 | 5/2013 | Woo |
| 2013/0116585 A1 | 5/2013 | Bouguerra |
| 2013/0144130 A1 | 6/2013 | Russell et al. |
| 2013/0158372 A1 | 6/2013 | Haisley |
| 2013/0172691 A1 | 7/2013 | Tran |
| 2013/0172724 A1 | 7/2013 | Aziz et al. |
| 2013/0225938 A1 | 8/2013 | Vlach |
| 2013/0245388 A1 | 9/2013 | Rafferty et al. |
| 2013/0245415 A1 | 9/2013 | Kumar et al. |
| 2013/0253285 A1 | 9/2013 | Bly et al. |
| 2013/0261422 A1 | 10/2013 | Gilmore et al. |
| 2013/0267854 A1 | 10/2013 | Johnson et al. |
| 2013/0296660 A1 | 11/2013 | Tsien |
| 2013/0296823 A1 | 11/2013 | Melker |
| 2013/0324812 A1 | 12/2013 | Brainard |
| 2013/0324816 A1 | 12/2013 | Bechtel et al. |
| 2013/0324855 A1 | 12/2013 | Lisogurski |
| 2013/0331665 A1 | 12/2013 | Libbus et al. |
| 2013/0338448 A1 | 12/2013 | Libbus et al. |
| 2013/0338460 A1 | 12/2013 | He et al. |
| 2014/0038147 A1 | 2/2014 | Morrow |
| 2014/0066726 A1 | 3/2014 | Costello |
| 2014/0066732 A1 | 3/2014 | Addison et al. |
| 2014/0066783 A1 | 3/2014 | Kiani et al. |
| 2014/0081152 A1 | 3/2014 | Clinton |
| 2014/0091926 A1 | 4/2014 | Gips et al. |
| 2014/0100432 A1 | 4/2014 | Golda et al. |
| 2014/0121557 A1 | 5/2014 | Gannon et al. |
| 2014/0206976 A1 | 7/2014 | Thompson |
| 2014/0228656 A1 | 8/2014 | Gonopolskiy et al. |
| 2014/0275869 A1 | 9/2014 | Kintz et al. |
| 2014/0276089 A1 | 9/2014 | Kirenko et al. |
| 2015/0057511 A1 | 2/2015 | Basu |
| 2015/0087948 A1 | 3/2015 | Bishay et al. |
| 2015/0087951 A1 | 3/2015 | Felix et al. |
| 2015/0094551 A1 | 4/2015 | Frix et al. |
| 2015/0094552 A1* | 4/2015 | Golda ............... A61B 5/0002 600/336 |
| 2015/0148622 A1 | 5/2015 | Moyer et al. |
| 2015/0148637 A1 | 5/2015 | Golda et al. |
| 2015/0148691 A1 | 5/2015 | Moyer et al. |
| 2015/0335288 A1 | 11/2015 | Toth et al. |
| 2015/0351690 A1 | 12/2015 | Toth et al. |
| 2016/0073954 A1 | 3/2016 | Meitav |
| 2016/0238440 A1 | 8/2016 | Chu et al. |
| 2016/0302674 A1 | 10/2016 | Moyer et al. |
| 2016/0345881 A1 | 12/2016 | Sarantos et al. |
| 2017/0027513 A1 | 2/2017 | Mulpuru |
| 2017/0095156 A1 | 4/2017 | Richards |
| 2017/0337412 A1 | 11/2017 | Bhat et al. |
| 2017/0337413 A1 | 11/2017 | Bhat et al. |
| 2018/0028122 A1 | 2/2018 | Golda et al. |
| 2018/0085068 A1 | 3/2018 | Telfort |
| 2018/0177459 A1* | 6/2018 | Eletr ............... A61B 5/0059 |
| 2018/0325385 A1 | 11/2018 | Deterding et al. |
| 2019/0029599 A1 | 1/2019 | Golda et al. |
| 2019/0282096 A1 | 9/2019 | Vardi |
| 2019/0320914 A1 | 10/2019 | Moyer et al. |
| 2020/0008749 A1 | 1/2020 | Golda et al. |
| 2020/0229767 A1 | 7/2020 | Eletr et al. |
| 2020/0237309 A1 | 7/2020 | Golda et al. |
| 2021/0059586 A1 | 3/2021 | Marriott et al. |
| 2021/0100514 A1 | 4/2021 | Golda et al. |
| 2021/0145293 A1 | 5/2021 | Moyer et al. |
| 2021/0212638 A1 | 7/2021 | Golda et al. |
| 2021/0236064 A1 | 8/2021 | Moyer et al. |

FOREIGN PATENT DOCUMENTS

| | | |
|---|---|---|
| CN | 201641985 U | 11/2010 |
| CN | 101984743 A | 3/2011 |
| CN | 102215747 A | 10/2011 |
| CN | 202288274 U | 7/2012 |
| CN | 105997103 A | 10/2016 |
| CN | 104812296 B | 5/2018 |
| EP | 0581073 A2 | 2/1994 |
| EP | 1737337 B1 | 5/2005 |
| EP | 1139858 B1 | 4/2007 |
| EP | 2438851 A2 | 4/2012 |
| EP | 2305103 B1 | 9/2013 |
| EP | 2903509 B1 | 9/2019 |
| EP | 3636148 A1 | 4/2020 |
| EP | 3099224 B1 | 5/2020 |
| EP | 3636148 A3 | 5/2020 |
| EP | 3769669 A1 | 1/2021 |
| JP | 52-052494 | 4/1977 |
| JP | 02172443 A | 7/1990 |
| JP | H05123305 A | 5/1993 |
| JP | H07213630 A | 8/1995 |
| JP | H09224917 A | 9/1997 |
| JP | 2001029318 A | 2/2001 |
| JP | 2001078974 A | 3/2001 |
| JP | 2002125944 A | 5/2002 |
| JP | 2002263075 A | 9/2002 |
| JP | 2004000474 | 1/2004 |
| JP | 2004016248 A | 1/2004 |
| JP | 2006000481 A | 1/2006 |
| JP | 2006158813 A | 6/2006 |
| JP | 3952082 B2 | 8/2007 |
| JP | 2007244531 A | 9/2007 |
| JP | 2007296266 A | 11/2007 |
| JP | 2011-147746 | 8/2011 |
| JP | 20120187404 A | 10/2012 |
| JP | 5408751 B2 | 2/2014 |
| JP | 6298063 B2 | 3/2018 |
| JP | 6539827 B2 | 7/2019 |
| JP | 6625682 B2 | 12/2019 |

(56) References Cited

FOREIGN PATENT DOCUMENTS

| | | | |
|---|---|---|---|
| JP | 2020513876 A | 5/2020 |
| WO | W09401039 A1 | 1/1994 |
| WO | WO9427494 A1 | 12/1994 |
| WO | WO0045696 A1 | 8/2000 |
| WO | WO0059374 A1 | 10/2000 |
| WO | WO01/043624 A4 | 6/2001 |
| WO | WO2001085019 A2 | 11/2001 |
| WO | WO2001093758 A1 | 12/2001 |
| WO | W00200094 A2 | 1/2002 |
| WO | WO2002085201 A1 | 10/2002 |
| WO | WO2002086792 A2 | 10/2002 |
| WO | WO2002086835 A1 | 10/2002 |
| WO | WO2002086837 A1 | 10/2002 |
| WO | WO2003077752 A1 | 9/2003 |
| WO | WO2005079429 A2 | 1/2005 |
| WO | WO2005060829 A1 | 7/2005 |
| WO | WO2005072237 A2 | 8/2005 |
| WO | W02006014806 A2 | 2/2006 |
| WO | WO2006044919 A2 | 4/2006 |
| WO | WO2006110488 A2 | 10/2006 |
| WO | W02006124788 A2 | 11/2006 |
| WO | WO2006124788 A2 | 11/2006 |
| WO | 2008092098 A2 | 7/2008 |
| WO | WO2008092098 A2 | 7/2008 |
| WO | WO2008092098 A3 | 10/2008 |
| WO | WO2009036321 A1 | 3/2009 |
| WO | WO2009036327 A1 | 3/2009 |
| WO | 2009112972 A2 | 9/2009 |
| WO | WO2010/055155 A2 | 5/2010 |
| WO | WO2010093900 A2 | 8/2010 |
| WO | WO2010104952 A2 | 9/2010 |
| WO | WO2010107913 A2 | 9/2010 |
| WO | W02011074004 A2 | 6/2011 |
| WO | WO2012104658 A2 | 8/2012 |
| WO | WO2012129498 A1 | 9/2012 |
| WO | WO2012150563 A1 | 11/2012 |
| WO | 2014027293 A2 | 2/2014 |
| WO | 2014027293 A3 | 2/2014 |
| WO | 2014055994 A1 | 4/2014 |
| WO | 2015113054 A1 | 7/2015 |
| WO | WO2013/071014 A2 | 5/2016 |
| WO | 2016210334 A1 | 12/2016 |
| WO | WO2018112401 A1 | 6/2018 |
| WO | 2020154697 A1 | 7/2020 |

OTHER PUBLICATIONS

Partial European Search Report for Application No. 19194996.5 issued by the European Patent Office, dated Feb. 6, 2020, 15 pages, EPO, Munich, Germany.

Transmittal of International Preliminary Report of Patentability and International Preliminary Report on Patentability for Application No. PCT/US2016/039374 issued by the International Bureau of WIPO, Geneva, Switzerland dated Jan. 4, 2018 which includes: The International Preliminary Report on Patentability dated Dec. 26, 2017 with Written Opinion of the International Searching Authority for International Application No. PCT/US2016/039374 dated Oct. 28, 2016 issued by the United States Patent Office, dated Oct. 28, 2016.

International Search Report and Written Opinion of the International Searching Authority. International Application No. PCT/US2016/039374 issued by the United State Patent Office, dated Oct. 28, 2016, 14 pages, Alexandria Virginia.

Chinese Office Action, Application No. 201780077645.7, dated Jun. 15, 2021, China National Intellectual Property Administration, Beijing, China.

Notification of transmittal of the International Search Report and the Written Opinion of the International Searching Authority for Application No. PCT/US2017/066805 issued by the International Searching Authority, Alexandria, VA dated Mar. 12, 2018, 1 page, which includes: The International Search Report completed Feb. 7, 2018 dated Mar. 12, 2018, 5 pages, with Written Opinion of the International Searching Authority for International Application No. PCT/US2017/066805 dated Mar. 12, 2018 issued by the United States Patent Office, Alexandria, dated Mar. 12, 2018.

Extended European Search Report including the Supplementary European Search Report for Application No. EP15740972 issued by the European Patent Office, Munich, Germany dated Aug. 29, 2017.

Extended European Search Report for Application No. EP19194996 issued by the European Patent Office, dated Apr. 22, 2020, 18 pages, EPO, Munich, Germany.

Palreddy, Surekha, Chapter 9—Signal Processing Algorithms, Design of Pulse Oximeters, Medical Science Series, Bristol [U.A.]; Institute of Physics Pub, GB, Jan. 1, 1997, pp. 124-158, 133-157, Taylor & Francis Group, LLC., New York, NY and Milton Park, Abingdon, Oxon, England.

International Search Report and Written Opinion of the International Searching Authority. International Application No. PCT/US20/15099 issued by the United State Patent Office, dated Jun. 4, 2020, 11 pages, Alexandria Virginia.

Yoo, Jerald et al., A 5.2 mW Self-Configured Wearable Body Sensor Network controller and a 12 uW Wirelessly Powered Sensor for a Continuous Health Monitoring System, IEEE Journal of Solid-State Circuits, Jan. 2010, pp. 178-188, vol. 45, Issue No. 1, Institute of Electrical and Electronics Engineers, Piscataway, NJ.

Japanese Office Action dated/transmitted Aug. 31, 2021 for Japanese Application No. 2019531741—original and translation.

Kansy, Robert J., Response of a Correlated Double Sampling Circuity to 1/f Noise, IEEE Journal of Solid-State Circuits, Jun. 1980, pp. 373-375, vol. SC-15, No. 3, IEEE, New York, NY, USA.

International Search Report and Written Opinion of the International Searching Authority. International Application No. PCT/US2013/063748 issued by the United State Patent Office, dated Feb. 27, 2014, 15 pages, Alexandria Virginia.

Timmerman, Luke, Xconomy, Inc., "UW Spinout Cardiac Insight Wins FDA OK for Heartbeat Monitor", published Jun. 6, 2013; website accessed Oct. 27, 2013, http://www.xconomy.com/seattle/2013/06/06/uw-spinout-cardiac-insight-wins-fda-ok-for-heartbeat-monitor/, Xconomy Inc., Cambridge, Massachusetts.

CardioNet, Inc., "CardioNet, Inc. Announces Launch of MCOTos 2:1 Device", published Jun. 19, 2013; website accessed Oct. 27, 2013, https://www.cardionet.com/index.htm, BioTelemetry, Inc., Conshohocken, Pennsylvania.

Heart Check, "The HeartCheck Pen, a Handheld ECG with SMART Monitoring", website accessed Oct. 27, 2013, http://heartcheckpen.com/, HeartCheckPEN.com, TAW Global, LLC, Portage, Michigan; CardioComm Solutions Inc., Toronto, ON, and Victoria, BC.

Corventis, Inc., "Nuvant Mobile Cardiac Telemetry", Copyright 2009-2013; website accessed Oct. 27, 2013, http://corventis.com/, Corventis, San Jose, California.

Transmittal of International Preliminary Report on Patentability dated Apr. 16, 2015 and International Preliminary Report on Patentability date of issuance of report dated Apr. 7, 2015 with Written Opinion of the International Searching Authority International Application No. PCT/US2013/063748 issued by the United State Patent Office, dated Feb. 27, 2014, 5 pages, Alexandria, Virginia.

International Search Report and Written Opinion of the International Searching Authority. International Application No. PCT/US2015/13113 issued by the United State Patent Office, dated Jun. 29, 2015, 14 pages, Alexandria Virginia.

Supplementary European Search Report for Application No. EP17880188 issued by the European Patent Office, dated Aug. 5, 2020, 8 pages, EPO, Munich, Germany.

Extended European Search Report for Application No. EP20175192 issued by the European Patent Office, dated Oct. 26, 2020, 12 pages, EPO, Munich, Germany.

International Search Report and Written Opinion of the International Searching Authority. International Application No. PCT/US2020/048603 issued by the United States Patent Office, dated Jan. 4, 2020, 18 pages, USPTO, Alexandria, Virginia, USA.

Supplementary European Search Report for Application No. EP16815429 issued by the European Patent Office, dated Jan. 17, 2019, 4 pages, EPO, Munich, Germany.

(56) References Cited

OTHER PUBLICATIONS

Allen, John, Photoplethysmography and its application in clinical physiological measurement, Physiological Measurement, Feb. 20, 2007, pp. R1-R39, vol. 28, No. 3, IOP Publishing Ltd., Bristol, United Kingdom.

Extended European Search Report including the Supplementary European Search Report (SESR) for Application No. EP13843561.5 issued by the European Patent Office, Munich, Germany dated Apr. 29, 2016.

\* cited by examiner

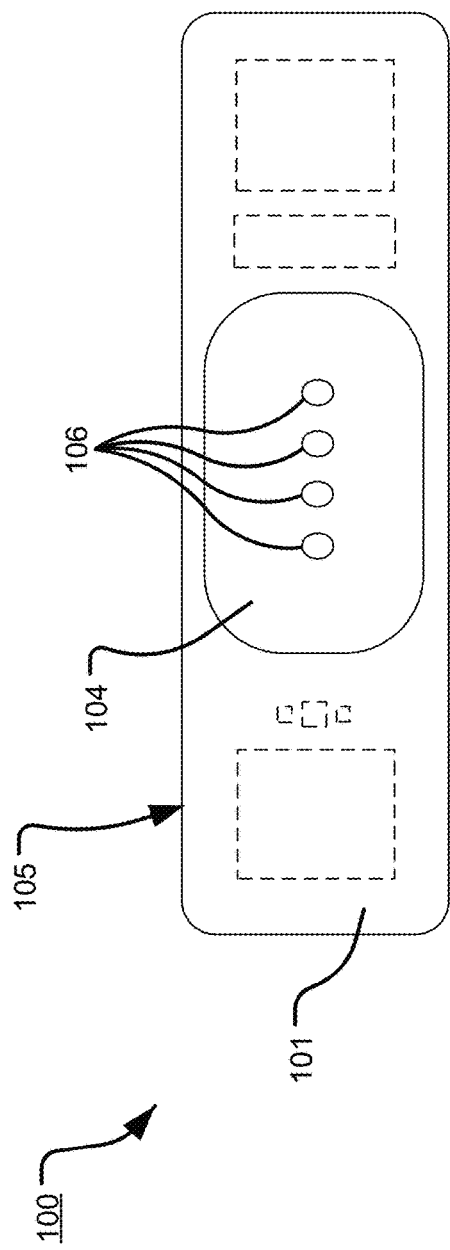
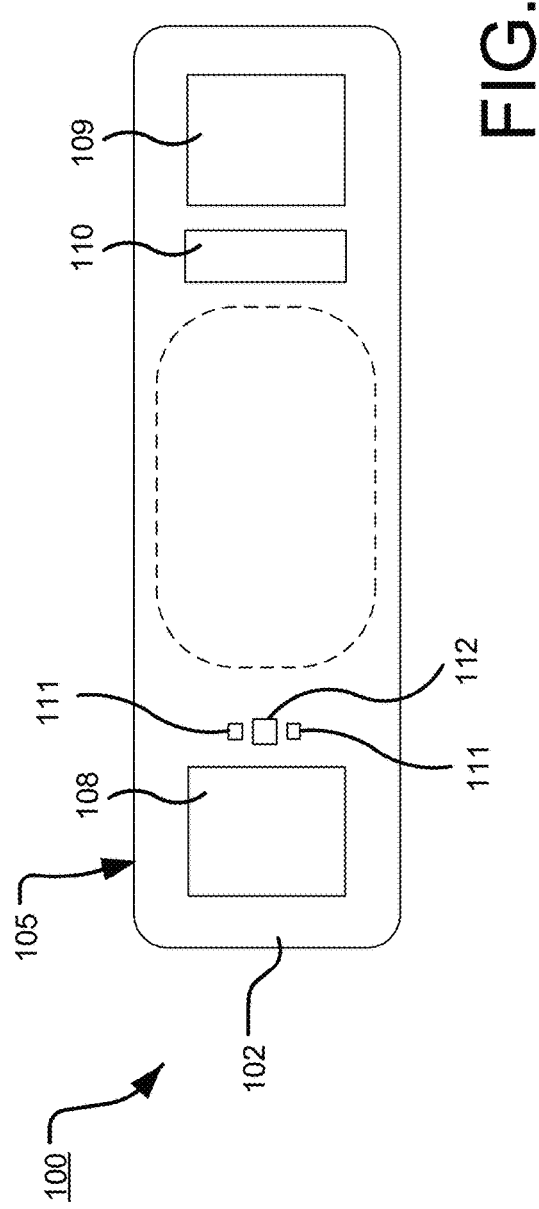

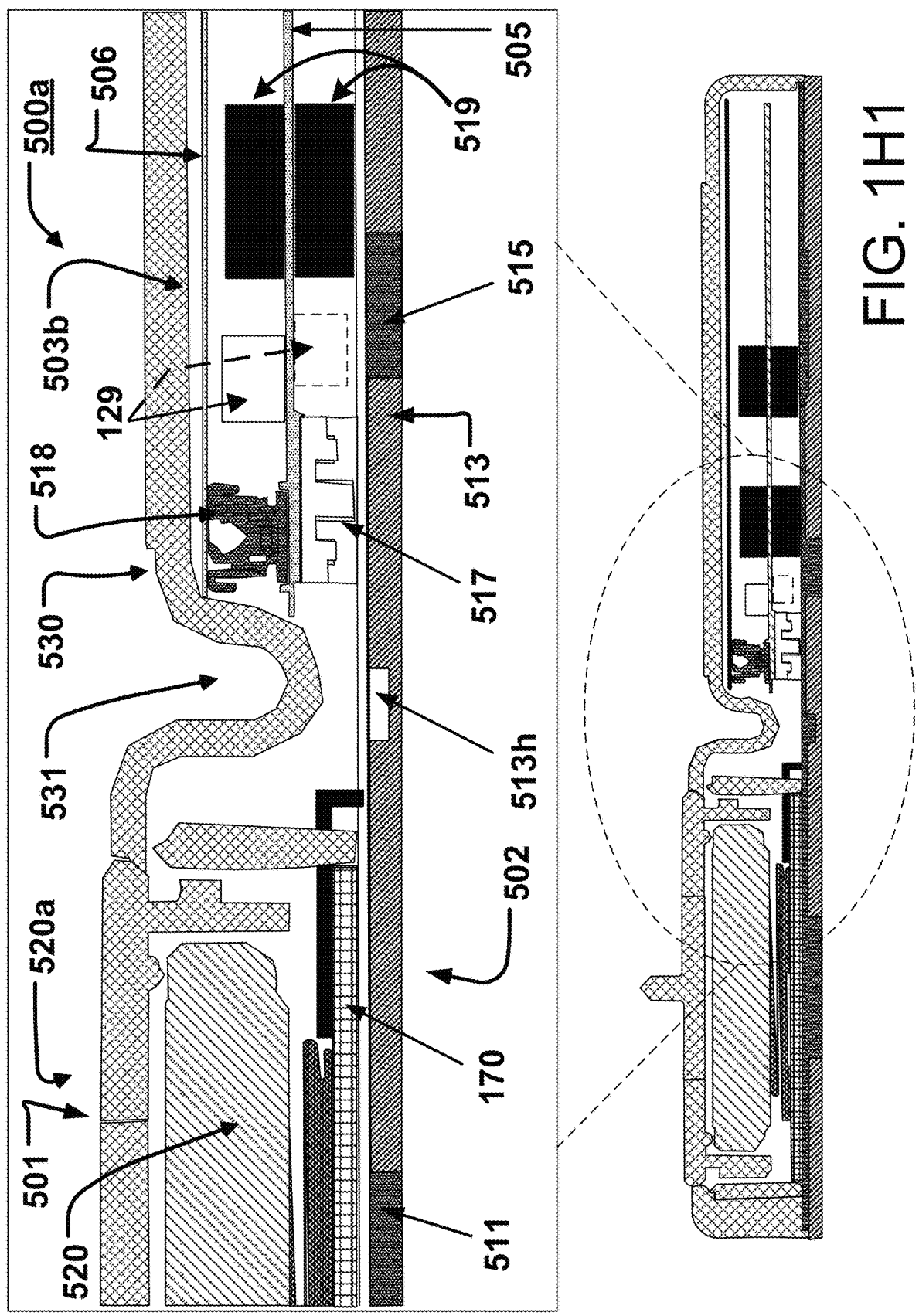

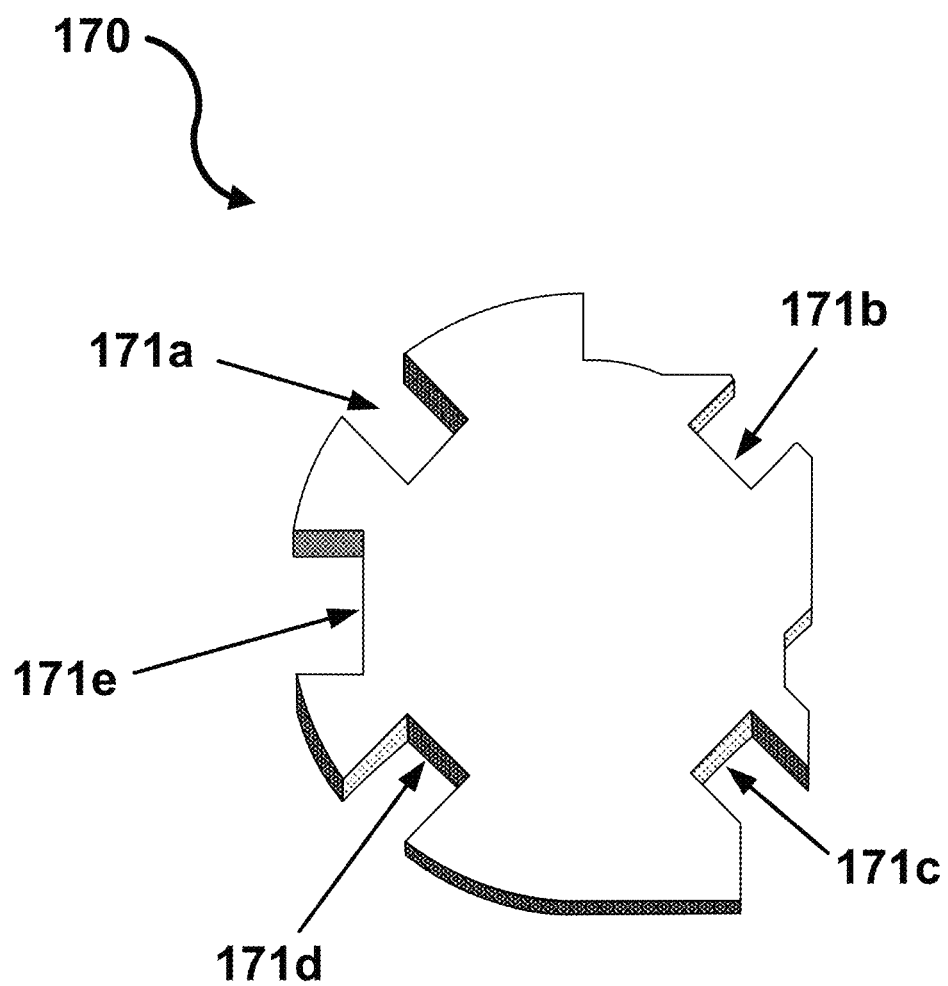
FIG. 1I1

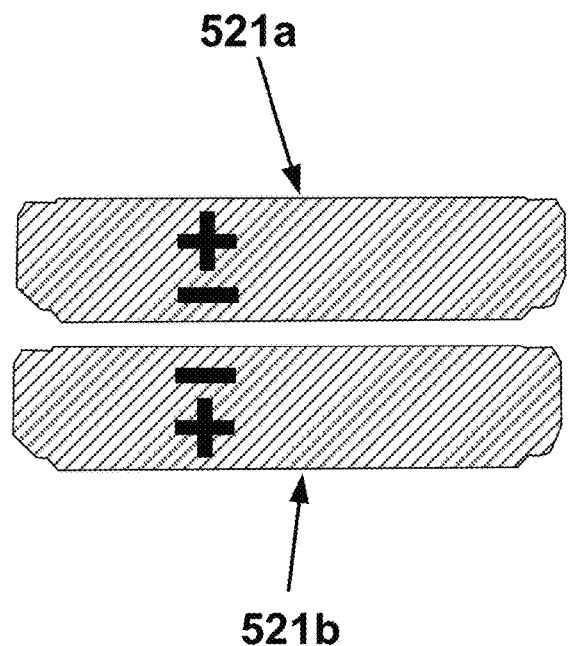
FIG. 1l2a
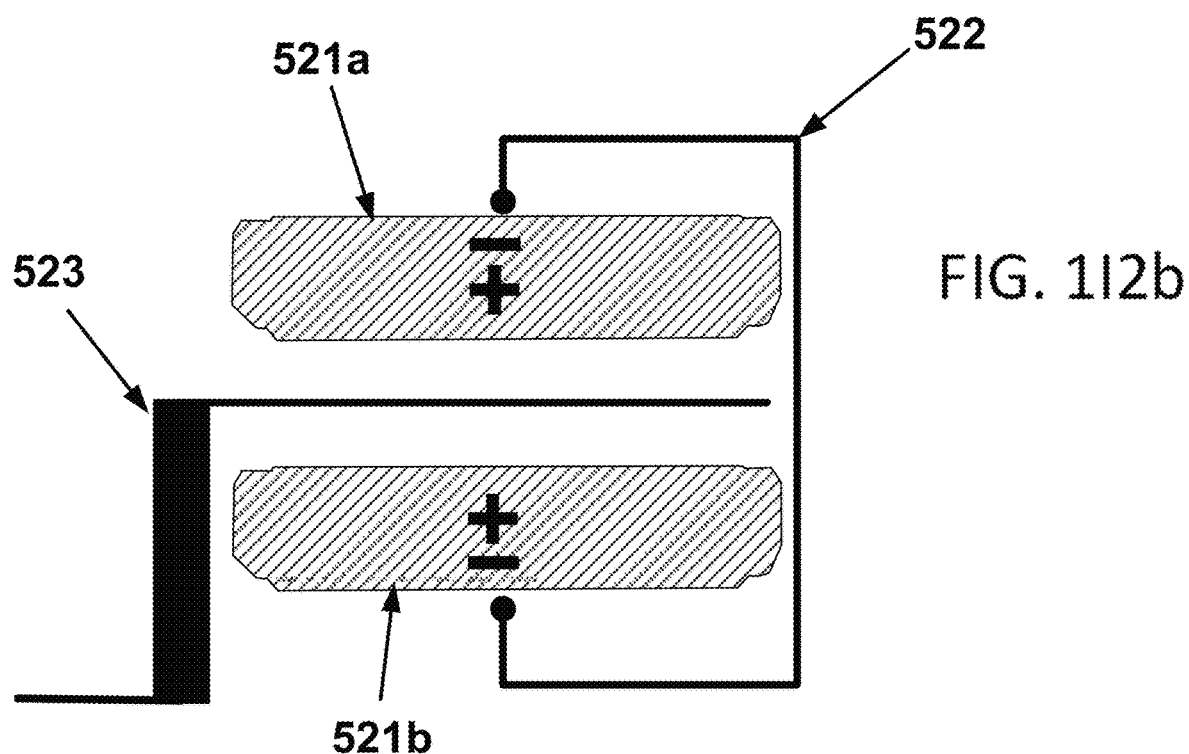
FIG. 1l2b

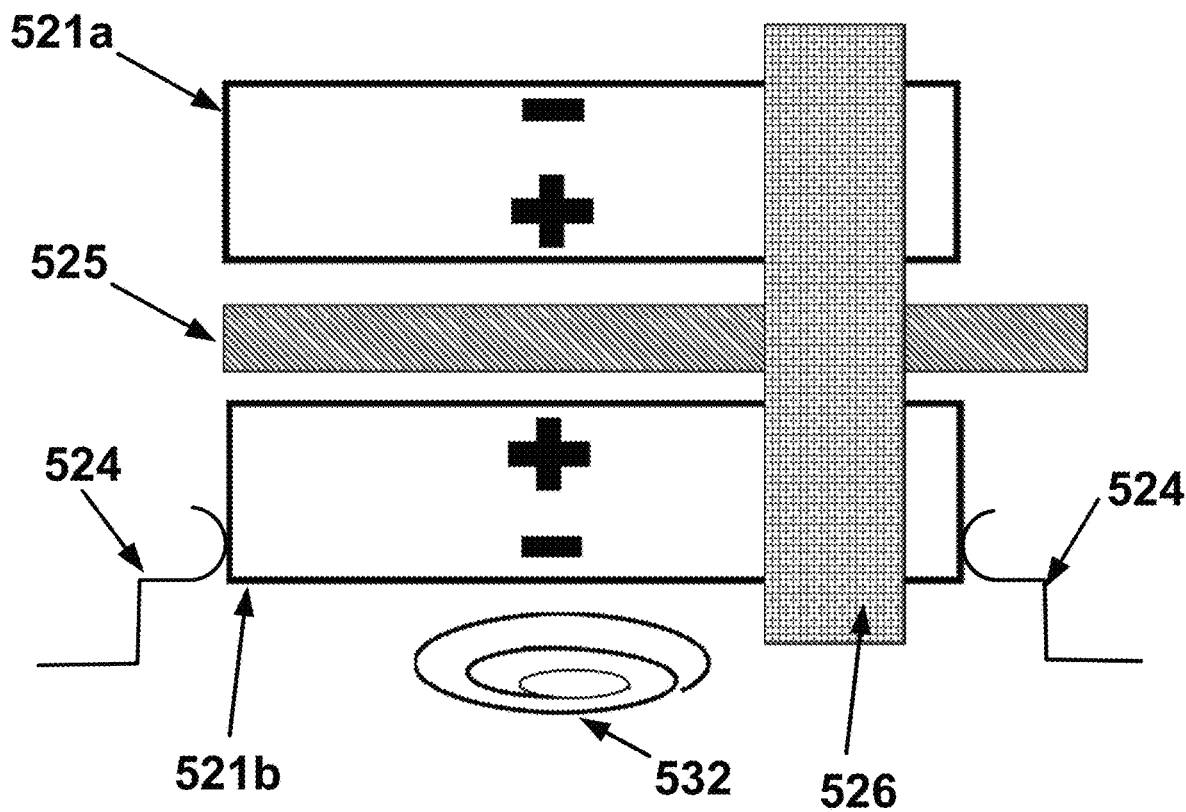
FIG. 1I2c
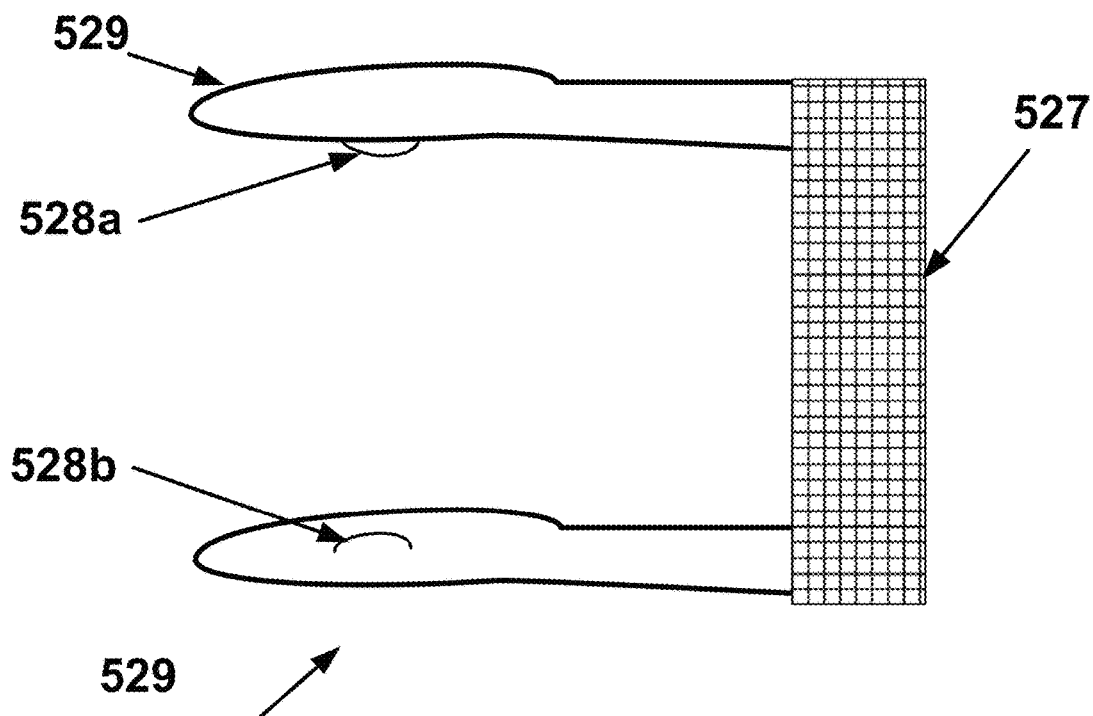
FIG. 1I2d

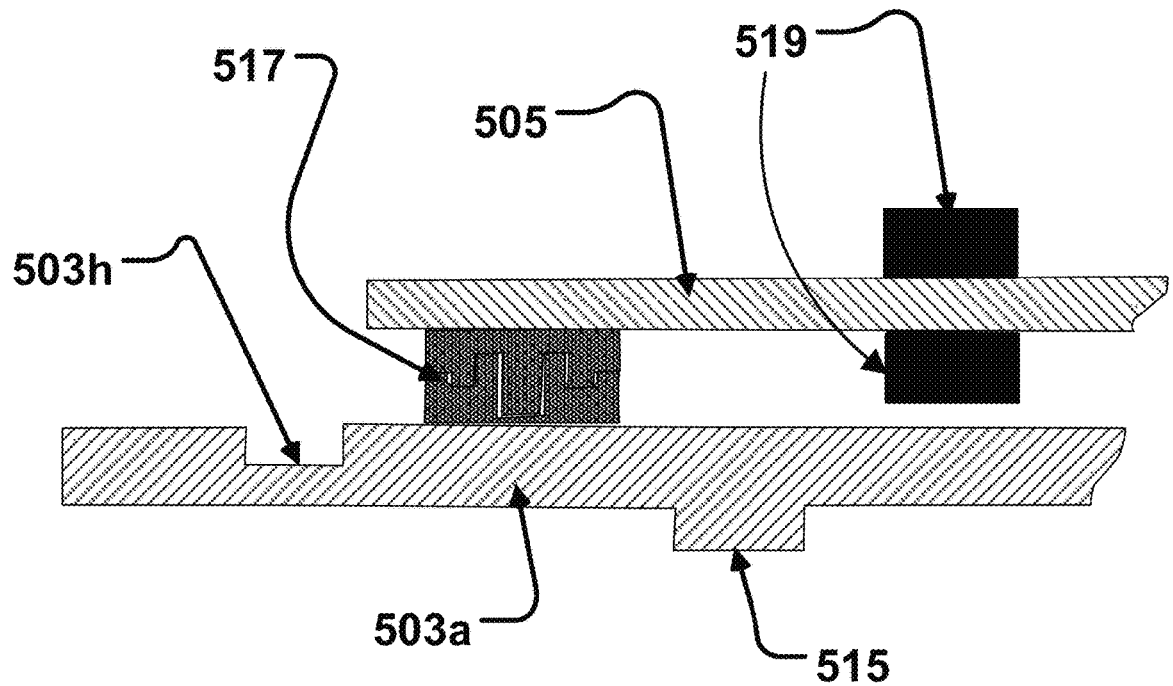
FIG. 1K
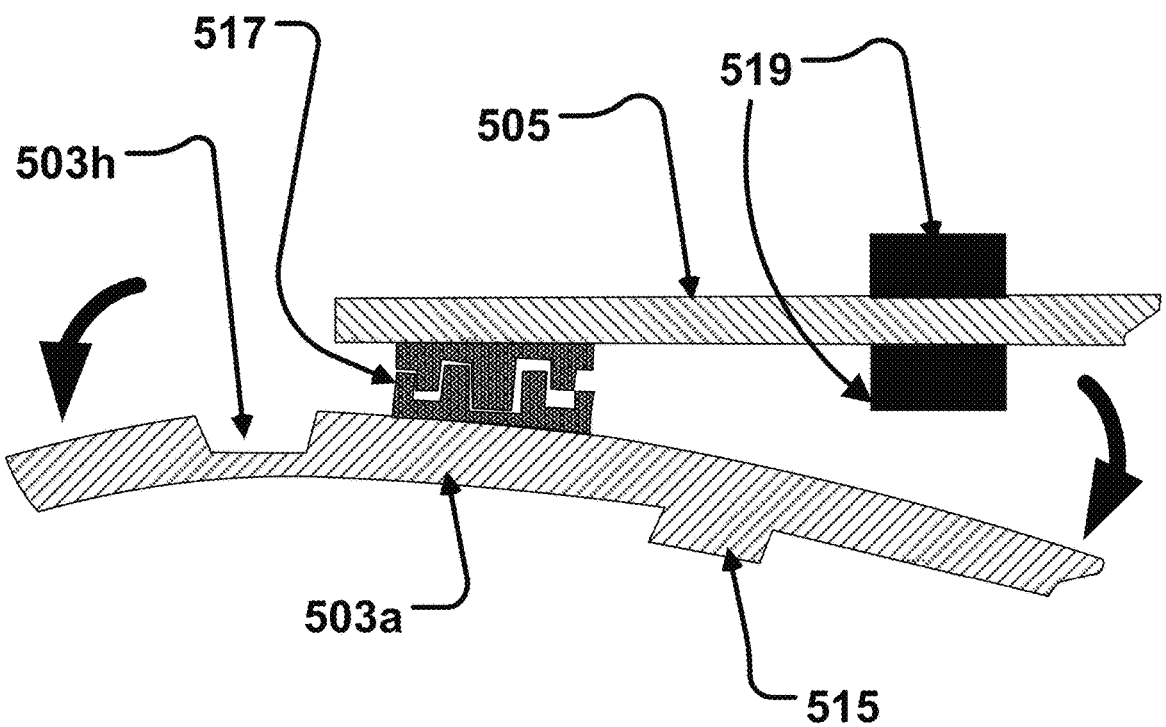
FIG. 1K1

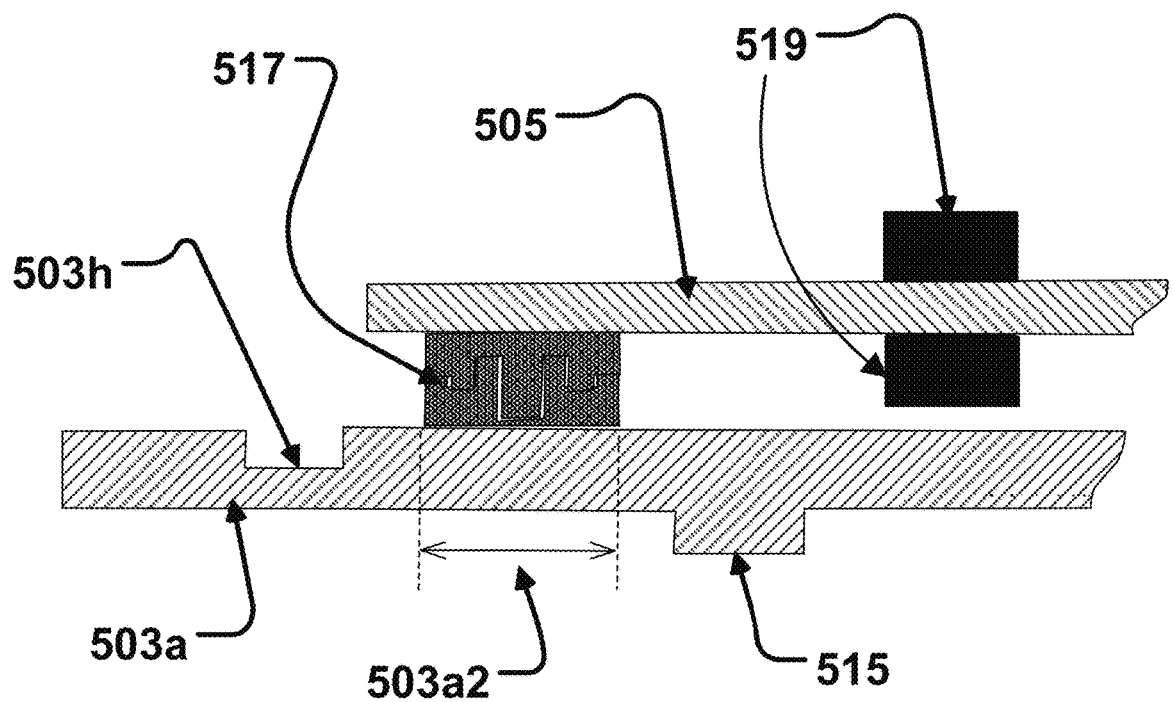
FIG. 1L
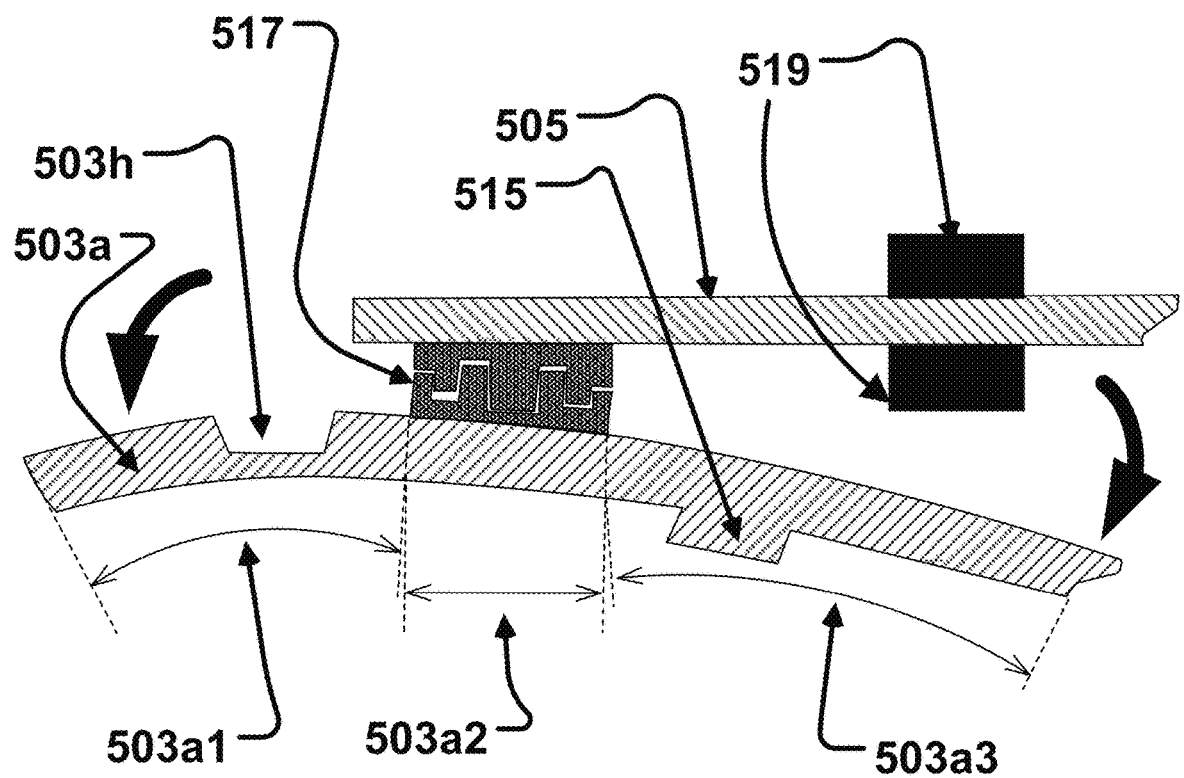
FIG. 1L1

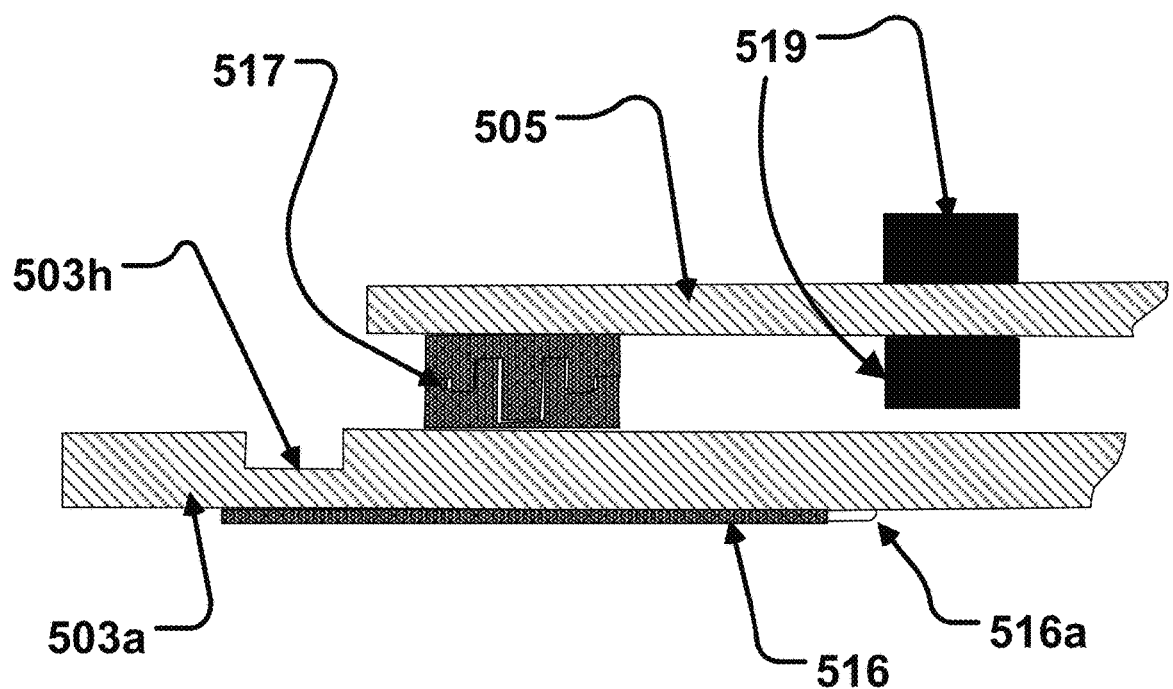
FIG. 1M
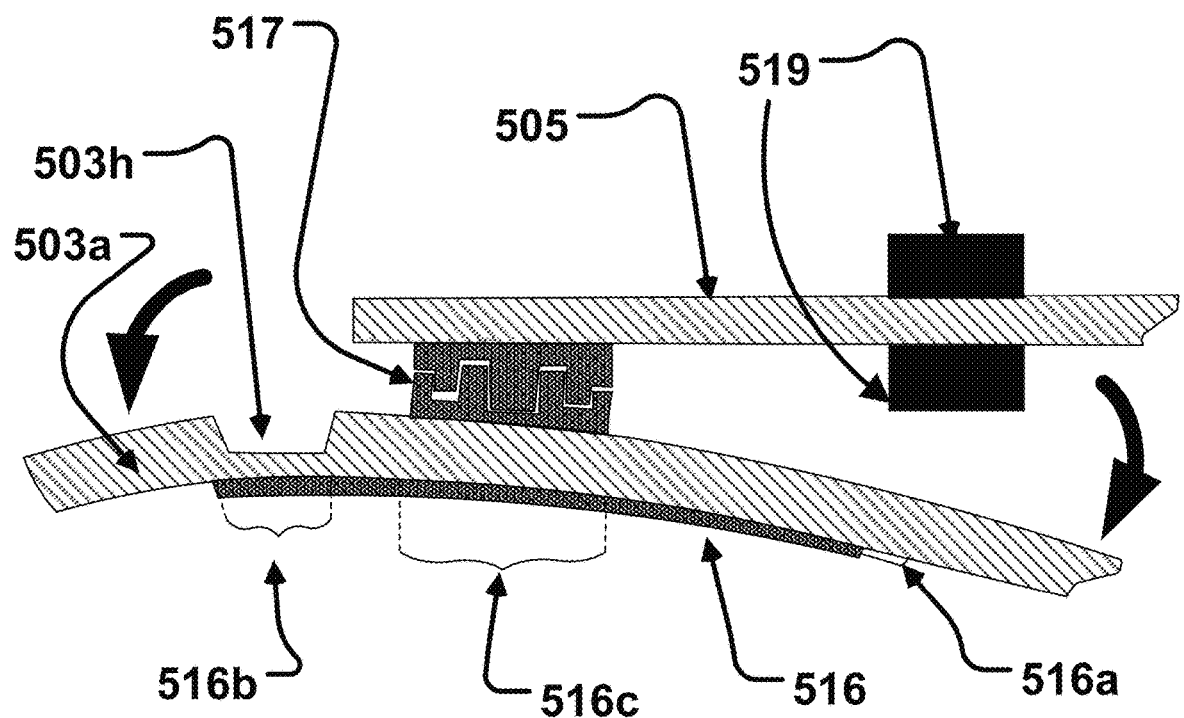
FIG. 1M1

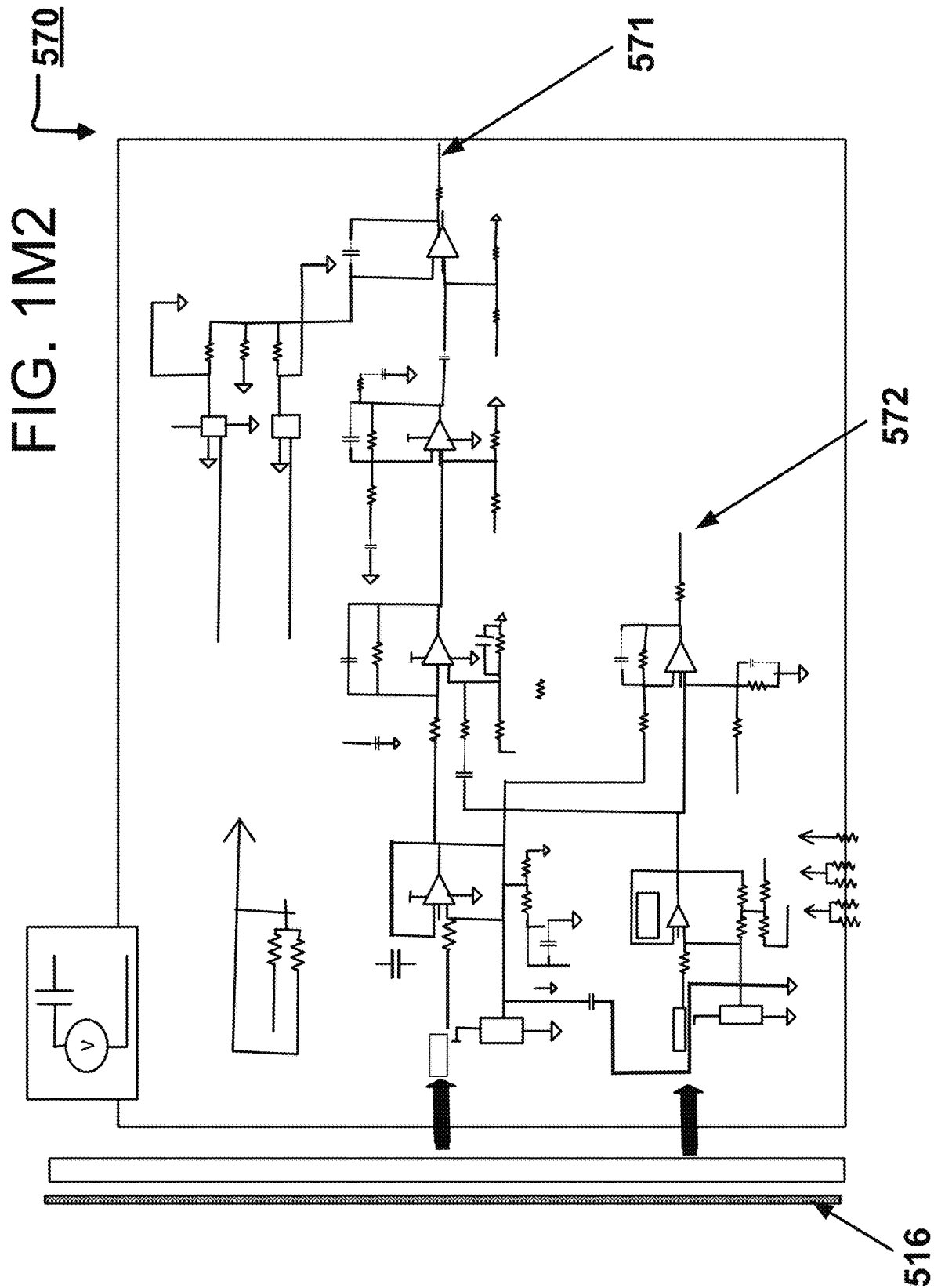
FIG. 1M2

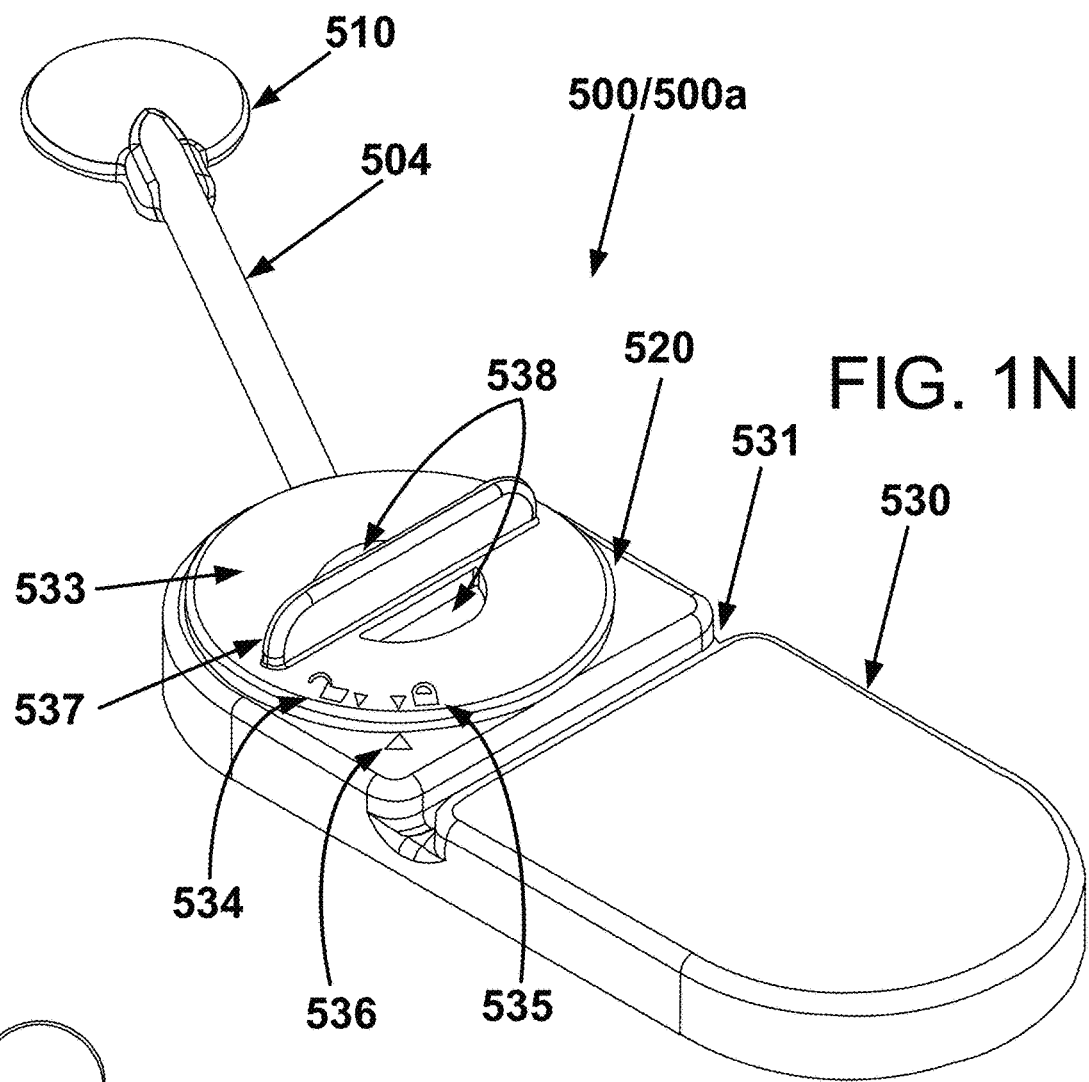
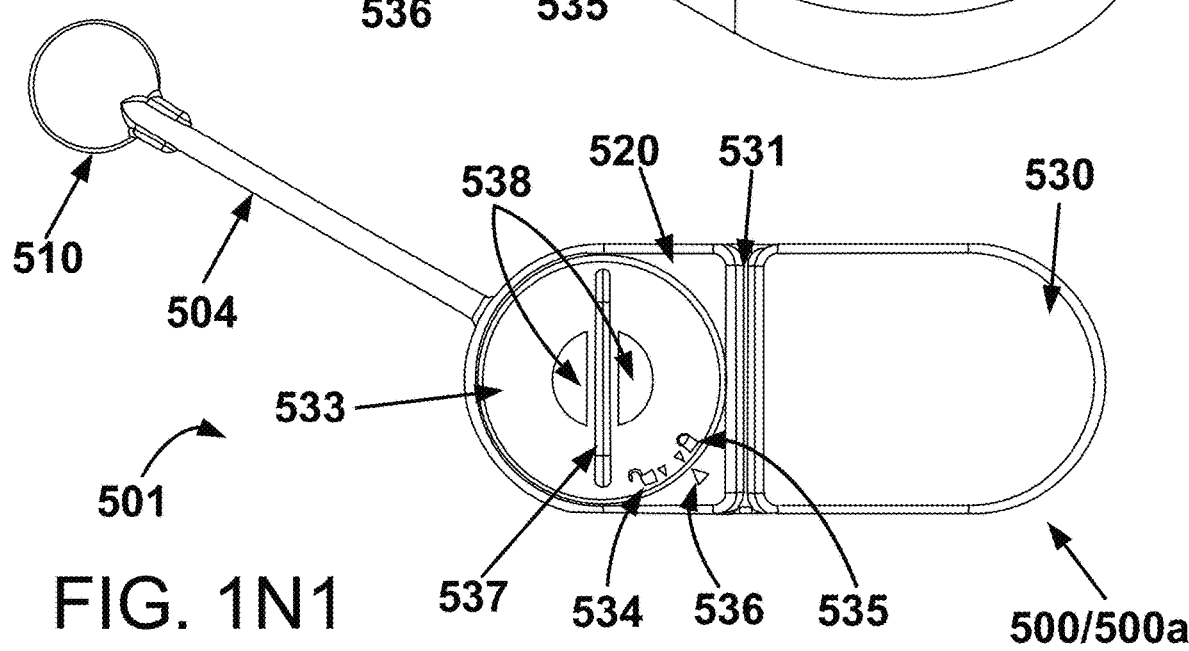

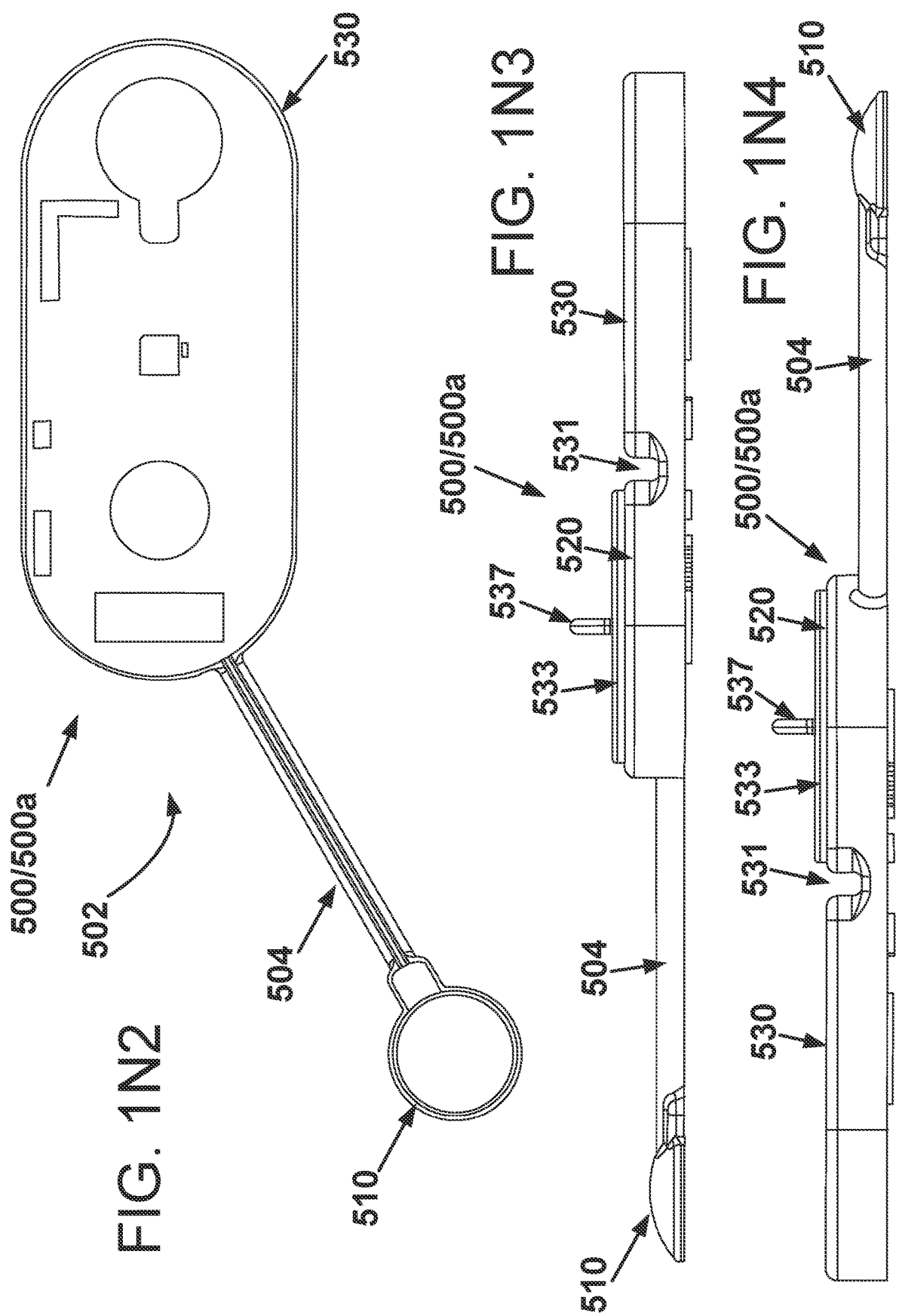

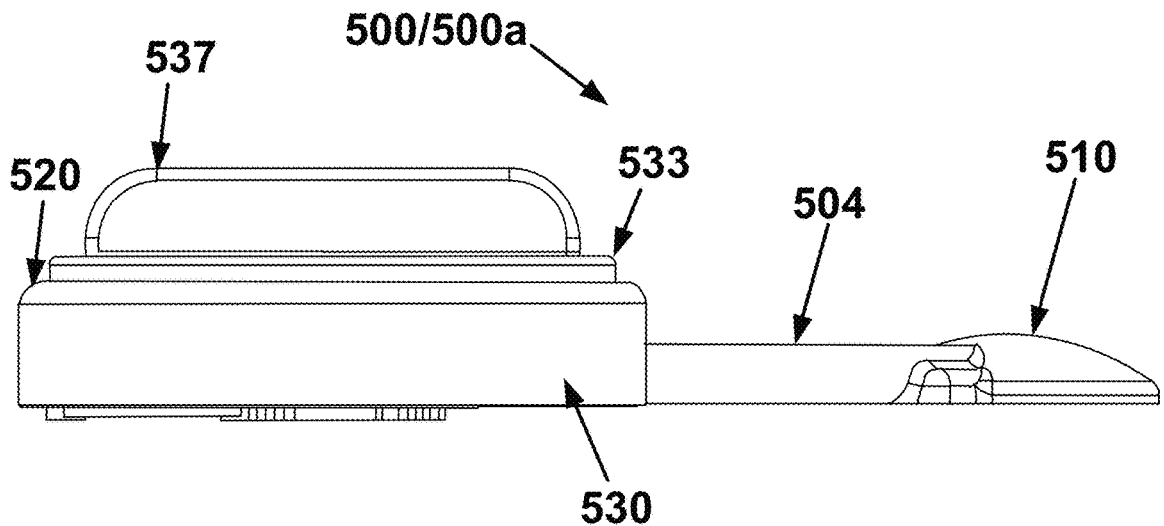
FIG. 1N5
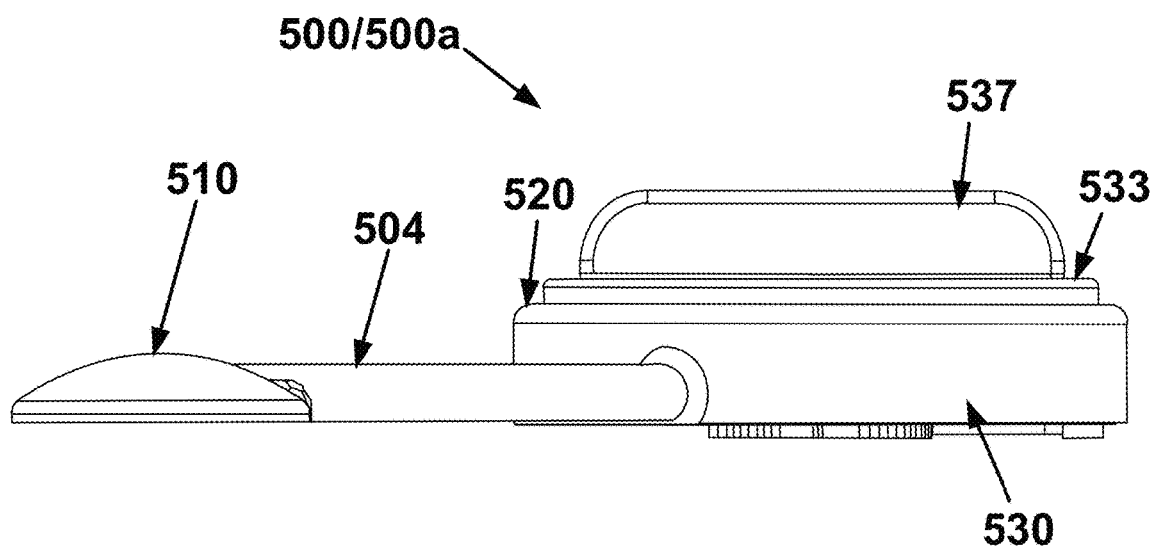
FIG. 1N6

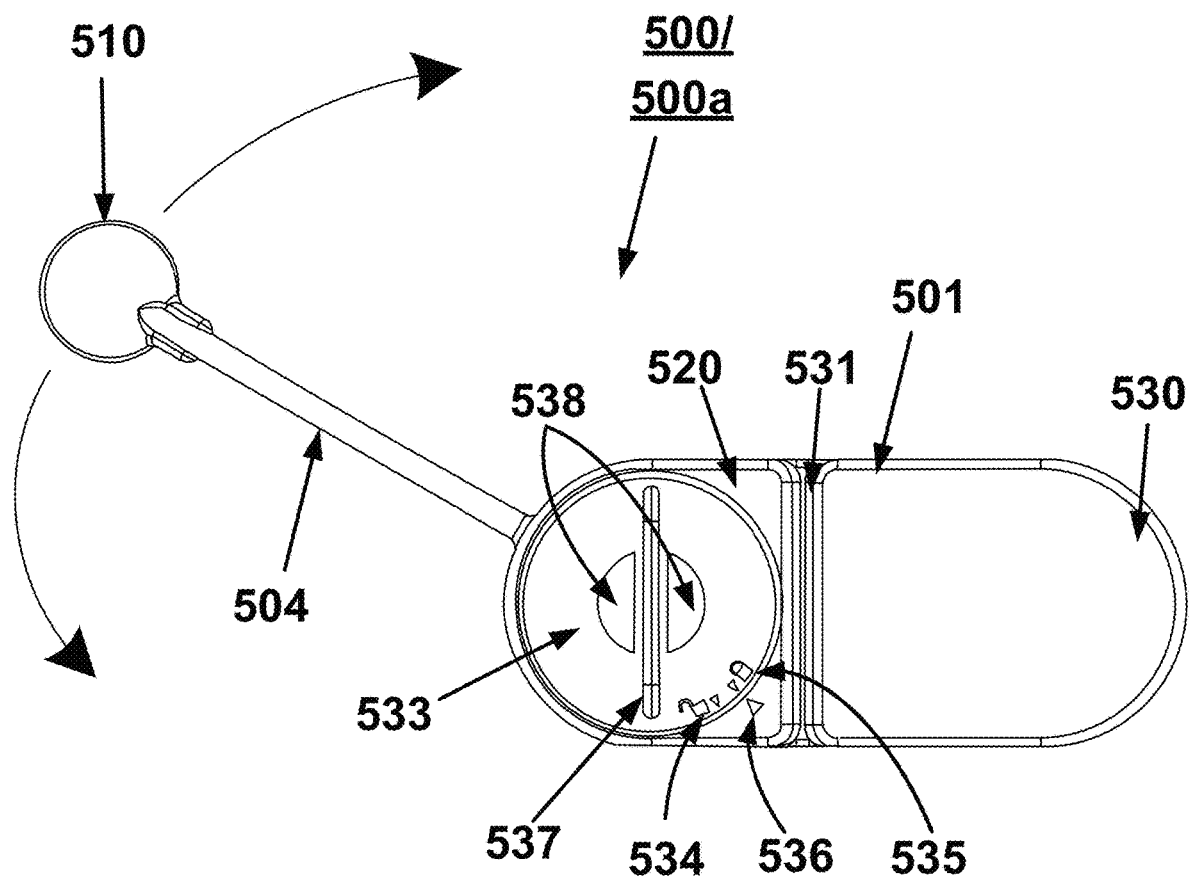
FIG. 1N7

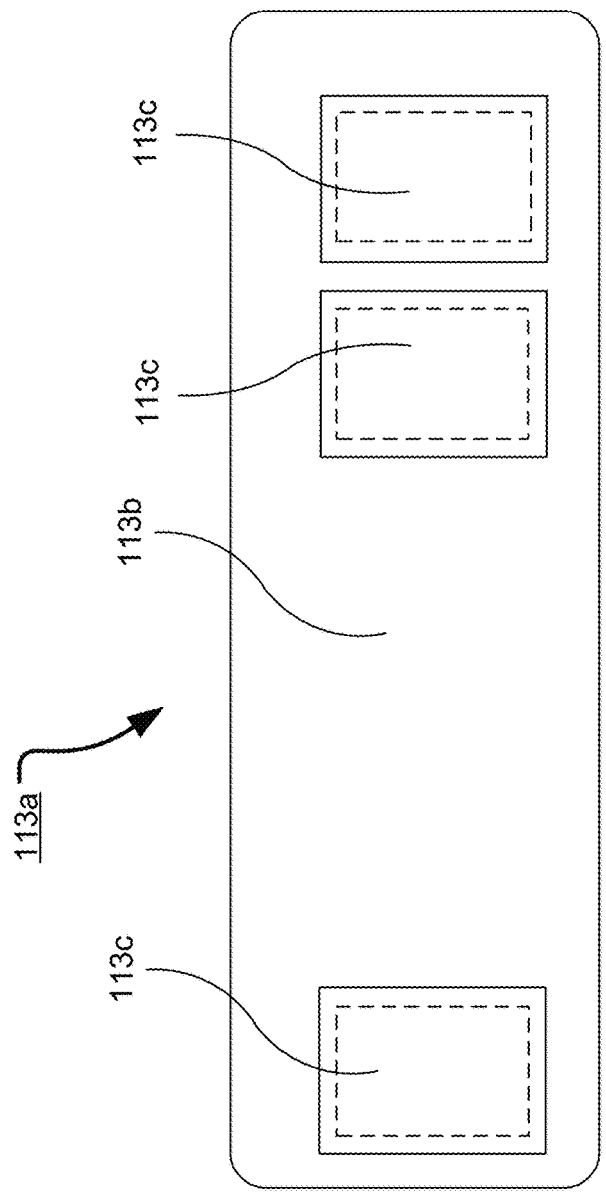
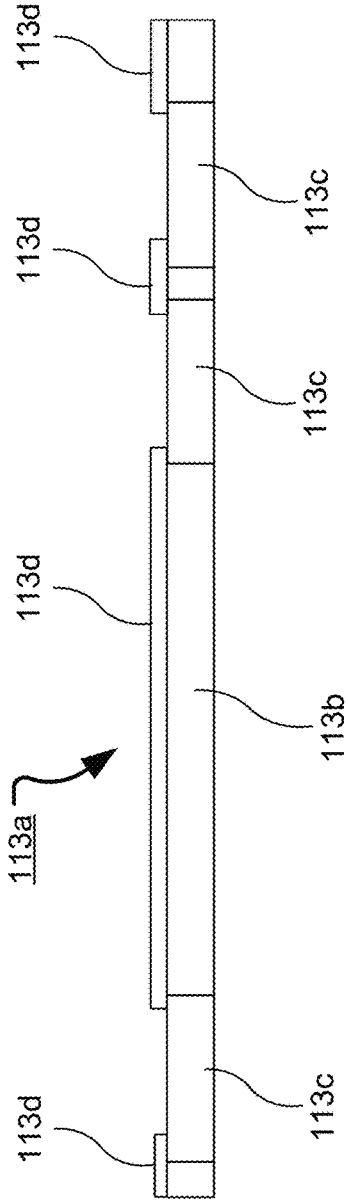
FIG. 10
FIG. 10I

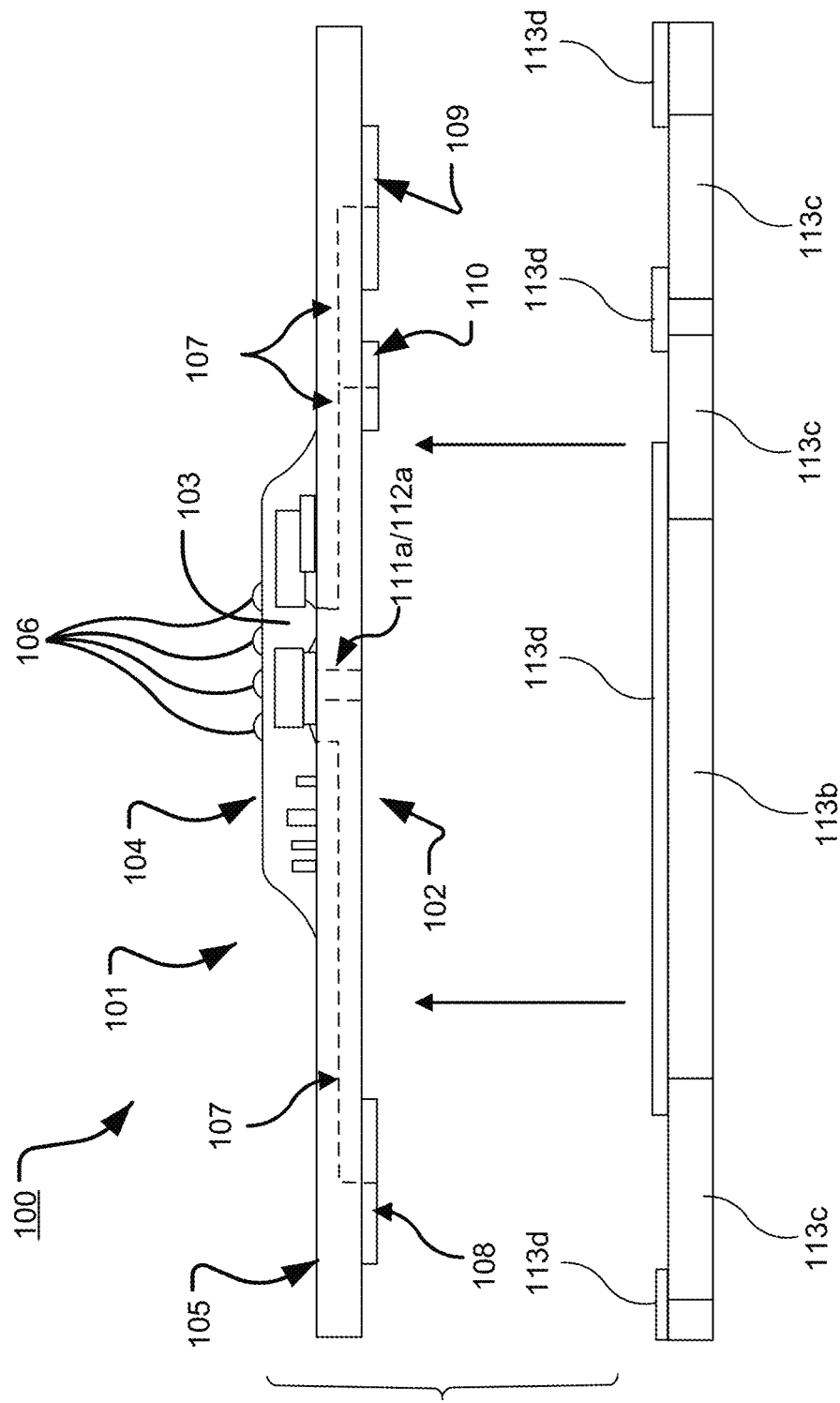

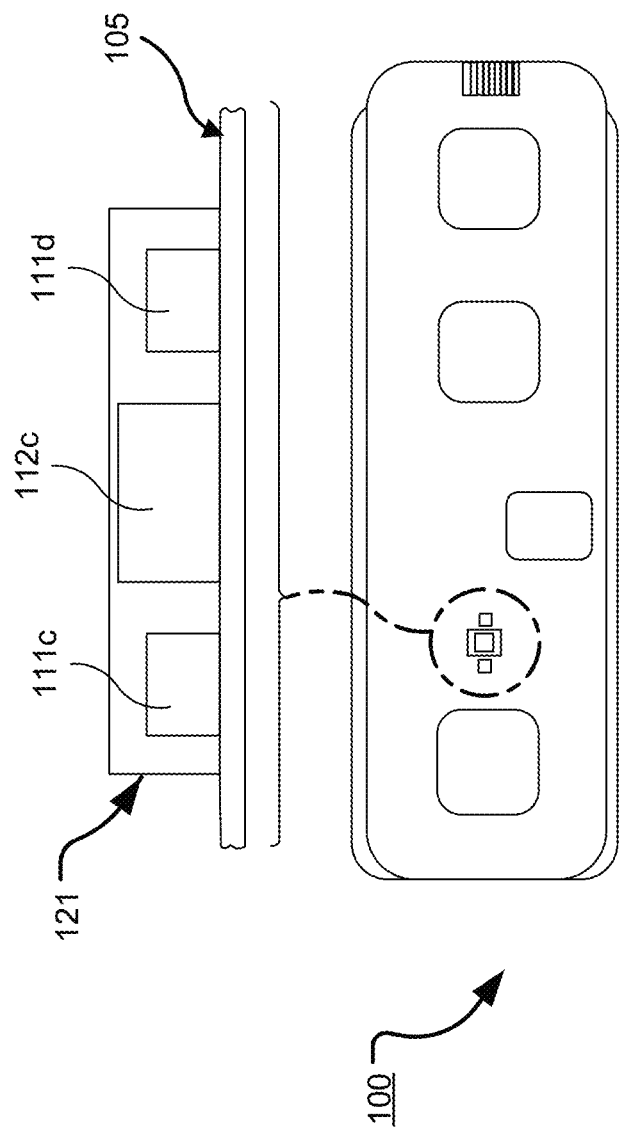

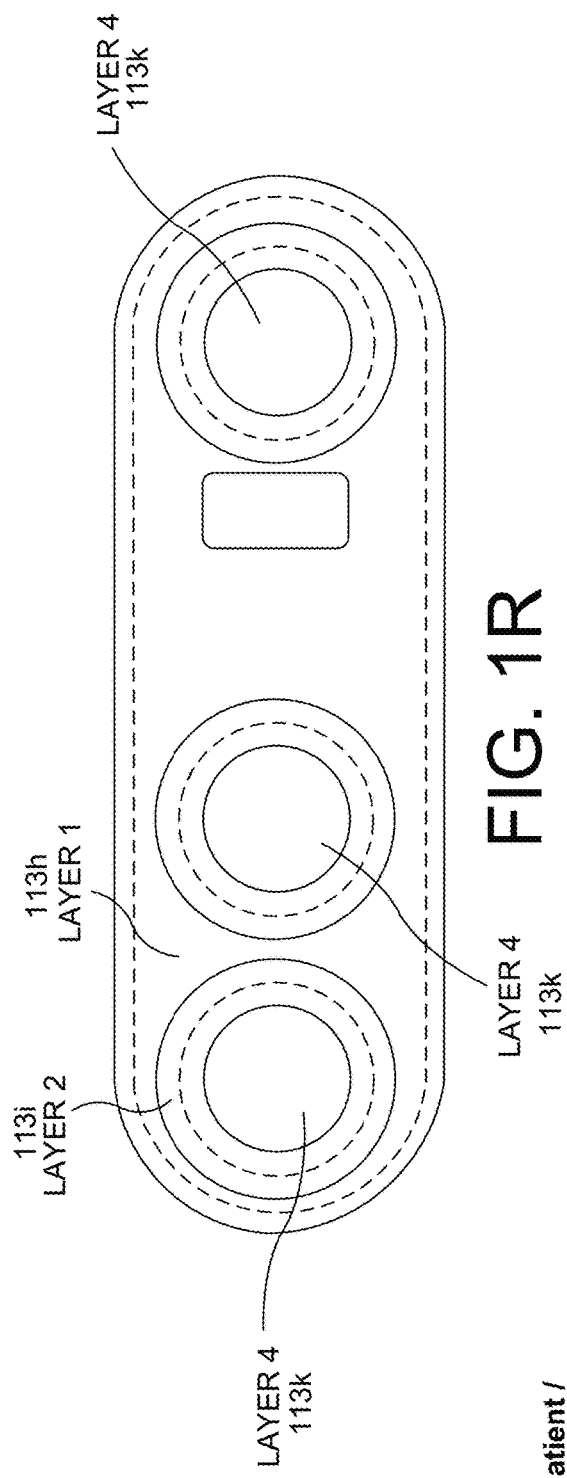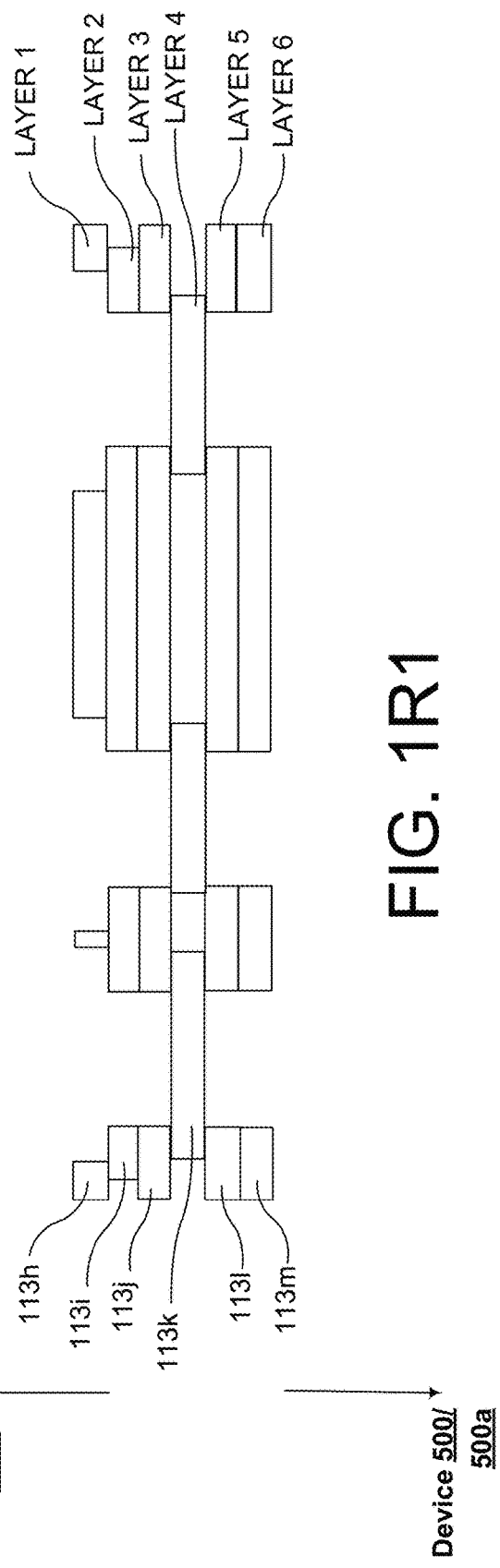

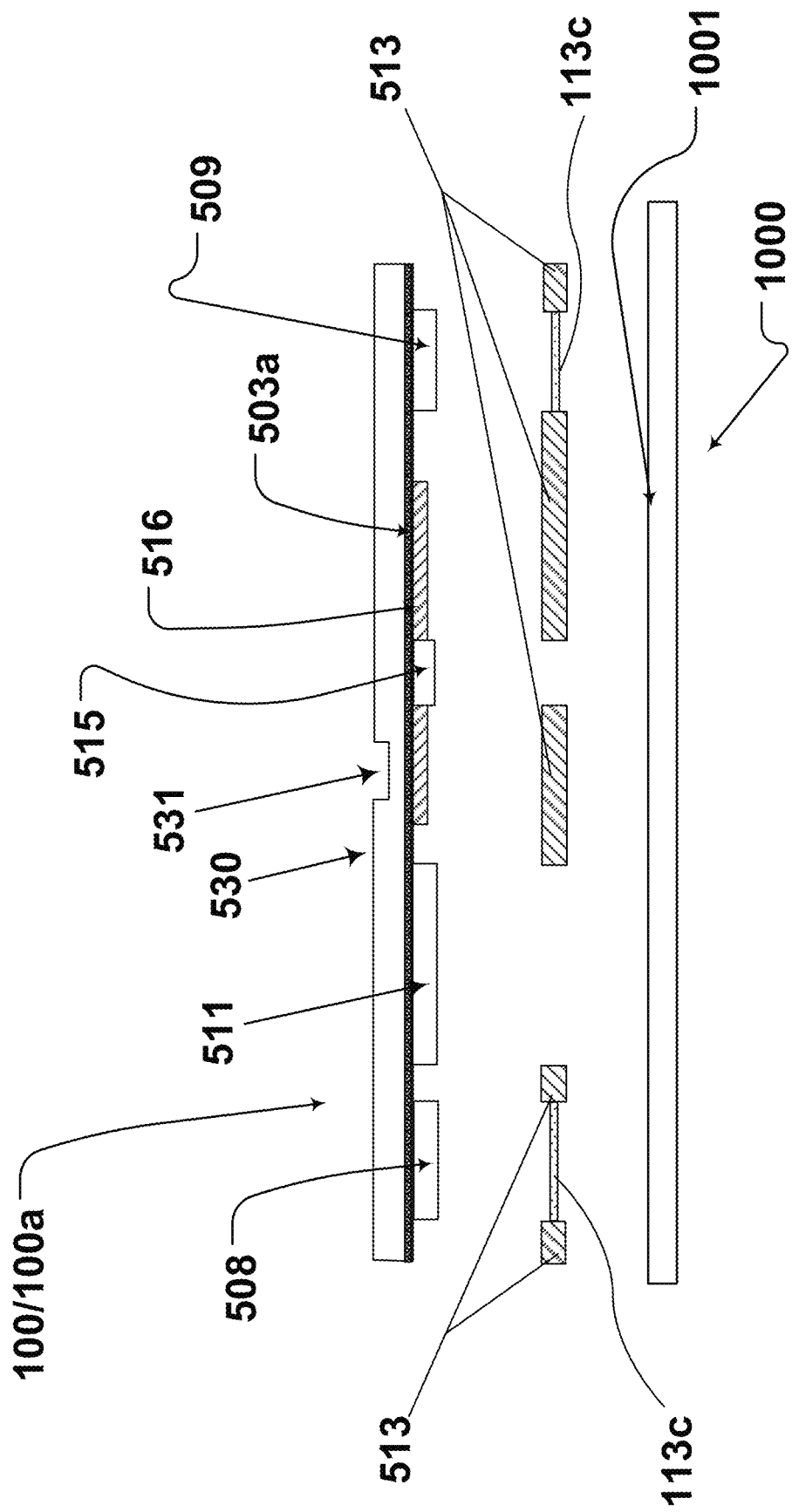
FIG. 1R2

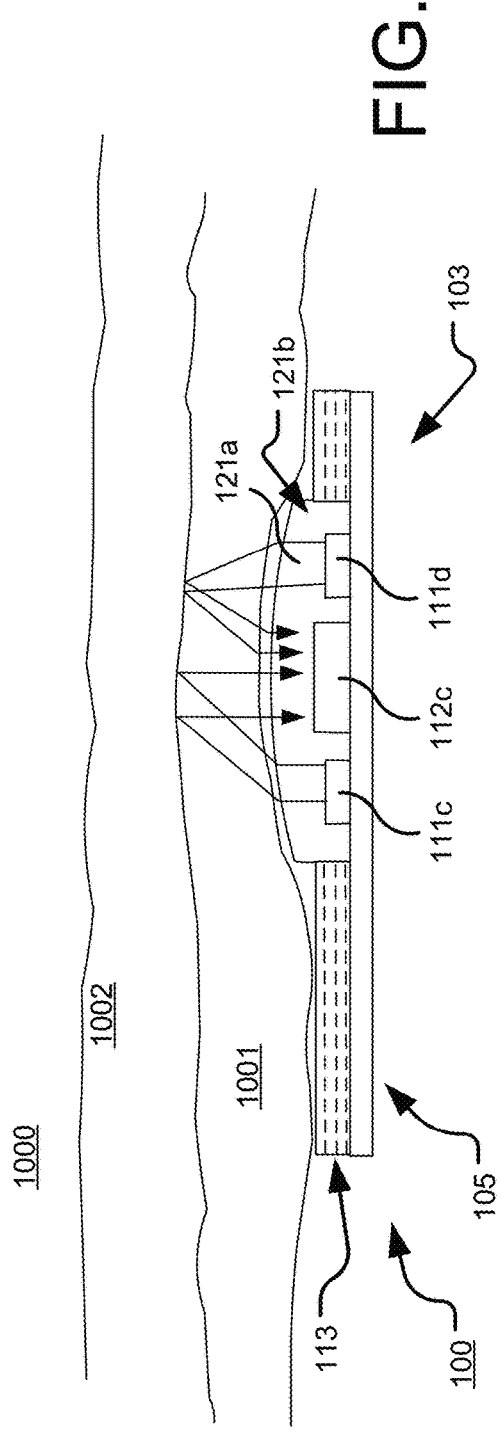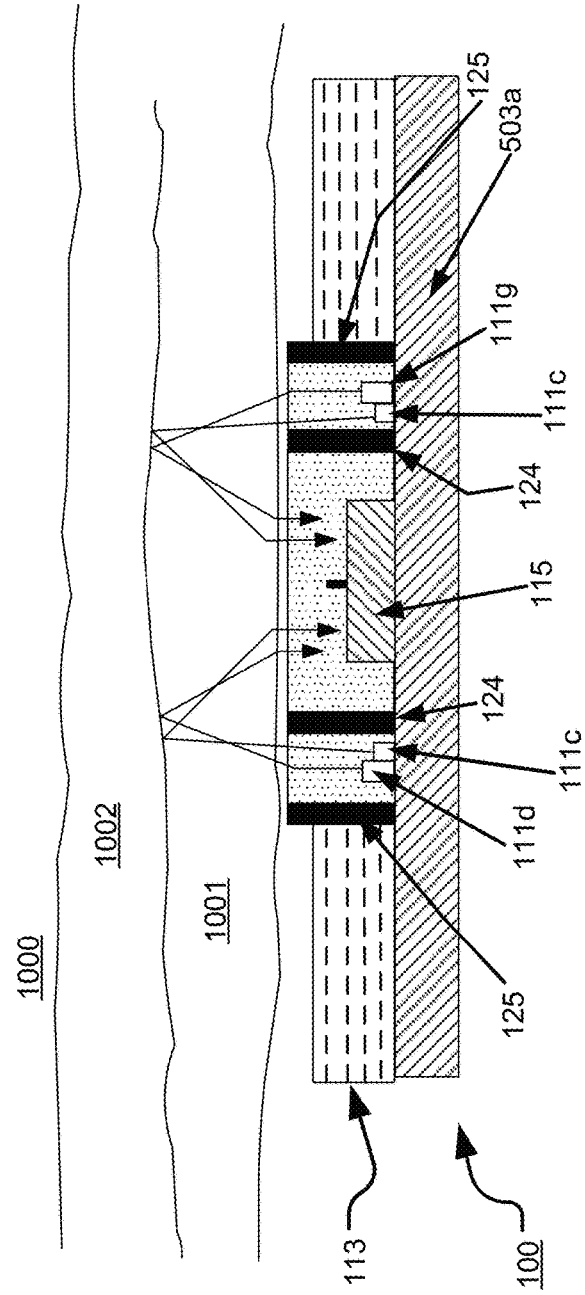

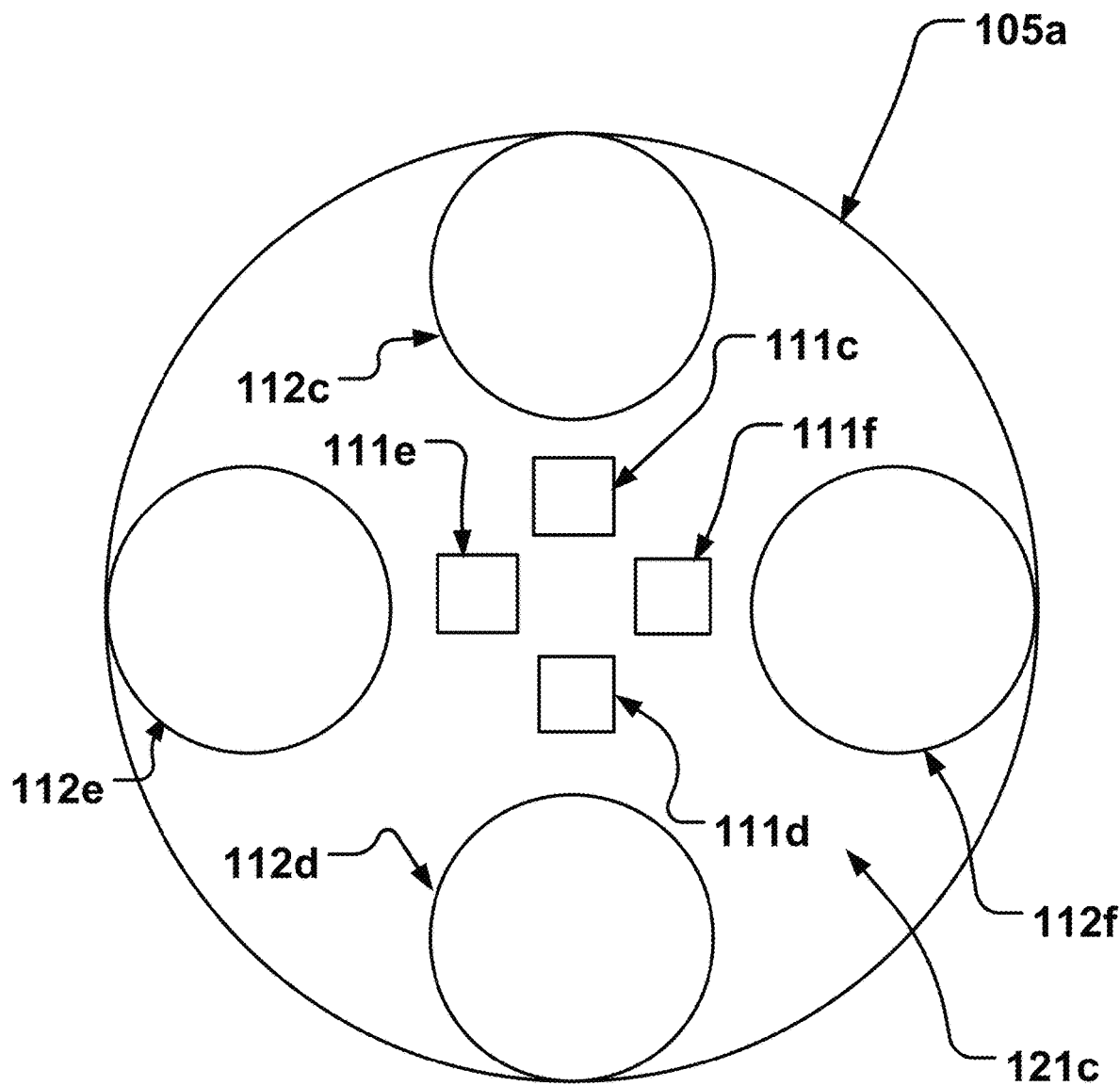
FIG. 1T1

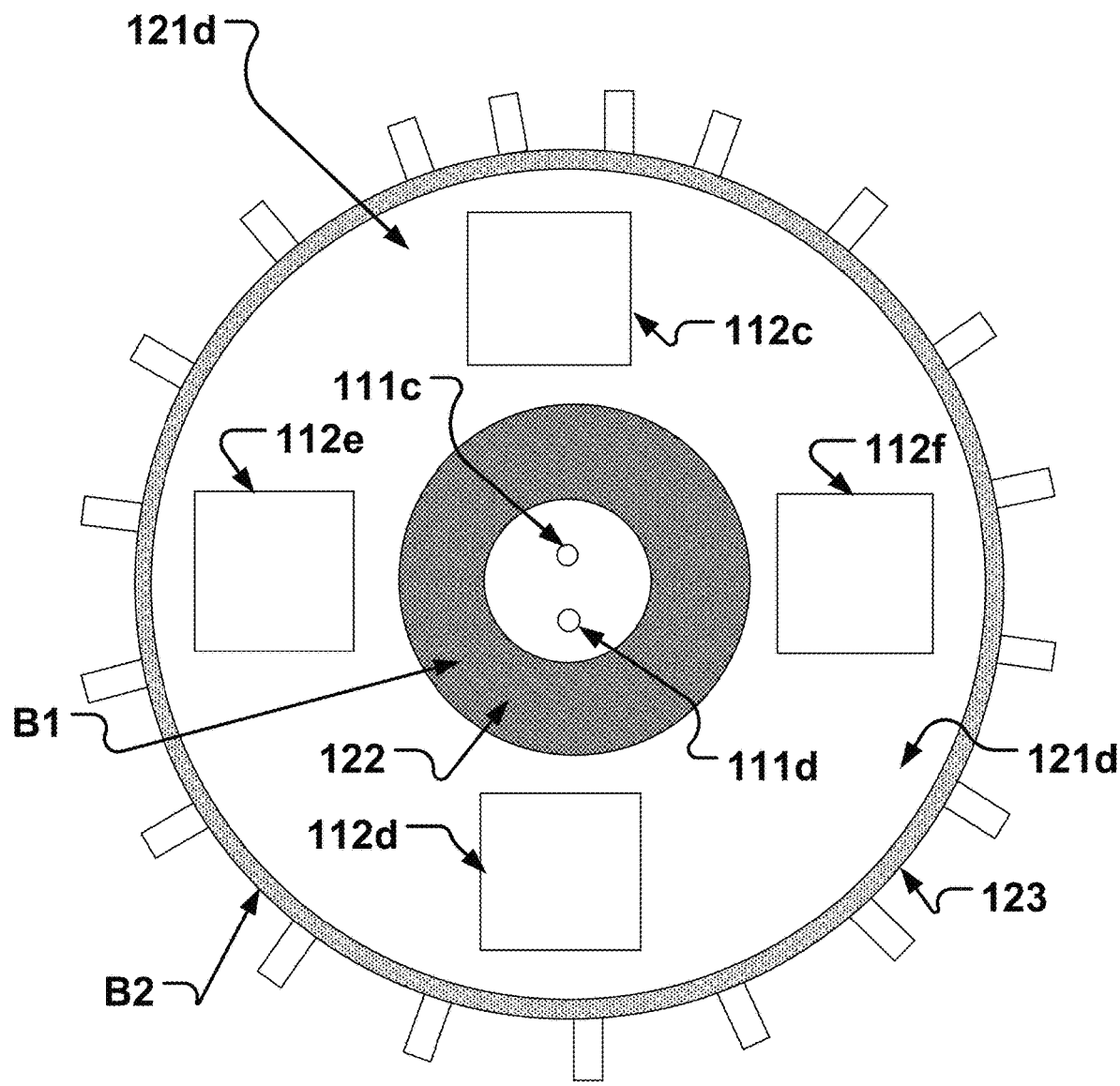
FIG. 1T2

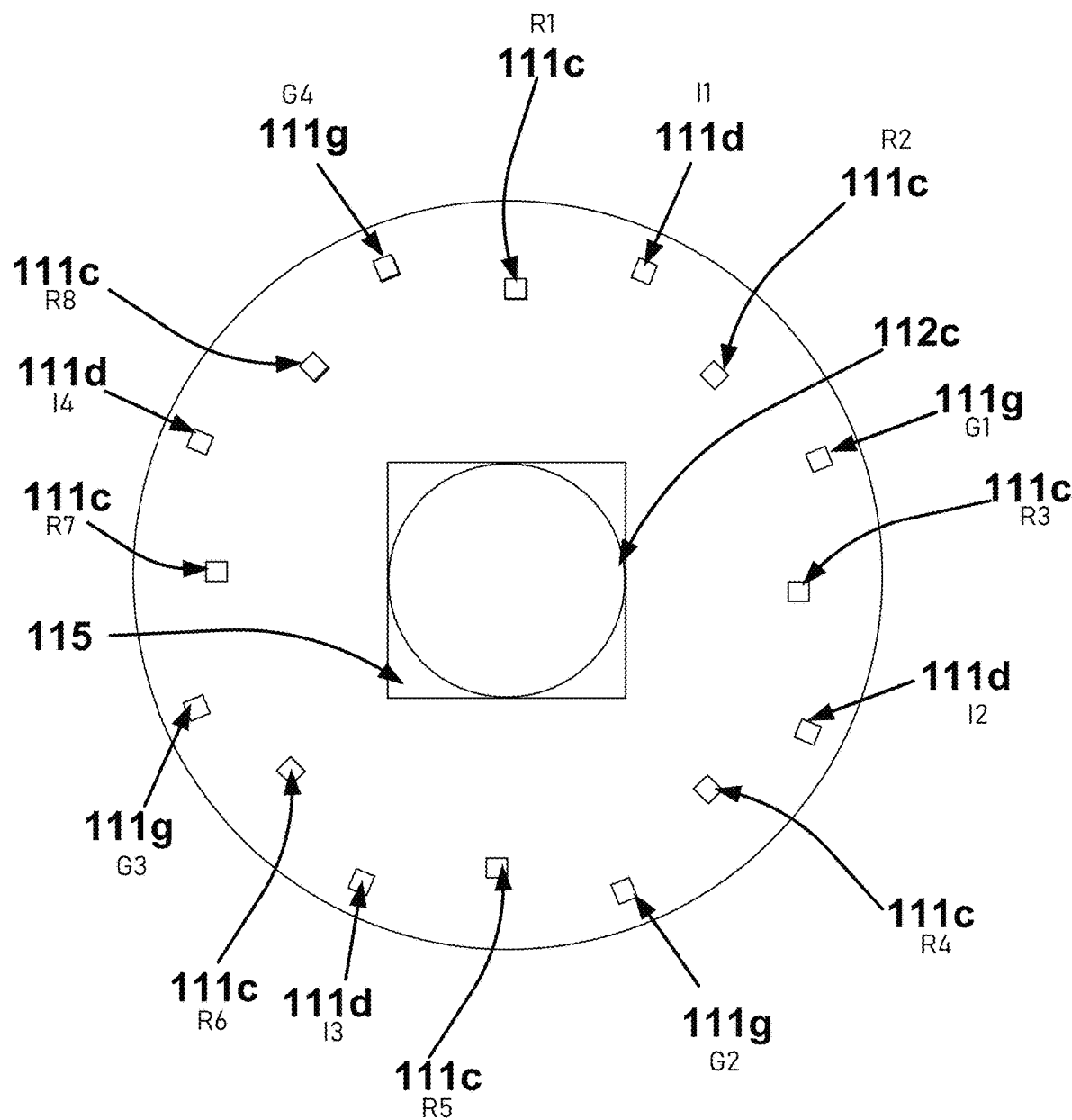
FIG. 1T3a

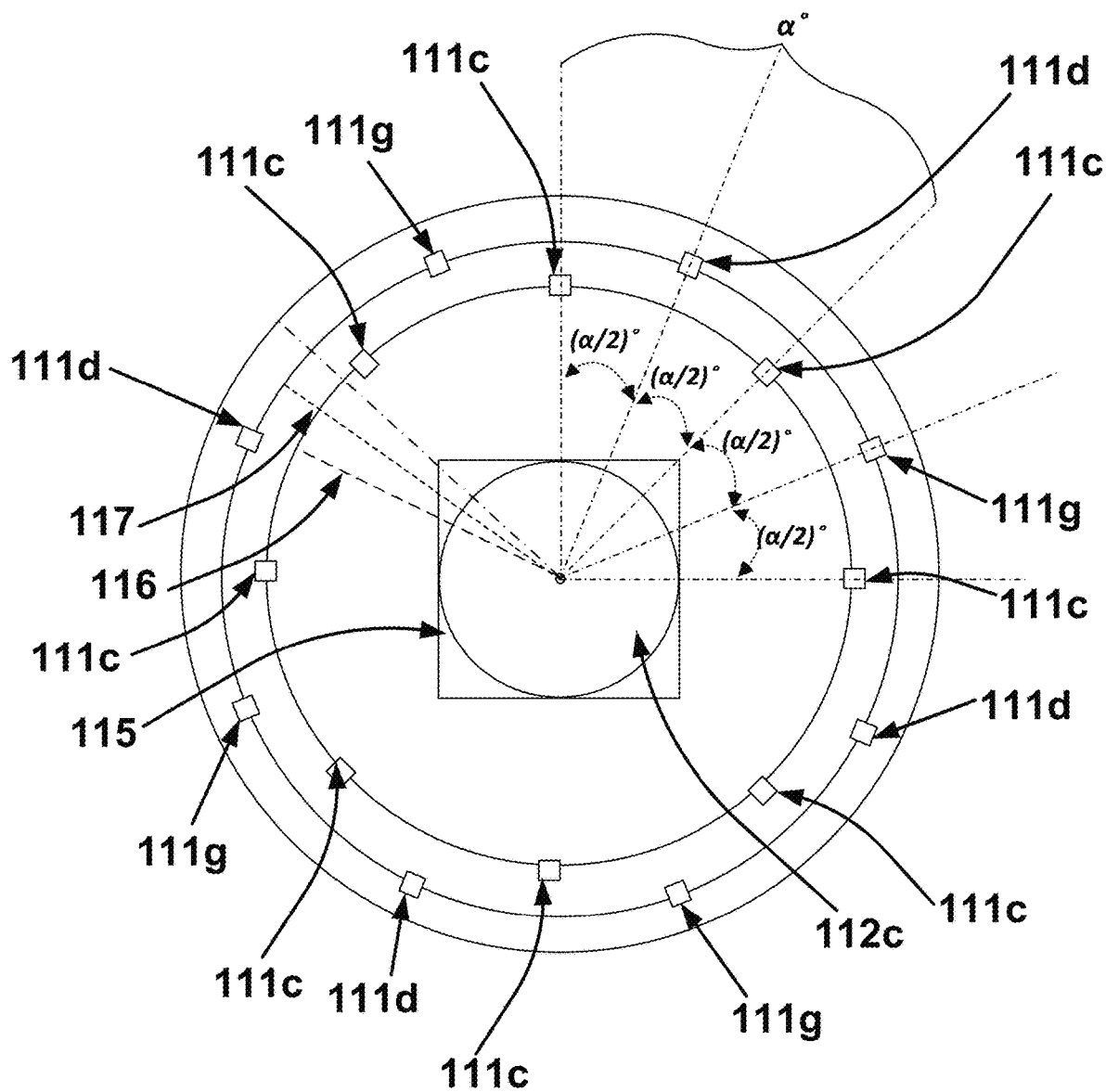
FIG. 1T3b

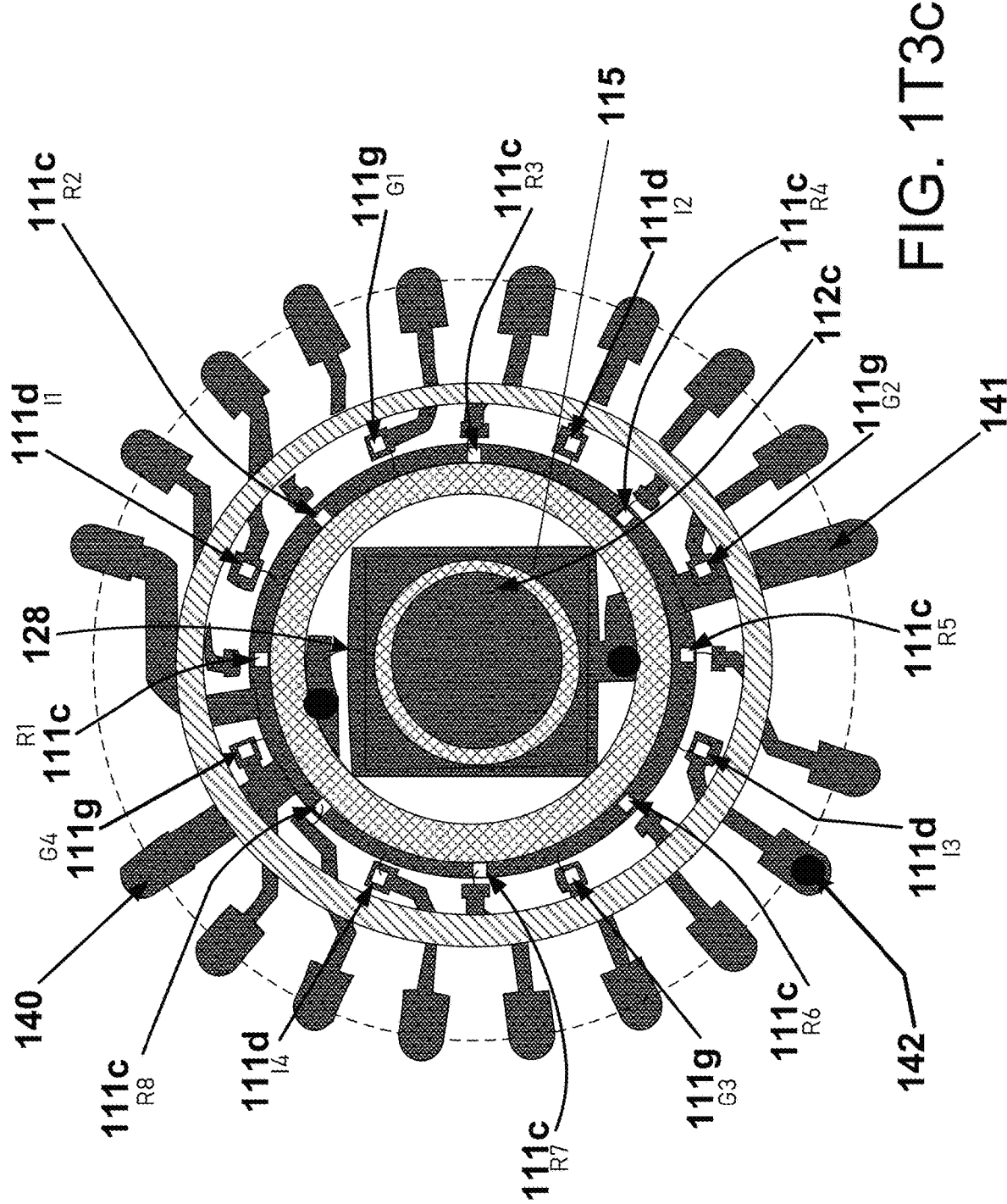
FIG. 1T3c

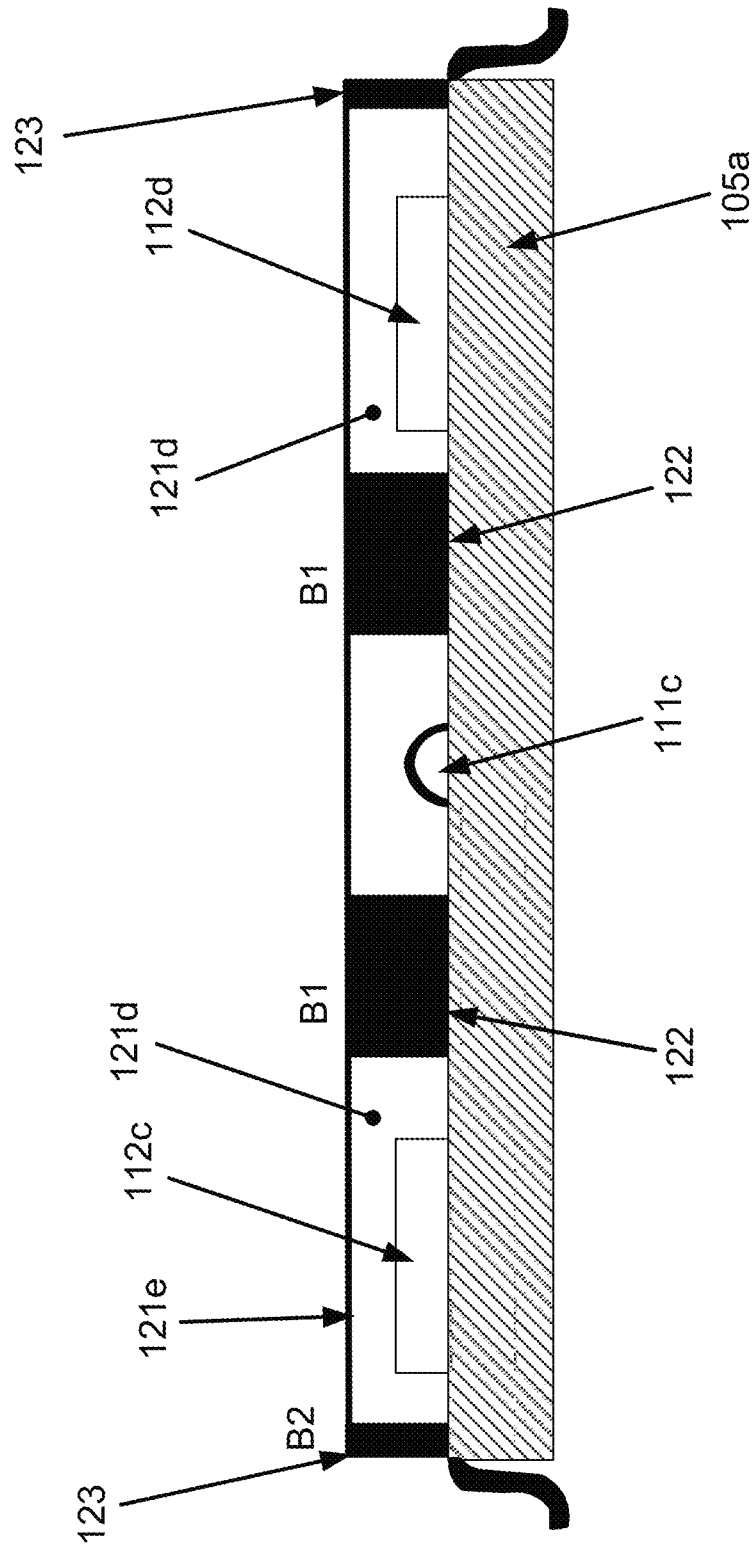

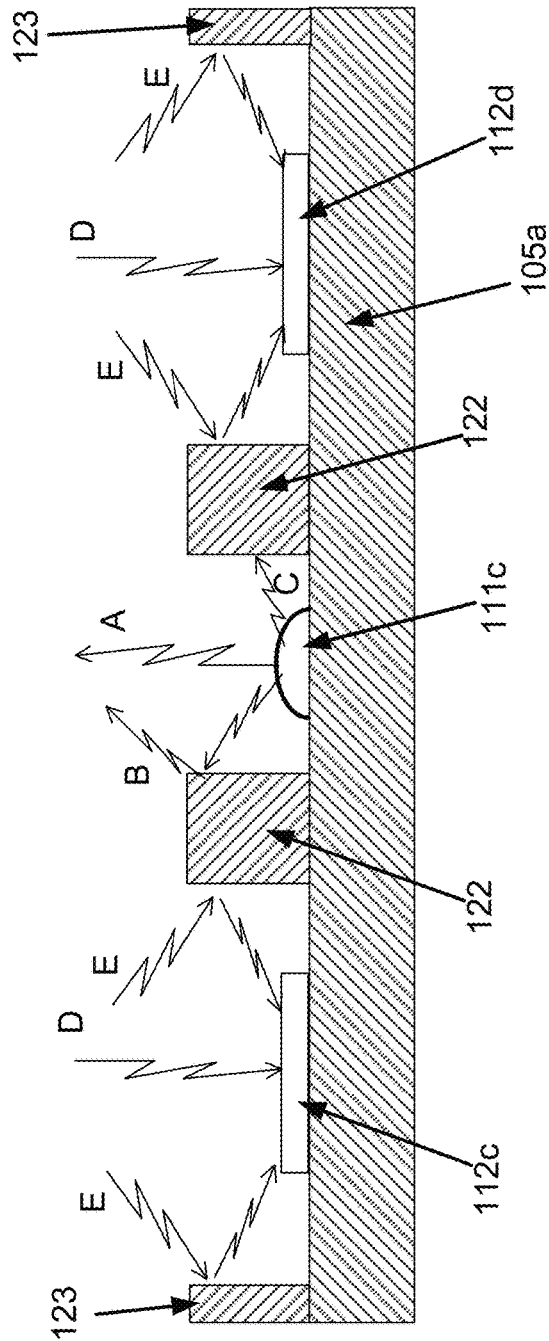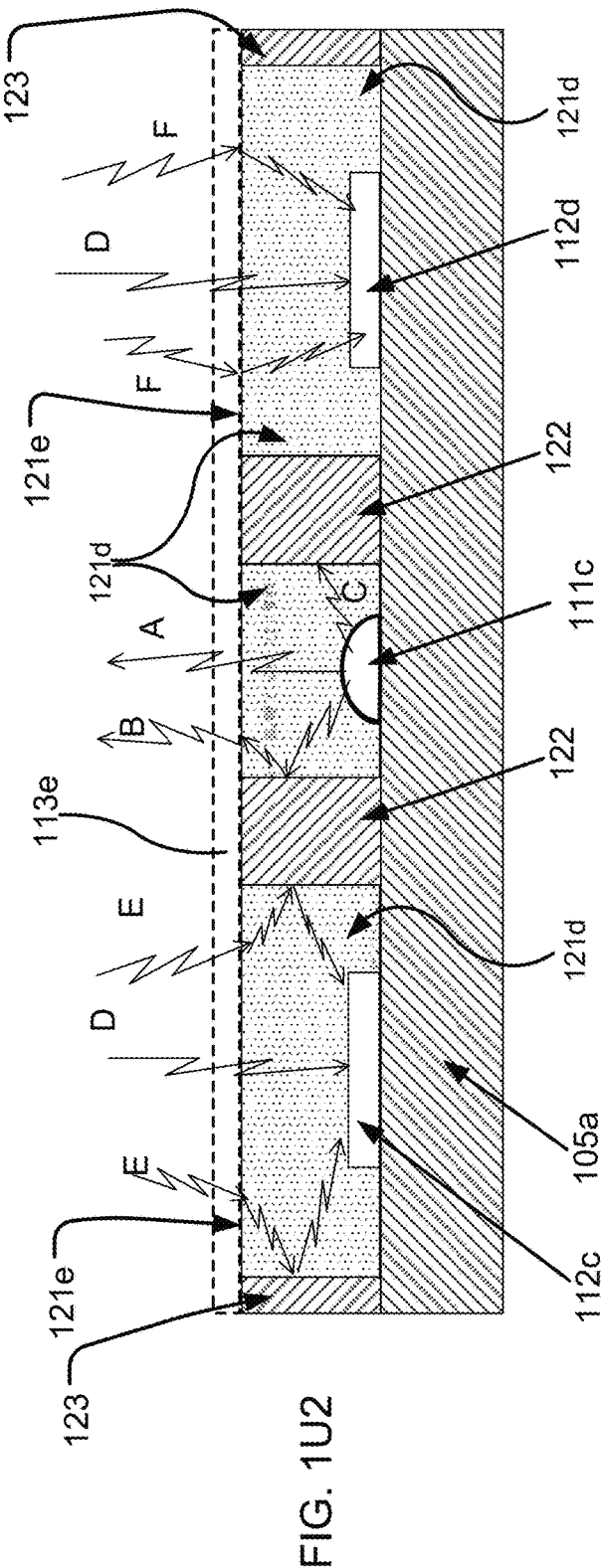

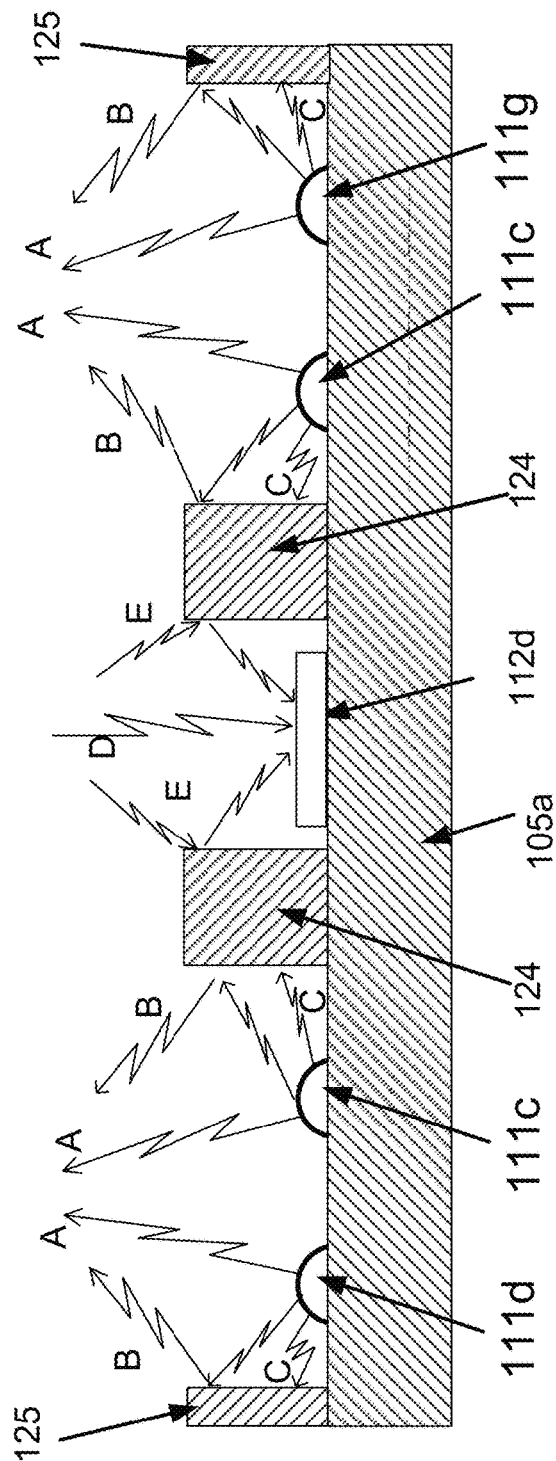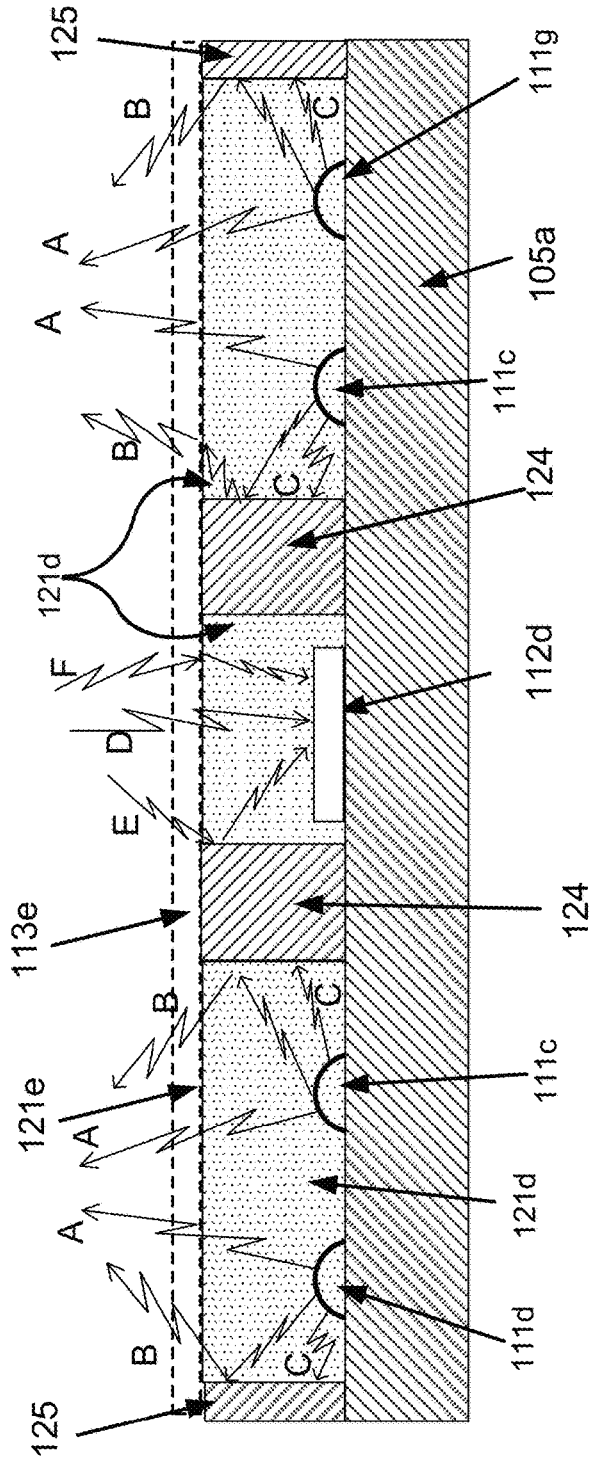
FIG. 1U2a
FIG. 1U2b

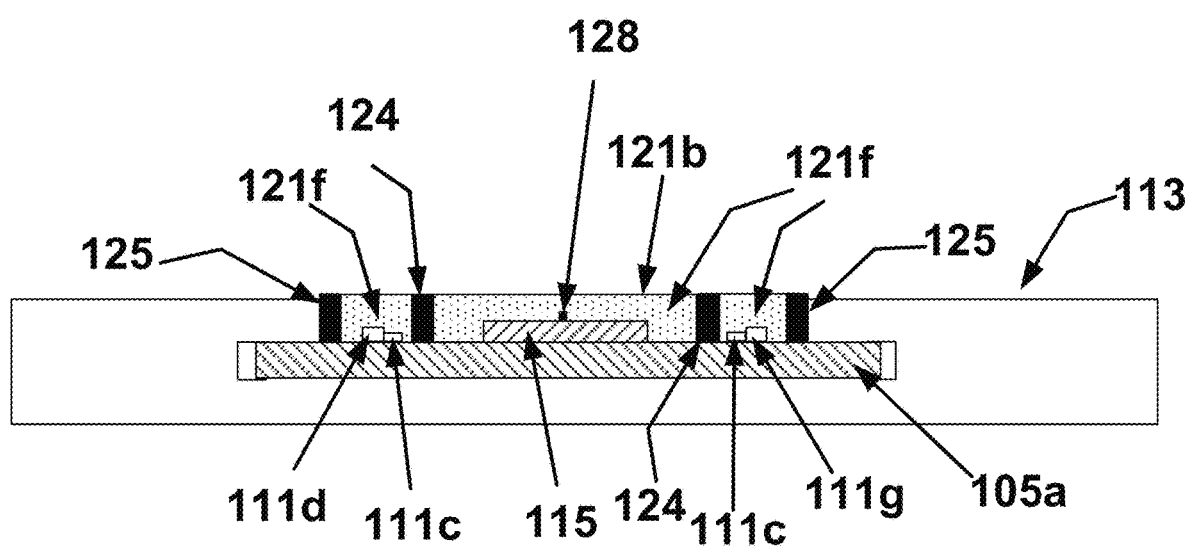
FIG. 1U3a

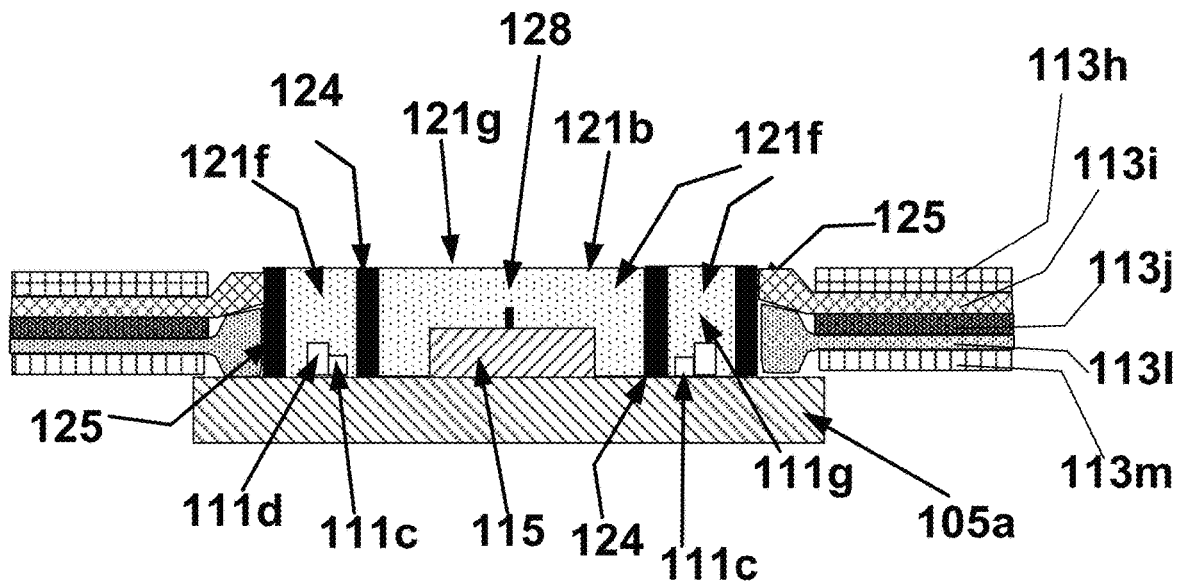
FIG. 1U3b
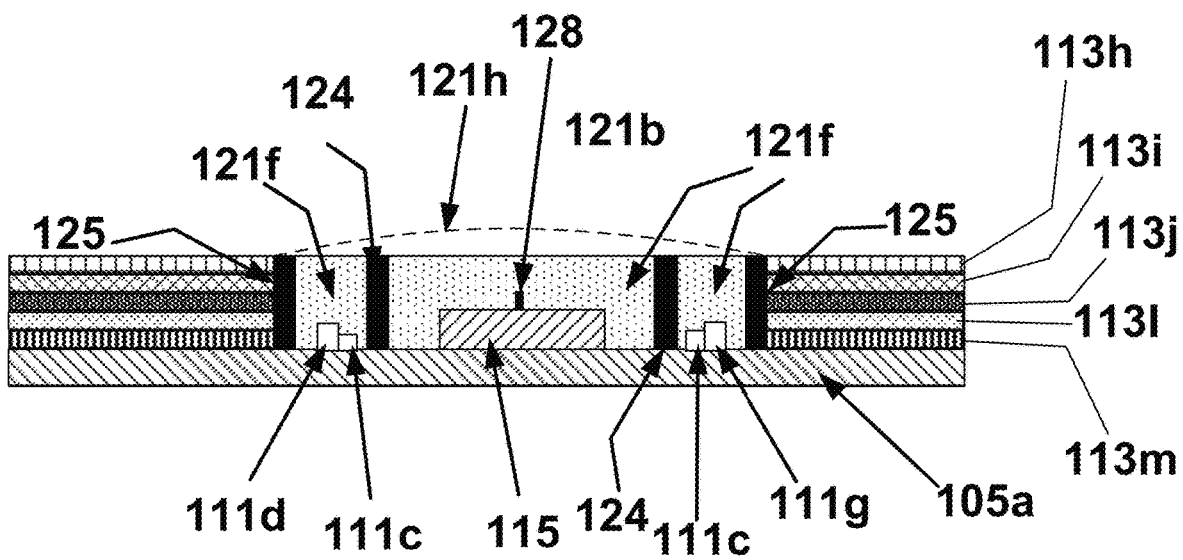
FIG. 1U3c

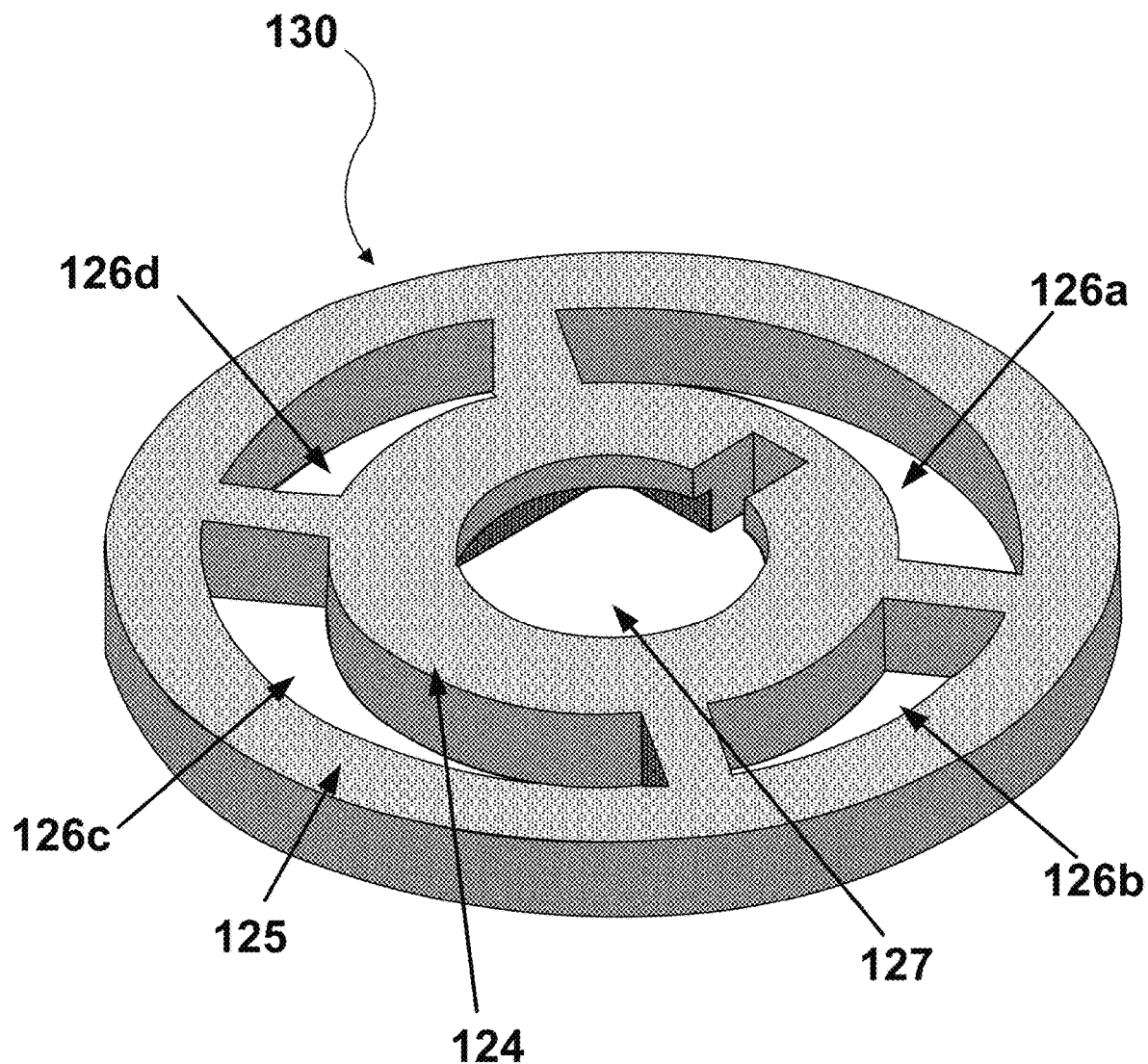
FIG. 1U3d

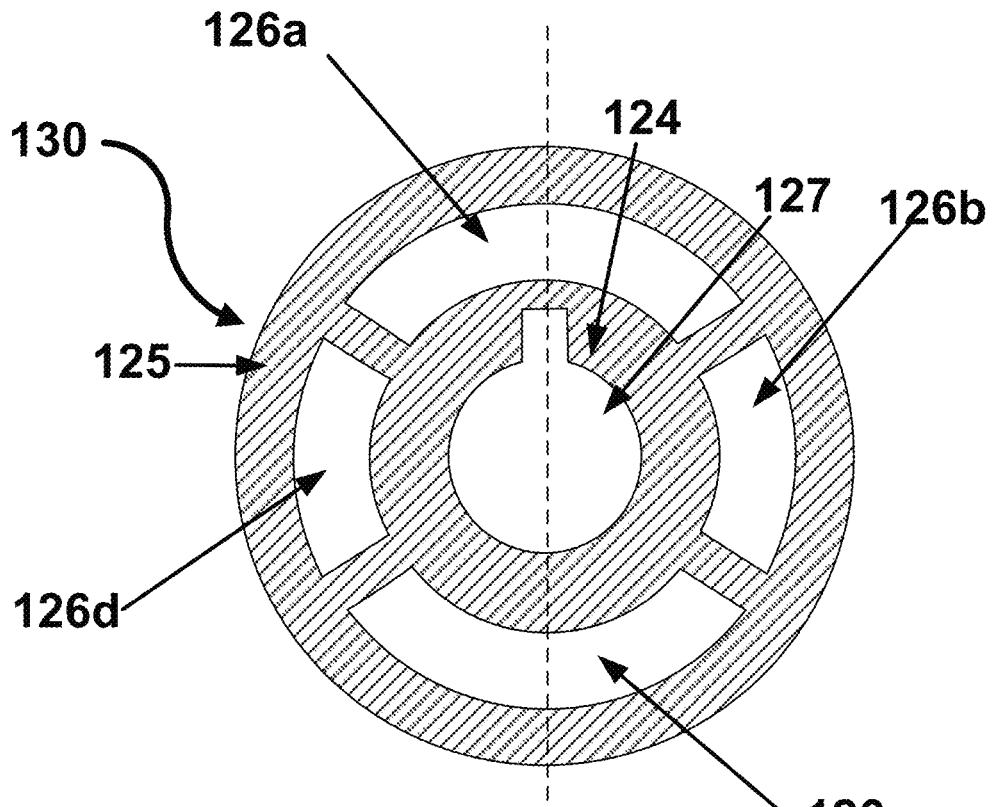
FIG. 1U3e
FIG. 1U3f
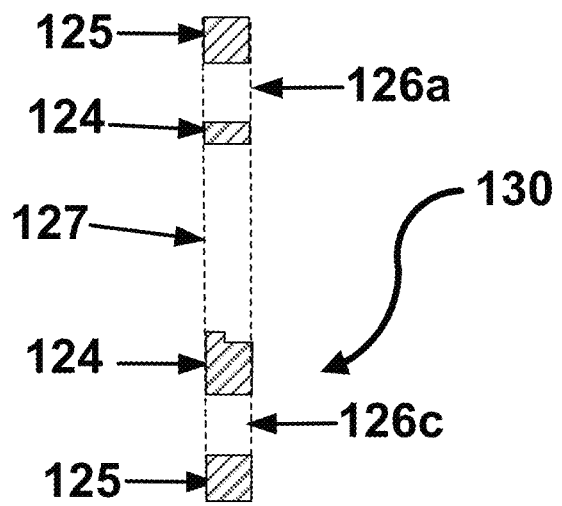

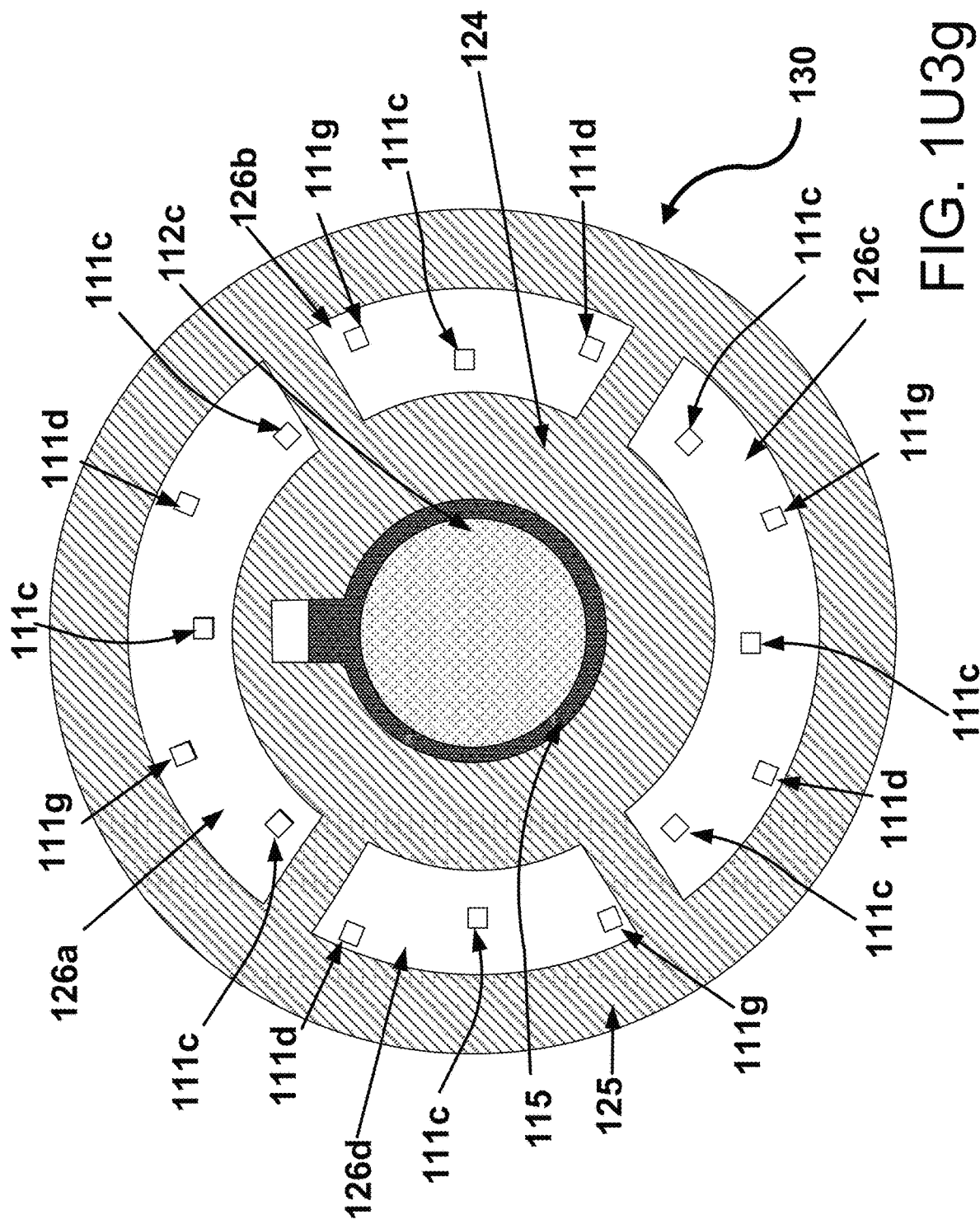

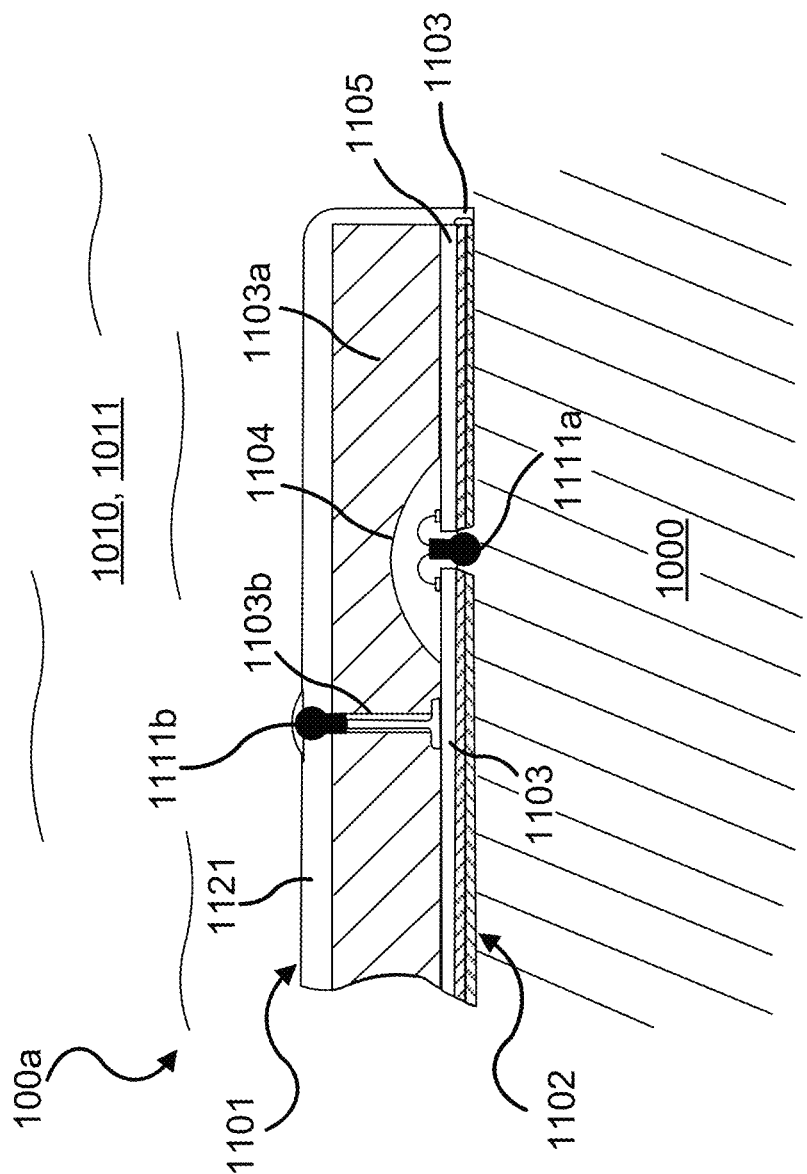

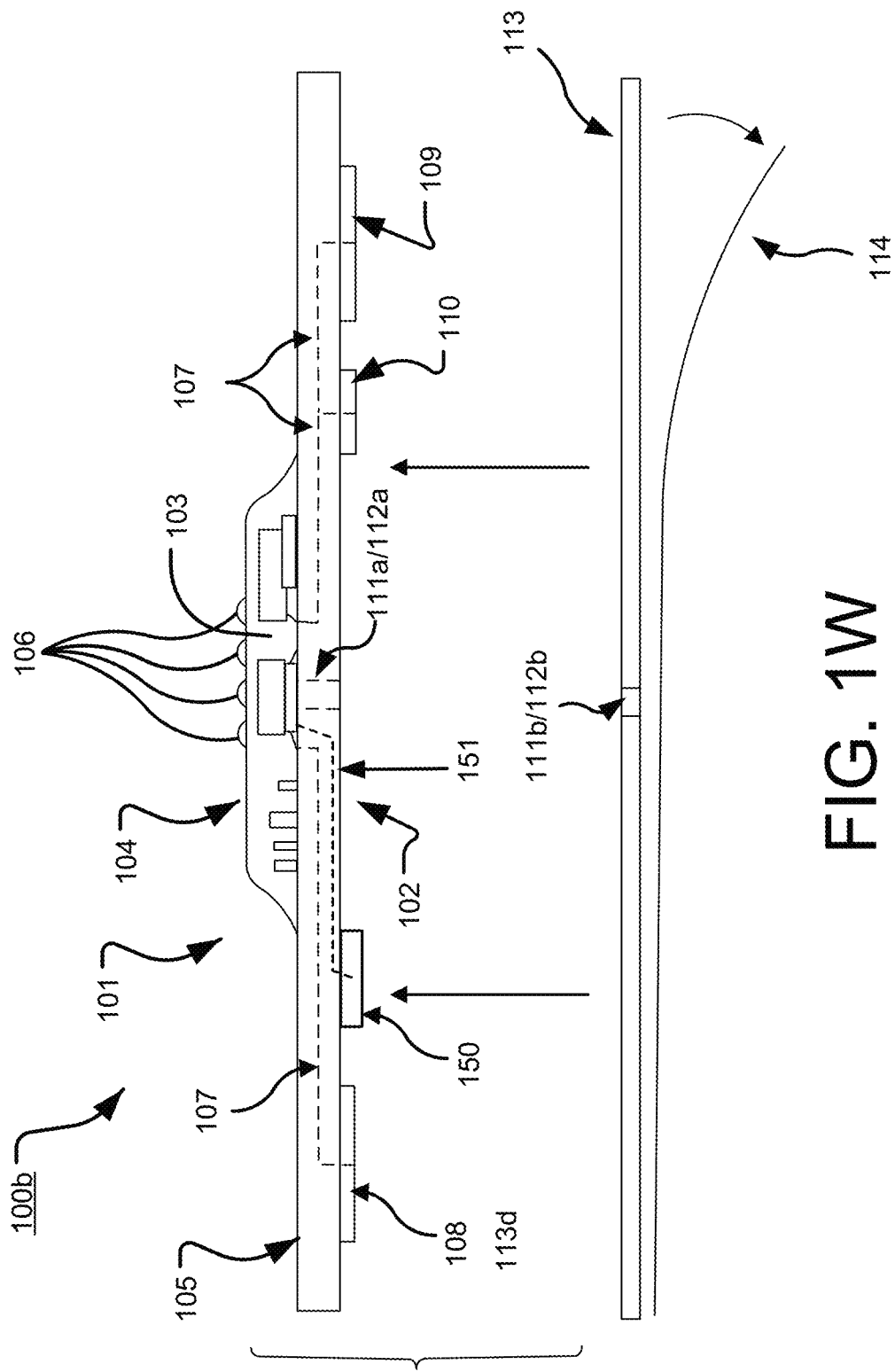

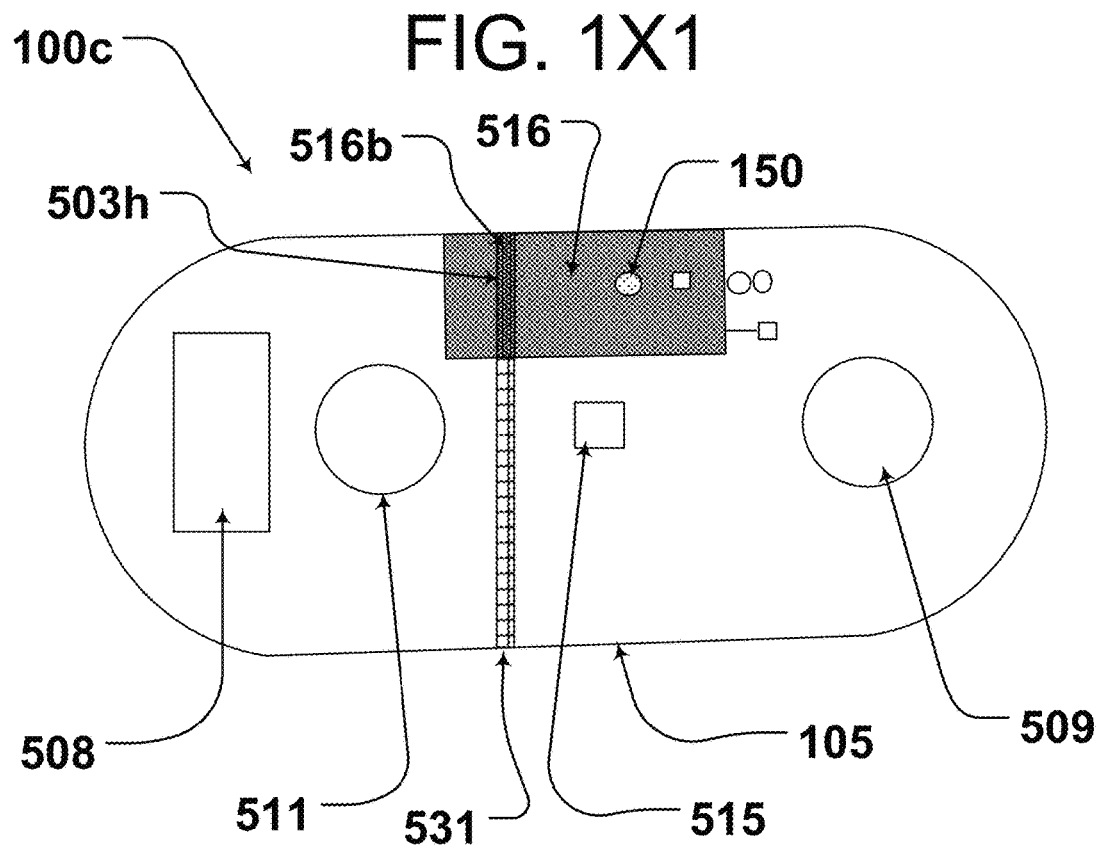
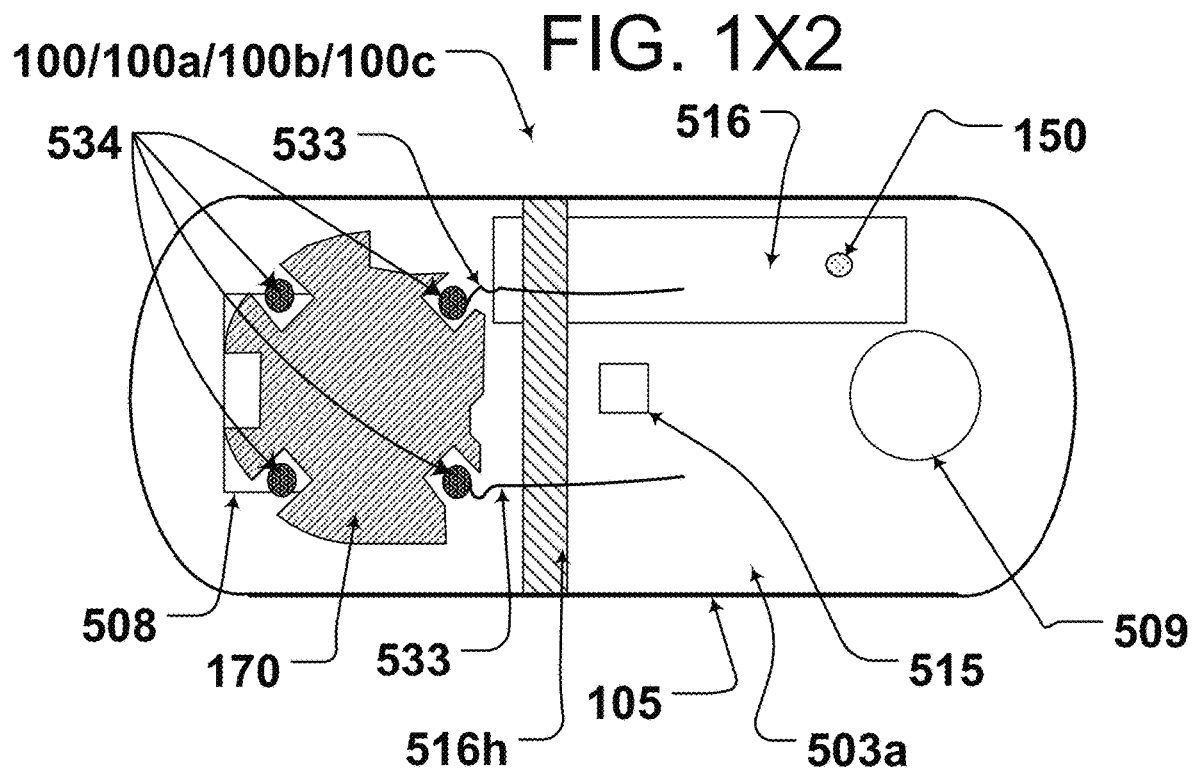

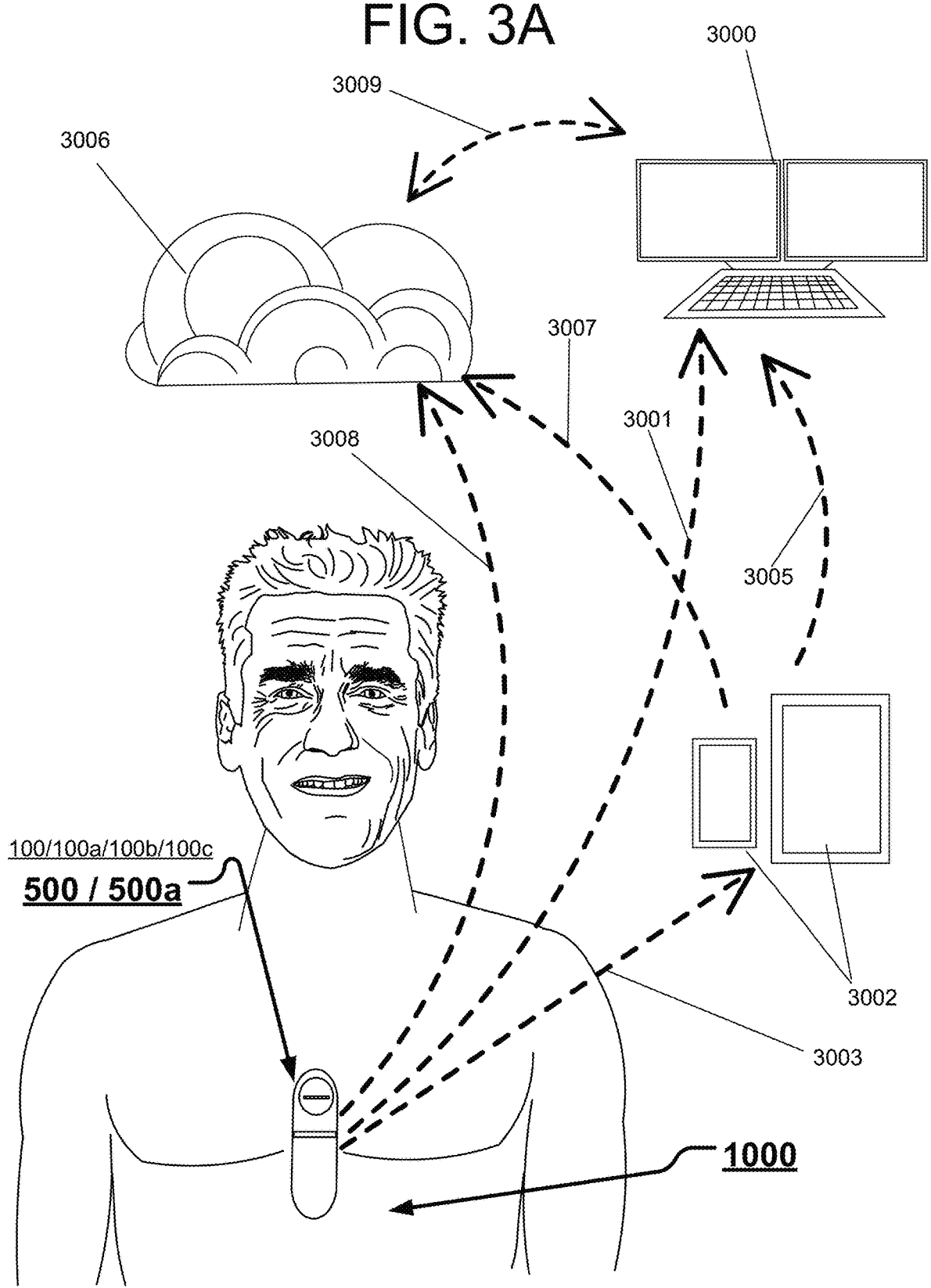

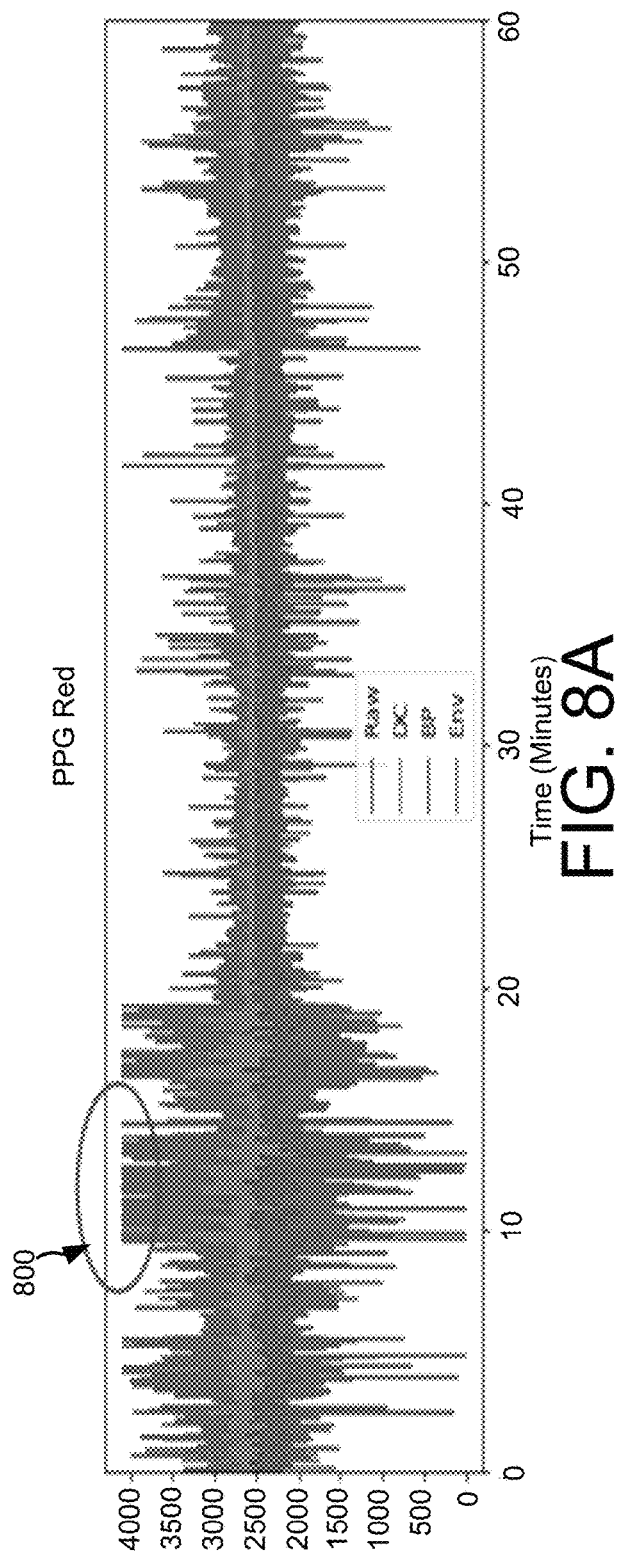
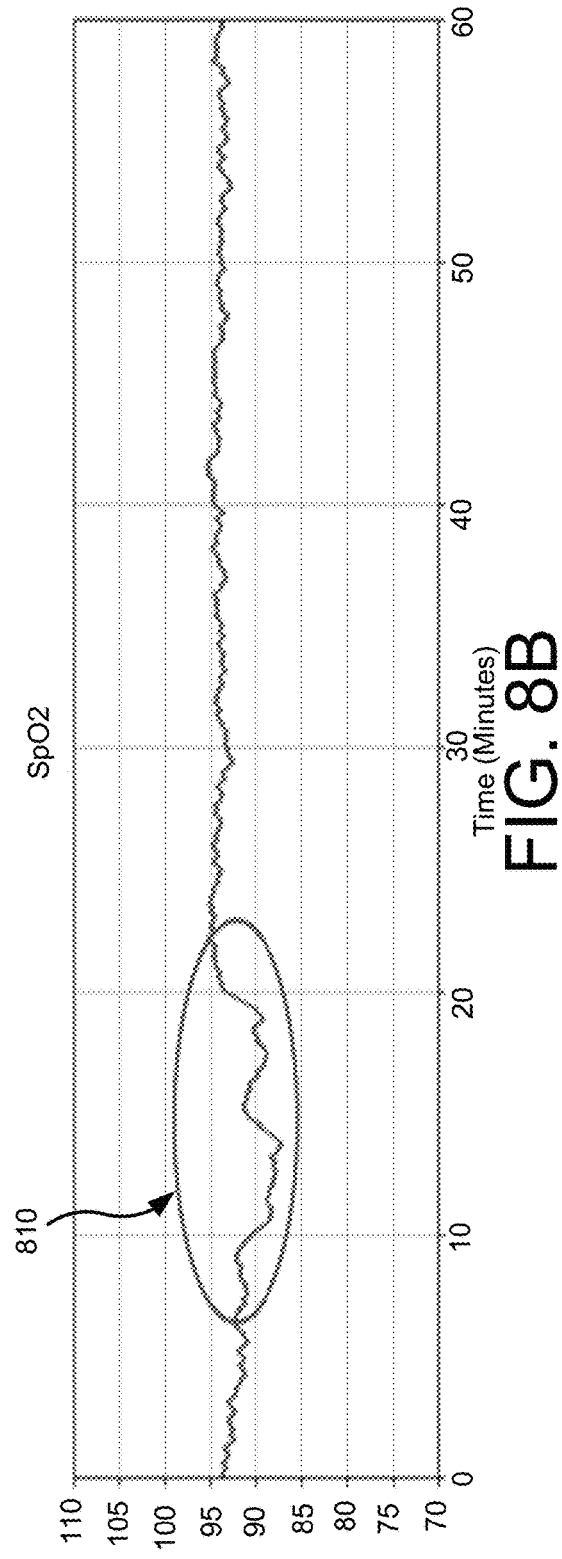

RDS: SpO2 v Time
Test: Light Skin (Fitzpatrick =2)

Finger Oximeter: SpO2 v Time
Test: Light Skin (Fitzpatrick =2)

RDS: SpO2 v Time
Test: Very Dark Skin (Fitzpatrick >6)

Finger Oximeter: SpO2 v Time
Test: Very Dark Skin (Fitzpatrick >6)

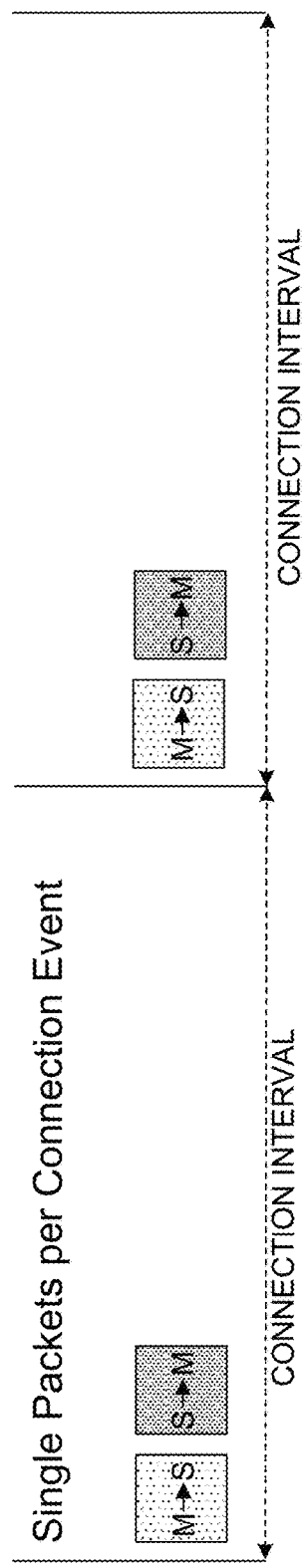
FIG. 10F1
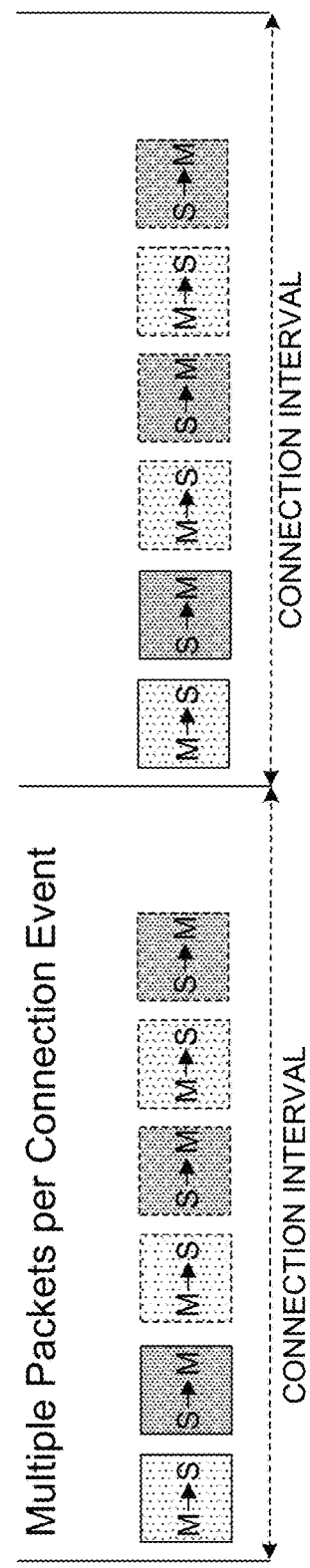
FIG. 10F2
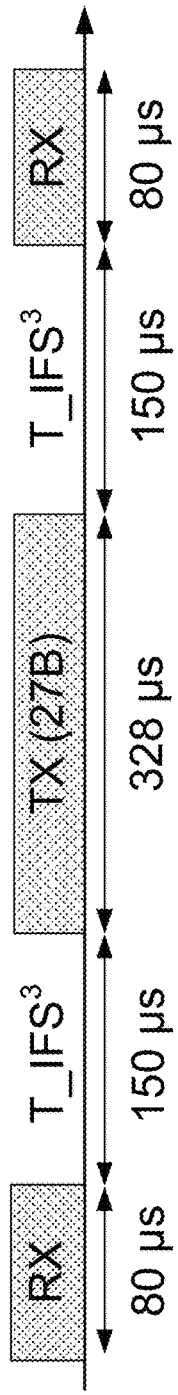
FIG. 10F3

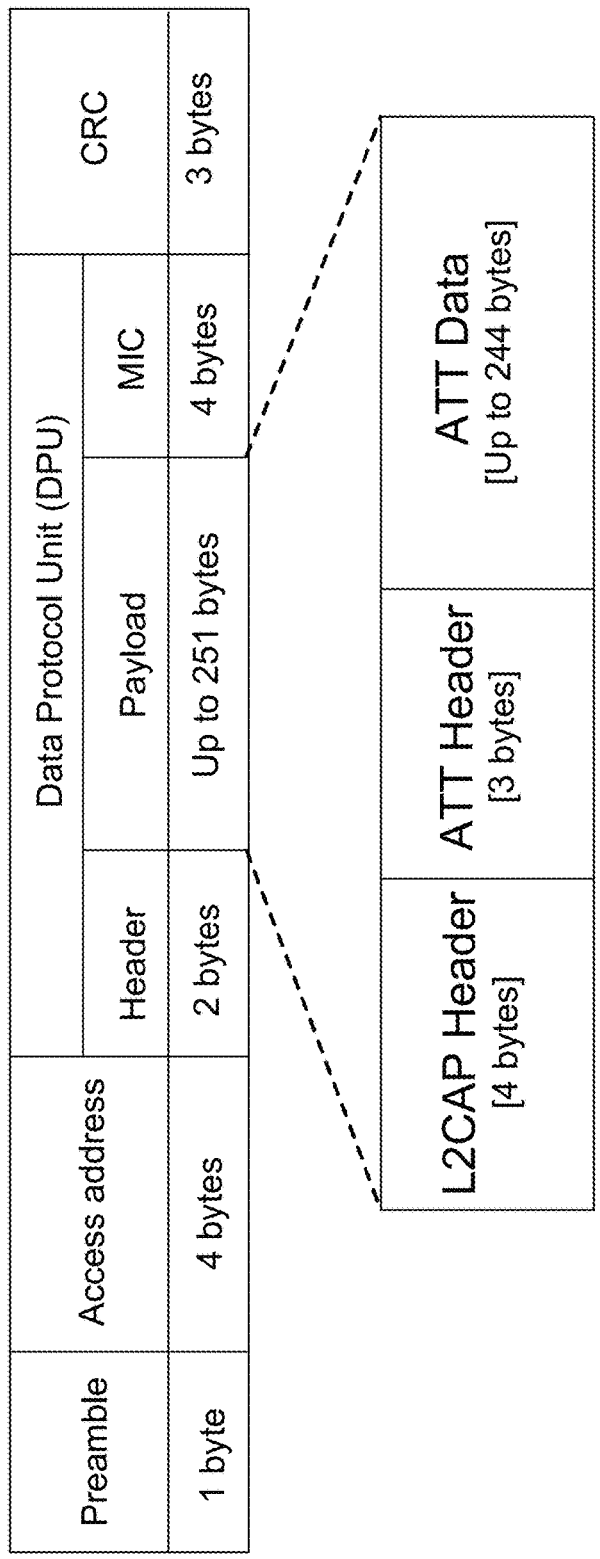
FIG. 10G1
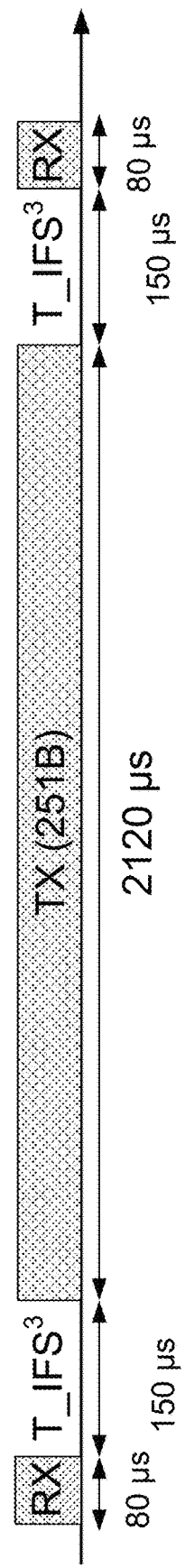
FIG. 10G2

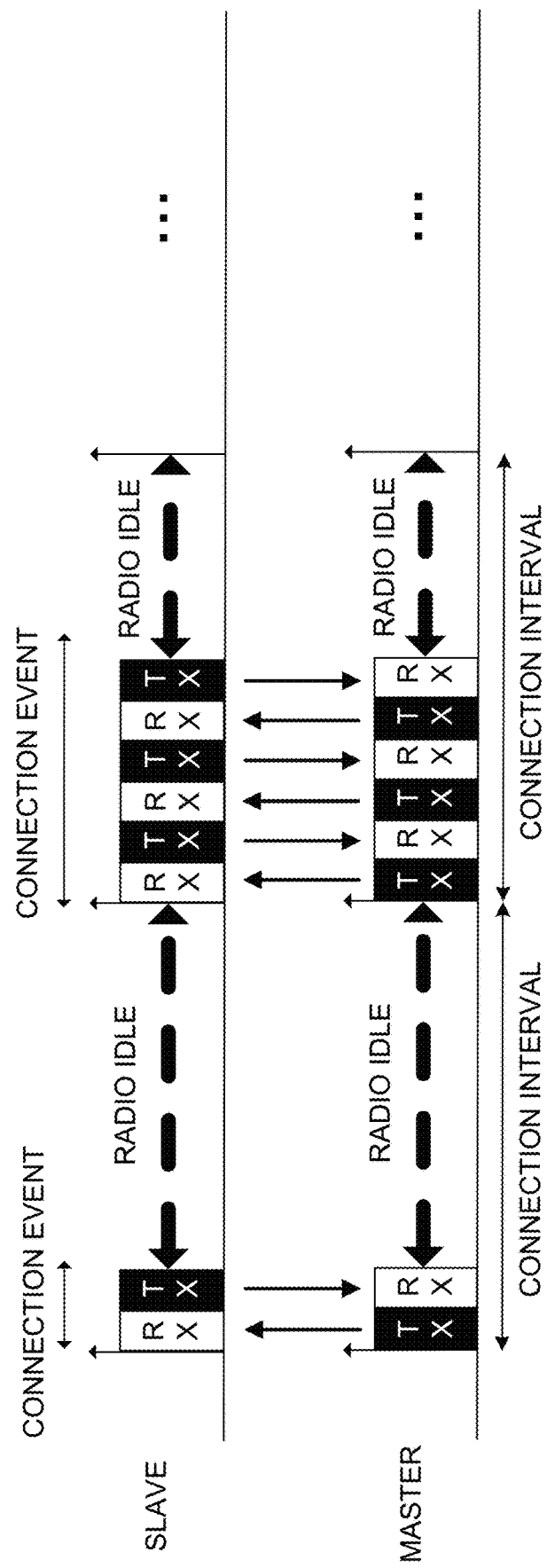

VITAL SIGNS MONITORING SYSTEMS AND METHODS

BACKGROUND

Advances in software, electronics, sensor technology and materials science have revolutionized patient monitoring technologies. In particular, many devices and systems are becoming available for a variety of vital signs or health monitoring applications. However, improvements may yet be desired for vital signs or health monitoring devices and systems that provide one or more of effective data collection and/or manipulation for parameter determination.

Further alternatives for patients and their physicians may then be developed to include robust and convenient monitors that in some instances may collect and transfer short-term or long-term data and/or monitor events in real-time, or substantial real-time, and in some cases may include multi-variable parameter determination.

SUMMARY

Described herein are several alternative medical monitoring devices, systems and/or methods for parameter determination, in some instances for long-term sensing and/or recording of cardiac and/or respiratory and/or temperature and/or audio data of one or more individuals, such as a neonate, infant, mother/parent, athlete, or patient. A number of alternative implementations and applications are summarized and/or exemplified herein below and throughout this specification.

In one alternative aspect, the developments hereof may include an implementation wherein a health device is configured for monitoring one or a plurality of physiological parameters of one or more individuals from time-concordant measurements collected by one or a plurality of sensors, including one or a variety of one or more of, but not limited to, electrodes for measuring ionic potential changes for electrocardiograms (ECGs), and/or one or more light sources and one or more photodetectors, in some cases including LED-photodiode pairs or groupings, for optically based oxygen saturation measurements, and/or one or more temperature sensors, and/or one or more xyz accelerometers for movement and exertion measurements, and/or one or more audio or acoustic pickups or piezo sensors or microphones and/or the like. In some implementations, methods and devices of the developments hereof may be used to generate a respiration waveform. Other implementations may include a circuit that mimics a driven right-leg circuit (sometimes referred to herein as "a proxy driven right-leg circuit") that may permit reduction in common mode noise in a small-footprint device conveniently adhered or having the capacity to be adhered to an individual.

In another alternative aspect hereof, a blood pressure determination may in some cases be made from a determination of pulse transit time. The pulse transit time is the time for the cardiac pressure wave to travel from the heart to other locations in the body. Measurements of pulse transit time may then be used to estimate blood pressure. Heart beat timing from ECG or otherwise and photoplethysmogram (aka PPG) signals can be used to generate pulse transit time. Note, such signals may be generated from conventional or other to-be-developed processes and/or devices or systems; or, such signals may be taken from one or more wearable health monitoring devices such as those also described hereinbelow.

In another alternative aspect, the developments hereof may include in some instances one or more methods and/or devices for measuring and/or determining oxygen saturation parameters from time concordant pulse oximetry signals and ECG signals. In some implementations, ECG signals may be used to define intervals, or "frames" of pulse oximetry data that are collected and averaged for determining the constant and main periodic components (e.g., DC and AC components) of the pulse oximetry signals from which, in turn, values for oxygen saturation may be determined.

These as well as other alternative and/or additional aspects are exemplified in a number of illustrated alternative and/or additional implementations and applications, some of which are shown in the figures and characterized in the claims section that follows. However, as will be understood by the ordinarily skilled artisan, the above summary and the detailed description below do not describe the entire scope of the inventions hereof and are indeed not intended to describe each illustrated embodiment or every possible implementation of the present inventions nor provide any limitation on the claims or scope of protection herein set forth below.

BRIEF DESCRIPTION OF THE DRAWINGS

The drawings include:

FIG. 2, which includes and is defined by sub-part FIGS. 2A-2D, provides circuit diagrams of alternatives to, in FIGS. 2A-2C, a driven right leg circuit, and in FIG. 2D, pulse oximetry.

FIGS. 3 and 3A are a flow chart and relational diagram including alternative methods of use.

FIGS. 8A and 8B set forth improvements in the measurement of SpO2 values.

FIGS. 10A, 10B, 10C, 10D, 10E, 10F1, 10F2, 10F3, 10G1, 10G2, 10H, 10I, 10J, and 10K provides exemplary data transmission diagrams with which implementations hereof may be utilized.

DETAILED DESCRIPTION

Figure 1A:
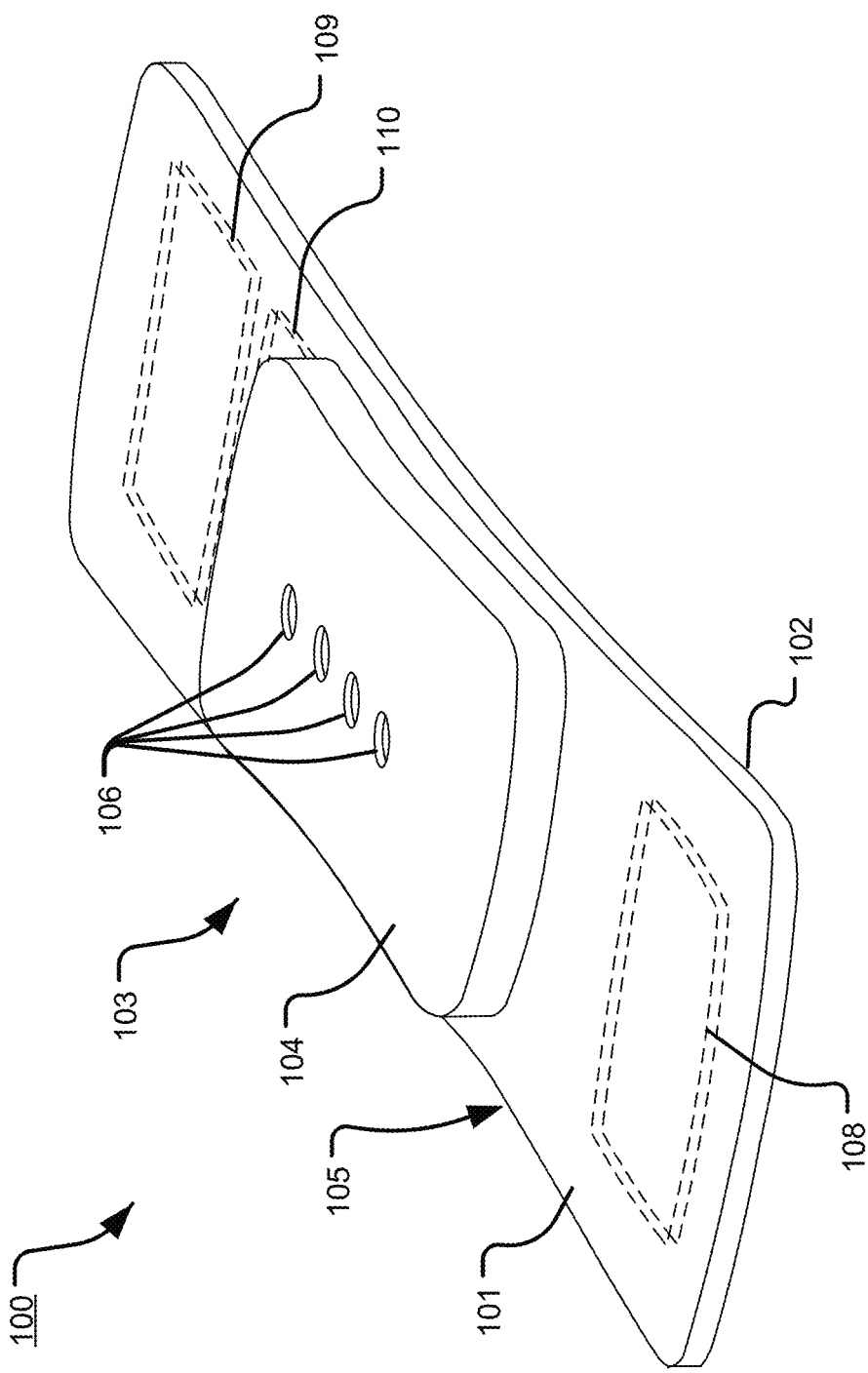
FIGS. 1A-1X2, illustrates several alternatives of the present developments, including a variety of isometric, top and bottom plan and elevational views of devices and alternative adhesive structures.

While the inventions hereof are amenable to various modifications and alternative forms, specifics hereof have been shown herein by way of non-limitative examples in the drawings and the following description. It should be understood, however, that the intention is not to limit the inventions to the particular embodiments described. The intention is to cover all modifications, equivalents, and alternatives falling within the spirit and scope of the inventions whether described here or otherwise being sufficiently appreciable as included herewithin even if beyond the literal words or figures hereof.

In general, included here are on-body, multi-function, biometric sensors. The devices monitor bodily functions such as one or more or all of ECG, PPG, temperature, respiration, and activity among other possible options. Such devices may in many cases be configured for operational attachment on a subject to, on, adjacent to, or nearby a subject's sternum or on a subject's chest, inter alia, with an adhesive, often a disposable or replaceable adhesive. Such devices may typically be in many instances, but not limited hereto, small and thin relative to a user (e.g., on the order of approx. +/−~1.5"×3"×¼" or approximately 30 mm×100 mm×6.3 mm; practical sizing not limited hereby, but may be dependent inter alia on body size and practical component availability among other features) and may typically be configured to be wearable by a wide range of subjects from infant to adult through to the morbidly obese.

In one aspect, a system hereof may include a device for monitoring physiological parameters such as one or more or all of electrocardiogram (aka ECG or EKG), photoplethysmogram (aka PPG), pulse oximetry, temperature, respiration, and/or patient acceleration or movement signals and/or audio or sound signals as for example heartbeat or breathing sounds.

Moreover, systems hereof may be established to measure and/or process such signals of a patient using or including any one or more of the following elements: (a) a circuit, sometimes flexible as in or on or forming a flexible or flex circuit board, embedded in or on a flat elastic or resilient substrate or board having a top surface and a bottom surface, the circuit having one or more of (i) at least one sensor mounted in or on or adjacent the bottom surface of the flat elastic or resilient substrate, the at least one sensor being capable of electrical or optical or acoustic or motion communication with the patient. In some implementations, a circuit may include (ii) at least one signal processing module for receiving and/or accepting signals from the at least one sensor in some implementations also providing for transforming such signals for storage as patient data; and/or (iii) at least one memory module for receiving and/or accepting and storing patient data, and/or (iv) at least one data communication module for transferring patient data, stored or otherwise to an external device, and/or (v) a control module for controlling the timing and operation of the at least one sensor, one or more of the at least one signal processing module, the at least one memory module, the at least one data communication module, and/or the control module capable of receiving commands to implement transfer of patient data by the at least one data communication module and to erase and/or wipe patient data from the at least one memory module. In some implementations, a system hereof may include (b) a conductive adhesive removably attached to the bottom surface of the flat elastic or resilient substrate, the conductive adhesive capable of adhering to skin of the patient or other user and in some non-limiting examples a system hereof may be capable of conducting an electrical signal substantially only in a direction perpendicular to the bottom surface of the flat elastic or resilient substrate, and/or in some implementations may include a conductive portion adjacent the sensor or sensors and a non-conductive portion. In some implementations, the conductive adhesive is an anisotropically conductive adhesive in that it comprises regions of material that conducts current substantially only in a direction perpendicular to the skin (i.e. "z-axis" conduction).

In some implementations, devices hereof may be for comprehensive long-term cardiac monitoring, inter alia. Features of such may but not necessarily include any one or more of a Lead 1 ECG, PPG, pulse oximeter, accelerometer, temperature sensor and/or a button or other indicator for manual patient event marking. Such a device may be adapted to communicate in real-time or near real-time to display vital signs as or very near in time as they are occurring. In some other implementations, such a device may rather store up to, for example, about two weeks of continuous data (though more or less will also be feasible in alternative implementations), which may in some implementations be downloaded to a clinic or other computer in a short time period, as for one example, in only about 90 seconds (though more or less time will be viable in alternative implementations) via computer connection, whether wireless or wired as in one example by USB or other acceptable data connection. In real-time or near real-time implementations, data communication may be via hard-wire connection, or may be by wifi, LAN, WAN, Bluetooth or other wireless data communication, and may be direct to a display monitor or computer for display, or may occur over a network, or even via cellular communication and may include data communication to one or more local or remote servers, e.g. the 'cloud' for further communication to a display or remote computer. A companion software data analysis package may be adapted to provide automated event capture and/or allow immediate or delayed, local data interpretation, including either or both waveform display or one or more snapshots.

Intermittent cardiac anomalies are often difficult for physicians to detect, interpret and/or diagnose, as they would typically have to occur during a physical examination of the patient. A device hereof may address this problem with what in some implementations may be a continuous or substantially continuous monitoring of one or a number of vital signs.

Some alternative features may include but not be limited to one or more of (i) a driven "Right Leg" circuit with electrodes located only on the chest, and/or (ii) a "z-Axis" or anisotropic conductive adhesive electrode interface that may permit electrical communication only between an electrode and a patient's skin immediately beneath the electrode, and/or (iii) data transmission to and interpretation by a local computer accessible to CCU/ICU personnel, and/or (iv) a unique combination of hardware that may allow correlation of multiple data sources in time concordance to aid in monitoring and/or diagnosis.

In some alternative non-limiting implementations, devices and systems hereof may provide 1) reusability (in some cases near or greater than about 1000 patients) that may allow recouping cost of the device in just about 10-15 patient tests; and/or 2) one or more of ECG waveform data, inertial exertion sensing, manual event marking, temperature sensing and/or pulse oximetry, any one or all of which in time concordance to better detect and analyze arrhythmic events; and/or 3) efficient water-tightness or waterproofing (for the patient/wearer to be able to bathe and/or swim while wearing the device); and/or 4) a comprehensive analysis package for typically immediate, local data interpretation. An alternative device may be adapted to take advantage of flex-circuit technology, to provide a device that is lightweight, thin, durable, and flexible to conform to and move with the patient's skin during patient/wearer movement.

In some alternative non-limiting implementations, the sensor systems may include expanded dynamic range of the signal acquisition circuitry. The signal of interest in the PPG signal is a small pulsatile wave. This pulsatile wave may be highly amplified to obtain the needed resolution for the calculation and derivation of the oxygen saturation (SpO2) levels. In certain instances, the amplification in or with the presence of motion artifacts may cause the signal to saturate the amplifier and may result in signal loss. For example, while using a 12 bit A/D (analog-to-digital) converter the range of measurement of the raw PPG signal may be about 4096 levels. The results of using this combination of amplifier and converter is shown in graphical form in FIG. 8A. The over-saturation and signal misrepresentation is shown by the circled area 800. This circled area shows where the PPG signal is saturating, or sometimes referred to as railing. In FIG. 8B, the circled area 810, shows how the derived SpO2 levels may be misrepresented and/or distorted as a result of the loss of signal from the PPG due to the saturating, or railing described in FIG. 8A. Increasing the A/D converter from 12 bits to 24 bits represents approximately a 60 dB gain in the dynamic range. The use of a 24 bit A/D converter may help eliminate the possibility of saturating the amplifier and the resulting distorted derived SpO2 levels as shown in FIGS. 8A and 8B.

In some alternative non-limiting implementations, the sensor systems may have dynamic automatic gain control for optimizing and maximizing signal acquisition depending on the physiology of the patient. A fixed gain amplifier may not be appropriate for all physiologies. For example, a very dark-skinned patient will require a relatively high level of gain; however, a light-skinned person may require a much lower level of gain. A fixed gain amplifier may limit the ability to maximize and optimize the pulsatile signal for all physiologies. Therefore, devices hereof may have many different levels of gain control, in some instances as many as 2, 3, 4, 5, 6, 7, 8, 9, or more different levels of gain control. These different levels of gain control may thus allow for automatic setting of the appropriate level of gain for different physiologies encountered.

In some implementations the device hereof may allow for 512 levels of DC Offset. With this control, the signal will always be placed in the middle of the amplifier range, allowing for maximum amplification and limited distortion. DC Offset allows for the signal to be set correctly in the middle of the amplifier input range. If the DC Offset is not incorporated in to the device hereof, very dark skin may cause the DC offset to be near the bottom of the range of the amplifier, limiting the ability to amplify the signal without significant distortion.

In some implementations the device hereof may have 256 levels of LED light control that may allow more efficient control for each physiology to increase efficiency of the device and extend the device wear time. As with amplifier gain, different physiologies require different amount LED light intensity. Since LED power is one of the largest consumers of battery power in the system, inefficient control, management, or usage of the LEDs may result in inefficient battery usage and thus decreased longevity or wear time.

Figure 9A:
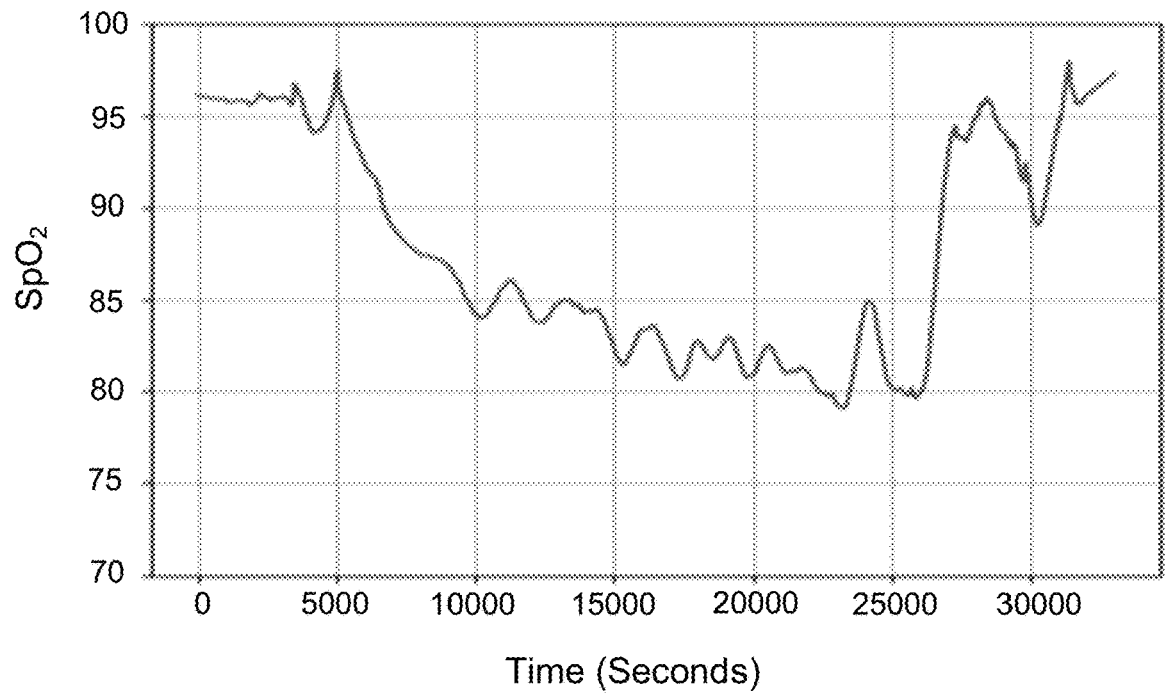
FIGS. 9A, 9B, 9C, and 9D provide graphed results of SpO2 measurements over time as obtained via the device hereof, or alternatively obtained via a finger oximeter, as set forth in each graph.
Figure 9B:
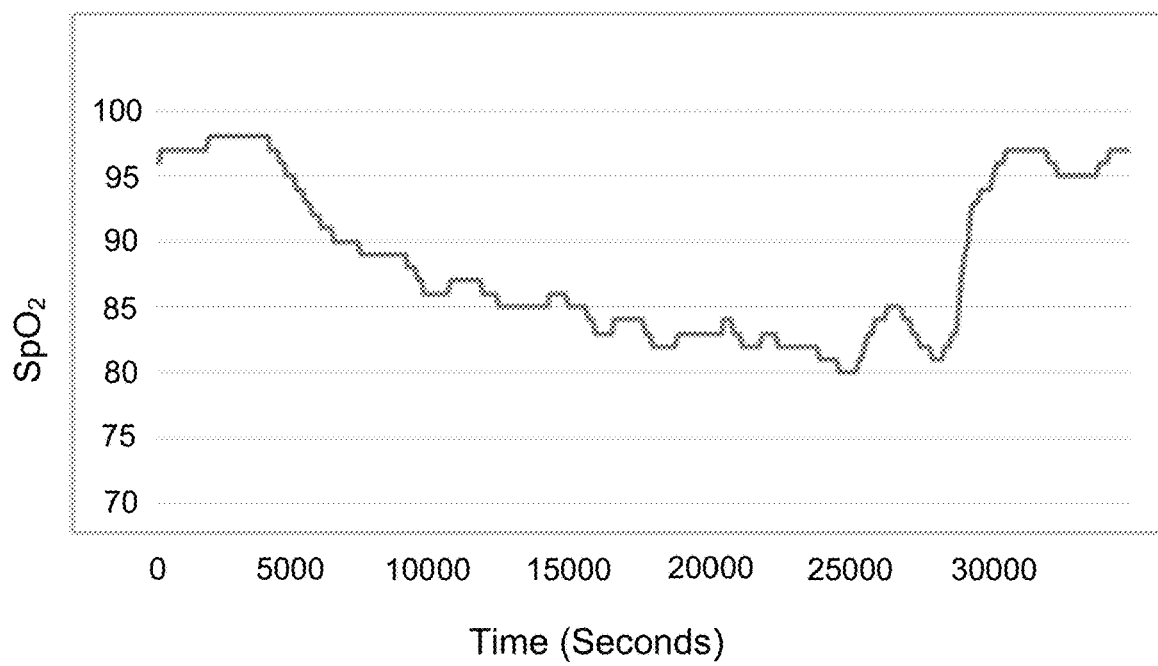
Figure 9C:
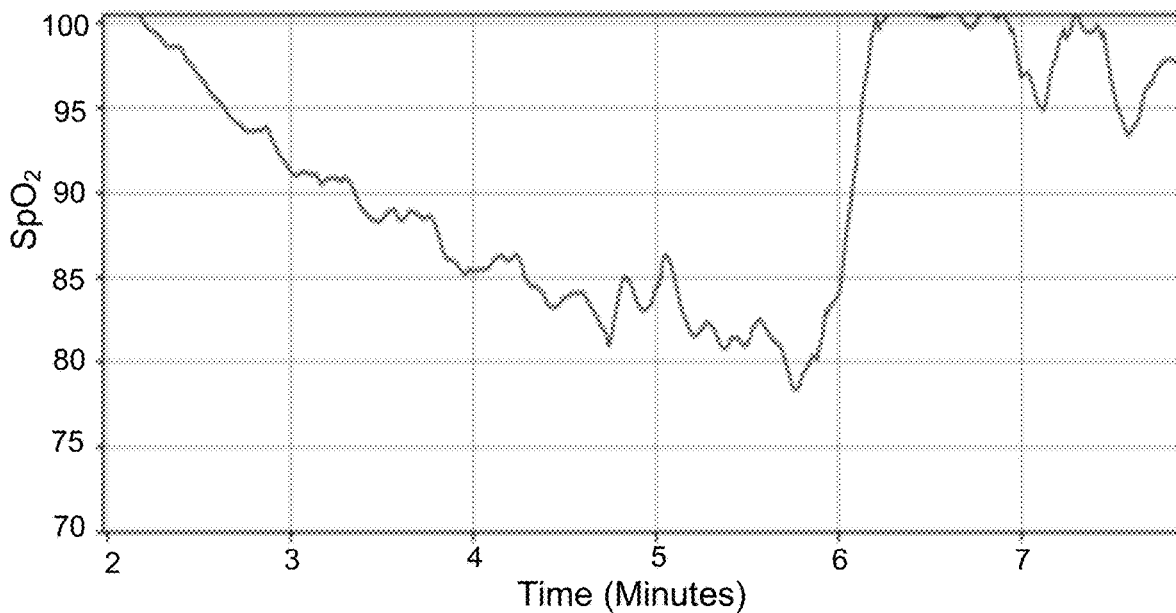
Figure 9D:
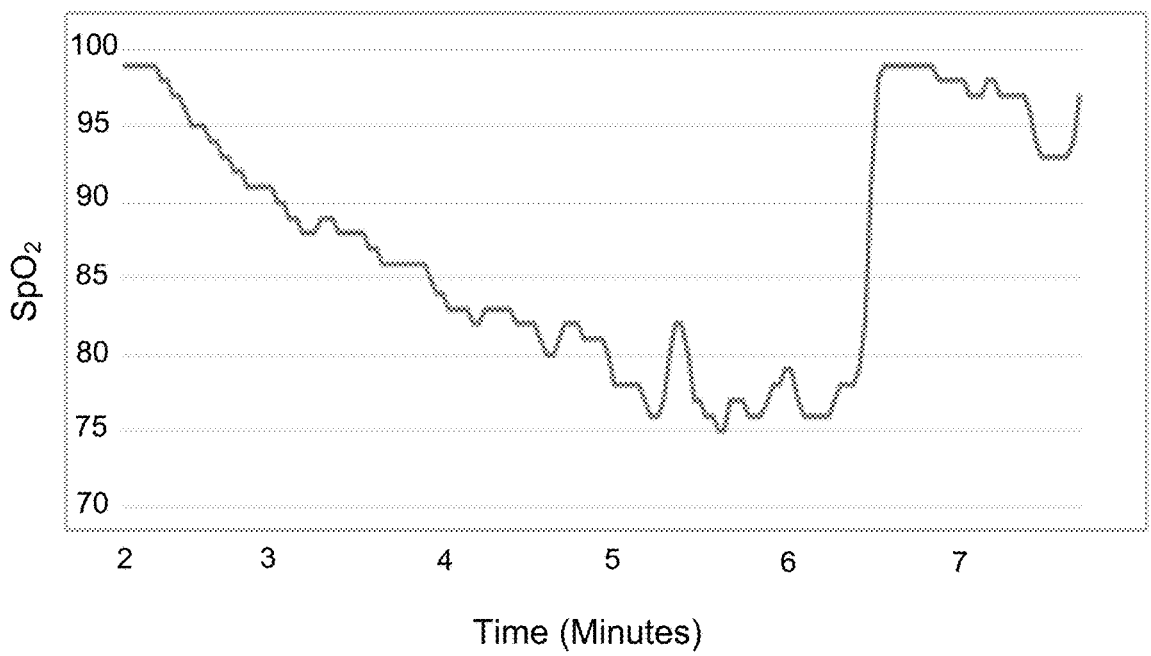

FIGS. 9A and 9C show the results of SpO2 measurements by the device hereof. FIGS. 9B and 9D provide the results of SpO2 measurements of a commercial finger oximeter. Note that in FIGS. 9A and 9B, the tests were performed simultaneously on an individual with light skin, with a Fitzpatrick score of 2. In FIG. 9A the device hereof was placed on the chest of the individual and in FIG. 9B the finger pulse oximeter was placed on the finger of the individual. Note that in FIGS. 9C and 9D, the tests were simultaneously performed on individuals with very dark skin, or a Fitzpatrick score of greater than 6. In FIG. 9C the device hereof was placed on the chest of the individual and in FIG. 9D the finger pulse oximeter was placed on the finger of the individual. In both tests, that is, whether on a very light skinned person or a very dark skinned person, the device hereof was capable of providing results very similar to those of a commercially produced finger pulse oximeter, which demonstrates that the device hereof may provide accurate information regarding SpO2 levels over time.

In some implementations the wearable device hereof may be approximately 80 mm (~3.149 inches) in length. In some aspects as shorter length may increase wear time of the device by decreasing the loss of adhesion of the device and electrode lifting or detachment which may occur if the device is too large for a particular physiological topography. Further in some implementations the device may incorporate a circuit board design that is more flexible which may enable a greater integrity of adhesion to the subject.

In some implementations the adhesive stack may be fabricated using advancements in adhesive technologies from 3M Company, Maplewood, Minnesota as further described in detail below. In some alternative implementations the adhesive is rated for up to 21 days of continuous wear and will not absorb moisture from the patient or wearer.

In some alternative implementations of the device hereof, in a Lead 1 arrangement, the device may utilize only two (2) electrodes for obtaining the data needed for the ECG measurements and calculations. In one aspect the use of two electrodes instead of three electrodes may increase the reliability of the device because there may be a lower or lesser change of electrode lifting and subsequent signal loss. Additionally, in some implementations one electrode may be integral to the main body of the strip, while the second electrode is tethered, which may de-couple the mechanical movement of the two electrodes and thus greatly reduce or decrease motion noise from the signals obtained from each electrode. The tethered electrode may allow different relative positioning of the electrodes as the tethered electrode is attached via a flexible electrode extender as described in more detail in FIGS. 1N to 1N7, inter alia. One benefit of a being able to change the relative positioning of the electrode may be that different ECG morphologies may be required for particular studies, and thus being able to change the placement of the electrode may allow the device to be used in studies requiring devices that can measure different ECG morphologies. Moreover, in some implementations an analog front-end (AFE or analog front-end controller (AFEC)) set of conditioning circuitry that utilizes high sensitivity amplifiers and filters along with the automatic gain control (described elsewhere herein) may allow for greater reliability and ECG resolution for all ages and physiologies.

In some alternative non-limiting implementations, the battery cage or container may allow the wearer, user, health aide, or health care provider to change the battery without removal of the device from the wearer or patient. In some instances, this may allow the device to be worn for an extended period of time such as 7, 10, 14, or 21 or more days.

In some alternative non-limiting implementations, an audio sensor may be incorporated into the device to capture the internal breathing sounds and respiratory artifacts. This audio sensor is described in more detail below.

In some alternative non-limiting implementations, Bluetooth capabilities may be utilized and incorporated into the device which may increase the range, bandwidth, and power efficiency of the device. In one aspect, the Bluetooth capabilities may utilizes Bluetooth Low Energy ("BLE") to transmit information from the device to a Bluetooth compatible smartphone, such as, for example, an Apple iPhone 8, iPhone X, iPhone 11 (Apple, Inc., Cupertino, CA), or Samsung Galaxy S8, Galaxy S9, Galaxy S10 (Samsung Group, Seoul, South Korea), or Google Pixel, Pixel 2, Pixel 3, or Pixel 4 (Google, Inc., Mountain View, CA), or to a Bluetooth compatible tablet, such as, for example an Apple iPad or iPad Pro (Apple, Inc. Cupertino, CA), or, to a Bluetooth enabled laptop computer, or, to a Bluetooth enabled desktop computer. In one alternative non-limiting implementation, the device utilizes BLE 4.0 standards and protocols. In another alternative non-limiting implementation, the device utilizes BLE 5.0 standards and protocols. The utilization of both BLE 4.x and BLE 5.x are described in more detail throughout the specification below.

FIGS. 1 and 2 (as defined by respective sub-part figures) illustrate examples of alternative implementations of devices that may be so adapted.

FIG. 1, which is defined by and includes all of sub-part FIGS. 1A-1X2, shows a device 100 that has a component side or top side 101, patient side or circuit side 102, and one or more inner electrical layer(s), generally identified by the reference 103 and an elongated strip layer 105. The strip layer 105 may have electronics thereon and/or therewithin. FIG. 1A shows isometrically these elements in what may in some non-limitative implementations together with some other elements that may be used herewith. FIG. 1B is more specifically directed to a top side 101 plan view and FIG. 1C to an underside, patient side 102 plan view and FIG. 1D a first elevational, side view.

Figure 1D:
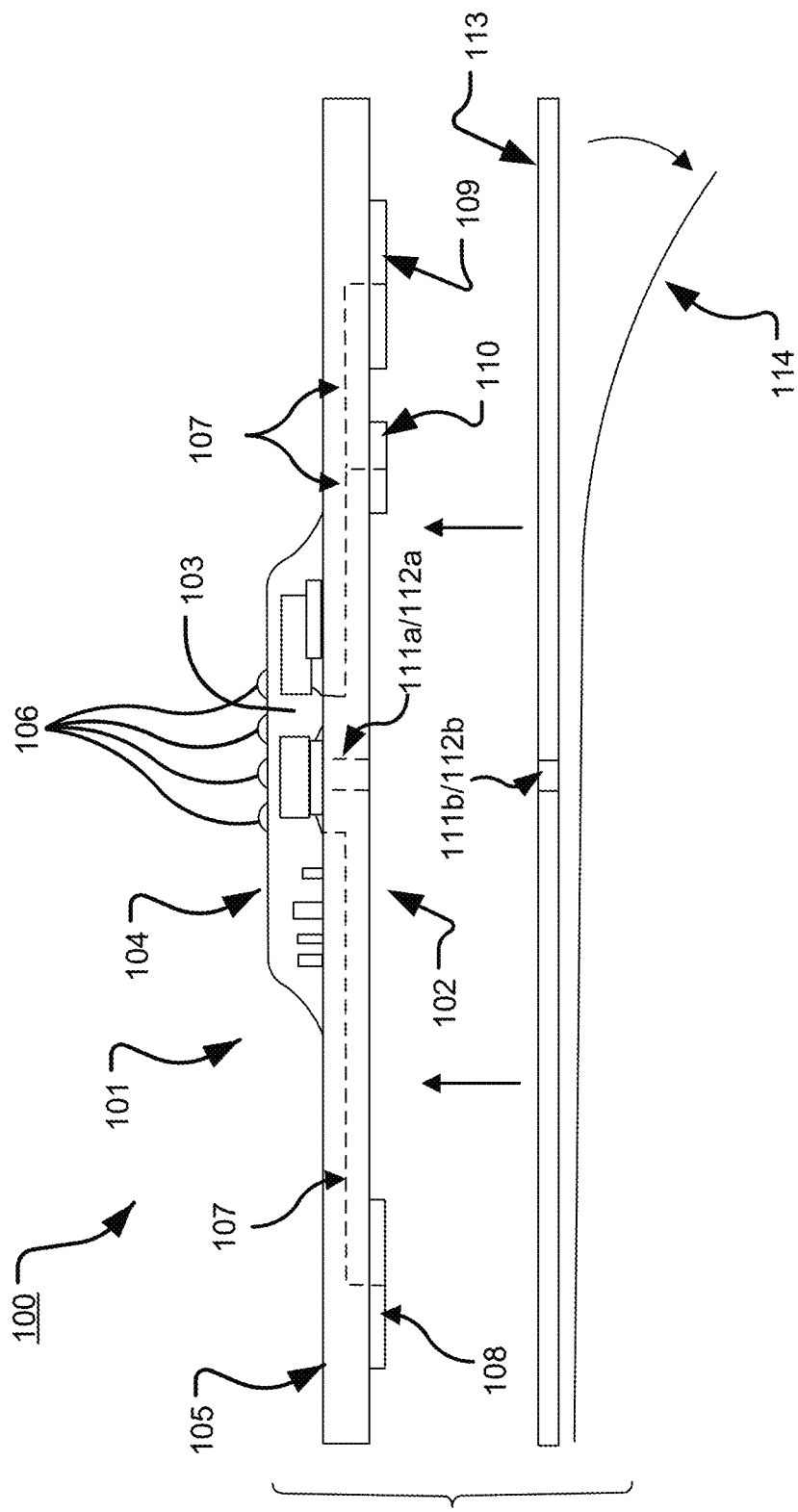
FIG. 1, which includes and is defined by sub-part

Many of the optional electronics hereof may be disposed in the electronics layer or layers 103, and as generally indicated here, the electronics may be encapsulated in a material 104 (see FIGS. 1A, 1B, 1D, and 1S for some examples, and see FIGS. 1T2, 1T3b, 1U, 1U1, 1U2, and 1U3 described further below, e.g.), medical grade silicone, plastic or the like, or potting material, to fix them in operative position on or in or otherwise functionally disposed relative to the elongated strip layer 105. The potting or other material may in many implementations also or alternatively provide a waterproof or watertight or water resistant coverage of the electronics to keep them operative even in water or sweat usage environments. One or more access points, junctions or other functional units 106 may be provided on and/or through any side of the encapsulation material 104 for exterior access and/or communication with the electronics disposed therewithin, or thereunder. FIGS. 1A, 1B and 1D show four such accesses 106 on the top side. These may include high Z data communication ports and/or charging contacts, inter alia. This upper or component side 101 of device 100 may be coated in a silicone compound for protection and/or waterproofing, with only, in some examples, a HS USB connector exposed via, e.g., one or more ports 106, for data communication or transfer and/or for charging.

The elongated strip layer 105 may be or may include a circuit or circuit portions such as electrical connections or leads or other inner layer conductors, for signal communications, e.g., leads 107 shown in FIG. 1D, for communication between the electronics 103 and the electrically conductive pads or contacts 108, 109 and 110 described further below (108 and 109 being in some examples, AgCl (printed or otherwise), high impedance/high Z silver or copper/silver electrodes for electrocardiograph, ECG, and 110 at times being a reference electrode). In many implementations, the strip layer 105 may be or may include flex circuitry understood to provide acceptable deformation, twisting, bending and the like, and yet retain robust electrical circuitry connections thereon and/or therewithin. Note, though the electronics 103 and electrodes 108, 109, 110 are shown attached to layer 105; on top for electronics 103, and to the bottom or patient side for electrodes 108, 109, 110; it may be that such elements may be formed in or otherwise disposed within the layer 105, or at least be relatively indistinguishably disposed in relative operational positions in one or more layers with or on or adjacent layer 105 in practice. Similarly, some of what may be myriad possible leads or traces 107 are shown embedded (by dashed line representation in FIG. 1D); however, these may be on the top or bottom side, though more likely top side to insulate from other skin side electrical communications. If initially top side (or bottom), the traces may be subsequently covered with an insulative encapsulant or like protective cover (not separately shown), and/or in many implementations, a flexible material to maintain a flexible alternative for the entire, or majority of layer 105.

Sophisticated electronics may be preferred for many of the functionalities described herein; indeed, many implementations may include large numbers and/or combinations of functions on the respective devices and sophisticated electronics may in some implementations even be required to achieve same in many cases. Flexible Circuit Boards (aka FCB or FCBs) and/or Flexible Printed Circuits (aka FCB, FPC or FPCs) can become quite rigid when populated with electronic components; merely adding multiple components makes even a flexible circuit board more relatively rigid. The soldered connections of larger integrated circuits (IC's) can in many cases be unreliable or become unreliably soldered under constant or otherwise significant flexure of the flexible substrate. The alternative implementations, designs and methods of FIGS. 1E-1N may be used to address these or like flexibility and/or reliability issues of manufacturing a multi-function, wearable biometric monitor.

In the implementations of FIGS. 1A-1D (among others also shown and described below), all the circuitry may be, as shown, attached relatively directly to the flexible circuit board 105, though still viable options, but may perhaps less preferred with other flexible substrates. However, in some alternatives, in order to make the subject-facing FPC relatively more flexible than the board 105 of FIGS. 1A-1D, many if not all of the large IC's and other components can be relocated to another, relatively rigid, Printed Circuit Board (aka PCB) that can be nevertheless operably connected to a flexible circuit board. Examples of these are shown in FIGS. 1E-1N7 in the devices 500 and 500a.

Figure 1E:
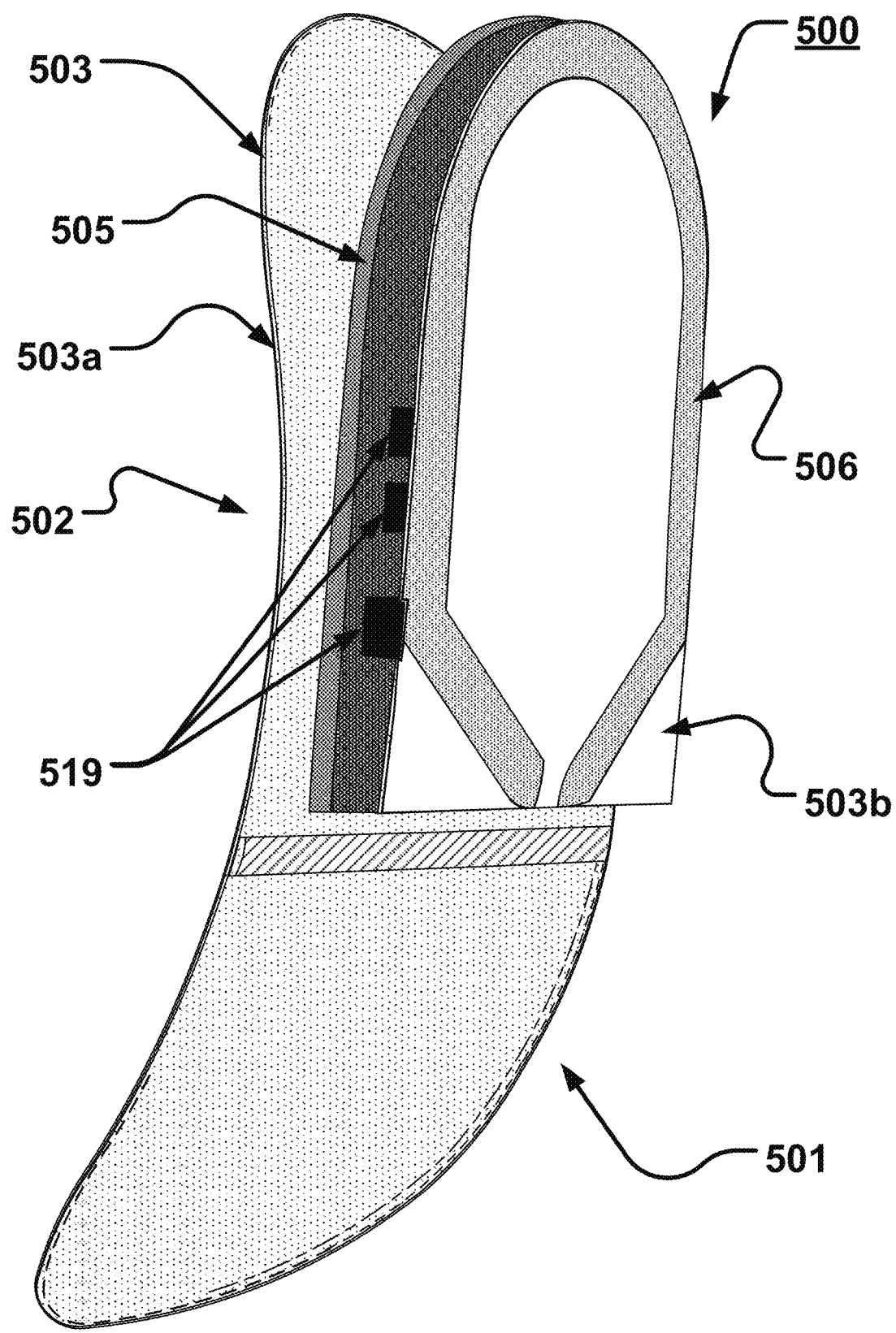
Figure 1F:
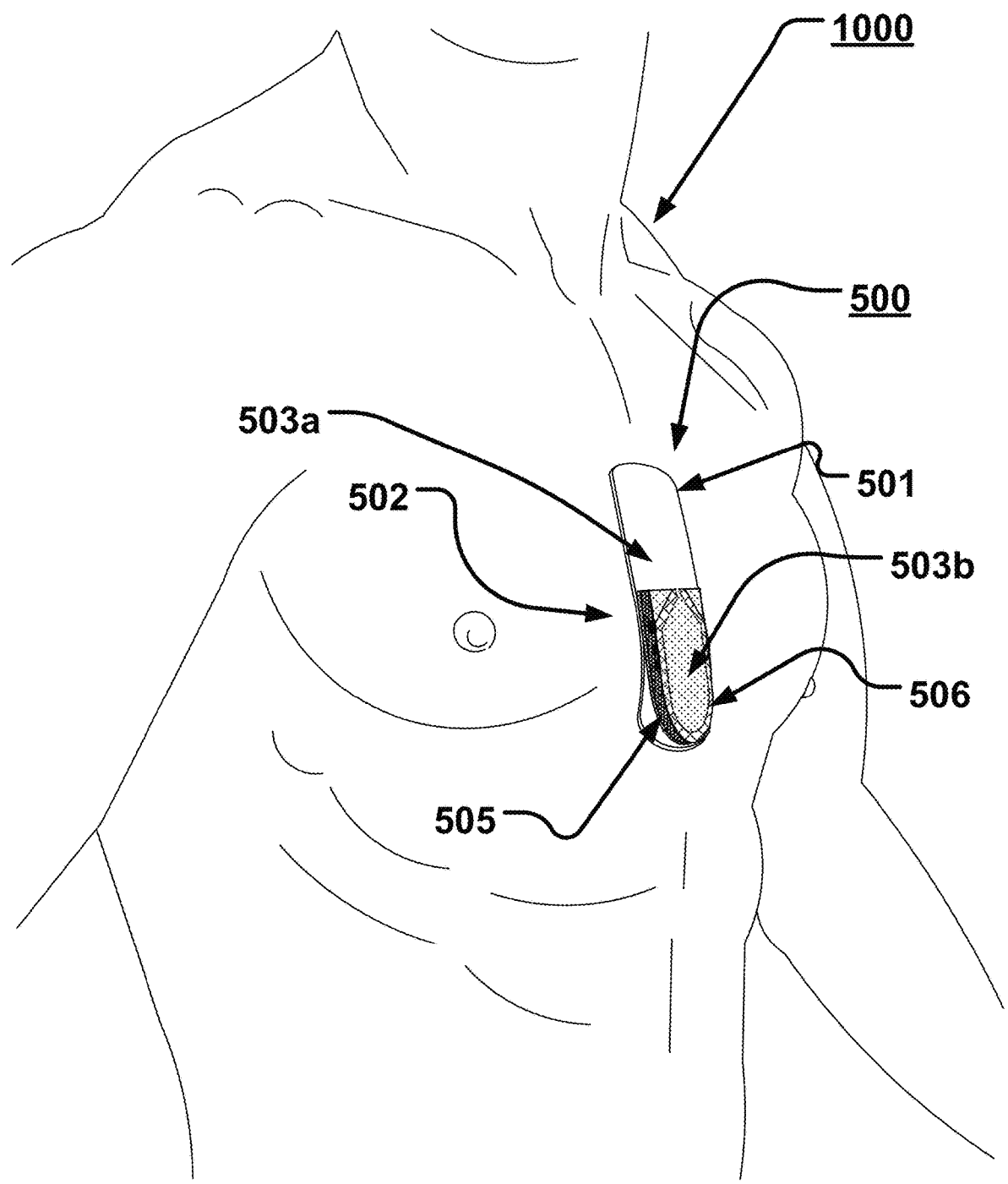

In more particularity, sub-part FIGS. 1E-1N7, show a device 500 or an alternative device 500a that each have a component side or top side 501, patient side or circuit side 502, and one or more generally electrical layer(s), generally identified by the reference 503, generally. Also here included is an elongated strip layer or circuit layer 505 disposed therewithin. The circuit layer 505 may have electronics thereon and/or therewithin, see e.g., components 519 described further below. FIGS. 1E and 1F show isometrically these in what may in some non-limitative implementations be as shown a substantially transparent or translucent device together with some other elements that may be used herewith. FIGS. 1E and 1F show two or more layers, generally one on top of the next, here including a first layer 503a which is a flexible or flex circuit layer shown noticeably flexed, here shown arched as it might be in use on a subject user (a user or wearer 1000 is identified generally in FIG. 1F). The second or middle circuit layer 505 is here a relatively rigid material board not intended to arc or arch or substantially otherwise flex to more readily maintain the electrical connections and/or circuit components connected thereon, thereto and/or therewithin. An optional third layer 503b, also here a flexible layer is also shown, here above the circuit layer 505; the third layer 503b here having data communication capability, via one or more data communication devices 506, here via an antenna 506.

Figure 1G:
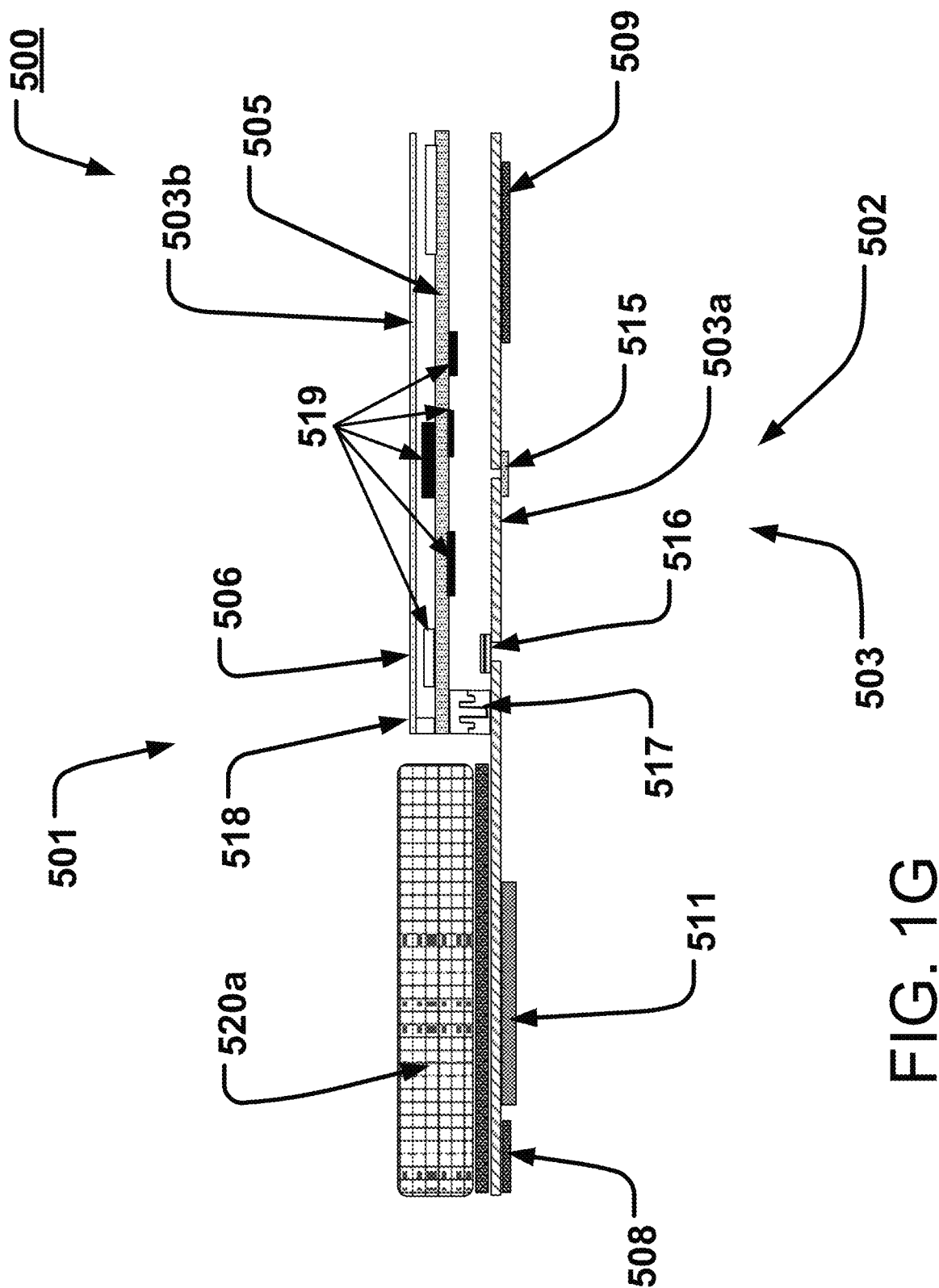
Figure 1H:
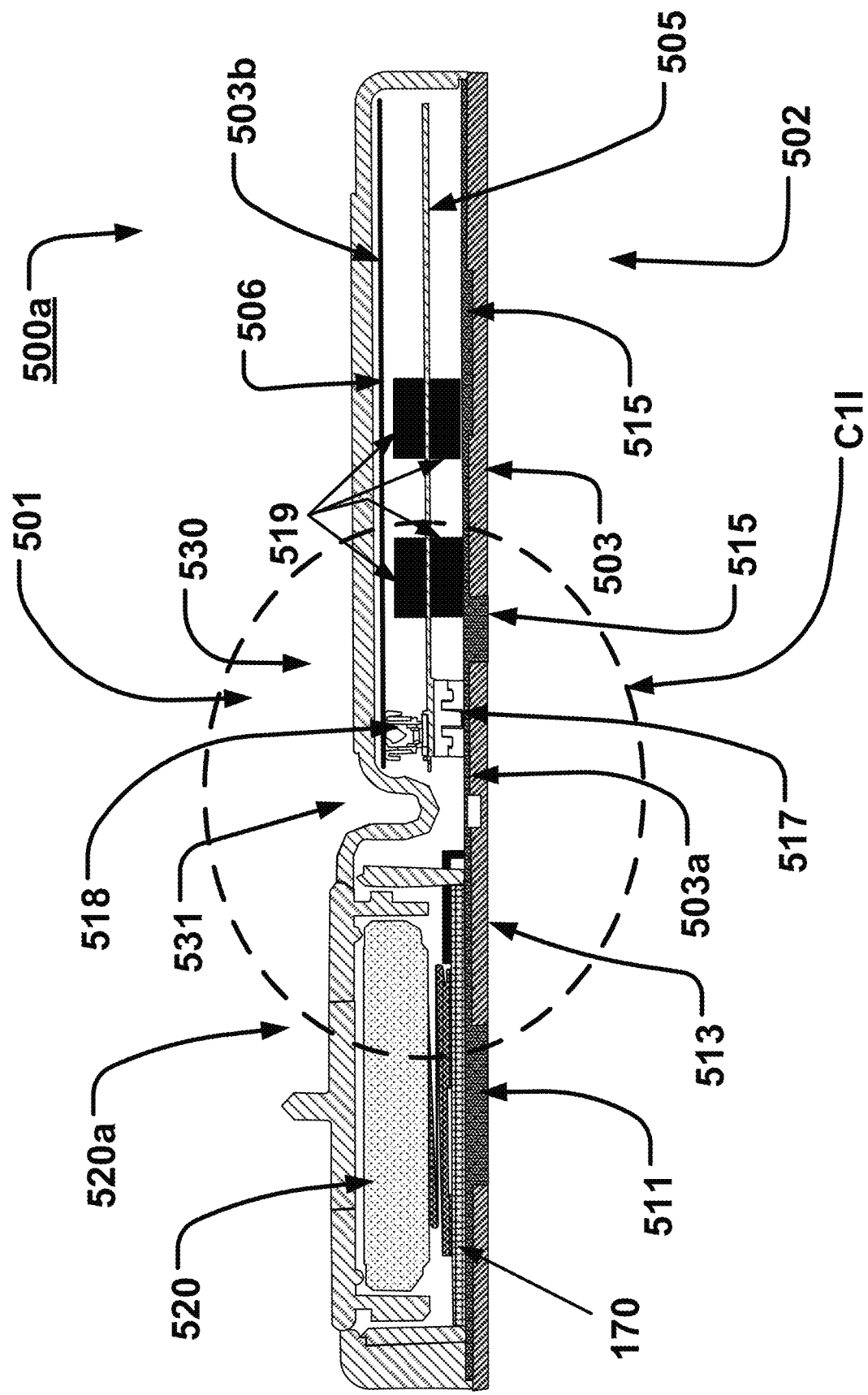
Figure 1I:
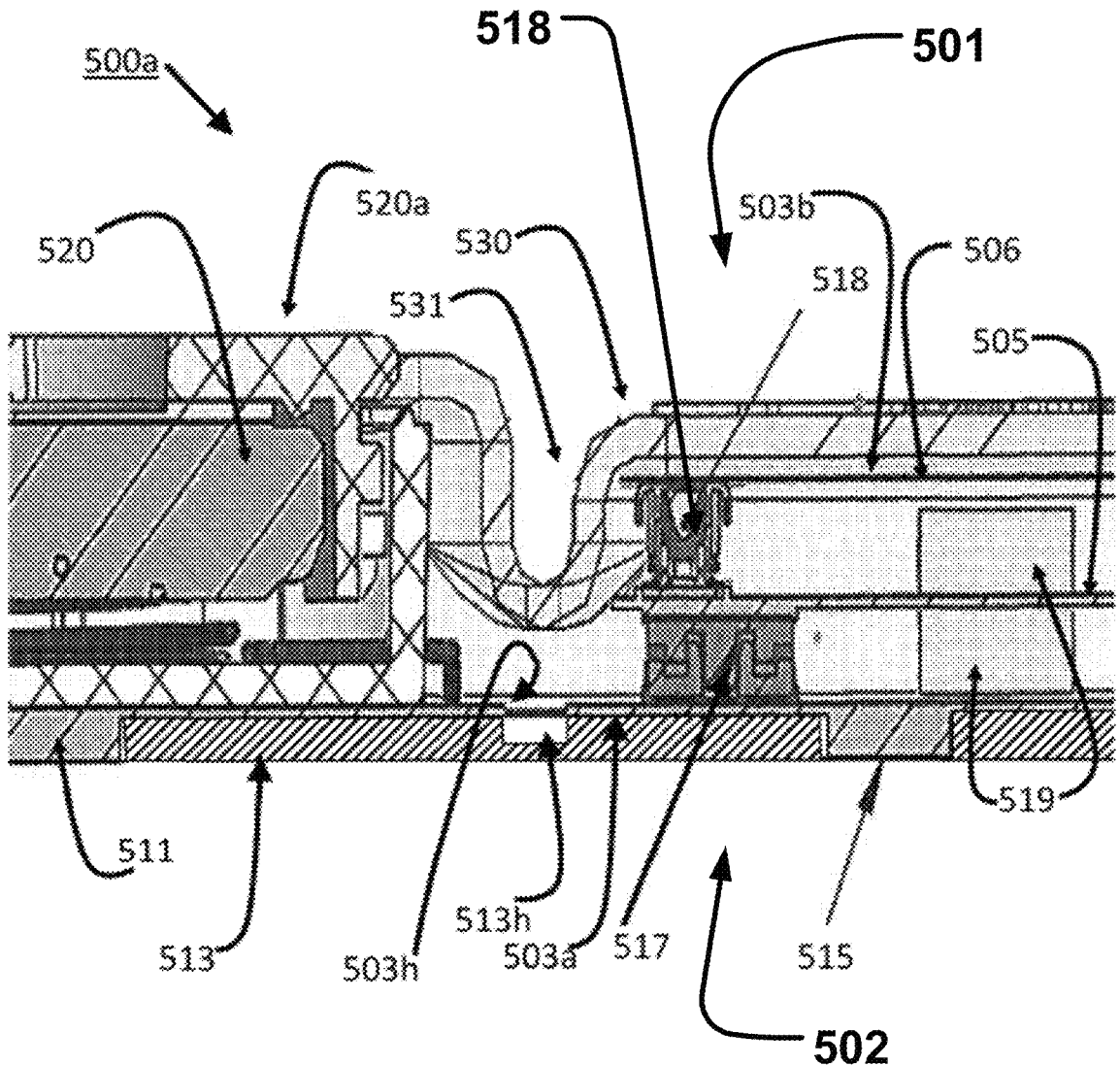

Cross-sectional views of respective versions of devices 500 and 500a are shown in respective FIGS. 1G and 1H and 1H1 and 1I. These also each have the top or external side 501, patient side 502, and the one or more generally electrical layer(s), generally identified by the reference 503, generally, including the elongated strip layer or circuit layer 505 therewithin. In these implementations, shown is the stacking of these two or more, and here as shown, three layers one on top of the other. An adhesive layer 513 is shown in FIGS. 1H and 1I as well, but left off the implementation of FIG. 1G merely for ease in showing/viewing other operational parts thereof as described below. Off to the side relative to these stacked circuit layers is a battery 520 and battery compartment or cage 520a. Other optional and/or preferred components are further explored/described below.

With many electrical components removed from the bottom, the subject facing layer, here layer 503a in FIG. 1G, this layer 503a remains flexible and has the capability to conform to a wide variety of body types, sizes and shapes and body motions. Only a few components remain on this lower layer 503a; typically, in this implementation, the actual sensors themselves, devices to be in contact with or near association with the patient 1000. These are the ECG electrodes 508 and 509, the PPG (photoplethysmograph) device/LEDs/sensor unit 511, a temperature sensor 515 and a microphone 516, e.g., a piezo microphone (shown and described in more detail below). The signals received by and/or through these sensors can then be passed to the next layer 505 thereabove, the "floating" relatively rigid PCB, through a micro-connector 517 placed in such a fashion to be a mechanical hinge point with electrical communication therethrough and/or therebetween. In some implementations, the processing electronics 519 may be disposed to reside on this rigid PCB 505, which may thereby, i.e., through relative rigidity, increase solder reliability, and thereby reliability and robustness of the electrical communications during use, whether moving or not; the electronic and/or processing components 519 having little cause for movement relative to the PCB 505. Also, taking electronic devices and processing electronics 519 such as integrated circuit(s) (IC(s)) from the flexible layer 503a may remove or reduce rigidity in or from the subject facing layer 503a disposed below the more rigid layer 505.

In some implementations, and as shown here in FIGS. 1G, 1H, 1H1, and 1I, above the rigid layer 505, another flexible layer 503b may be disposed. In some situations, this may be an antenna 506, as for a non-limiting example, a Bluetooth antenna, connected to Layer 505 by a micro coaxial connector 518, placed adjacent the above-mentioned hinge point 517. This Third Layer 503b may be configured to be either rigid or otherwise flexible in order to, in some examples, keep the overall stack of three circuit boards flexible.

An exterior housing 530 is shown in FIGS. 1H, 1H1, and 1I as it might be disposed over and contain the other parts. This might be made of a pliable or flexible silicone, typically of a medical grade, and may be a molded part to provide shape substantially as shown. Also shown is a pleat 531 or fold, or tuck or crease in such a housing 530; such a pleat providing even further allowance for bending movement, here near the center of the device, and/or near the connection of the rigid board 505 to the flexible substrate 503a. This connection area is shown and described in more detail in and relative to FIG. 1I, et seq; the FIG. 1I generally being an enlarged approximate portion of FIG. 1H taken at about circle C1I of FIG. 1H.

In FIG. 1I, the primary substrate 503a is shown with adhesive 513. Connected to the substrate 503a is the rigid board 505, connected via the electrical/data connector 517. Generic electrical components 519 are shown on both sides of board 505; both sides being optionally usable to maximize usage of real estate or surface area on board 505, yet keeping the overall size, width and length, of board 505 to a relative minimum. This is optional; only one side may be used in some implementations. Also shown in FIG. 1I for general reference are the PPG light source/sensor components or unit 511 and sensor 515 on substrate 503a, the battery 520 and battery cage 520a (which may take other forms, not shown), inter alia. The third level, or layer or third circuit 503b is shown housing the antenna 506, and as connected to PCB 505 via connector 518. However, as introduced in FIG. 1H, a better view of pleat 531 of cover 530 is shown in FIG. 1I, pleat 531 allowing for greater flexure of substrate 503b. Here also, more visible are two gaps, or hinges 503h and 513h, formed in the respective substrate 503a and adhesive 513; each gap at the hinge being disposed to allow flexibility. In a simplistic model or view, these may be formed by a lack of or reduction of material at these points. (Note, in an implementation herein described, an adhesive may be formed by six layers strategically disposed, and for the relative gap/hinge 513h, only one or another number of few or fewer of the six (6) layers, may be/remain existing at this point 513h; the reduction of material being representative of the concept.) It is noted that the gap and the adhesive are not shown in the alternative implementation shown in FIG. 1G, showing thus the optionality, but, also noting that same could be incorporated into the implementation of FIG. 1G.

FIG. 1H1 provides a similar view as FIG. 1H; however, FIG. 1H1 also provides an accelerometer 129, that may be disposed on the rigid printed circuit board (PCB) 505. Understanding here also that it may be preferred to reduce the sensor and electronic components that are to be disposed on the flex circuit board 503a to those that are needing more direct access to the human skin/patient body—where on the other hand, componentry or sensors, as for example an accelerometer are less or not needing direct access themselves to the patient or the patient skin, these may then be removed to the second level, relatively rigid PCB 505. The optional accelerometer 129, may be a high-resolution accelerometer for a variety of possible uses, including without limitation, respiration, respiration rate, movement of the body, position of the body and/or optionally ballistocardiography (with or without also using output from a piezo 516, see below)—ballistocardiography being a representation of cardiac and/or other body forces, movement and/or vibrations relative to the expulsion of blood into the aorta with each heart beat caused by the mechanical movement of the heart; the push or expulsion has different information than the movement during valve closure, chamber filling and relative muscle relaxation—a high resolution accelerometer and/or piezo can/may be able to gather this information for ballisto-analaysis. In some implementations, the accelerometer is placed at or near or as near as reasonably possible to the hinge 513h and near the pleat 531. Placing the accelerometer in this manner reduces the distance the accelerometer changes in distance from the skin, and thus may help to assure minimal movement of the accelerometer due to flexing movement of the flex circuit board, which may not be relative to the particular parameter being measured; similarly, minimized movement may be preferred where the accelerometer is on the rigid board, but, not moving as in some cases might be desired relative to the flex circuit due to the accelerometer being placed on the floating, but relatively rigid PCB 505—a possibly undesirable divergence of or increased distance from the body might be experienced by an accelerometer disposed away from the central/hinge area of the overall device; the divergence not maybe being relatively calibrated for as or relative to the actual motion of the patient body, if this contributes to the desired data to be achieved from the accelerometer. Also shown in 1H1 is a PPG source and sensor device or unit 511, a battery 520, a silicone cover 530, a temperature sensor 515, and a connector 517. As shown in FIG. 1H1, the accelerometer may be placed on the top side or the bottom side (dashed line version) of the rigid PCB 505. FIG. 1H1 also shows relatively how and where a battery and/or PPG stiffener 170 might be disposed in or adjacent the battery cage 520a. FIG. 1I1 provides an exemplar, non-limiting stiffener 170 which may in some instances be a battery stiffener 170 and/or a PPG stiffener 170. This stiffener may be constructed from stainless steel or other relatively rigid material, often exhibited by metallic materials, and may have an anodized exposed stainless steel surface. Optionally, this stiffener may be disposed on or above, below or even in some circumstances within the flex circuit board 503a but preferably below the battery cage described in FIGS. 1H and 1I, above and above the PPG sensor unit described below. The stiffener provides a localized rigidity in the local area of one or both the battery compartment and/or the PPG sensor/source unit or other components or connections to reduce the effects of a flexible movement relative thereto. In more detail, the flexible circuit in the area of a battery compartment might lead to movement of the battery or batteries relative to the electrical connections or leads therein and result in some possible undesirable failure of continuous connection of the power source (battery or batteries) with the electrical circuitry. Similarly, a flexible circuit board in and around the PPG devices may lead to a possible undesirable movement of one or more of these devices relative to the patient, and more particularly relative to and perhaps undesirably away from constant, or substantially constant, contact with the skin. In either case, power interruption/failure or PPG disconnection from the skin, inefficiencies or failures of data may be experienced. The battery and/or PPG stiffener 170 may have one or more indentations, or cut-outs or mounting holes, 171a-171e (171a, 171b, 171c, 171d and 171e), around the perimeter of the stiffener. These indentations or mounting holes may allow for the stiffener and battery cage and PPG to be affixed to the flex circuit board, the mounting holes providing access to the flex circuit board for the battery cage, and electrical communication through to the PPG.

Figure 2A:
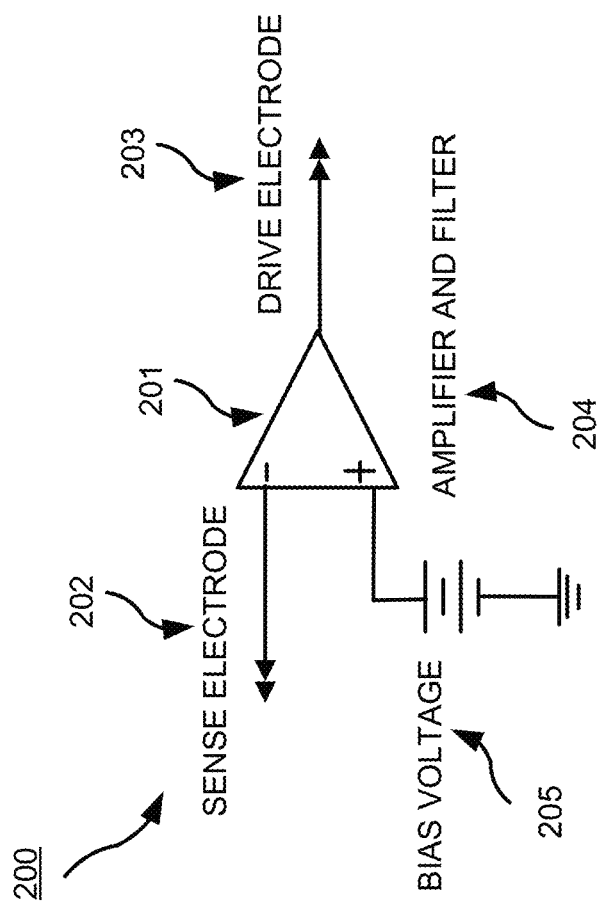

FIGS. 1I2a, 1I2b, 1I2c, and 1I2d show several different optional battery arrangements that may be utilized to power the device. As described elsewhere, one or more batteries 520, may be used to power the device. Similarly, in some implementations two (or in some instances more batteries) may be used. FIG. 1I2a provides batteries 521a and 521b, in these examples, flat watch-type batteries with one pole on the top surface and the opposing pole on the bottom surface. In this implementation the two batteries are shown with the two negative terminals schematically facing each other, which would not be operable if they touched—one would rather, in some more typical battery dispositions, have a positive of one battery would be adjacent the negative of the adjacent battery, one of which thus needing flipped from what is shown in FIG. 1I2a.

Figure 2C:
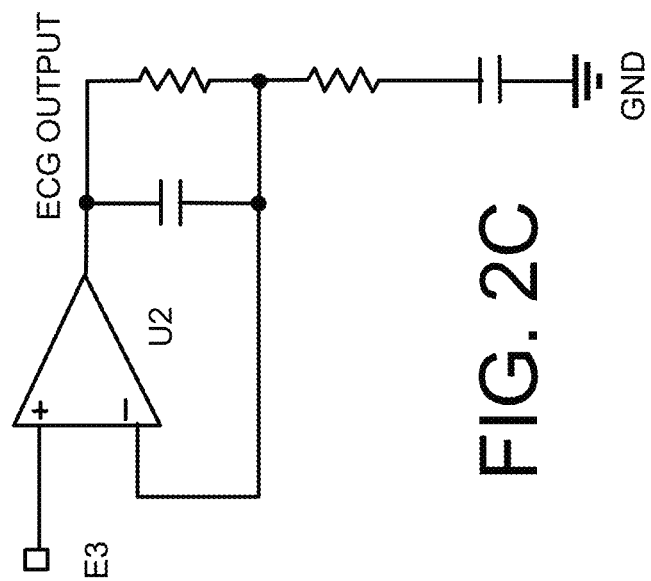
Figure 2B:
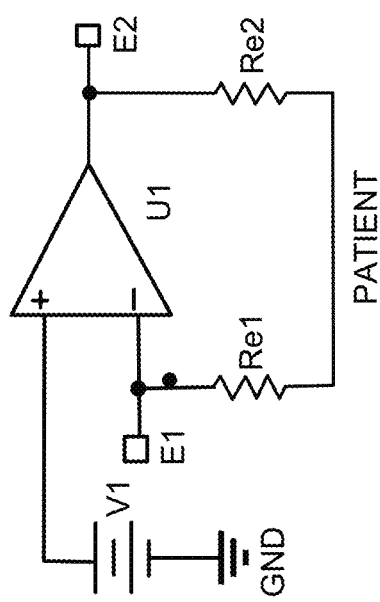

For one example of an implementation for the two batteries operationally adjacent, FIG. 1I2b provides batteries 521a and 521b, metal clip 522, and an insulated circuit divider 523. In this implementation, the batteries 521a and 521b are secured into a metal clip or metal clips 522, but are insulated from directly touching each other by an insulator 523, the insulator 523 nevertheless providing electrical connection of the here positive poles therethrough, without interfering one with the other. In this implementation, the two batteries may be secured together and then lowered as a unitary assembly into the battery cage or battery holder, described elsewhere herein. Note, with an insulating separating portion 523, the option of providing for both negative poles or both positive poles to be adjacent each other is also provided. Note, then, the central portion 523 would also provide an electrical contact for that combined pole orientation, if desired. I.e., not shown in FIGS. 1I2b and 1I2c are the options of having like poles disposed adjacent each other in the middle separated by an insulator 523, or as in FIG. 1I2c, air spacer 525. In such orientations, an electrical conductor (not directly shown) would also be needed to provide for electrical connection to these interior poles. When disposed such that both positives are pointed to the interior 523, 525, then both negatives would be pointed outwardly. Then, the connection 522 in FIG. 1I2b and the connections 526 and 527 in FIGS. 1I2c and 1I2d (described further below) would be known as "negative-to-negative" connections or clips; i.e., connecting two negative poles.

FIG. 1I2c provides a schematic diagram of yet another alternative implementation including batteries 521a, 521b; electrical contacts 524, air spacer 525, negative-to-negative clip 526, and spring 532. In this implementation, the negative-to-negative clip connects the negative terminal of one battery 521a to the negative terminal of the other battery 521b and then the battery assembly may be lowered in to the holder.

Figure 2D:
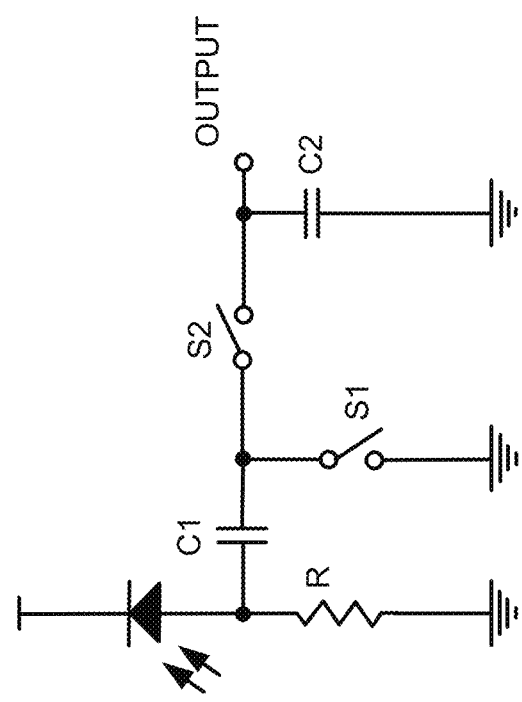

FIG. 1I2d provides a schematic diagram of yet another option related to the negative-to-negative clip scenario as described in FIG. 1I2c. Here, a spring tube 527 connects one or more disc-shaped mounting contact(s) 529, that may have contact nubs/contact buttons 528a and 528b.

Figure 1J:
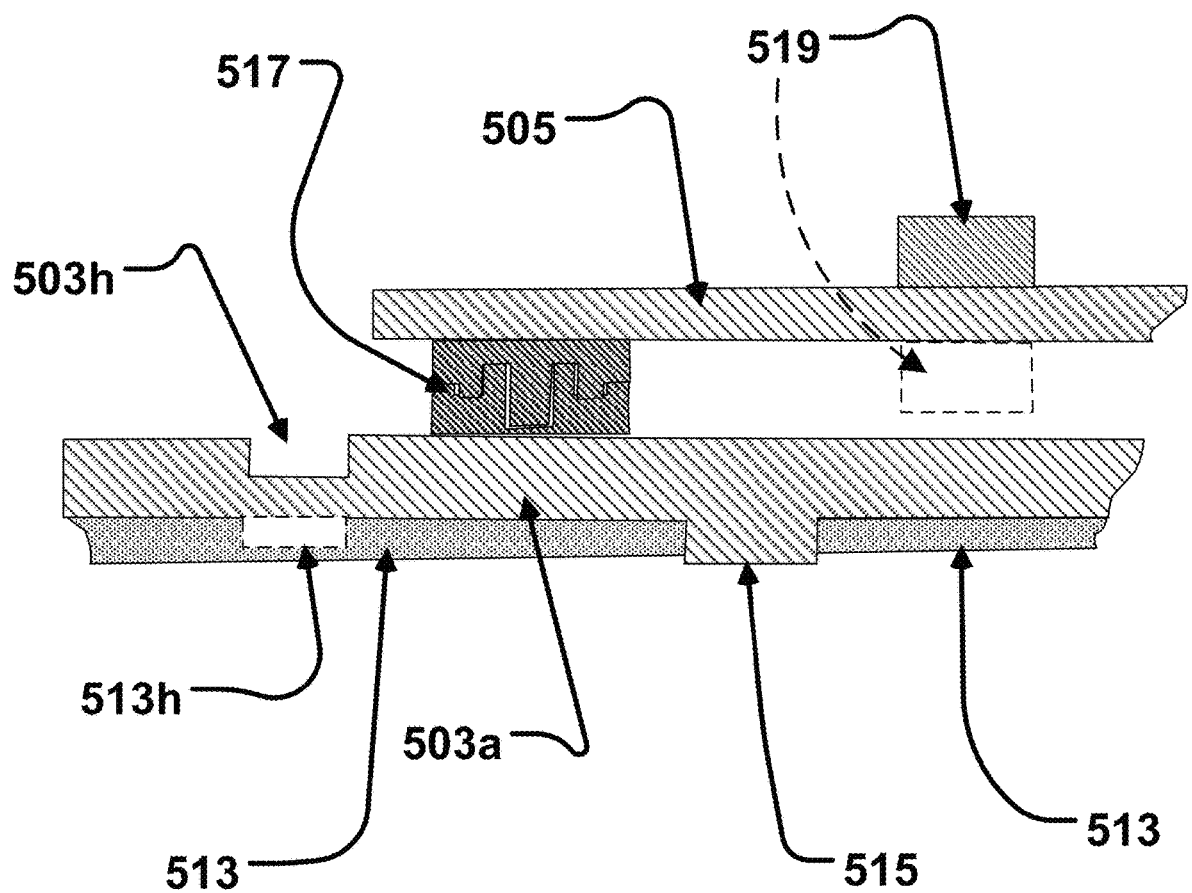
Figure 102:
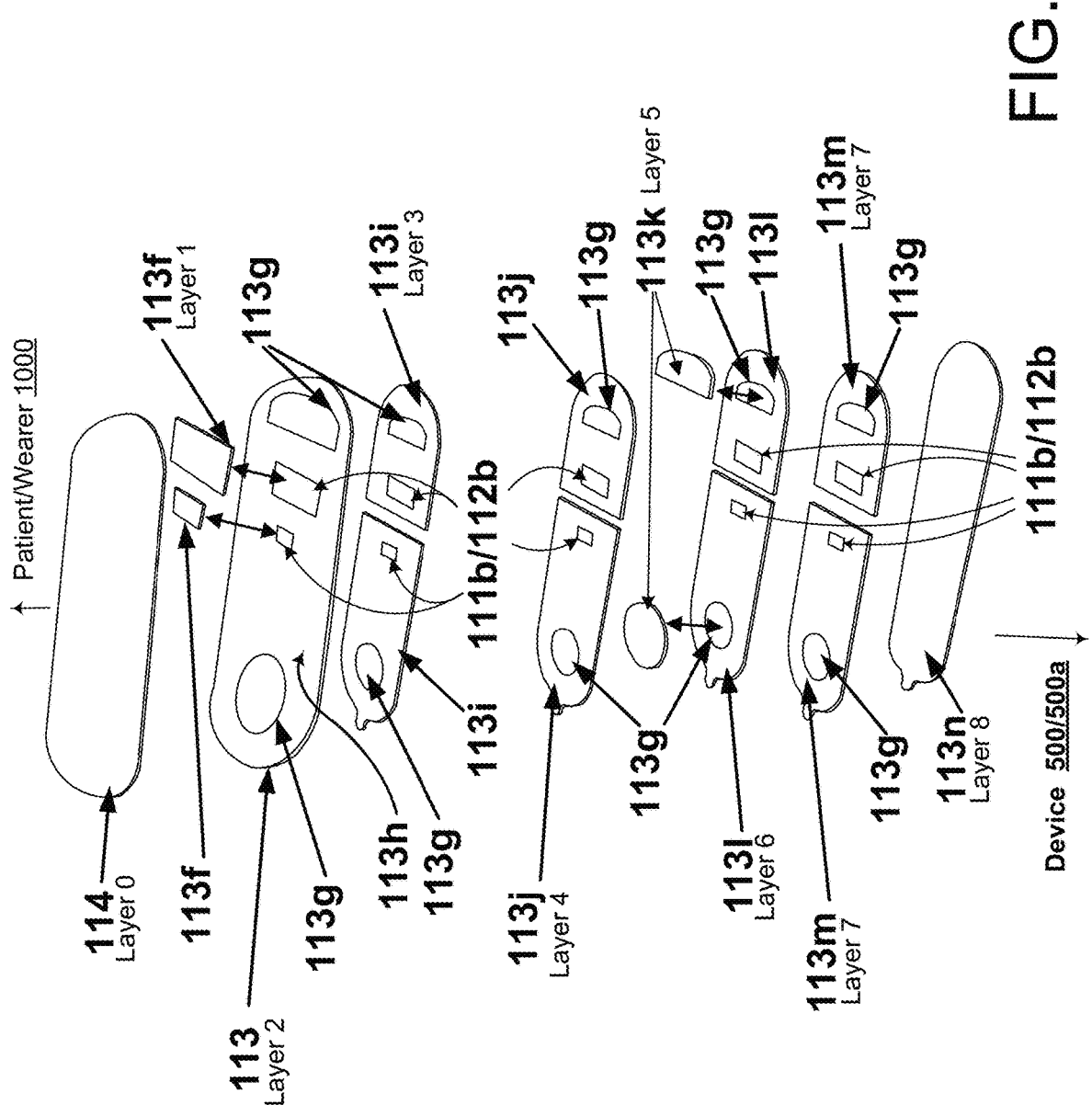

FIG. 1J, a more schematic view showing some options, shows the gap/hinge 503h in substrate 503a and an optional representation (dashed lines) of a gap/hinge 513h in adhesive 513. A representative sensor element, here temperature sensor 515 is shown as it may be schematically attached to substrate 503a. Relatively rigid board 505 is shown as it might be attached via connector 517 to flexible substrate 503a. An electrical component 519 is shown on the top/external side of board 505, with a dashed line/optional representation of s second component 519 on the underside of board 505; this to schematically show the optionality of these connections/dispositions; the top side being just as optional as the bottom side, though not so indicated here.

FIGS. 1K, 1K1 are not unlike FIG. 1J, though with even more schematical representation, by removal of the adhesive, and removal of the optionality/dashed line representations. In a primary view, the FIG. 1K implementation shows a relatively un-flexed flexible circuity board 503a. By comparison, the FIG. 1K1 implementation shows the same componentry with a flexed disposition of the substrate 503a. The flex arrows generally show the movement. FIG. 1K1 shows what may not be ideal depending upon the type of connector 517. Preferably, a connector 517 is chosen which may allow for some rotational movement; however, the preferred implementation will provide a robust secure electrical connection at 517. In FIG. 1K1, some space may be seen to perhaps demonstrate a disconnect; however, the intent is to show a connection device, if available, that may allow for some relative rotational movement and yet continue to provide a robust electrical and/or data communication connection.

In a further alternative as shown in FIGS. 1L and 1L1, the flexible circuit board 503a may be disposed to be relatively rigid in the area under/adjacent the connector 517; this relative rigidity may be a feature of the board 503a or may be imposed thereon by the connector 517. In either case, this implementation of a "Flexible Stack—Rigid Connector" may provide a relative correction over the FIG. 1K1 implementation which shows instead the connector mating surfaces not distorting during flexure. As shown, the device may be more relatively flexible in the regions identified generally as 503a1 and 503a3 and may be more relatively rigid in the region 503a2. The connector itself will, in this implementation, have little or no movement. In FIG. 1K1, the connector parts appeared to skew slightly; and this may also occur, though more slightly in FIG. 1L1; but, in many implementations, the connector 517 will have locking ears to prevent any movement within the connector, keeping all 60 pins in contact with each other. Some connectors found to meet some preferences include the 60 pin connector 517, male and female made by Samtec (Samtec, Inc., New Albany, IN). Shown in 1I, Hirose (Hirose Electric Co., Ltd., Downers Grove, IL) is a manufacturer for a Coax connector on/from the antenna 506 to the connector 518, where the mating coax connector 518 on double sided board 505 may come from Amphenol (Amphenol Corp., Wallingford, CT).

As a note for the implementations of FIGS. 1I-1L; the temperature sensor 515, which may in many implementations be an "Insulated Skin Temp Sensor", the location of the sensor may be found to have a more desirable disposition located near the rigid portion of the stack, and/or as well as in the center of area of the device. The location near the rigid portion may provide better if not optimum skin contact (relative rigidity providing for more consistent skin contact and resulting consistent data acquisition), while the location at the center of area may allow maximum distance in the x and y direction from the edges. Combined with the adhesive stack (which in this application, may act as a thermal insulator), allows the temperature sensor to come to thermal equilibrium with the skin quickly, thus increasing accuracy.

FIGS. 1M and 1M1 show a "Flexible Microphone" as may be implemented herein. The microphone technology used herein may be a flexible piezo strip 516, also known as a piezoelectric sensor, which will emit a voltage having an amplitude that is proportional to the amount of flexure or movement input that it is subjected to (note, a piezo will typically be sensitive to either or both motion and sound, so it can be referred to as an audio sensor or microphone, or as vibration sensor or motion sensor depending upon the movement, e.g., flexure thereof, and thus output therefrom can be indicative of movement or sound or vibration or any combination or all of these). A thin-film piezo 516 connected to the substrate 503a by electrical connection 516a may be employed allowing the device to be sensitive to movement input in two bandpass frequencies: about 0 to about 10 Hz, here a low bandpass, and centered around a bandpass of around about 1100 Hz, here a high bandpass. A placement of the piezo 516 as shown in FIG. 1M is described here. The piezo 516 may be placed on the patient side of the substrate 503a such that it crosses the hinge point. By placing part of the piezo in the area 516b (an area of relative maximum deflection) over and/or around the flexible hinge 503h, and part of it over a less flexible area 516c (an area of relatively less or minimum deflection), the microphone 516 may be sensitive to the relatively large chest movement that occurs during breathing (in the 10 Hz range) yielding respiration rate from relatively low or ultra-low frequency sound. The portion over the more flexible portion (516b) is sensitive to mid-range sound of relatively higher frequency 1100 Hz, yielding breath sound data such as sounds within in the breathing cavity or lungs, as e.g., normal breathing, breathing depth or breathing with artifacts, wheezing, obstruction volume of air, or perhaps abnormality due to disease (mechanical or bacterial (e.g., pneumonia) or viral (e.g., orthopneumovirus (RSV, e.g.) or perhaps coronavirus), etc. Since the hinge point is where the maximum flexure (516b) will occur, it will generate the maximum voltage possible during respiration of the patient. This modulated voltage is then processed using digital signal processing (DSP) techniques to provide an accurate measure of the patient's respiration rate and depth. Outputs may be in waveform form.

FIG. 1M2 shows exemplar schematic views of a piezo circuit 570, where a thin-film piezo 516 may be employed allowing the device to be sensitive to two frequencies, represented by relative high and low bandpasses. The piezo film 516 may be capable on obtaining one signal which may then be processed and conditioned using the circuitry, amplifiers, resistors, and filters to provide two outputs: (1) a high frequency output (<1100 Hz) 571 which may be used to measure and record respiratory sounds and (2) a low frequency output (0-10 Hz) 572, which may be used to measure and record respiration rate of the patient. The circuitry generating outputs 571 and 572 may be referred to as filters; e.g., a high frequency filter for output 571 and a low frequency filter for output 572. The output would typically be in waveforms, relatively simultaneous reduction of the input voltage into two parts, or two signals from one composite voltage input signal, and generating corresponding outputs, a low frequency waveform and a high frequency waveform.

A description of the antenna 506 (see FIGS. 1E, 1F, 1G and 1H, inter alia) is that it may preferably be disposed to fit, e.g., may be custom fit, within the envelope of the device 500/500a. It may be resonant at 2.4 GHz with a Minimum Standing Wave Ratio and Maximum Forward Power. In order to achieve this, active element length, width, and dielectric thickness may be optimized in-situ, on the human body, with the circuit boards, silicone cover 530, and adhesives 513 in place. A novel feature may normally be a dipole antenna normally constructed with two elements of equal length at the resonant frequency (one passive, one active). The herein shown and described implementation of a dipole may use an active element at the resonant frequency, but the human body as the passive element.

FIGS. 1N and 1N1-1N6 show various external views of a device 500 or 500a or the like. FIG. 1N is a three-dimensional top view; FIG. 1N1 is more specifically directed to a top side 501 plan view and FIG. 1N2 to an underside, patient side 502 plan view and FIG. 1N3 a first elevational, side view, and FIG. 1N4 is a second elevational side view. FIG. 1N5 is a front elevational view, and FIG. 1N6 is a back side elevational view. In FIG. 1N7 a top side 501 plan view of the device 500 or 500a also provides an optional flexible electrode extender 504 and optional third electrode or optionally disparately disposed second electrode 510 for optional additional use in the ECG/EKG measurements described elsewhere herein.

FIG. 1N provides a three-dimensional top view of a device 500 or 500a or the like, including optional second or third electrode 510, optional for a second electrode meaning optionally disparately disposed from the circuit board or boards, electrode extender 504, silicone cover 530, pleat 531, battery cage 520, and removable battery cage cap or cover 533. The removable battery cage cover 533 may be a turnable friction-fit type (or alternatively a bayonet style) of cap that allows the cap to be secured in place relative to the battery cage 520. In some implementations, the removable battery cage cover 533 may have an unlock indicator 534 and lock indicator 535, that align with a point of reference marking 536 to help a user determine whether the removable battery cage cover 533 is secured in place relative to the battery cage and the device more generally. Further, in some implementations the battery cage cover 533 may further have a handle 537 that protrudes from the surface of the battery cage cover that may assist the user in turning (screwing or unscrewing) and securing the battery cage cover. Alternatively, the battery cage cover 533 may also have one or more indentations 538 to assist the user in turning (screwing or unscrewing) the battery cage cover. In some instances the battery cage cover may have a sealing material of silicon, rubber, or other suitable material (not shown in diagrams) around the circumference of the bottom-side of the cap to provide for waterproofing of the battery compartment from the exterior conditions.

FIG. 1N1 is a top side 501 plan view of a device 500 or 500a or the like, including optional second or third electrode 510, flexible electrode extender 504, silicone cover 530, pleat 531, battery cage 520, removable battery cage cover 533, unlock indicator 534, lock indicator 535, reference marking 536, handle 537, and indentations 538.

FIG. 1N2 provides an underside, patient side 502 plan view of a device 500 or 500a or the like, including optional second or third electrode 510, flexible electrode extender 504, and silicone cover 530.

Figure 3:
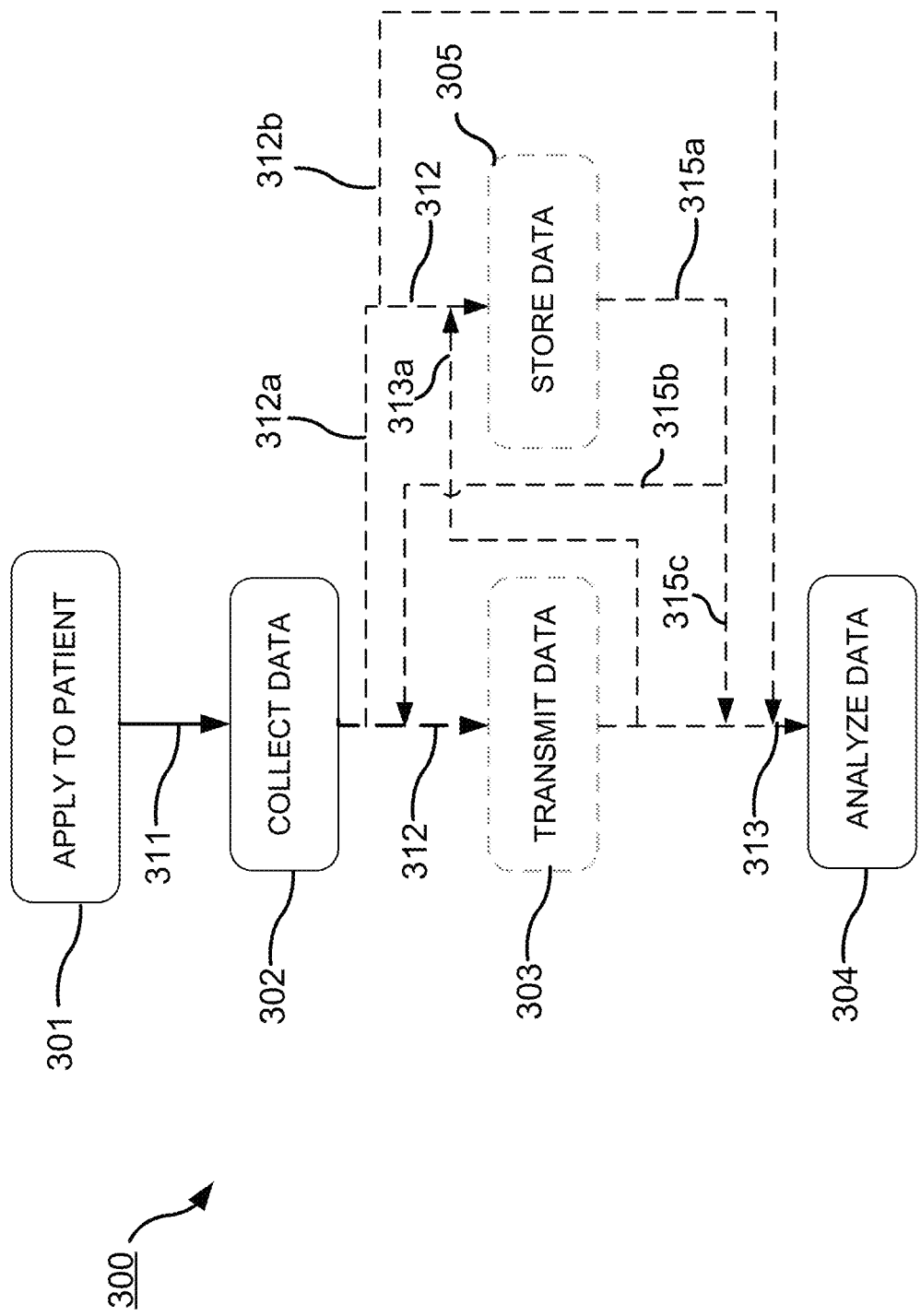
Figure 4:
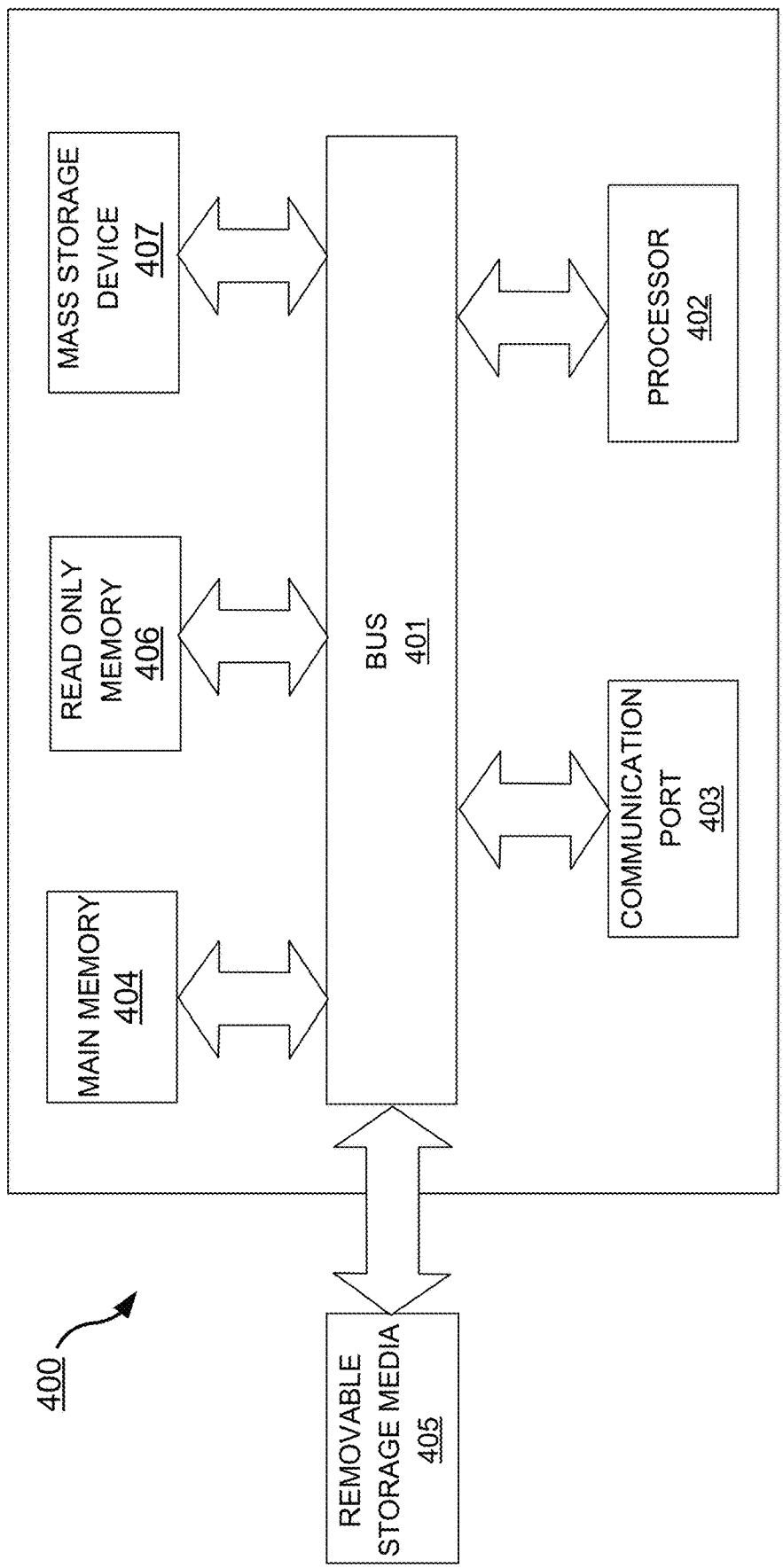
FIG. 4 illustrates an exemplary computer system or computing resources with which implementations hereof may be utilized.

FIG. 1N3 provides a first elevational side view of a device 500 or 500a or the like, including optional second or third electrode 510, flexible electrode extender 504, silicone cover 530, pleat 531, battery cage 520, removable battery cage cover 533, and handle 537.

FIG. 1N4 provides a second elevational side view of a device 500 or 500a or the like, including optional second or third electrode 510, flexible electrode extender 504, silicone cover 530, pleat 531, battery cage 520, removable battery cage cover 533, and handle 537.

FIG. 1N5 is a front elevational view of a device 500 or 500a or the like, including optional second or third electrode 510, flexible electrode extender 504, silicone cover 530, pleat 531, battery cage 520, removable battery cage cover 533, and handle 537.

FIG. 1N6 is a back elevational view of a device 500 or 500a or the like, including optional second or third electrode 510, flexible electrode extender 504, silicone cover 530, pleat 531, battery cage 520, removable battery cage cover 533, and battery cage cover handle 537.

FIG. 1N7 provides a top side 501 plan view of the device 500 or 500a or the like, including optional second or third electrode 510, flexible electrode extender 504, silicone cover 530, pleat 531, battery cage 520, removable battery cage cover 533, unlock indicator 534, lock indicator 535, reference marking 536, battery cage cover handle 537, and indentations 538.

Another alternative implementation is shown in FIG. 1W. Herein shown is an audio pickup and adhesive structure and/or methods to reduce audio, audible or acoustic noise; in particular, typically, though not limited hereto, for reducing the audible noise in either a worn device (FIG. 1W). Application of an audio pickup device or sensor or microphone or the like to a patient, the very interaction between the pickup sensor or like device and the skin, and particularly movement of the sensor relative to the skin imparts undesirable noise to the sensor or to the sensitive mechanical membrane of the sensor, if it has one, possibly masking important or desirable physiological sounds. This is even more pronounced on/in/with electronically amplified or otherwise very sensitive audio sensors which may be disposed to introduce noise.

An implementation hereof may involve a removable, double-sided silicone adhesive, in some implementations with one or both sides initially protected by a release liner. In such an implementation, application of one adhesive side to the audio sensor, then the other side may be applied to the patient (person to be monitored), and then at least some, and in perhaps other implementations as much as all, of the motion noise that would have been imparted by the movement of the sensor relative to the skin can be eliminated or substantially reduced.

In one or more primary implementations, no other adhesives may typically be included (e.g. without a composite adhesive or without stacked composite adhesive, even typically without conductive areas or layers); however, other uses with or including such other adhesives or adhesive portions in other possible implementations, whether used with an audio sensor, or, as for example when used together with/on a wearable health monitoring device having other sensors and/or electrodes included. In the primary implementation of FIG. 1W, inter alia, the adhesive may typically be a single, thin, double-sided silicone adhesive or tape. Typically, this may be a silicone adhesive approved or otherwise acceptable for skin contact thus eliminating mechanical noise. This would/could also and/or alternatively apply to a wearable device by providing a relatively immovable or very restrictedly movable coupling between the microphone and skin, thus reducing mechanical noise. In some implementations, the silicone adhesive may be disposed to be applied once or several times on/to a particular patient. Moreover, in some implementations, with appropriate selection of the adhesive, removal of hair may not be required.

In FIG. 1W, for a particular first non-limiting example, in a wearable health monitoring device 100b, for example, a microphone or other audible, acoustic or audio sensor 150 may be disposed on or in or otherwise operably associated with a substrate 105 of the device 100b for ultimate operational application to or in relation to a patient or other wearer (not shown in FIG. 1W). A dashed line representation of an electrical/audio signal connection 151 is also shown for communication of sound data from the patient via the sensor or microphone 150 to the central data collection and/or communication devices of health monitoring device 100*b* (see other descriptions of optional alternative operational data acquisition and/or manipulation devices that can be disposed on a substrate 105 and used herefor) for appropriate handling. An adhesive 113 is shown to be disposed (not unlike description above) over and operationally in position relative to the acoustic sensor or microphone 150 (in this example, the adhesive is configured to be disposed over other devices 108, 109, 110 and substrate 105 as well). The adhesive 113 would be exposed by removal of the release liner 114 (not unlike description herein elsewhere) also be connected to the patient for ultimate operation and collection of physiological signals or sounds, as for example heartbeats. The adhesive would operate to isolate and/or maintain operational disposition of the device 150 relative to the skin and/or patient to eliminate and/or reduce movement of the device 150 and consequent noise, noise that would otherwise interrupt or potentially obliterate the sound or signal data of interest.

A particular use may be on a device 100*b* as shown with one or more other sensors, electrodes and/or optical equipment (emitters and/or receivers); or, alternatively, particular uses may involve only the audio sensor or microphone. Adult or child uses are both envisioned with possible enhanced benefit for child heartbeat sensing and/or capture.

In FIGS. 1X1 and 1X2, for a particular second non-limiting example, in a wearable health monitoring device 100*c*, for example, a microphone or other audible, acoustic or audio sensor 150 may be disposed on or in or otherwise operably associated with a substrate 105 of the device 100*c* for ultimate operational application to or in relation to a patient or other wearer (not shown in FIGS. 1X1 and 1X2). Further, the view of FIGS. 1X1 and 1X2 also show how the ECG electrodes 508 and 509 may be operably disposed on opposite length-wise sides of the device 100*c*. The ECG electrodes 508/509 may be plated or printed out of silver-silver chloride (silver/silver chloride or Ag/AgCl) on polyimide. These ECG electrodes made from, printed from, or plated with silver-silver chloride may be extremely durable and electrically stable when used with hydrogels. In some implementations the silver-silver chloride electrodes may be adhered to polyimide, polyester, vinyl, urethane, polycarbonate, and other plastic substrates. In some implementations, such as the device 100*c*, a temperature sensing component or temperature sensor component 515 may be placed at the centroid of the device 100*c*. In this respect, when placed at the centroid of the device 100*c*, the temperature sensor 515 may be relatively isolated from the ambient temperature. The temperature sensor 515 may be surrounded by the adhesive stack (not shown in FIGS. 1X1 and 1X2) for further insulation and to help the temperature sensor quickly achieve equilibrium and be useful for measurement of the temperature of the wearer. The PPG light device/sensor unit 511 is also on or in or otherwise operably associated with a substrate 105 or 503*a* of the device 100*c*. The PPG light device/sensor unit 511 is described in greater detail below. The piezo film 516 may also be on, in, or otherwise operably associated with a substrate 105 of the device 100*c*. Note that in some implementations such as that of the device 100*c* shown in FIGS. 1X1 and 1X2 that the piezo film extends across the hinge 503*h* and the area over the hinge 516*b*. Also shown in FIGS. 1X1 and 1X2 is a generalized indication of where the pleat 531 of the cover would be disposed in relation to the hinge 503*h*. FIG. 1X2 provides a top plan view of one non-limiting implementation of the device 100/100*a*/100*b*/ and/or 100*c*, including in a wearable health monitoring device 100/100*a*/100*b*/and/or 100*c*, for example, a microphone or other audible, acoustic or audio sensor 150/516 may be disposed on or in and/or through (see e.g., MIC 516 with through-hole of FIG. 1G; note, typically a piezo or like device 516 would be used instead of not usually together with a distinct type of audio sensor or microphone as reference 150 might rather indicate as a generalized audio device—though it is possible for two or more such devices to be used) or otherwise operably associated with a substrate 503*a* of the device 100/100*a*/100*b*/ and/or 100*c* for ultimate operational application to or in relation to a patient or other wearer (not shown in FIG. 1X2). Further, the top side plan views of FIG. 1X2 also shows how the ECG electrodes 508 and 509 may be operably disposed on opposite/under sides of the device 100*c*; i.e., though shown here, would be on the under side not actually visible. The ECG electrodes are described in more detail in several figures including FIGS. 1G, 1H, 1I, 1X1 and 1X2. In some implementations of the device 100/100*a*/100*b*/ and/or 100*c*, a temperature sensing component or temperature sensor component 515 may be placed at or near the centroid of the device 100/100*a*/100*b*/ and/or 100*c* (see e.g., again FIG. 1G). In this respect, when placed at the centroid of the device 100/100*a*/100*b*/ and/or 100*c*, the temperature sensor 515 may be isolated from the ambient temperature. The temperature sensor 515 may be surrounded by or disposed poking through the adhesive stack (not shown in FIG. 1X2) for further insulation and to help the temperature sensor quickly achieve equilibrium and be useful for measurement of the temperature of the wearer. A piezo film 516 is also shown in FIG. 1X2, on, in, or otherwise operably associated with a substrate 503*a* of the device 100, 100*a*, 100*b*, and/or 100*c*, though like the electrodes would more likely be on the underside of 503*a* and not visible therethrough. Note that in some implementations such as that of the device 100/100*a*/100*b* and/or 100*c* shown in FIG. 1X2 that the piezo film may extend to or may extend across the hinge 503*h* (identified as 516*h* in FIG. 1X2). FIG. 1X2 also shows a battery/PPG stiffener 170 which may be used to stiffen, strengthen, or rigidify the battery cage or the area around and about the PPG sensor/source group (neither shown in FIG. 1X2). The battery/PPG stiffener 170 may be connected to or disposed with or relative to the battery compartment soldering points 534 that are soldered or otherwise secured (mechanically via small machine screws) to the substrate 503*a*. The power wires 533 provide power from the batteries to the flexible circuit layer or substrate 503*a*. The position of the power wires is arbitrarily shown in FIG. 1X2, and may rather be at or adjacent a cut-out area of the stiffener 170; as for example the small cut-out adjacent the hinge—the other cut-outs being possibly disposed to achieve electronic communication (not shown) to the electrode 508 and or to the piezo 516 as these respective cut-outs appear in relation thereto. The power wires 533 may alternatively be disposed in a discrete flexible circuit substrate to electrically connect the battery or batteries to the circuitry to power the device.

Returning to description of other components, on the patient side 102, as in FIG. 1C, the ECG electrodes 108, 109 and 110 may be left exposed for substantially direct patient skin contact (though likely with at least a conductive gel applied therebetween); and/or, in many implementations, the patient side electrodes 108, 109 and/or 110 may be covered by a conductive adhesive material as will be described below. The electrodes may be plated with or may be a robust high conductive material, as for example, silver/silver chloride for biocompatibility and high signal quality, and in some implementations may be highly robust and, for one non-limiting example, be adapted to withstand over about one thousand (1000) alcohol cleaning cycles between patients. In some instances these silver/silver chloride electrodes may be printed directly on the flexible circuit board or flexible printed circuit, and yet in other instances the silver/silver chloride electrodes may be attached or fastened to the flexible circuit board or flexible printed circuit as a discrete and separate step in the fabrication process. Windows or other communication channels or openings 111, 112 (FIG. 1C) may be provided for a pulse oximeter, for example, for LEDs and a sensor. Such openings 111, 112 (e.g., FIG. 1C) would typically be disposed for optimum light communication to and from the patient skin. An alternative disposition of one or more light conduits 111a/112a (and 111b/112b) is shown in a non-limiting example in FIG. 1D more nearly disposed and/or connected to the electronics 103. A variety of alternative placements may be usable herein/herewith, some of which further described below.

The devices and systems and methods hereof typically employ a technique referred to as "Reflectance Pulse Oximetry" to obtain O2SAT data (oxygen saturation data) from the strip device. In many implementations hereof, two or three or more wavelengths of light are shined onto and into the skin and into the capillary bed, then reflected back to the photodiode sensor. These reflected wavelengths are then used to calculate O2sat, also referred to herein as oxygen saturation, pulse-ox, and SpO2, inter alia. In some implementations, sampling of the ambient light (with the LEDs off) may be provided, and then subtracting this from each of the pulse-ox signals in order to cancel out the noise caused by sunlight or other ambient light sources.

The LEDs and one or more photodiode sensors may also and/or alternatively be covered with a layer of silicone to remove any air gap between the sensor/LEDs and the patient skin. Some examples of such are set forth in respective FIGS. 1Q and/or 1S and/or 1T and/or 1T1 and/or 1T2 and/or 1T3a and/or 1T3b and/or 1T3c, 1U, 1U1 1U2, 1U2a, and 1U2b. In some of these, a silicone layer or covering 121 and/or 121a and/or 121b and/or 121c and/or 121d is shown covering/surrounding the light conduits and/or sensors 112c/112d/112e and LEDs 111c/111d/111g. LED 111c (FIGS. 1Q and/or 1S and/or one or more of 1T, 1T1, 1T2, 1U, 1U1, 1U2, 1U2a and 1U2b) might be a Red LED, LED 111d (FIGS. 1Q and/or 1S and/or one or more of 1T-1U2b) might be an IR (infrared) LED and the device 112c (FIGS. 1Q and 1S and/or one or more of 1T-1U2)) might be a sensor. Alternative and/or additional LEDs might be provided; for a first example, one or more additional or alternative colors of LEDs (not shown) might be provided not unlike those shown in the FIGS. LED 111g might be a Green LED (see FIGS. 1T3a, 1T3b, 1T3c, 1U2a, 1U2b, 1U3a-c). Additionally, 1Q and/or 1S and/or one or more of 1T-1U2, as for example a Green LED for additional and/or alternative functionality as described further below.

Figure 1T:
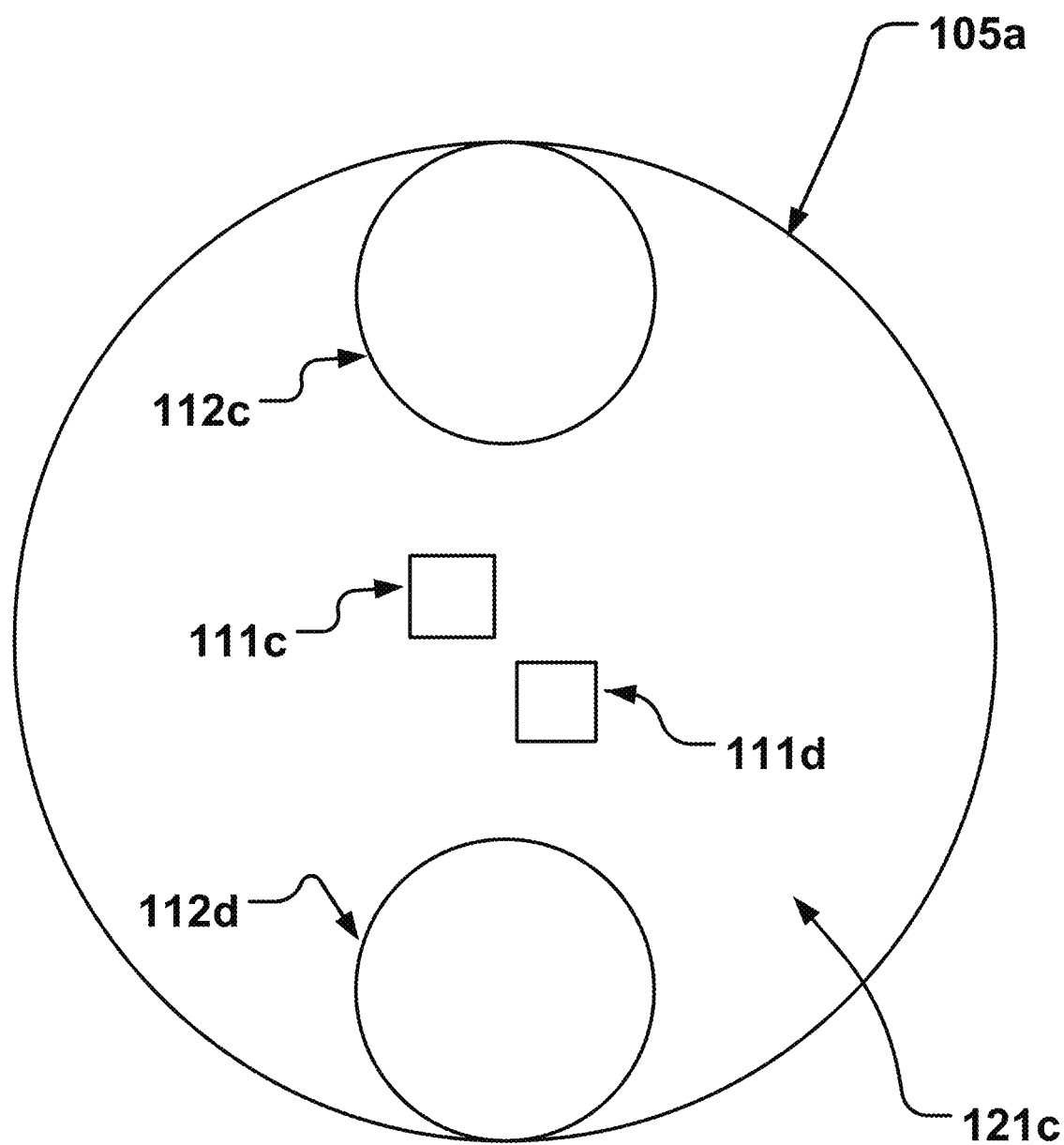

Other alternative LED and sensor arrays or arrangements are shown in FIGS. 1T and 1T1 wherein one or more LEDs are more centrally disposed within epoxy/light-pipe 121c and/or 121d on a substrate 105a and one or more sensors or photodiodes are more peripherally disposed. The opposite alternative of a central sensor or sensors is shown, e.g., in FIGS. 1T3a, 1T3b, and 1T3c, see descriptions below. In FIG. 1T two LEDs 111c and 111d (not unlike LEDs 111c and 111d of FIGS. 1Q and/or 1S, but for positioning/geometry) are shown relatively centrally disposed relative to one or more sensors, here, two sensors or photodiodes 112c and 112d. As above-described for FIGS. 1Q and/or 1S, LED 111c might be a Red LED, and LED 111d might be an IR (infrared) LED and the devices 112c and/or 112d might be one or more sensors, here two sensors or photodiodes 112c and 112d. In FIG. 1T1, four LEDs 111c, 111d, 111e and 111f (not unlike LEDs 111c and 111d of FIGS. 1Q and/or 1S and/or 1T, but for number, positioning and/or geometry) are shown relatively centrally disposed relative to one or more sensors, here, four sensors or photodiodes 112c, 112d, 112e and 112f. As above-described for FIGS. 1Q and/or 1S and/or 1T, LED 111c might be a Red LED, and LED 111d might be an IR (infrared) LED, and/or 111e might also be a Red LED, and LED 111f might be an IR (infrared) LED and the devices 112c, 112d, 112e and/or 112f might be one or more sensors, here four sensors or photodiodes 112c, 112d, 112e and 112f.

Another alternative arrangement of LED and sensor arrays is shown in FIG. 1T2. In this alternative example, red and infrared (IR) LEDs, 111c and 111d, respectively, are positioned toward the center of a circle and surrounded by a barrier wall 122 or B1. When powered on, these LEDs, 111c and 111d, project light into the skin of a wearer, where the light is scattered by the tissue and then reflected back toward the device and through light pipe epoxy 121d to four sensors or photodiodes 112c, 112d, 112e, and 112f. The light is thus absorbed and measured by photodiodes 112c, 112d, 112e, and 112E A second barrier wall 123 or B2 assists in preventing outside or unwanted light from being cast toward the sensors or diodes of 112c, 112d, 112e, and 112f.

Yet another alternative arrangement of LED and sensor arrays or arrangements is shown in the FIGS. 1T3a and 1T3b, wherein one or more LEDs are disposed in circular arrays within epoxy/light pipe/s 121, 121a, 121b, 121c, 121d and/or 121e (not shown in the 1T3 series of FIGS.) on a substrate and one or more sensors or photodiodes, here one sensor 112c is/are disposed or positioned at the center of the concentric circles of LEDs. In FIG. 1T3a, a total of sixteen (16) LEDs are shown arranged in a circular array around a centrally disposed sensor or photodiode 112c. In FIG. 1T3a, eight (8) red LEDS 111c (not unlike LEDs 111c of FIGS. 1Q and/or 1S and/or 1T, but for number/positioning/geometry) are disposed circularly around a central sensor or photodiode 112c. Without being limited to any particular dimensions, in this arrangement, the red LEDS 111c can be as shown placed approximately 3.2 mm from the center of the middle the sensor or diode 112c. The red LEDs 111c (R1, R2, R3, R4, R5, R6, R7 and R8) may be evenly spaced (or may be irregularly disposed) and disposed at every 45 degrees around the circumference of a circle to surround the sensor or diode 112c. In FIG. 1T3a, four (4) IR (infrared) LEDs (I1 I2, I3, I4) 111d (not unlike LEDs 111d of FIGS. 1Q and/or 1S and/or 1T, but for number/positioning/geometry) may be disposed and arranged in a circular array around the centrally disposed sensor or photodiode 112c. In this arrangement, also without any limitation to dimensions, the infrared LEDs 111d are placed approximately 3.724 mm from the center of the sensor or diode 112c. Further, in this arrangement the infrared LEDs 111d may be spaced, but not limited hereby, and disposed 90 degrees apart around the circumference of a circle with a radius of approximately 3.724 mm. In FIG. 1T3a, four (4) green LEDs (G1, G2, G3 and G4) 111g, are disposed and arranged in a circular array around the centrally disposed sensor or photodiode 112c. In this arrangement, the green LEDs 111g may be placed approximately 3.724 mm from the center of the sensor or diode 112c. Further, in this arrangement the green LEDs 111g may, but not limited hereto, be spaced and disposed 90 degrees apart around the circumference of a circle with a radius of approximately 3.724 mm. Furthermore, as shown in FIG. 1T3a, the infrared LEDS 111d and green LEDS 111g may be alternated, but not limited hereby, around the circumference of the circle that has a radius of approximately 3.724 mm. The sensor or diode 112c may be located on top of or within a die 115. The photodiode 112c is in one aspect connected to the PCB 105a (not shown) via a bond wire 128 (shown in FIG. 1T3c).

FIG. 1T3b provides a similar arrangement as FIG. 1T3a, including red LEDs 111c, infrared LEDs 111d, green LEDs 111g, sensor, diode, or photodiode 112c, and die 115. Additionally, FIG. 1T3b provides additional illustration and representation of an alternative positioning and geometry of eight (8) red LEDS 111c located on a circle with a radius of approximately 3.2 mm 116, and the four (4) infrared (IR) LEDs 111d and four (4) green LEDs 111g located on a circle with a radius of approximately 3.724 mm 117. Moreover, FIG. 1T3b provides additional illustration to demonstrate that each LED (whether red LEDs 111c, infrared LEDs 111d, or green LEDs 111g) is positioned approximately $(\alpha/2)°$ from other LEDs. In the non-limiting example of FIG. 1T3b, each LED is positioned approximately 22.5° from other LEDs; however, it is possible and contemplated that each LED may be alternatively disposed, for example at less than 10°, 10°, 12.5°, 15°, 17.5°, 20°, 22.5°, 25.0°, 27.5°, 30.0°, 32.5°, 35°, or greater than 35° apart, thus in some aspects depending on the size of the PPG unit and the number of LEDs utilized in the PPG. Thus, placement in this manner as provided in FIG. 1T3b or alternatively contemplated may provide for the sensor to capture light emitted from discretely arranged red, infrared, and green LEDs.

FIG. 1T3c is a plan view of alternative circuitry of a PPG combination or unit including a central photodiode 112c, optional die 115, 8 Red LEDs 111c (in this drawing R1-R8), 4 infrared LEDs 111d (in this drawing I1-I4), and 4 green LEDs 111g (in this drawing G1-G4). Also provided is the photodiode (sensor) anode 140 which provides the electrical current to the photodiode, and the photodiode cathode 141 through which the electrical current leaves the photodiode. The die (or photodiode die) 115 is here a square having sides that measure approximately 3.048 mm (0.120 inches) a piece; however, the dimensions hereof should not be a construed as a limitation as to the PPG, as alternative implementations contemplate larger and smaller dimensions and shapes of the photodiode and photodiode die. The PPG board may, in some implementations, measure approximately 12.0 mm in diameter and may have nineteen (19) mounting holes (or pads) 142 located along the perimeter of the board (these are not individually identified in FIG. 1T3d). The mounting holes may provide castellated to the PCB or substrate and through this provide both an electrical connection and be secured in place. Note that the photodiode bond wire 128 may be disposed to connect the PCB to the sensor or photodiode 112c. The devices of FIGS. 1T3a-1T3c may be preferentially disposed to be operative with and combined with the elements of FIGS. 1U2a-1U2b and 1U3a-1U3g, see below.

When a central sensor is used, only a single or relatively small number of sensors may be optimally placed among many light sources, if desired. However, optionally to the opposite, when placing the LEDs in the more centrally disposed positioning of FIGS. 1T and 1T1 and surrounding those more centrally disposed LEDs with sensors or photodiodes, as opposed to the more or relatively conventional method of a central sensor or photodiode surrounded by LEDs, provides a geometry that may in some instances be disposed to capture a desirable percentage of the emitted light, emitted from the LEDs. If used, in the geometries of and/or described for FIGS. 1T and 1T1, in some implementations, more light, perhaps as much as virtually all of the emitted light may be captured by the sensors or photodiodes, or in some cases, a significantly higher efficiency capture than conventional. Due to the higher efficiency light capture, fewer LEDs might thus be required than conventional Multi-LED integrated sensors. This may contribute to significantly reducing power consumption and yet achieve similar or better measurement results. In sum, a geometry of LEDs, such as the red and IR combinations described above, combined with an array of photodiodes (or sensors) is shown and described that may enable a higher concentration of light into the subcutaneous region of the subject (patient/infant/neonate/mother/athlete, e.g.).

The combination of LEDs and photodiodes/sensors might also be referred to in some implementations as a High-Efficiency Integrated Sensor. This arrangement may be implemented in determination of SpO2 (peripheral capillary oxygen saturation). Note, in some practical implementations, the sensors shown in FIGS. 1T, 1T1, 1T3a, e.g., may be about 5 mm² and the diameter of the exterior circle encompassing the sensors and LEDs might be a corresponding about 8 mm. In some implementations, it may be that about 3.2 mm red may be set for a preferred distance from the center of the red LED light sources to the center of the corresponding sensor or sensors, and may be a preferred distance of about 3.7 mm set from the center of the IR LED light sources and green LED light sources to the corresponding sensor or sensors therefor.

The silicone layer or covering or encapsulant 121/121a/121b/121c/121d/121e/121f (as in FIGS. 1U, 1U2, 1U2b, 1U3a, 1U3b, 1U3c) may reduce the light lost to reflection off the skin, and thereby greatly increase the signal and reduce the noise caused by motion of the skin relative to the sensor. In some implementations this silicone might be referred to as a light pipe or lens and in some situations may alternatively and/or additionally be clear, colorless, and/or medical grade silicone. As described further below, the silicone layer or covering 121 and/or 121a and/or 121b and/or 121c and/or 121d and/or lens surface 121e and/or 121f (sometimes referred to herein in short by 121/121a/121b/121c/121d/121e/121f but having the same meaning hereof) may also/alternatively be referred to as a light pipe or lens 121/121a/121b/121c/121d/121e/121f herein inasmuch as how it may be involved in light transmitting or to be transmitted therethrough, whether upon emission or received upon reflection or both.

In one or more implementations, an encapsulant and/or lens 121/121a/121b/121c/121d/121e/121f hereof may be made from a medical grade silicone that is one or more of clear, colorless, soft, low durometer. Exemplars of such specialized silicones that may be used herewith are known as "tacky gels" (several suppliers), and typically have very high-tack adhesives, preferably embedded on both sides. A low durometer silicone combined with double-sided adhesive on the tacky gel allows the construction of a lens 121/121a/121b/121c/121d/121e/121f that may be both conforming to the electronic sensors and skin, as well as, in some implementations, exhibiting properties of motion artifact reduction by limiting movement between the skin-lens-sensor interface. A lens according hereto may also/alternatively be specially shaped such that it can be trapped between layers of the composite adhesive strip (see e.g., alternatives of FIGS. 1D, 1P and 1R and 1R1), and in some implementations, with a raised portion the size of the opening, often a rectangular opening, in the adhesive strip that allows the lens to protrude slightly on the patient side of the adhesive strip (see further detail relative to FIG. 1S, described below).

In FIG. 1S an implementation of a further alternative silicone covering or encapsulant 121*a* for the LEDs and sensor 111*c*/111*d*/112*c*, may include a convex lens at or adjacent the covering external surface 121*b*. In many implementations, the external surface and lens are one and the same and/or the lens may be defined by the surface 121*b* of the encapsulant material 121*a*. What this provides is a structure and method for interfacing pulse oximetry LED emitters 111*c*/111*d* and one or more photodiode sensors 112*c* with the skin surface, whether chest or forehead (e.g., infant or neonate) or otherwise mounted on the patient or user body. In FIG. 1S1 an implementation of a further alternative option demonstrates how the PPG is attached to the flexible substrate 503*a* and may protrude slightly from the adhesive layer 113 and make contact with the skin 1001 of the wearer 1000. Note that in this implementation the device 100 may be operably connected to the PPG unit including LEDs 111*c* (Red LED), 111*d* (IR LED), and 111*g* (Green LED), and sensor (112*c* not shown) is disposed on the top side of the die 115. Barrier wall 124 separates the sensor from the LEDs and barrier wall 125 separates the LED from the rest of the device and provides other functionality as described in further detail below. The LEDs project light into the skin of the patient where it penetrates the tissue and then is reflected or scattered back towards the photodiode or photosensor. In FIGS. 1S and 1S1, the bone 1002 of the patient is shown in the diagram as well.

In FIG. 1U3*a* an implementation of a further alternative silicone covering or encapsulant 121*f* for the sensor 112*c* and red, infrared, and green LEDs 111*c*, 111*d*, and 111*g*, respectively, may include a flat lens at or adjacent the covering external surface 121*b*. In many implementations, the external surface and lens are one and the same and/or the lens may be defined by the surface 121*b* of the encapsulant material 121*f*, as shown in FIG. 1U3*a*. As stated previously, in other optional non-limiting implementations, a lens that may be a discrete, thin, structure, may cover the entirety of the area of the sensor and LEDs (111*c*, 111*d*, and 111*g*).

More particularly, as otherwise described herein, a system and/or device 100 hereof may utilize one or multiple LED emitters 111*c*/111*d* (and/or 111*e* and/or 111*f*; and/or 111*g*) of selected wavelengths and one or multiple photodiode sensors. However, in order to maximize coupling of the LED/sensor combination to the skin 1001 of a wearer 1000, an encapsulant and/or lens 121/121*a*/121*b*/121*c*/121*d*/121*e*/121*f*/121*g* comprised of optically clear, medical grade silicone may be molded onto or molded such that it may be later attached in covering relationship on the LED/sensor combination 111*c*/111*d*/112*c*. In many implementations, as for example in FIG. 1S, the lens 121*b* may be partially spherical or perhaps hemispherical in nature, though it need not be; see e.g., FIGS. 1T2-1U2, and FIGS. 1U3*a*-1U3*b*, described below. Curvature of other shapes may be useful as well, for example see FIG. 1U3*c*. Curvature may reduce loss of skin contact when the device 100 may be moved, whether by wearer motion or otherwise. I.e., motion of the wearer 1000 or the device 100 relative to the wearer 1000 in FIG. 1S can result in a quasi-rolling contact of the lens on and in relation to the skin 1001. Better maintained skin contact means better data acquisition without interruption and/or with reduced noise. In some implementations, including those above and below (though not directly shown therein, i.e., alternatively included or not included therewith), or as described with specific reference to FIG. 1U2 below, a thin silicone adhesive 113*e* may be used on and between the silicone layer 121/121*a*/121*b*/121*c*/121*d*/121*e*/121*f*/121*g* to assist with maintenance of the skin contact relative to the silicone encapsulant 121/121*a*/121*b*/121*c*/121*d*/121*e*/121*f*/121*g*. See description of FIGS. 1U2, 1U3*a*, 1U3*b*, 1U3*c*, and 1U3*d* below, e.g.

Moreover, related to the function of maintaining contact is the light piping effect that may be achieved when LEDs and sensors, even of different heights are communicating substantially with little or substantially without air gap interruption through the light pipe of the encapsulant material 121*a*/121*c*/121*d*/121*e*/121*f* from the emission to the skin and back from the skin to the sensors. With no air gap from emitter to and through the light pipe 121*a*/121*c*/121*d*/121*e*/121*f*/121*g* and/or sometimes including a curved surface 121*b* or 121*h* substantially constant contact with the skin, there is thus no air gap or with little or substantially no air gap interruption in transmission into and through and reflected back on return from within the skin and back to the sensor via the same light pipe material 121*a*/121*c*/121*d*/121*e*/121*f* (transmission and reflection both referring to light travel). This reduces inefficiencies caused by light wave scattering at air gap interfaces (air gaps allow for light to bounce off the skin or other surface). I.e., encapsulation of the LEDs and the sensor; provides no air-gap and a light pipe effect to and the curved surface provides high quality low scattering transmission into the skin and reception of reflection from the skin and bone. The light pipe and flat or curved lens surface maintain uninterrupted contact between the skin and lens and thus may reduce lost signals due to skin reflection. The signal to noise ratio may go down and data acquisition may go up in quality.

Such an encapsulant 121/121*a*/121*c*/121*d*/121*f* and/or a lens 121*b*/121*e*/121*g*/121*h* flat or curved may thus serve one or multiple purposes, including in some instances, inter alia: 1) providing a "light-pipe" effect to assure equal or otherwise high quality coupling of the different height LEDs and sensors, as well as substantially constant coupling to the skin to reduce motion artifact; 2) focusing of emitted light through the skin to the bone; and, 3) focusing of reflected light through the skin to the photodiode sensors.

As a further note, for a curved lens 121*b* option as from FIG. 1S (or curved lens 121*h* as from FIG. 1U3*d*), the radius of the lens may be designed to maximize 1) through 3). The height of the lens may be designed to allow it to protrude above composite adhesive 113 of the device 100 and into the skin, but not deep enough to disturb the capillary bed which would also result in bad data. Moreover, the radius of curvature and the angles of LED lightwave emission are not necessarily highly controlled and in some cases need not be because the LEDs used to penetrate the skin, e.g., the red and infra-red and/or green LEDs; provide a very wide array of angles of emission, and thus a large number of reflected array of lightwaves will be focused back to the sensor by a large variety of surfaces, curved surfaces or flat. I.e., the curved surface may in some instances be helpful for maintaining contact through movement (accidental or on purpose), and may in some instances be less important to the angles of transmission through the skin and reflection back to the sensor. In other words, many different radii of curvature may be effective with very little difference in data/wave transmission and reflection; the wide angle emission of LED may take care of what might be a variety of radii. Rather, the curvature may have more limitation in the maintenance of contact due to movement of the device 100—e.g., flatter curvatures may not roll readily, and very small radii of curvature will not transmit or receive as much data.

In some implementations, radii of curvature may be between about 20 and 40 (e.g., 20.34 mm and 39.94 mm radii of curvature) for a device having LEDs and sensors in a compartment of about 12.6 mm by 6.6 mm. It may be noted further that LEDs may be on one side or another or on two opposing sides or perhaps at four or more substantially equi-distant points around a sensor and may provide desirable results.

Note further, pulse oximetry hereof may be with multiple light sources and/or sensors as may be one interpretation of the dispositions of FIGS. 1Q and 1S, and/or any one or more of 1T-1U2, e.g. Typical pulse oximetry circuitry uses one light source (LED) per wavelength (typically red, infrared, and sometimes others including green or long time averages of red/IR for further examples as described below). However, devices and/or methods hereof may make use of multiple light sources for each wavelength, for example see FIG. 1T3a-FIG. 1T3c, wherein eight red LEDS 111c, four infrared LEDs 111d, and four green LEDs 111g are used as light sources for each wavelength. This may allow for interrogation of a wider area of capillary bed in/on the patient/wearer in order to reduce the effects of a local motion artifact. Similarly, multiple sensors may be used for the same or similar purpose or advantage.

Furthermore, a combination of driven right leg and/or proxy driven right leg together with pulse oximetry can provide additional benefits. The right leg circuit, proxy right leg and/or driven right leg, whether for chest or forehead or other electrode placement, can remove common mode and power line noise that would/might otherwise be capacitively-coupled into the pulse oximetry sensor and reduce effectiveness thereof. A combination of driven right leg and/or proxy driven right leg and improved pulse oximetry with a lens as described in and for FIG. 1S, S1 and FIGS. 1U3b and 1U3d, and/or the light pipes of FIG. 1Q and/or any one or more of FIGS. 1T-1U3c may significantly reduce such noise, and thereby enhance data acquisition. For driven electrodes see further detail below.

Thus, measurement of arterial blood oxygen content can be made using optical signals (sometimes also referred to as heart beat optical signals), typically from Red and Infra-Red and often also green pulsed sources, which exhibit different optical absorptions dependent on oxy-haemoglobin presence or absence. In sum, a transmissive system is used with light sources and optical detectors. In many implementations as described following (and in part above), a light pipe that encapsulates either or both or three or more light source or sources and the one or more sensors may be employed, particularly a light pipe encapsulating, meaning having substantially no air gaps, may be used for providing either or both increased efficiency in light emission to the skin and/or capturing otherwise lost photons upon collection.

Herein, reflective systems are typical, and these often have some advantages being less intrusive, and perhaps being more portable. As described herein, such reflective systems typically employ a red and an infra-red and often a green source and a photo-diode sensor or detector, or multiple arrangements of these components. Also as described, one implementation/method employs one or more central large area photo-diodes/sensors/detectors, with one or more LED sources, often one or more of each of a red, and an infra-red and often green LED sources adjacent to the photo-diode or in an array around it. Also as described, an alternative arrangement uses a central LED set of one or more light sources, with one or more of each wavelength type (Red, InfraRed, Green, etc.), and multiple large area photo-diodes or light sensors surrounding the central LEDs. Such an arrangement might use two or three or four such detectors around the LEDs to collect more light scattering from the LEDs through the skin and other tissues; see e.g., FIGS. 1T and/or 1T1.

Herein, reflective systems are typical, and these often have some advantages being less intrusive, and perhaps being more portable. As described herein, such reflective systems typically employ a red, an infra-red, and a green source and a photo-diode sensor or detector, or multiple arrangements of these components. Also as described, one implementation/method employs one or more central large area photo-diodes/sensors/detectors, with one or more LED sources, often one or more of each of a red, an infra-red, and green LED sources adjacent to the photo-diode or in an array around it. Also as described, an alternative arrangement uses a central LED set of one or more light sources, with one or more of each wavelength type (Red, InfraRed, Green, etc.), and multiple large area photo-diodes or light sensors surrounding the central LEDs. Such an arrangement might use two or three or four such detectors around the LEDs to collect more light scattering from the LEDs through the skin and other tissues; see e.g., FIGS. 1T and/or 1T1.

A further alternative implementation may employ structural enhancements to and/or around the light sources and/or the one or multiple photo-diodes. Described first are one or more such enhancements disposed in relation to the central LED arrangement described above, though the following could be used with or relative to the prior described central sensor arrangement as well. The optical enhancing structures may provide minimal intrusion in the collection area and may reduce photo-diode areas or reduce numbers of photodiodes. Cost benefits and/or increased efficiency may thus result.

In FIGS. 1T2, 1U, 1U1 and 1U2, in the light pipe 121d, the central LED sources 111c and 111d are isolated from the peripheral photo-detectors 112c, 112d, 112e and 112f on the substrate 105a by a surrounding barrier wall 122 (here also identified by the alternative reference B1). A further optional external barrier 123 surrounding the sensor area is also shown. The barrier wall 122 (or B1) and/or wall 123 (or B2) is/or preferably opaque and/or reflective to both red and IR (or to whatever other color or wavelength of light is being used, e.g., green etc.) in order to prevent crosstalk between the LEDs and the sensors. i.e., preferably want all of the light leaving the LED area to go into the skin rather than some of the light rays finding a path to enter the sensors directly. A preferable surface for the barrier would be diffuse-reflective (as opposed generally to relative absorptive and/or mirror-shiny). An example may be clear anodized aluminum. Another would be textured white paint. Operation is shown and described relative to FIGS. 1U1 and/or 1U2; see below.

The shape and size of the wall 122 can be chosen appropriate to the shape and size of the LED sources, here sources 111c and 111d. For example, the wall 122 could be, as shown, a circle, or could be a square or rectangular shape or otherwise (not shown) around the LEDs 111c, 111d (noting here also that more or fewer light sources might be included within or enclosed by the wall 122). The width or thickness of and the material used for the barrier wall 122 can be variable or varied as needed or desired as well; indeed, the width may depend upon the material and/or vice versa in that the relative opacity of any particular material may mean less or more width necessary to provide a particular level of opacity or relative diffuse reflectivity. The particular wavelengths of light, i.e., type of light used, and/or the type or types of sensors and/or the relative and/or overall geometrical relationships (sensors to light sources, sensors to sensors, and/or light sources to light sources) may also figure into the relative dimensions and/or material used for and/or due to the relative opacity in relation to the particular wavelengths. There may be situations where the relative thicknesses may have more to do with the type of material of the wall, or the opacity or relative diffuse reflectivity thereof. In some implementations, the barrier/wall may be machined, anodized aluminum, or other similar material, but other implementations are of plastic, e.g., a molded plastic. For Red and Infra-Red usage, a driving consideration can be that the material would perhaps preferably be opaque or reflective or diffuse reflective to both 660 and 940 nanometers. Thus, in many situations, very thin aluminum meets this criteria, and thicker plastic does as well.

The options for wall 122 will primarily be for the provision of an optical barrier to sideways propagation of either the radiation from the LEDs (e.g., as here thus far, the Red or the Infra-Red light from, e.g., LEDs 111*c*/111*d*), and the wall 122 is preferably level or slightly higher than the optical exit window of the LEDs. It is preferred that the barrier wall 122 also has a width sufficient to prevent optical crosstalk of light rays that never enter the skin or scattering material, but not so wide that light from the LEDs that is scattered from the skin or other flesh material, is prevented from reaching the photo-diode detectors outside the barrier wall.

An optional external barrier wall 123 might also be employed. This one assisting with collection of light reflected from the patient or user. Similar considerations for size and thickness and material may be employed with wall 123; the difference being primarily in collection as opposed to light generation.

Where these developments may provide improvement with external detectors as described here, FIGS. 1T2/1U, and/or 1U1/1U2, is that an optical collecting structure is added that can collect light from other regions where detector diodes are not present, and conduct or reflect some of that radiation in such a way as to reach one or more of the detectors. Note, central detectors with otherwise separately isolated light sources (as shown in FIGS. 1T3*a*-1T3*c*, and 1U3*a*-1U3*d*) may also have similar improvements.

Preferred structures of this type may include a transparent optical medium, here the light pipe material 121*d* and/or 121*f*. This light pipe material may be molded into a shape within and/or surrounding the relatively opaque barrier wall 122 (see e.g., FIGS. 1U2 and 1U3*a*, described further below), and contain sources 111*c* and/or 111*d* and/or 111*g* (and/or others if/when present) within the wall 122 and/or contain outside the wall 122 (between wall 122 and wall 123) the diode detectors 112*c*, 112*d*, 112*e* and/or 112*f* (and/or others if/when present) embedded in that structure 121*d* with little or substantially no air gaps between the detectors and the light pipe material. The detector devices 112*c*, 112*d*, 112*e* and/or 112*f* may be molded into the optical medium, i.e., light pipe material, itself, or could be inside pre-molded cavities in that optical medium. Optical structures of this type, may generally be referred to as "light pipes".

Alternatively, structures with central detectors with otherwise separately isolated light sources (as shown in FIGS. 1T3*a*-1T3*e*, and 1U3*a*-1U3*g*) may include a transparent or substantially transparent optical medium, here the light pipe material 121*d* and/or 121*f*. This light pipe material may be molded into a shape within and/or surrounding the relatively opaque barrier wall 122, 124 and/or 125 (also B1 and/or B2) (see. E.g. FIG. 1U3*a*, described further below), and contain light sources (LEDs or light emitters) 111*c* and/or 111*d* and/or 111*g* (and/or others if/when present) situated between the interior barrier wall 124 and exterior barrier wall 125, and the diode detector 112*c* (and/or diode detectors 112*d*, 112*e*, and/or 112*f*) embedded in that structure 121*f* (or 121*d*) with little or substantially no air gaps between the detectors and the light pipe material. The detector device(s) (diode detector(s)) 112*c* may be molded into the optical medium, i.e. light pipe material, itself, or could be insides pre-molded cavities in that optical medium. Optical structures of this type, i.e., structures and/or materials through which light passes, may generally be referred to as "light pipes".

As shown in FIG. 1U2, the shape of the light pipe structure 121*d* and/or surface 121*e* can be chosen in a variety of ways, depending on the number and size or shape of the detector diodes, and may be designed in such a way as to capture scattered light received from the skin or flesh material not directly in contact or above any detector diode, and contain it by total internal reflection, and using scattering reflective surfaces, to redirect rays in a direction towards one or more of the photo diodes. In this way, light that would be lost in previous designs, is captured by devices of these present implementations. In FIGS. 1T2 and 1U, the epoxy (light pipe) 121*d* is relatively flat, i.e., presenting a relatively flat surface 121*e*, not concave or convex, though it may be that curvature will work with some implementations of a barrier wall or walls hereof. In FIG. 1U2, also a relatively or substantially flat surface 121*e* is shown.

Shown also in FIG. 1U2 is an optional adhesive 113*e* on surface 121*e* which may be used to relatively adhere the device to the skin (not shown here) to reduce movement of the device relative to the skin and enhance light transmission and reception. If used, such an adhesive may preferably be as thin as operably possible so as not to interfere with or provide refraction of light waves passing therethrough. A 0.2 mm thickness may be so operable. Also, it may be that a similar refractive index of the adhesive to the epoxy/encapsulant/light pipe 121/121*a*/121*b*/121*c*/121*d*/121*e* might be preferred. This choosing of a similar refractive index may be of assistance or may be related to thickness as well as material of adhesive to be used. E.g., an appropriate refractive index similarity may result from or lead to an operable 0.2 mm thickness.

FIGS. 1U1 and 1U2 show some operative examples and/or alternatives. In FIG. 1U1, where no light pipe is shown for simplicity, though could be an operable alternative example, light wave emissions A, B and C are shown emanating from the exemplar LED 111*c*. Wave A is a relative direct emission meeting no obstacle on its way from the device to the skin (not shown), whereas wave B is shown as reflected off the wall 122 (note though waves are sometimes described, it is understood that light energy in whatever form is intended herewithin, whether for example it is or may better be understood as photons which are more particularly as understood as emitted and/or collected). Less preferred is a wave C shown not reflected off wall 122; here shown merely for highlighting the preference toward most if not all waves leaving the LED finding a way to be reflected to exit the LED area and enter the skin of the user (not shown here). Light collection is shown relative to the exemplar sensors 112*c* and 112*d*, where in FIG. 2P, relatively direct waves D are shown as they might enter the sensor area and be captured by the sensors 112*c* and/or 112*d*. Reflected waves E are also shown as they might be reflected off the walls 122 and/or 123. Note, the floor or top surface of the substrate 105*a* might also be diffuse reflective to the waves and assist in reflecting these ultimately for sensor collection.

In FIG. 1U2, the light pipe/s 121*d* are shown as is an optional adhesive 113*e*. The relative refractive indices of these materials may or may not affect, or largely affect the light passing therethrough. Preference is for similarity of refractive indices to minimize refraction. Even so, some refraction may occur as shown for example by emitting light wave B in FIG. 1U2 and in collected waves E and F, F differing from E by not also being reflected of the walls 122 and/or 123 as is light wave E. Light wave B is shown both reflected and refracted. Choice of materials and sizes and shapes of relative structures can assist in management of relative reflection and/or refraction toward increasing efficiency in light emission and/or capture.

In FIGS. 1U2*a* and 1U2*b*, in the light pipe 121*d*, the peripheral LED sources 111*c*, 111*d*, and 111*g* are isolated from the central photo-detectors 112*d* on the substrate 105*a* by a surrounding barrier wall 124. A further optional external barrier 125 surrounding the sensor area is also shown. The barrier wall 124 and/or wall 125 is/or preferably opaque and/or reflective to both red and IR (or to whatever other color or wavelength of light is being used, e.g., green etc.) in order to prevent crosstalk between the LEDs and the sensors. i.e., preferably want all of the light leaving the LED area to go into the skin rather than some of the light rays finding a path to enter the sensors directly. A preferable surface for the barrier would be diffuse-reflective (as opposed generally to relative absorptive and/or mirror-shiny). An example may be clear anodized aluminum. Another would be textured white paint.

FIGS. 1U2*a* and 1U2*b* show some operative examples and/or alternatives. In FIG. 1U2*a*, where no light pipe is shown for simplicity, though could be an operable alternative example, light wave emissions A, B and C are shown emanating from the exemplar LEDs 111*c*, 111*d*, and 111*g*. Waves A are relative direct emissions meeting no obstacle on the way from the device to the skin (not shown), whereas waves B are shown as reflected off the walls 124, 125 (note though waves are sometimes described, it is understood that light energy in whatever form is intended herewithin, whether for example it is or may better be understood as photons which are more particularly as understood as emitted and/or collected). Less preferred is a wave C shown not reflected off walls 124, 125; here shown merely for highlighting the preference toward most if not all waves leaving the LED finding a way to be reflected to exit the LED area and enter the skin of the user (not shown here). Light collection is shown relative to the exemplar sensors 112*d*, where in FIG. 1U2*a* and FIG. 1U2*b*, relatively direct waves D are shown as they might enter the sensor area and be captured by the sensor 112*d*. Reflected waves E are also shown as they might be reflected off the wall 124. Note, the floor or top surface of the substrate 105*a* might also be diffuse reflective to the waves and assist in reflecting these ultimately for sensor collection.

In FIG. 1U2*b*, the light pipe/s 121*d* are shown as is an optional adhesive 113*e*. The relative refractive indices of these materials may or may not affect, or largely affect the light passing therethrough. Preference is for similarity of refractive indices to minimize refraction. Even so, some refraction may occur as shown for example by an emitting light wave B in FIG. 1U2*a* and in collected waves E and F, F differing from E by not also being reflected of the walls 124 as is light wave E. Light wave B is also shown both reflected and refracted in some instances. Choice of materials and sizes and shapes of relative structures can assist in management of relative reflection and/or refraction toward increasing efficiency in light emission and/or capture.

FIGS. 1U3*a*-1U3*d* and 1U3*g*, provide another implementation that employs structural enhancements to and/or around the light sources and one photo diode. Alternatively, although not pictured, multiple sensors or diodes could be placed at the center of the structure. Described first are one or more such enhancements disposed in relation to the circular LED arrangement or arrays described above (such as those described in FIG. 1T3*a*-1T3*c*), though the following could be used with or relative to the prior described multiple external detectors as described here, FIGS. 1T2/1U, and/or 1U1/1U2. The use of several LEDs may provide additional light for refraction through the skin and measurement of the corresponding absorption at the diode or sensor. The use of sixteen LEDs, though not herein being limited to any particular number, arrangement, geometry or relative dimensions, as described previously may provide for additional light and thus benefits such as more light for the centrally located sensor to absorb and use for its functioning.

In FIGS. 1U3*a*, 1U3*b*, and 1U3*c*, in the light pipe 121*f*, the LED sources 111*c*, 111*d*, and 111*g*, are isolated from the centrally located photo-detector (diode/sensor), on the substrate 105*a* by a surrounding exterior barrier wall 125 (here also identified by the alternative reference B2). A further interior barrier wall 124 (here also identified by the alternative reference B1) separates the LEDs from the centrally located photo-detector 112*c*. The photodiode 112*c* may be located on or embedded substantially on or in the die 115. The exterior barrier wall 125 (or B2) and/or interior barrier wall 124 (or B1) is/are preferably opaque and/or reflective and/or diffuse reflective to red, IR, and green (or to whatever other color or wavelength of light is being used, e.g. orange/yellow/blue/indigo/violet, or other light of the spectrum) in order to prevent crosstalk between the LEDs and the sensors, as it may be preferable to have (as much as possible or practical) of the light leaving the LED area go into the skin rather than some of the light rays finding a path to enter the sensors directly. A preferable surface for the barrier would be diffuse-reflective (as opposed generally to relative absorptive and/or mirror shiny). As described earlier, clear anodized aluminum may be appropriate. Another possible material may be textured white paint. Operation is shown and described relative to FIGS. 1U3*a* and/or 1U3*b*, see below.

The shape and size of the wall 124 can be chosen appropriate to the shape and size of the LED sources, here sources 111*c*, 111*d*, and 111*g*. For example, the interior wall 124 could be, as shown in FIG. 1U3*e*, a circle; however, the interior wall 124 could also be a square or rectangular shape or otherwise (not shown) around the sensor 112*c*. Similarly, the exterior wall 125 could be, as shown in 1U3*e*, a circle; however, the exterior wall 125 could also be a square or rectangular shape or otherwise (not shown) around the LED sources 111*c*, 111*d*, and 111*g*. The width or thickness of the material used for the barrier wall 124 can be variable or varied as needed or desired as well; indeed, the width may depend upon the material and/or vice versa in that the relative opacity or relative diffuse reflectivity. The particular wavelengths of light, type of light used, type of sensors used, and the relative and overall geometrical relationships (for example, sensors to light sources, light sources to lights sources and/or sensors to sensors) may also play a role in determining the relative dimensions and/or material used for and/or due to the relative opacity in relation to the particular wavelengths. There may be situations where the relative thickness may have more to do with the type of material of the wall, or the opacity or relative diffuse reflectivity thereof. Similar to the barrier walls 122 and 123, the barrier walls 124 and 125 may be machined, anodized aluminum, or other similar material, but in other implementations are of plastic, e.g. a molded plastic. Furthermore, likewise with barrier walls 122 and 123, when red and infrared light sources are used, a factor to be considered when choosing the material for barrier walls 124 and 125, may be that the material preferably be opaque or reflective or diffuse reflective to both 660 and 940 nanometers. Thus, again, very thin aluminum may meet the criteria, and thicker plastic may as well.

The options for wall 124 will primarily be for the provision of an optical barrier to sideways propagation of either the radiation from the LEDs (e.g. as here thus far, the red, infrared, or the green light from, e.g. LEDs 111c, 111d, 111g), and the wall 124 is preferably at least level or slightly higher than the optical exit window of the LEDs. It is preferred that the barrier wall 124 also has a width that is sufficient to prevent optical crosstalk of light rays that never enter the skin or scattering material, but not so wide that light from the LEDs that is scattered from the skin or other flesh material, is prevented from reaching the photo-diode detectors inside the barrier wall 124. Importantly and preferably, barrier wall 124 should be utilized to prevent light rays from the LEDs from directly encountering the sensor 112c, as the intention is to have the light rays emitted into the skin and reflected or scattered back from the blood to the photo-diode detector (or detectors).

An optional exterior barrier wall 125 may also be employed. This one may assist with directing the light rays from LEDs 111c, 111d, and 111g, toward or into the subject. Similar considerations may be employed with wall 125 as those with 124, and those of considerations of other barrier walls, such as barrier walls 122 and 123, of other implementations. However, due to the unique considerations of the arrangement of a central sensor surrounded by an array of lights, as in FIG. 1U3b, a skilled artisan may make changes necessary for the operation of the device as intended and to optimize the light sources and detection.

In FIG. 1U3a-1U3c, the shape of the light pipe structure 121f and/or surface 121b may be chosen in a variety of ways depending on the number and size or shape of the detector diodes (and LEDs) and may be designed in such a way as to capture scattered light received from the skin or flesh material in contact therewith or in some instances not directly in contact or above any detector diode and contain it by internal reflection, and using scattering reflective surfaces, to redirect rays in a direction towards one or more of the photo diodes. In FIGS. 1T3a-c and FIGS. 1U3a-c, the epoxy (light pipe) 121f is relatively flat, i.e. presenting with a relatively flat surface 121b, not concave or convex, though it may be that curvature will work with the barrier wall or walls hereof. Note, however, that in FIG. 1U3c, the epoxy (light pipe) 121h presents with a convex structure, which is meant to show that the epoxy (light pipe) may be formed in such a structure as described elsewhere herein.

Not shown also in FIG. 1U3b is an optional silicone adhesive 113f on the lens 121g (although in other implementations the thin silicone adhesive 113f could be applied directly to the surface 121b) which may be used to relatively adhere the device to the skin (not shown here) to reduce movement of the device relative to the skin and enhance light transmission and reception. If used, such an adhesive may preferably be as thin as operably possible so as not to interfere with or provide refraction or light waves passing therethrough. A 0.2 mm thickness may be so operable. Also, it may be that a similar refractive index of the adhesive to the epoxy/encapsulant/light pipe 121/121a/121b/121c/121d/121e/121f might be preferred. This choosing of a similar refractive index may be of assistance or may be related to thickness as well as material of adhesive to be used, e.g. an appropriate refractive index similarity may result or lead to an operable 0.2 mm thickness. Note that in FIG. 1U3a the PPG sensor is proud, or protruding slightly, from the adhesive layer 113. The lens 121g or surface of the light pipe 121b may in some implementations be designed to slightly protrude from the adhesive surface 113. The protrusion or proudness of the PPG sensor may be about 0.036" or 0.91 mm. This slight protrusion of the PPG sensor compared to the adhesive strip may help the PPG sensor to stay in contact with the skin and perform its function in the desired manner.

FIGS. 1U3a-1U3c also show some operative examples and/or alternatives of how the PPG may be associated, united, or disposed within the flexible adhesive layers described in FIGS. 1A-1E, FIGS. 1O-1R2, inter alia. FIG. 1U3b and FIG. 1U3c both provide a cross-sectional view and demonstrate how a PPG mounted to a PCB and attached to and slightly protruding from the surface of the adhesive layers. The first layer 113h may be made from a non-conductive adhesive material such as 3M Medical Tape 4076, Polyester Spunlace Nonwoven Extended Wear (3M Company, Maplewood, Minnesota) or equivalent. The first layer 113h may be approximately 0.170 mm thick. These constructs may provide the effect of creating a low electrical impedance path in between the layers of the device. The second layer 113i may be constructed from a double-sided high tack adhesive transfer medical tape, such as 3M 1504XL High Tack Adhesive Transfer Medical Tape (3M Company, Maplewood, Minnesota) or equivalent. The second layer 113i may be approximately 0.114 mm thick. The next layer 113j (the third layer) may be constructed from a double sided transparent polyethylene such as 3M Medical Tape 9889, Double Sided Transparent Polyethylene (3M Company, Maplewood, Minnesota) or equivalent. This third layer 113j may be about 0.130 mm thick. The next layer 113l (the fourth layer) may be constructed from a double-sided high tack adhesive transfer medical tape, such as 3M 1504XL High Tack Adhesive Transfer Medical Tape (3M Company, Maplewood, Minnesota) or equivalent. This fourth layer 113l may be about 0.114 mm thick. The next layer 113m (the fifth layer), may be formed from an acrylic pressure sensitive adhesive such as Flexcon H-566 (FLEXcon Company, Inc., Spencer, MA). This fifth layer 113m may be about 0.076 mm in thickness. Note that the layers of hydrogel (113k) is not shown in FIGS. 1U3b and 1U3c because these drawings do not show the ECG electrodes.

FIG. 1U3d provides a three-dimensional top view of an exemplar unitary barrier wall structure or frame 130 that may be used with/as a part of a PPG unit 511 (lights, sensor/s and barrier wall structure with encapsulant combined as a combination or unit), central sensor/detector and LEDs, of FIG. 1T3a-1T3c and incorporated in FIG. 1U3a-1U3d. The unitary barrier wall structure or frame 130 may be relatively disc-shaped with apertures for light emission and collection. In this non-limiting example, the barrier walls 124, 125 walls are substantially circular in shape and provide LED apertures 126a-126d and a central sensor/diode aperture 127. The unitary barrier wall structure or frame 130 may be configured to be suitable for being placed and positioned around the PPG (central sensor/detector and LEDs) of FIGS. 1T3a-1T3c. When appropriately placed and secured, the unitary barrier wall structure or frame 130 may provide structure for connection and/or disposition of the lights, sensor and encapsulant as well as for the intended purpose of preventing or limiting sideways propagation of light rays from the LEDs directly to the sensor, preventing the sensor from receiving light rays that have not been emitted into the skin, preventing and/or reducing optical crosstalk, and generally assisting in directing the light rays emitted by the LEDs into the skin and scattered back to the photodiode detector or sensor.

In this implementation, the unitary barrier wall structure frame 130 may be formed by either injection molding using resin or machined from a block of non-conductive light blocking resin to form the structure of the proper size and shape for integration with the PPG sensor and LEDs. In this implementation of the unitary barrier wall structure 130, the resin used may have a volume resistivity of greater than $10^{12}$. Further, in this implementation the resin selected should be a dark color such as opaque black and, in some instances, a higher concentration of black colorant may be combined with the resin to achieve a desired level of opacity or diffuse-reflectivity, in this case full opacity. However, a colorant for the resin may not always be required, as a suitably opaque paint or film may be applied to the surface of the barrier walls to achieve the desired opacity or diffuse-reflectivity. The final shape of the barrier wall assembly should be fully formed with no underfills or voids on the structure in order to prevent light from escaping after emission by LEDs.

FIG. 1U3*e* provides a plan view of the unitary barrier wall structure 130 that may be used with the PPG, central sensor/detector and LEDs, of FIG. 1T3*a*-1T3*c*. Like in FIG. 1U3*d*, this non-limiting example, the barrier walls 124, 125 walls are substantially circular in shape and may provide LED apertures 126*a*, 126*b*, 126*c* and/or 126*d* and a central sensor/diode aperture 127.

FIG. 1U3*f* provides a cross-section of a side view of the unitary barrier wall structure 130. As previously described, in this implementation the unitary barrier wall structure 130 may be disc-shaped (although not pictured in this view) with LED apertures 126*a*-126*d* (126 generally) and central sensor/diode aperture 127. The interior barrier wall 124 provides separation of the central sensor/diode from the LEDs. The exterior barrier wall 125 provides separation of the LEDs from other surroundings, as further shown and described in FIG. 1U3*a*-1U3*d*, above. An internal ledge is optional and is shown formed in the space 127 which may be of a shape to accommodate particular sensor or die or light structures.

FIG. 1U3*g* provides a top view of how the unitary barrier wall structure 130 might fit relative to and/or around the LEDs 111*c*, 111*d*, and 111*g*, and sensor 112*c*. Note that the sensor die 115 is partially visible from this view. Further, barrier wall 124 provides a partition between the LEDs and sensor as described previously. Additionally, barrier wall 125 provides separation from outside areas and may perform the functions described above.

Returning to the adhesive alternatives, FIG. 1D provides a first example of an adhesive 113 that may be used herewith. The adhesive layer 113 is here a double-sided adhesive for application to the bottom side 102 of the device 100 or alternatively the device 500, and a second side, perhaps with a different type of adhesive for adhering to the skin of the human patient (not shown). Different types of materials for adhesion might be used in that the material of choice to which the adhesive layer is to be attached are different; typically, circuit or circuit board material for connection to the device 100/500, and patient skin (not separately shown) on the patient side. A protective backing 114 may be employed on the patient side until application to the patient is desired. Note, in many applications, the adhesive 113 is anisotropic in that it may preferably be only conductive in a single or substantially a single direction, e.g., the axis perpendicular to the surface of adhesive contact. Thus, good electrically conductive contact for signal communication can be had through such adhesive to/through the adhesive to the electrical contacts or electrodes, 108, 109 and 110. Note, a corresponding one or more light apertures 111*b*/112*b* are shown in the adhesive of 113 of the example of FIG. 1D to communicate light therethrough in cooperation with the light conduit(s) 111*a*/112*a* in/through layer 105 for communication of light data typically involved in pulse oximetry and/or temperature sensing.

The adhesive may thus be placed or disposed on the device 100/500, in some implementations substantially permanently, or with some replaceability. In some implementations, the device as shown in FIGS. 1A-1D and/or 1P without (or with in some implementations) the adhesive may be reusable. In many such cases, the adhesive layer 113 may be removed and replaced before each subsequent use, though subsequent re-use of and with a layer 113 is not foreclosed. In a first or subsequent use with a replaceable adhesive layer 113, it may be that the user applying the device to the patient, e.g., the physician or technician or even the patient, him/herself, applies the conductive transfer adhesive 113 to the patient side 102 of the device 100/500. The protective backing 114 may then be removed, and the device adhered to the patient and activated.

Activation of the device after application to a patient/wearer may occur in a number of ways; in some, it may be pre-set that an affirmative activation interaction may not be necessary from the doctor or patient or like due to either an inertial and/or a pulse oximeter activation which may be substantially automatically activating, e.g., upon receiving sufficient minimum input (movement in case of inertial system/accelerometer or light reflection of blood flow via e.g. a PPG combination for pulse oximetry); however, a button may be provided at an access 106 or in some other location adjacent the electronics to allow the patient to start or stop the device or otherwise mark an event if desired. In one exemplar implementation the device may be worn for a period such as two weeks for collection of data substantially continuously, or at intervals as may be preferred and established in or by the systems hereof.

After a monitoring period is over, a physician, technician, patient or other person may then remove the device from the patient body, in some instances remove the adhesive, in some instances with alcohol, and may establish a data communication connection for data transfer, e.g., by wireless communication or by insertion/connection of a USB or like data connector to download the data. The data may then be processed and/or interpreted and in many instances, interpreted immediately if desired. A power source on board may include a battery and this can then also be recharged between uses, in some implementations, fully recharged quickly as within about 24 hours, after which the device could then be considered ready for the next patient or next use. Alternatively, in some implementations a Bluetooth Low Energy (BLE) connection may be substantially employed for the duration of the wearing of the device which may negate the need for a USB or like data connector to download the data.

Some alternative conductive adhesives may be used herewith. FIGS. 1O, 1O1, 1O2 and 1P show one such alternative conductive adhesive 113*a*; a bottom plan view in FIG. 1O and elevational side views thereof in FIGS. 1O1 and 1P (as being in process of being connected to a device 100 in FIG. 1P). In some implementations, the conductivity may be anisotropic as introduced above; in some conductive primarily if not entirely in the direction of the Z-Axis; perpendicular to the page (into and/or out of the page for plan views) in FIG. 1O, and/or vertically or transversally relative to the long horizontal shown axis of device 100 in the implementation view of FIG. 1O1.

The implementation of this particular example includes a composite adhesive 113a which itself may include some non-conductive portion(s) 113b and some one or more conductive portions 113c. The adhesive composite 113a may, as described for adhesive 113 above be double sided such that one side adheres to the patient while the other side would adhere to the underside 102 of the device 100 (see FIG. 1P) so that one or more conductive portions 113c may be disposed or placed in electrically communicative and/or conductive contact with the integrated electrodes on the electronic monitoring device 100. Since the electrodes would operate better where they may be electrically isolated or insulated from each other, yet each making electrical contact or communication with the patient's skin, the adhesive may further be more specifically disposed in some implementations as follows.

As shown in FIGS. 1O and 1O1, three isolated conductive portions 113c may be disposed separated from each other by a body portion 113b which may be non-conductive. These could then correspond to the electrodes 108, 109, 110 from the above-described examples, and as more particularly shown schematically in FIG. 1P (note the scale is exaggerated for the adhesive 113a and thus, exact matching to the electrodes of device 100 is not necessarily shown). In some examples, the electrode areas 113c may be a conductive hydrogel that may or may not be adhesive, and in some examples, may be made of a conductive adhesive material such as 3M Corporation 9880 Hydrogel adhesive (3M Company, St. Paul, Minnesota). These areas 113c may then be isolated from each other by a non-conductive material 113b such as 3M Corporation 9836 tape or 3M double-sided Transfer Adhesive 9917 (3M, St. Paul, MN) or equivalent. The additional layer 113d, if used, might be a 3M 9917 adhesive together with the 113b of a 9836 material. These constructs may provide the effect of creating a low electrical impedance path in the Z-axis direction (perpendicular to page for FIG. 1O and vertically/transversally for FIGS. 1O1 and 1P) for the electrode areas 113c, and high electrical impedance path between the electrodes in the X/Y directions. (See FIGS. 1O, 1O1 and 1P; coplanar with the page in FIG. 1O and horizontal and perpendicular to the page in FIGS. 1O1 and 1P.) Thus, a composite adhesive strip can ensure not only device adhering to the patient, but also that the electrodes whether two or as shown three electrodes are conductively connected by conductive portions of the adhesive strip, where the combination of conductive and non-conductive portions can then reduce signal noise and/or enhance noise free characteristics. Electrodes that move relative to skin can introduce noise; that is, electrodes electrically communicative/connected to the skin via a gel may move relative to the skin and thus introduce noise. However, with one or more conductive adhesive portions in a composite adhesive connected to respective electrodes and then substantially securely connected to the skin will keep the respective electrodes substantially fixed relative to the skin and thereby reduce or even eliminate electrode movement relative to the skin. Removal of such movement would then remove noise which would thereby provide a clean signal that can allow for monitoring cardiac P waves which enhances the possibility to detect arrhythmias that couldn't otherwise be detected. Further description is set forth below.

In some implementations, a further optional connective and/or insulative structure 113d may be implemented as shown in FIGS. 1O1 and/or 1P, to provide further structural and insulative separation between electrodes with connected to a device 100 on the underside 102 thereof (see FIG. 1P). Though shown separate in FIGS. 1O1 and 1P, it may be contiguous with the insulative adhesive 113b of these views.

As shown in the non-limiting example of FIG. 1O2, adhesive layer 113 provides two apertures 113g for two isolated conductive portions 113c (not shown) and two other data acquisition apertures 111b/112b to mount the temperature sensor and the PPG sensor through, which are separated by body portion 113h which may be non-conductive. On the side of the adhesive layer 113 that is placed toward the patient or wearer 1000, optionally shown are thin silicone adhesive strips 113f, which may be fashioned from a transparent double sided thermoplastic elastomer tape such as 3M Medical Silicone Tape 2477P, Double Sided Silicon (3M Company, Maplewood, Minnesota) or equivalent, that are placed and secured substantially over the two temperature and light apertures 111b/112b. The body portion 113h may be made from a non-conductive adhesive material such as 3M Medical Tape 4076, Polyester Spunlace Nonwoven Extended Wear (3M Company, Maplewood, Minnesota) or equivalent. These constructs may provide the effect of creating a low electrical impedance path in between the layers of the device. The next layer 113i, in this example layer 3, optionally formed from two pieces of adhesive that have been split to accommodate the hinge, may be constructed from a double-sided high tack adhesive transfer medical tape, such as 3M 1504XL High Tack Adhesive Transfer Medical Tape (3M Company, Maplewood, Minnesota) or equivalent. Like the adhesive layer 113, this layer 3 113i, provides two apertures 113g for two isolated conductive portions and two temperature and light apertures 111b/112b. The next layer 113j, in this example layer 4, may be constructed from a double sided transparent polyethylene such as 3M Medical Tape 9889, Double Sided Transparent Polyethylene (3M Company, Maplewood, Minnesota) or equivalent. Again, this layer 4, 113j, provides two apertures 113g for two isolated conductive portions and two temperature and light apertures 111b/112b. Next, a layer of hydrogel 113k (layer 5) is provided to cover only the areas of the apertures 113g for the two isolated conductive portions for the ECG (not shown in FIG. 1O2). The conductive hydrogel 113k may be M865 Hydrogel tape (R&D Medical Products, Lake Forest, CA) or equivalent suitable for skin applications and compatible with silver inks, tin, and conductive carbon substrates. The hydrogel layer may allow for improved contact and communication between the ECG leads or conductors that will occupy the two apertures of 113g and the users skin, and this may result in better efficiency in the performance of the electrodes. The next layer 113l, in this example layer 6, may be constructed from a double-sided high tack adhesive transfer medical tape, such as 3M 1504XL High Tack Adhesive Transfer Medical Tape (3M Company, Maplewood, Minnesota) or equivalent. Like the adhesive layer 113, this layer 3 113i, provides two apertures 113g for two isolated conductive portions and two temperature and light apertures 111b/112b. The next layer 113m, in this example, layer 7, may be formed from an acrylic pressure sensitive adhesive such as Flexcon H-566 (FLEXcon Company, Inc., Spencer, MA). The bottom most layer, 113n, in this example, layer 8, may be a silicone or polymer liner, such as Loparex (Loparex, LLC, Cary, NC) which allows the layered assembly to be attached to the device. The arrangement of these adhesives in the order described above may impart desirable properties and characteristics to the device such as maintaining a waterproof seal, providing electric isolation, providing a flexible foundation for attachment to the wearer and other desirable benefits.

Further alternatives related to the adhesive may be used. In some implementations, a composite adhesive strip may be used having properties to reduce one or more motion artifacts. Typical ECG attachment systems use a conductive gel located over the electrode. Here, however, a hydrogel adhesive, e.g., 113k, may be used which is embedded in a continuous sheet of laminated adhesives that cover the selected regions or the entire footprint of the device. The fact that the hydrogel itself has strong adhesive properties coupled with the complete coverage of the device with adhesives may assure a strong bond between the device and the patient's skin. Contributing to motion artifact reduction may be an alternative vertical placement of the device on the sternum which results in reduced motion artifacts for one or more of ECG signals, photoplethysmography waveforms, and oxygen saturation signals.

In some implementations, composite adhesive improvements may include water resistant or water-proof encapsulation of the hydrogel adhesive to prevent ohmic impedance reduction resulting in reduction of signal amplitude. This may also help prevent hydrocolloid adhesive degradation. In particular, as shown the non-limitative alternative exemplar in FIGS. 1R and 1R1; several layers may be used. Herein, Layer 1 (113h) may be a hydrocolloid that is an adhesive designed for long term skin contact by absorbing sweat and cells. Layer 2 (113i) may then also be a layer designed for long-term skin contact, however, this Layer 2 (113i) isolates Layer 3 (113j) from contacting the skin. The smaller dimensions of Layer 2 113i create a gap between Layer 1 113h and Layer 3 113j. When Layer 1 (113h) and Layer 3 (113j) bond together, it forms a water resistant or water-tight seal around Layer 2 (113i). This layer, Layer 2 (113i), also isolates the Hydrocolloid from the Hydrogel Adhesive, protecting the adhesive properties of the Hydrocolloid. Layers 3 (113j) and 5 (113l) would then generally be water resistant or water-proof layers that are electrically isolating, double-sided adhesives. These two layers encapsulate the hydrogel adhesive, preventing a "short circuit" described relative to Layer 4 (113k) below. Layer 4 113k is the hydrogel adhesive that is the conductive element hereof. The three islands of hydrogel adhesive of Layer 4 must be kept electrically isolated from each other. However, as the hydrocolloid in Layer 1 113h absorbs sweat, it too becomes conductive and creates a potential "short circuit" between the three islands of hydrogel adhesive in Layer 4 113k, reducing signal amplitude. Nevertheless, this "short circuit" may be substantially prevented by Layer 3 113j and Layer 5 113l, described above.

FIG. 1R2 provides an exploded and cross-sectional view of one example of how the device 100/100a/500 might be layered or attached to the adhesive 513 and placed on the skin 1001 of the patient or wearer 1000. Further, this view demonstrates how the ECG electrodes 508/509 may be affixed to opposite ends of the flexible substrate 503a. The PPG light source and sensor unit 511 and temperature sensor 515 are also electronically connected to the flexible substrate 503a, as is the piezo strip 516. A pleat 531 in the housing 530 is also shown. These features are described in more detail above and below.

In some one or more additional alternative implementations, temperature may be a parameter determined hereby. This may be by a single sensor or plural sensors as described herein. In some temperature implementations, infant or neonate temperature may be sought data for capture hereby, or temperature may be used with other users, adult or otherwise.

Infant and/or neonate temperature sensing can be of significant assistance in health monitoring. Forehead or other use may be one such application. Another set of possible applications may include methods and apparatuses for sensing the temperature of both an infant and a mother engaged in so-called "Kangaroo Care". There is evidence that pre-mature infants may benefit more from constant contact with a parent's or the mother's skin than from being placed in an incubator. There is also evidence of lower mortality rates.

An apparatus 100a for dual temperature sensing, the infant wearer 1000 and the mother 1010 or ambient air 1011, is shown in the accompanying figure, FIG. 1V. The substrate 1105 is preferably a small, flexible circuit board, in some examples, approximately twenty (20) mm X thirty (30 mm. The board 1105 may be disposed to contain circuitry 1103 for, for example, sensing relative X-Y-Z position and/or acceleration, and/or Bluetooth or other wireless data/signal connectivity, as well as, in many examples, a replaceable and/or rechargeable battery for extended use, as for example, seven (7) days of continuous monitoring (circuit element alternatives not all separately shown in FIG. 1V). The conductive portion 113c covers the two ECG electrodes 508/509 and acts as a conductive, yet isolated element as described in detail above. The apparatus 100a may be held to the infant with an adhesive, such as the composite adhesive 1113 shown in FIG. 1V, which may further be, for example, a disposable, medical grade, double-sided adhesive.

As shown in FIG. 1V, each of two temperature sensors 1111a and 1111b may be disposed on alternative opposing sides 1101, 1102 of the apparatus 100a, and may be thermally isolated from each other, as well as often being waterproof, water tight or water resistant. A thermally insulating or isolation layer 1103a may provide the thermal isolation of the electronics 1103 and/or sensors 1111a and 1111b. A further spacer 1103b may be disposed through the insulating/isolating layer 1103a to provide a throughway for electronic communication of the sensor 1111b to the electronics layer 1103. A silicone bead 1104 may be provided for isolating and assisting in giving a waterproof or water-resistant seal on the "infant side" 1102, and a silicone cover 1121 may provide a waterproof or waterproof barrier on the "mother side" 1101. The sensor 1111b on the "mother side" or top or exterior side 1101 may be slightly protruding relative to the cover 1121 with in many implementations a thin/thinner layer of covering material and/or silicone thereover. The sensor 1111a on the child side or patient or circuit side 1102 may be protruding past, or through the adhesive and/or disposed exposed or also/alternatively covered with a thin protectant layer for water proofness, or tightness or resistance.

The thermally insulating layer may provide one or two or more functions. It may provide for or allow the "infant side" sensor 1111a to reach equilibrium, thus providing an accurate "core temperature" of the infant. It may also or alternatively isolate the infant's temperature reading from the mother's or ambient. The "mother side" sensor 1111b does not have to provide an accurate core temperature for the mother. Typically, the function of sensor 1111b would be to differentiate whether or not the infant is in the correct direct contact with the mother's skin; i.e., to provide a relative measurement for determining whether the infant is in relative contact or not in relative contact with the mother. If the infant is facing the wrong way, but is still in the "pouch" the sensor will read that environment's ambient temperature. If the infant is out of the pouch, it will read the room ambient temperature. The relative differences would be interpretable to provide an indication of what position the infant is in; whether in contact, or in close association in a controlled "pouch" environment (but not in contact), or outside the pouch in a further removed environment.

An alarm from a Bluetooth or otherwise wirelessly connected device may be used to alert the mother (or health care professional) that the infant is no longer in the correct desired position, or no longer in the "pouch".

Some alternative implementations hereof may include either use of two fixed electrodes—fixed in relation to each other on a device 100/100a/500, inter alia, or two electrodes with one on the device and another connected by tether (see FIG. 1N, et al.), or two fixed electrodes fixed on the device with an optional third electrode either on the device or connected by tether (see FIG. 1N, et al.). Other alternatives, e.g., with a third electrode can include one of which having a third electrode used in a driven right leg ECG circuit with one or more chest only electrodes ("Driven Chest Electrode"). In addition to the electrodes used to measure a single or multiple lead electrocardiogram signal, a device 100 may use an additional electrode, as for example the reference electrode 110 (see FIGS. 1A, 1C, 1D and 1P, e.g.) to reduce common mode noise. Such an electrode may function in a manner similar to the commonly-used driven right leg electrode, but may here be located on the patient's chest rather than on the patient's right leg but nevertheless this third/reference electrode may play the role of the leg electrode. This chest electrode may thus mimic a right leg electrode and/or be considered a proxy driven right leg electrode. A circuit, or portion of an overall circuit, adapted to operate in this fashion may include one, two, three, or more of a number of amplifier stages to provide gain, as well as filtering to ensure circuit stability and to shape the overall frequency response. Such a circuit may be biased to control the common mode bias of the electrocardiogram signal. This driven chest electrode implementation may be used in conjunction with a differential or instrumentation amplifier to reduce common mode noise. In this case, the sense electrode may be used as one of the electrocardiogram electrodes. Alternatively, a single-ended electrocardiogram amplifier may be used where the differential electrocardiogram signal is referenced to ground or to some other known voltage.

A circuit or sub-circuit 200 using a transistor 201 as shown in FIGS. 2A-2D may be such a circuit (aka module) and may thus include as further shown in FIG. 2A, a sense electrode 202, a drive electrode 203, and an amplifier 204. Both the sense and drive electrodes 202, 203 are placed on the patient's chest such that they provide an electrical connection to the patient. The amplifier 204 may include gain and filtering. The amplifier output is connected to the drive electrode, the inverting input to the sense electrode, and the non-inverting input to a bias voltage 205. The amplifier maintains the voltage of the sense electrode at a level close to the bias voltage. An electrocardiogram signal may then be measured using additional electrodes. Indeed, as was the case for the improved conductivity through use of anisotropic adhesive portions above, here also or alternatively, the use of this third electrode as a proxy for a right leg electrode (i.e., proxy driven right leg electrode) can provide signal reception otherwise unavailable. Clean signals may thus allow for receiving cardiac P waves which enhances the possibility to detect arrhythmias that couldn't otherwise be detected.

Further alternative descriptions of circuitry include that which is shown in FIGS. 2B and 2C; in which are shown non-limiting alternatives in which three adjacent electrodes E, E2, and E3 may be used to pick up the ECG signal, one of which electrodes playing the role of the distant limb electrode of traditional ECG monitors. Because the electrode-patient interface has an associated impedance (Re1 and Re2), current flowing through this interface will cause a difference in voltage between the patient and the electrode. The circuit may use a sense electrode (E1) to detect the patient voltage. Because this exemplar circuit node has a high impedance to circuit ground (GND), very little current flows through the electrode interface, so that the voltage drop between the patient and this node is minimized. The first of these alternative, non-limiting circuits (FIG. 2B) also contains an amplifier (U1) whose low-impedance output is connected to a separate drive electrode (E2). The amplifier uses negative feedback to control the drive electrode such that the patient voltage (as measured by the sense electrode E1) is equal to the bias voltage (V1). This may effectively maintain the patient voltage equal to the bias voltage despite any voltage difference between the driven electrode (E2) and the patient. This can include voltage differences caused by power line-induced current flowing between the drive electrode and the patient (through Re2). This arrangement differs from a traditional 'driven-right-leg' circuit in at least two ways: the driven electrode is placed on the patient's chest (rather than the right leg), and the ECG signal is a single-ended (not differential) measurement taken from a third electrode (E3). Because all electrodes are located on the patient's chest in a chest-mounted example, a small device placed there may contain all the necessary electrodes for ECG measurement. One possible benefit of the single-ended measurement is that gain and filtering circuitry (U2 and associated components (FIG. 2C)) necessary to condition the ECG signal prior to recording (ECG Output) requires fewer components and may be less sensitive to component tolerance matching. The examples of FIGS. 2A, 2B and 2C are non-limiting examples and not intended to limit the scope of the claims hereto as other circuits with other circuit elements can be formed by skilled artisans in view hereof and yet remain within the spirit and scope of claims hereof.

In many implementations, a system hereof may include other circuitry operative together with the ECG electrodes, which may thus be accompanied by other sensors to provide time concordant traces of: i) ECG p-, qrs-, and t-waves; ii) O2 Saturation, as measured by Pulse Oxymetry; and/or iii) xyz acceleration, to provide an index of physical activity. Such circuitry may be implemented to one or more of the following electrical specifications. The overall system might in some implementations include as much as two weeks (or more) of continuous run time; gathering data during such time. Some implementations may be adapted to provide as many or even greater than 1000 uses. Alternatives may include operability even after or during exposure to fluids or wetness; in some such examples being water resistant, or waterproof, or watertight, in some cases continuing to be fully operable when fully submerged (in low saline water). Other implementations may include fast data transfer, as for an example where using an HS USB for full data transfer in less than about 90 seconds. A rechargeable battery may typically be used.

A further alternative implementation may include an electronic "ground": In a device hereof, mounted entirely on a flexible circuit board, the ground plane function may be provided by coaxial ground leads adjacent to the signal leads. The main contribution of this type of grounding system may be that it may allow the device the flexibility desired to conform and adhere to the skin. Note that this alternative implementation is not depicted in the drawings hereof.

For electrocardiograph; EKG or ECG, some implementations may include greater than about 10 Megohms input impedance; some implementations may operate with a 0.1≠48 Hz bandwidth; and some with an approximate 256 Hz Sampling Rate; and may be implementing 12 Bit Resolution. For PPG and Pulse Oximeter, operation may be with 660 and 940 nm Wavelength; about 80-100 SpO2 Range; a 0.05-4.8 Hz Bandwidth; a 16 Hz Sampling Rate; and 12 bit resolution. For an accelerometer: a 3-Axis Measurement may be employed, and in some implementations using a ±2 G Range; with a 16 Hz Sampling Rate; and a 12 Bit Resolution. Some implementations hereof may operate with a 0.1-48 Hz bandwidth, and some with an approximate 256 Hz Sampling Rate; and may be implementing 24-bit resolution. Using an A/D converter with 24 bits may represent an approximately 60 dB gain in dynamic range, and may reduce the possibility of "saturating" or "railing" the amplifier and thus reducing errors or loss of signal issues that may have been generated by the PPG if only 12 bit resolution is used. ±2 G Range; with a 16 Hz Sampling Rate; and a 12 Bit Resolution.

In some implementations, two electrodes may be used instead of the often conventional three, the third electrode here, e.g., 510 of FIG. 1N, et seq. being optional; 508 and 509 being more primary. Thus, two are relatively internal, one optional one being external, either on device or connected by tether. A conventional TI chip or processor is one way to achieve same; TI being Texas Instruments Corporation. Another option is from Microchip Corporation (Corporate Office 2355 West Chandler Blvd. Chandler, AZ 85224-6199), PIC24FJ1024GA610/GB610 FAMILY 16-Bit Microcontrollers with Large, Dual Partition Flash Program Memory and USB On-The-Go (OTG). To do so, one or two oscillators can be used to provide for analysis of two ECG and one PPG on one chip, thus always in synchronicity (AFE device). Three electrodes is more difficult for a couple of reasons, including e.g., could cause blisters on the skin, particularly with a driven electrode. Temperature, piezo and accelerometer, also may prefer to have or use processor power for synchronicity. A dco or digitally controlled oscillator can be used to calculate from the two electrode inputs a sufficient LEAD 1 output. A DCO hereof may be internal to a printed integrated circuit or chip (pic), or integrated circuit, or processor as mentioned above (TI or Micron, e.g., without limitation). In some instances, one oscillator (one DCO) may be used, but, in other instances two DCOs might be used. Also allows more options, not just the removal of the third electrode; have choice of electrodes, physiological difference (skin color as above), Automatic Gain Control AGC, for PPG, may be provided also, as for example to adjust for skin color, or other light sensitivities. 24 bits vs prior 12 bits, can provide or have control over the gain. Also, can provide a DC offset, via the TI chip which allows to DC, vs, ripple.

For pulse oximetry, an option for PPG ambient light subtraction may be included. A method and circuitry for reducing errors in pulse oximetry caused by ambient light is described and a circuitry option shown in FIG. 2D. Here, a correlated double sampling technique is shown for use to remove the effect of ambient light, photo-detector dark current, and flicker noise.

The schematic shown in FIG. 2D may be used where, first, the noise signal may be measured. The light sources are turned off, switch S1 is closed, and switch S2 is open. This allows charge proportional to the noise signal to accumulate on C1. Then switch S1 is opened. At this point the voltage on C1 is equal to the noise signal voltage. Next, the light signal may be measured. The light source is turned on, switch S2 is closed, and charge is allowed to flow through C1 and C2 in series. Then, S2 is opened, and the voltage is held on C2 until the next measurement cycle when the whole process is repeated.

If C1 is much larger than C2, nearly all the voltage will appear on C2, and the voltage on C2 will be equal to the noise-free signal (s). Otherwise, the voltage on C2 will be a linear combination of the previous C2 voltage (p) and the noise-free signal: $(C2*s+C1*p)/(C1+C2)$. This has the effect of applying a first-order, low-pass, IIR discrete-time filter to the signal. If this filtering effect is not desired, the voltage on C2 may be discharged to zero before the signal is measured each cycle, so that the signal held on C2 is simply: $(C2*s)/(C1+C2)$.

This circuit may be used with a trans-impedance amplifier in place of resistor R, a phototransistor in place of the photodiode, and FETs in place of the switches. The output may be followed by additional buffering, amplification, filtering and processing stages. Some implementations may include a fixed gain amplifier, however, this gain may not be appropriate for all physiologies. For example, a very dark skinned person will require a very high gain, while a light skinned person will require a much smaller gain. A fixed gain amplifier limits the ability to maximize the pulsatile signal for all physiologies. An alternative, may include a dynamic gain control, which in some implementations may have multiple, in some cases as many as nine (9) different levels of amplifier gain, thus allowing for automatic setting appropriate level for physiologies encountered.

Another option may include a sequencer. Power control is interesting for a variety of reasons; for example, Zincare battery approved for human use (not lithium) provides different power considerations. Limitations: peak current, high inrush, could see high amperage, 1 milliamp. To work with this may include using a power sequencer, providing for power-up parts so that can minimize inrush which can overwhelm some hardware. Can include a hardware solution, current to any of devices minimized when device is in re-set, e.g., first boost regulator, done with RC and comparator. Part of problem is that not doable in firmware. Other advantages taking other devices out of reset, eliminating the de-bouncing the RCs are designed to empirically ensure that the voltage/s is/are stable, instead of de-bounce the RCs allow power to stabilize. Power down, once battery gets less than 0.8 volts, everything oscillates—which can kill some things like Bluetooth, and could be, but, may want to power down completely instead of this cascade. A voltage of 1.2 volts is likely acceptable for continued operation, but, when below 1.1 volts, e.g., preference is to kill LEDs first, and send signals to shut everything down. In some examples, where might want to start the shut down is when the power detection gets below one volt.

For power up:
Power Sequencing Order
1. Digital Power Rail enabled
2. Printed Integrated Circuit, aka PIC, Microcontroller enabled 3. Bluetooth enabled
4. Flash memory enabled
5. LED Power supply enabled
6. PPG/ECG Integrated Circuit, aka IC, Analog supply enabled
7. PPG/ECG IC Digital supply enabled
8. PPG/ECG IC LED supply enabled
9. PPG/ECG IC enabled For power down:

Power Down Sequencing Order
1. The first power down comparator detects that power is failing, and sends a state change to the PIC microcontroller. The microcontroller will then disable the flash memory, and the Bluetooth, and will wait for the power supplies to be disabled by hardware.
2. The second power down comparator disables the main digital supply.
3. When the main digital supply is disabled, the LED supply is subsequently disabled.

Some summary methodologies may now be understood with relation to FIG. 3, though others may be understood through and as parts of the remainder of the disclosure hereof. A flow chart 300 as in FIG. 3 may demonstrate some of the alternatives; where an initial maneuver 301 might be the application of the device 100 to the patient. Indeed, this might include some one or more of the alternatives for adhesive application as described here above, whether by/through use of an adhesive such as that 113 of FIG. 1D, or that of FIGS. 1O, 1O1, 1O2 and/or 1P. Then, as shown, in moving by flow line 311, a data collection operation 302 may be implemented. Note, this might include a continuous or substantially continuous collection or an interval or periodic collection or perhaps even a one-time event collection. This may depend upon the type of data to be collected and/or be dependent upon other features or alternatives, as for example whether a long term quantity of data is desired, for ECG for example, or whether for example a relative single data point might be useful, as in some cases of pulse oximetry (sometimes a single saturation point might be of interest, as for example, if clearly too low, though comparison data showing trending over time, may indeed be more typical).

Several alternatives then present in FIG. 3, flow chart 300; a first such might be the following of flowline 312 to the transmission of data operation 303, which could then involve either wireless or wired (e.g., USB or other) data communication from the device 100 to data analysis and/or storage devices and/or systems (not separately shown in FIG. 3; could include computing devices, see e.g., FIGS. 3A and/or 4 described below, or the like). Options from this point also appear; however, a first such might include following flow line 313 to the data analysis operation 304 for analyzing the data for determination of the relative health and/or for condition diagnosis of a patient. Computing systems, e.g., a computer (could be of many types, whether hand-held, personal or mainframe or other; see FIGS. 3A and/or 4 and description below) could be used for this analysis; however, it could be that sufficient intelligence might be incorporated within the electronics 103 of device 100 such that some analysis might be operable on or within device 100 itself. A non-limiting example, might be a threshold comparison, as for example relative to pulse oximetry where when a low (or in some examples, perhaps a high) threshold level is reached an indicator or alarm might be activated all on/by the electronics 103 of the device 100, or alternatively communicated wirelessly to a cellphone or tablet computer to alert the user.

A similar such example, might be considered by the optional alternative flow path 312a which itself branches into parts 312b and 312c. Following flow path 312a, and then, in a first example path 312b, a skip of the transmit data operation 303 can be understood whereby analysis 304 might be achieved without substantial data transfer. This could explain on board analysis, whether as for example according to the threshold example above, or might in some instances include more detailed analysis depending upon how much intelligence is incorporated on/in the electronics 103. Another view is relative to how much transmission may be involved even if the transmission operation 303 is used; inasmuch as this could include at one level the transmission of data from the patient skin through the conductors 108, 109 and/or 110 through the traces 107 to the electronics 103 for analysis there. In other examples, of course, the transmission may include off-board downloading to other computing resources (e.g., FIGS. 3A and/or 4). In some cases, such off-loading of the data may allow or provide for more sophisticated analysis using higher computing power resources.

Further alternatives primarily may involve data storage, both when and where, if used. As with intelligence, it may be that either some or no storage or memory may be made available in/by the electronics 103 on-board device 100. If some storage, whether a little or a lot, is made available on device 100, then, flow path 312a to and through path 312c may be used to achieve some storing of data 305. This may in many cases then, though not necessarily be before transmission or analysis (note, for some types of data multiple paths may be taken simultaneously, in parallel though perhaps not at the same time or serially (e.g., paths 312b and 312c need not be taken totally to the exclusion of the other), so that storage and transmission or storage and analysis may occur without necessarily requiring a completion of any particular operation before beginning or otherwise implementing another). Thus, after (or during) storage 305, flow path 315a may be followed for stored data which may then be transmitted, by path 315b to operation 303, and/or analyzed, by path 315c to operation 304. In such a storage example, which in many cases may also be an on-board storage example, data can be collected then stored in local memory and later off-loaded/transmitted to one or more robust computing resources (e.g., FIGS. 3A and/or 4) for analysis. Frequently, this can include long term data collection, e.g., in the manner of days or weeks or even longer, and may thus include remote collection when a patient is away from a doctor's office or other medical facilities. Thus, data can be collected from the patient in the patient's real-world circumstances. Then, after collection, the data can be transmitted from its storage on device 100 back to the desired computing resource (FIGS. 3A and/or 4, e.g.), and such transmission might be wireless or wired or come combination of both, as for example a Bluetooth or Wi-Fi connection to a personal computer (FIGS. 3A and/or 4 for one example) which might then communicate the data over the internet to the designated computer for final analysis. Another example might include a USB connection to a computer, either to a PC or a mainframe (FIGS. 3A and/or 4), and may be to the patient computer or to the doctor computer for analysis.

If little or no storage or memory is resident on device 100 (or in some examples even where there may be a large amount of resident memory available), then, relatively soon after collection, the data would need to or otherwise might desirably either or both be transmitted and then stored, see path 313a after operation 303, and/or transmitted and analyzed, paths 312 and 313. If path 313a is used, then, more typically, the data storage may be in/on computing resources (not shown in FIG. 3, but see FIGS. 3A and/or 4 described below) off-board (though on-board memory could be used as well), and then, any of paths 315a, 315b and 315c may be used.

Some detailed options for communication may include the following. In FIG. 3A, a device 100, or 100/100a/100b/100c/500 and/or 500a may include a Bluetooth communication therefrom to a further device as for example a computer or display device 3000 via a wireless transmission path 3001; or in some cases intermediately or rather more directly to a mobile communication device 3002 such as a hand-held telephone or tablet via a wireless transmission path 3003 which may thereafter communicate the data through either a closed circuit communication 3005 to a destination computer or display 3000 or to a remote data storage device or location via transmission path 3008 which in some cases could include a residence perhaps temporarily in the "cloud" 3006 from which the data may further be stored or further communicated via transmission path 3009 to a desired end receiver computing device and/or display 3000 for use, reading and/or interpretation by appropriate personnel. Communication can thus be either straight from the patient device 100/500 (or alternatives), either to a cloud 3006 or to a computer 3000 with analysis and/or display capacity (cloud 3006 can provide analysis or mere storage and re-communication to an analysis/display device 3000), or to a hand-held or other intermediate communication device 3002, which can then either communicate to cloud 3006 (via path 3007) or to analysis and/or display device 3000. Further note, the paths 3001 and 3008 are included in the drawings, FIG. 3A as alternative optionality/implementations of the device. It should also be appreciated that path 3001 to computer 3000 or to hand held 3002 could be via wireless or wired connection. Moreover, the connection 3008 would typically be wireless; though not necessarily so, however, it is also noted that path 3009 is typically a bi-directional arrow between cloud and computer, indicating possible communication both ways to and from the cloud and to and from the computer device 3000.

Operating in such a system or method or with a device in FIG. 3A, e.g., included are alternatives such as or included within the following. A health monitoring system, device or method can be included herein for monitoring health of a subject including: a wearable device for gathering health data from a user, the wearable device including a substrate for removable fixation to a subject, and disposed on the substrate one or more sensors and processing circuitry and transmission circuitry for gathering data from the one or more sensors and transmitting the data; a personal communication device; a server sub-system; at least first and second data communications networks; and, a receiver display device; the personal communication device being communicatively connected to the wearable device and via the first data communication network to the server sub-system; the receiver display device being communicatively connected via the second data communications network to the server sub-system; the health data being first gathered by the wearable device and then communicated via the personal communication device then through the first data communication network to the server sub-system, the receiver display device then receiving communication of the health data from the server sub-system for one or more of display, use, reading, processing and/or interpretation.

Alternatives may include without limitation; the wearable device including one or more sensors for gathering health data of one or more of: temperature; photoplethysmography; pulse oximetry or oxygen saturation; electrocardiography; pulse transit time or blood pressure heart rate; respiration rate; respiration depth; or motion or exertion. Alternatively, included may be one or both of the processing circuitry and transmission circuitry being or including: conditioning circuitry; conditioning circuitry including high sensitivity amplifiers and filters; an oscillator; two oscillators; one or two digitally-controlled oscillators; an integrated circuit; a processor; and, an analog front-end (AFE) device. Still further possible alternatives may include the personal communication device being: a computer or display device or a mobile communication device or a hand-held telephone or smartphone or tablet or communication module built into the wearable device. Yet still further possible alternatives may include the first data communication network being: a wireless transmission path; a wifi system; Local Area Network (LAN); Bluetooth or Bluetooth LE; Wide Area Network (WAN); a cellular or mobile telephone network; the internet; closed-circuit; or hard-wire network. And further alternatives may include the server sub-system being or including: one or more local server; one or more remote servers; a 'cloud' server; or a local or remote computer. Another set of potential alternatives includes the second data communication network being: an internet connection; a closed-circuit connection; or a cellular or mobile telephone network; Wide Area Network (WAN); Local Area Network (LAN); Bluetooth or Bluetooth LE; a wifi system; a wireless transmission path; or hard-wire network.

A health monitoring system, device or method hereof for monitoring health of a subject according may further include the receiver display device one or both: has the server sub-system directly connected for direct communication, or the receiver sub-system is: a computer with associated display or monitor; a remote terminal; or, a vital signs monitor. Alternatively, a health monitoring system for monitoring health may further include: a third data communication network; the third data communication network connecting the wearable device with the personal communication device. This third data communication network may be: a wireless transmission path; a wifi system; Local Area Network (LAN); Bluetooth or Bluetooth LE; Wide Area Network (WAN); a cellular or mobile telephone network; the internet; closed-circuit; or hard-wire network.

Hereof, a health monitoring system, device or method for monitoring health of a subject may further include; the data after having been gathered by the wearable device is one or more of: when a data communication module is resident on the wearable device, the data is communicated to the server sub-system or the receiver display device; the wearable device communicates via Bluetooth or BluetoothLE to the personal communication device; the personal communication device communicates to the server sub-system via a cellular data network; the receiver display device receives communication from the server sub-system via the internet or closed circuit communication. Alternatively, the data being subject to one or more of storage, processing or analysis for ultimate presentation in waveform display or one or more snapshots, within any one or more of: the wearable device; the personal communication device; the server sub-system; the receiver display device. Still further a method may include gathering health data via a wearable device disposed on a subject; communicating the health data via a personal communication device through a first data communication network to a server sub-system, receiving at a receiver display device communication of the health data from the server sub-system; displaying via the receiver display device the health data. Or, a method may include;

after having been gathered by the wearable device the method further comprising one or more of: communicating the data, when a data communication module is resident on the wearable device, to the server sub-system or the receiver display device; communicating the data from the wearable device via Bluetooth or BluetoothLE to the personal communication device; communicating the data via the personal communication device to the server sub-system via a cellular data network; receiving the data at the receiver display device from the server sub-system via the internet or closed circuit communication. A device for practicing the method according hereof may be one or more of: a wearable device, a personal communication device, and, a receiver display device.

Figure 10A:
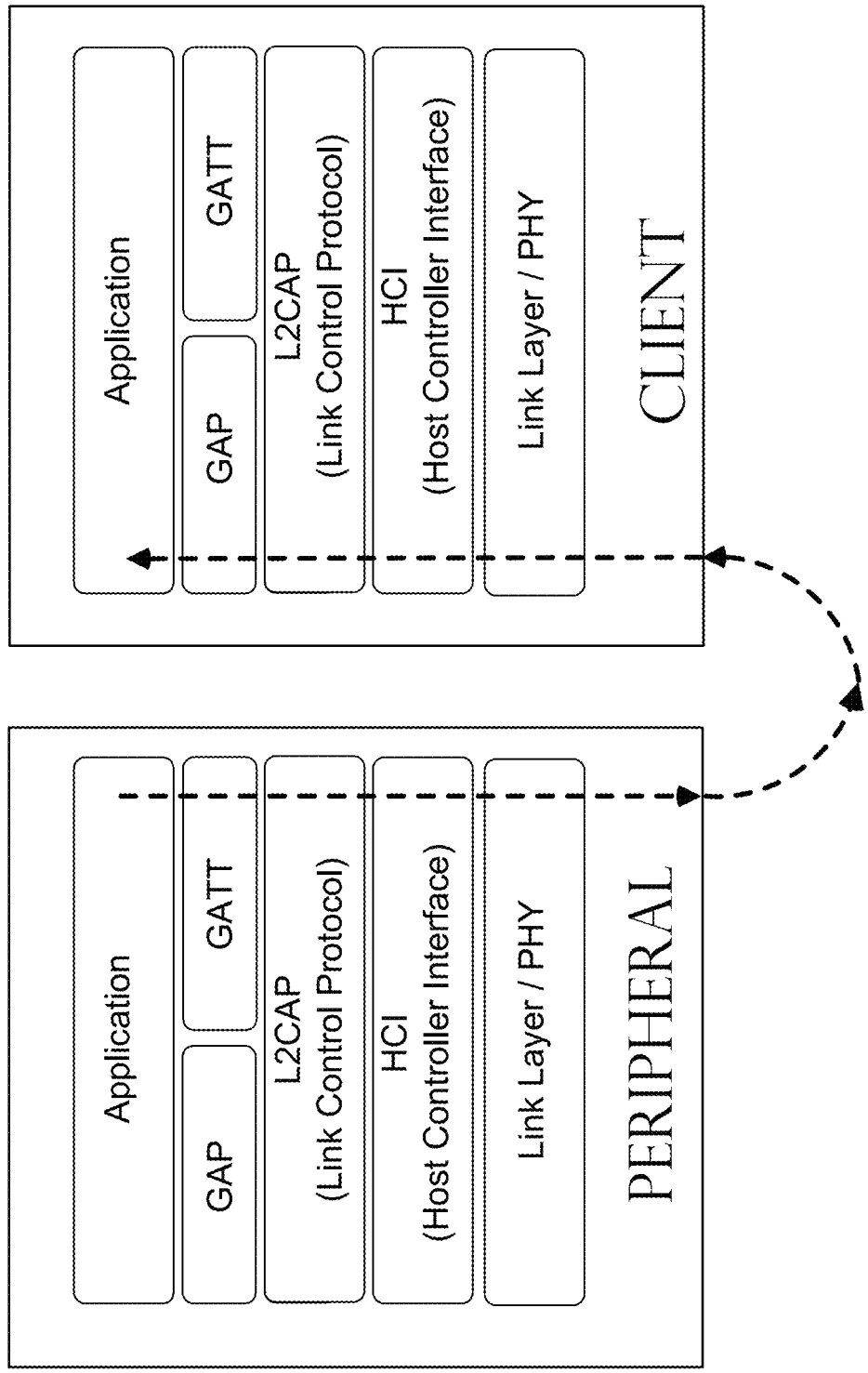
Figures 10B, 10C:
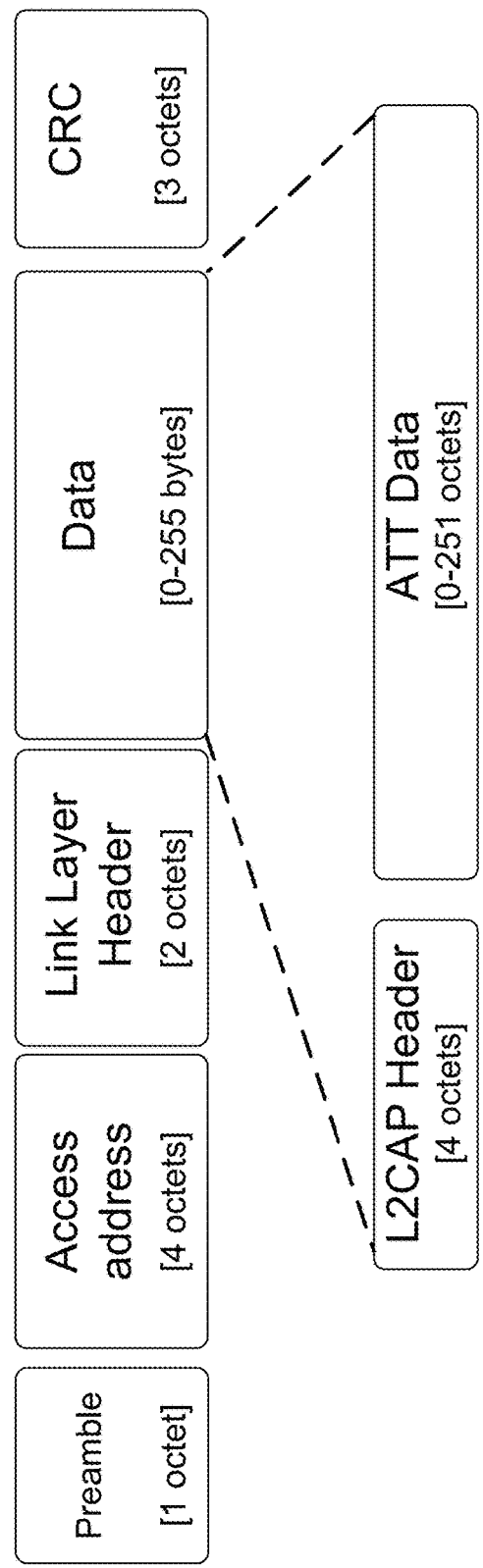
Figure 10D:
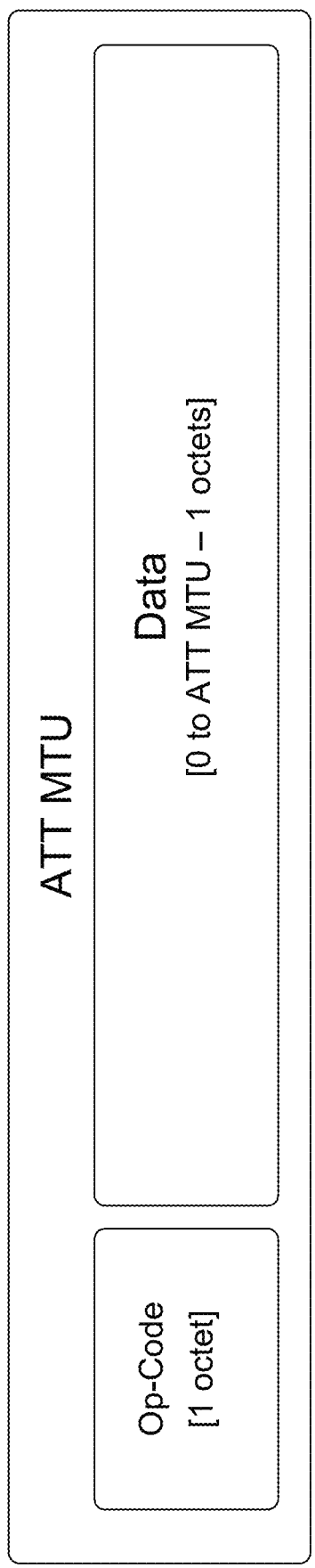
Figure 10E:
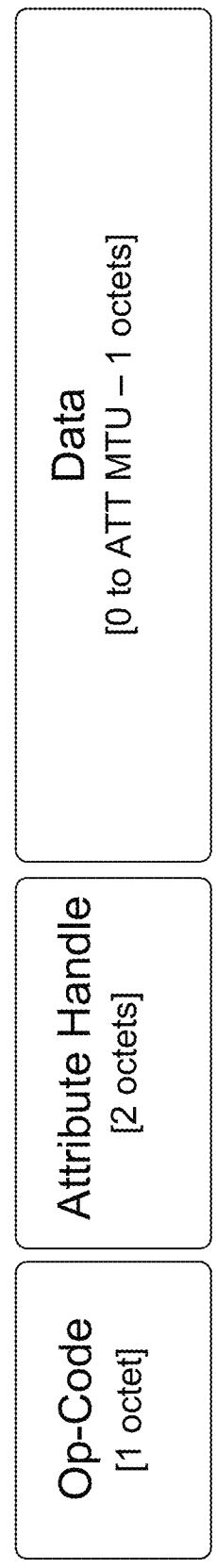
Figure 10H:
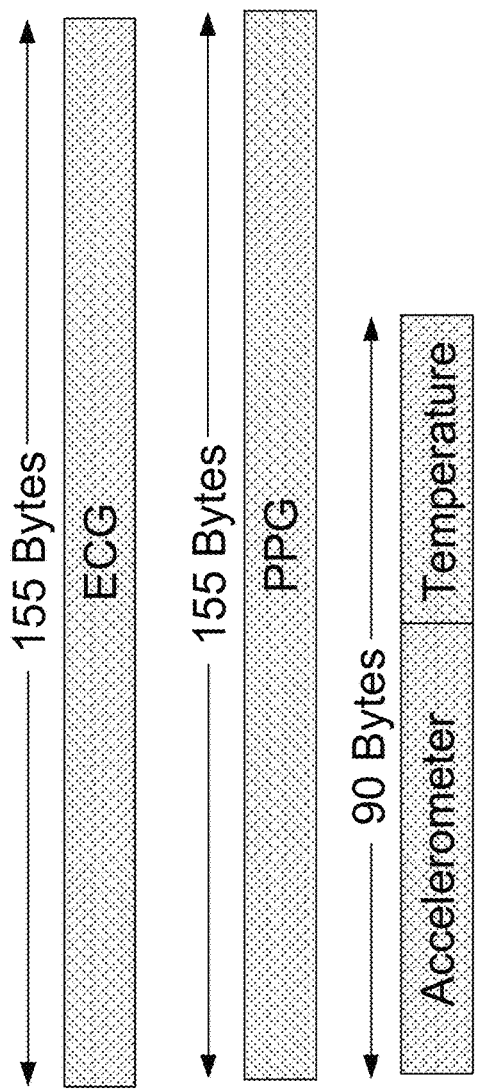
Figure 10I:
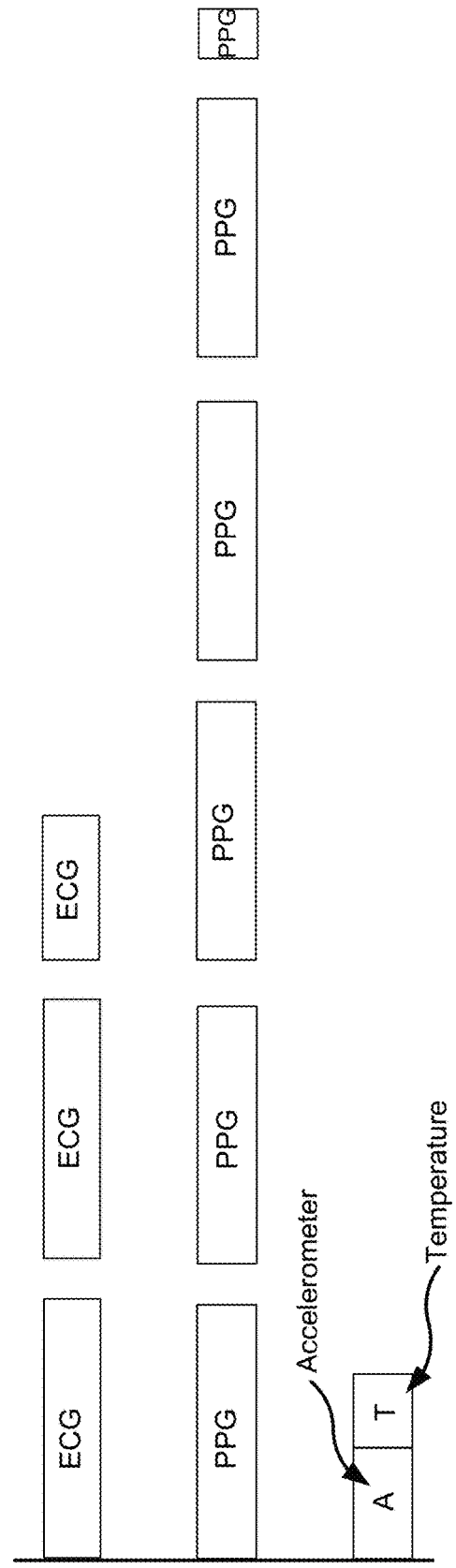
Figure 10K:
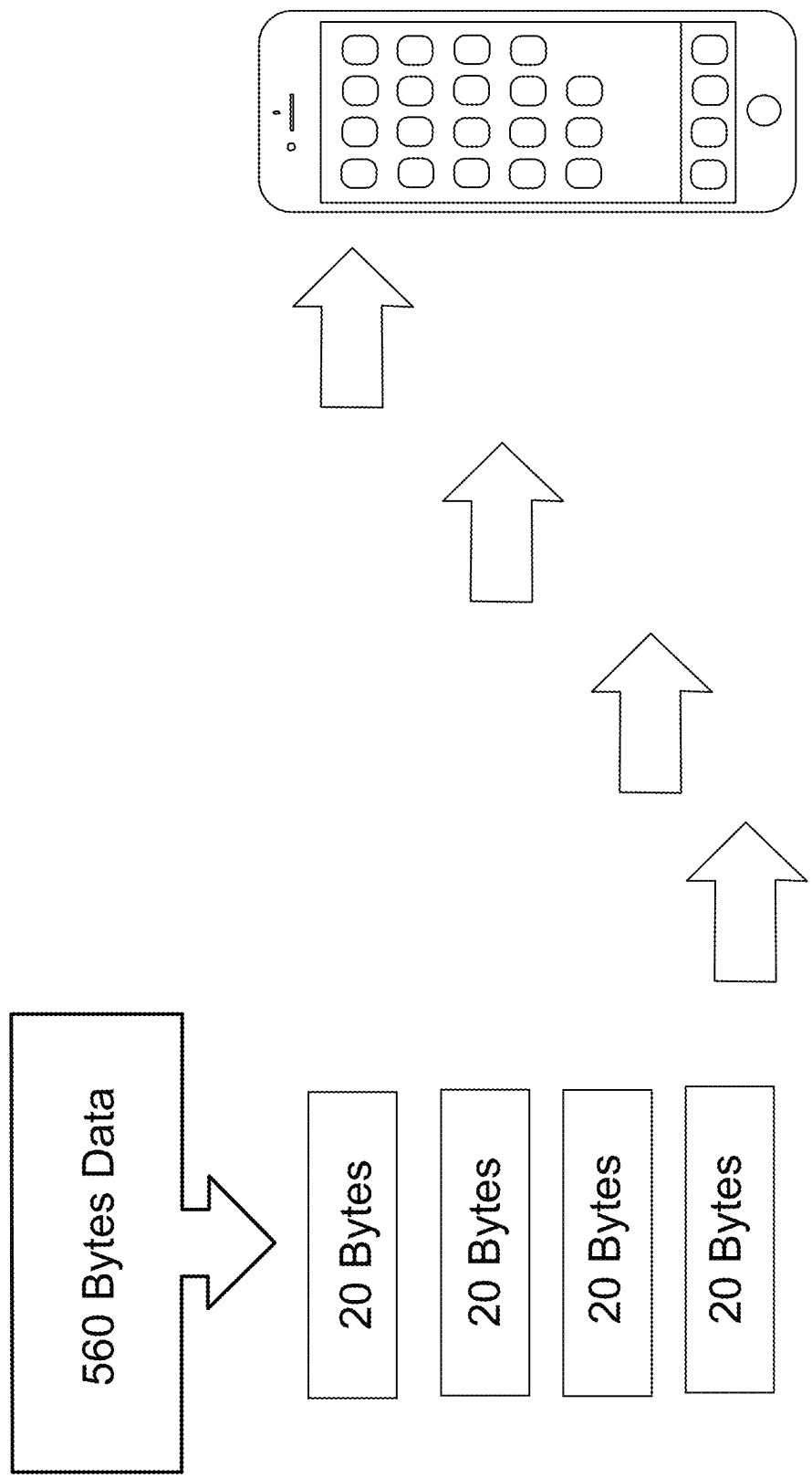

In using a Bluetooth system, to a hand-held mobile or other intermediate communication device 3002 (e.g. and hereafter, without limitation, a cell phone or mobile phone or tablet device or laptop or other portable communication device), a process and/or system as shown here may be used. An example may be or include without limitation Wi-Fi or Bluetooth or Bluetooth LE, which is Bluetooth Low Energy (Bluetooth LE, BLE, also marketed as Bluetooth Smart) which is a wireless personal area network technology. Using a BLE example, a Bluetooth LE Protocol Stack may be as set forth in FIG. 10A. Accordingly, a BLE 4.1 packet may be constructed using the format set forth in FIG. 10B. In BLE 4.1 a L2CAP (Link Control Protocol) uses four (4) bytes from the data payload as set forth in FIG. 10C. Additionally, the ATT Layer uses 3 more bytes as set forth in FIGS. 10D and 10E, which results in only 20 bytes being available left for data. This results in 21 bytes of overhead being used to send 20 bytes of data. The Packets and connection events used by BLE 4.1 is described in FIG. 10F1-10F3. The BLE 4.1 packet timing is set forth in FIG. 10F3 and it should be noted that 558 µs of overhead to send 150 µs of data, which means that only approximately 23% of the transfer is being utilized to transfer data.

BLE 4.2 may improve the throughput because it allows the payload to increase to 251 bytes from 27 bytes allowed by BLE 4.1. Consequently, the ATT Data increased from 20 bytes to 244 bytes. This is improvement is set forth in FIGS. 10G1 and 10G2. Accordingly, efficiency may increase significantly as only 558 µs of overhead is needed to send 1,952 µs of data, which improves the efficiency to 78%. Additional alternatives and implementations descriptions are shown in and relative to FIGS. 10H, 10I, 10J, and 10K.

A feature hereof may include an overall system including one or more devices 100 and computing resources (see FIGS. 3A and 4, for example) whether on-board device(s) 100, or separate, as for example in personal or mobile or hand-held computing devices (generally by FIGS. 3A and 4), the overall system then providing the ability for the physician or doctor to have immediate, in-office or otherwise on-site, hospital, hospice, clinic, etc., analysis and presentation of collected test or vital signs data. This would in some implementations allow for on-site data analysis from the device without utilization of a third party for data extraction and analysis.

Alternative implementations hereof may thus include one or more hardware and software combinations for multiple alternative data source interpretations. As noted above, a device 100 hereof includes hardware that monitors one or more of various physiologic parameters, then generates and stores the associated data representative of the monitored parameters. Then, a system which includes hardware such as device 100 and/or the parts thereof, and software and computing resources (FIG. 4, generally) for the processing thereof. The system then includes not only the collection of data but also interpretation and correlation of the data.

For example, an electrocardiogram trace that reveals a ventricular arrhythmia during intense exercise may be interpreted differently than the same arrhythmia during a period of rest. Blood oxygen saturation levels that vary greatly with movement can indicate conditions that may be more serious than when at rest, inter alia. Many more combinations of the four physiologic parameters are possible, and the ability of software hereof to display and highlight possible problems will greatly aid the physician in diagnosis. Thus, a system as described hereof can provide beneficial data interpretation.

Some of the features which can assist toward this end may be subsumed within one or more of operations 303 and 304 of FIG. 3, wherein data collected on a device 100 can rather simply be communicated/transmitted to computing resources (again, whether on-board device 100 or discrete therefrom as e.g., FIGS. 3A and/or 4). For an example, when a patient having had a device applied (operation 301) may return to a physician's office after a test period wherein data was collected (operation 302) the device is connected via one or more data transmission alternatives, as for example, USB to a computer (Windows or Mac) (generally with reference to FIGS. 3A and/or 4 and description thereof) in the office, allowing immediate analysis by the physician while the patient waits (note, the device 100 may first have been removed from the patient or might remain thereon pending transmission and analysis for determination of whether more data may be desired). In some implementations, data analysis time may be relatively quick, at approximately less than 15 minutes, less than 10 minutes, and less than 5 minutes in some implementations or even within seconds or parts of a second, and might be achieved with a user-friendly GUI (Graphic User Interface) to guide the physician through the analysis software.

The analysis/software package may be disposed to present the physician with results in a variety of formats. In some implementations, an overview of the test results may be presented, either together with or in lieu of more detailed results. In either case, a summary of detected anomalies and/or patient-triggered events may be provided, either as part of an overview and/or as part of the more detailed presentation. Selecting individual anomalies or patient-triggered events may provide desirable flexibility to allow a physician to view additional detail, including raw data from the ECG and/or from other sensors. The package may also allow data to be printed and saved with annotations in industry-standard EHR (Electronic Health Record) formats.

In one implementation, patient data may be analyzed with software having the one or more of the following specifications. Some alternative capabilities may include: 1. Data Acquisition; i.e., loading of data files from device; 2. Data Formatting; i.e., formatting raw data to industry standard file formats (whether, e.g., aECG (xml); DICOM; or SCP-ECG) (note, such data formatting may be a part of Acquisition, Storage or Analysis, or may have translation from one to another (e.g., data might be better stored in a compact format that may need translation or other un-packing to analyze)); 3. Data Storage (whether local, at a clinic/medical facility level or e.g., in the Cloud (optional and allows offline portable browser based presentation/analysis); 4. Analysis which inter alia, may include, e.g., noise filtering (High pass/Low pass digital filtering); and/or QRS (Beat) detection (in some cases, may include Continuous Wave Transform (CWT) for speed and accuracy); and/or 5. Data/Results Presentation, whether including one or more graphical user interface(s) (GUIs) perhaps more particularly with an overall Summary and/or General Statistics and/or Anomaly Summary of Patient triggered event(s); presentation of additional levels of detail whether of Strip view(s) of anomaly data by incident (previous, next) Blood Oxygen saturation, stress correlation or the like; and/or allowing care provider bookmarking/annotations/notes by incident and/or Print capability.

Further, on alternative combinations of hardware with proprietary software packages: (i) One on-device software package may be adapted to store the measurements from the data signals acquired from one or more of EKG/ECG (whether right leg and/or p-, qrs- and/or t-waves), or O2 saturation, or x-y-z acceleration, in a time concordant manner, so that a physician may access a temporal history of the measurements (say, in some examples, over a 1-2 week interval), which would provide useful information on what the patient's activity level was prior to, during, and after the occurrence of a cardiac event; (ii) an alternative to alternately manage the real-time transmission of the real-time measured parameters to a nearby station or relay; and/or, (iii) an off-device ECG analysis software aimed at recognizing arrhythmias.

The software mentioned above may be industry understood software provided by a 3rd party, or specially adapted for the data developed and transmitted by and/or received from a wearable device 100 hereof. Thorough testing using standard (MIT-BIH/AHA/NST) (Massachusetts Institute of Technology—Beth Israel Hospital/American Heart Association—Noise Stress Test) arrhythmia databases, FDA 510(k) approvals preferred. Such software may be adapted to allow one or more of automated ECG analysis and interpretation by providing callable functions for ECG signal processing, QRS detection and measurement, QRS feature extraction, classification of normal and ventricular ectopic beats, heart rate measurement, measurement of PR and QT intervals, and rhythm interpretation.

In many implementations, the software may be adapted to provide and/or may be made capable of supplying one or more of the following measurements:

TABLE 1

1. Heart Rate Min, Max and Average
2. QRS duration average
3. PR interval average
4. QT interval average
5. ST deviation average and, may be adapted to recognize a broad range of arrhythmias such as those set forth here:

TABLE 2A

1. SINUS RHYTHM
2. SINUS RHYTHM + IVCD
3. SINUS BRADYCARDIA
4. SINUS BRADYCARDIA + IVCD
5. SINUS TACHYCARDIA
6. PAUSE
7. UNCLASSIFIED RHYTHM
8. ARTIFACT

This first group of 8, Table 2A, given above are arrhythmia types that may be recognizable even if there is no discernible P wave. They are the ones typically recognized by existing products in the outpatient monitoring market that the devices, systems, and methods hereof propose to address.

A second set or group of arrhythmias; Table 2B below, may require a discernible and measurable P wave. Some implementations hereof may be adapted to be able to detect and recognize them, as device 100 may be able as described above to detect P waves, depending of course, and for example, on whether the strength of the P wave which may be affected by device 100 placement or patient physiology.

TABLE 2B

Figure 5A:
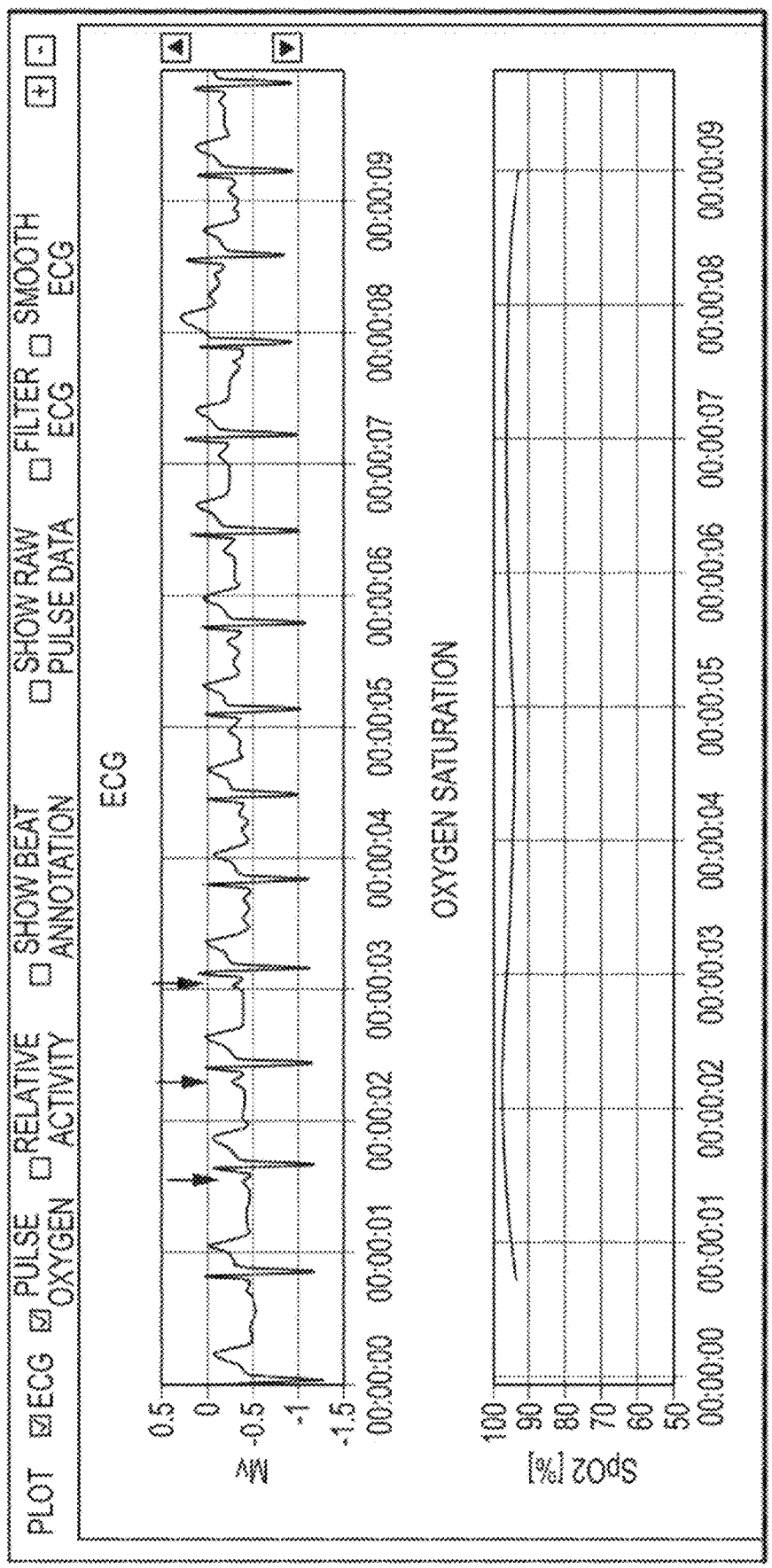
FIG. 5, which includes and is defined by sub-part FIGS. 5A-5D, provides alternative screenshots of alternative software implementations according hereto.

9. ATRIAL FIBRILLATION/FLUTTER SVR (slow)
10. ATRIAL FIBRILLATION/FLUTTER CVR (normal rate)
11. ATRIAL FIBRILLATION/FLUTTER RVR (rapid
12. FIRST DEGREE AV BLOCK + SINUS RHYTHM
13. FIRST DEGREE AV BLOCK + SINUS TACHYCARDIA
14. FIRST DEGREE AV BLOCK + SINUS BRADYCARDIA
15. SECOND DEGREE AV BLOCK
16. THIRD DEGREE AV BLOCK
17. PREMATURE ATRIAL CONTRACTION
18. SUPRAVENTRICULAR TACHYCARDIA
19. PREMATURE VENTRICULAR CONTRACTION
20. VENTRICULAR COUPLET
21. VENTRICULAR BIGEMINY
22. VENTRICULAR TRIGEMINY
23. IDIOVENTRICULAR RHYTHM
24. VENTRICULAR TACHYCARDIA
25. SLOW VENTRICULAR TACHYCARDIA Further in alternative software implementations; some sample screenshots are shown in FIG. 5. A first such alternative is shown in FIG. 5A, which is an example screenshot showing ECG and Oxygen Saturation data taken by using a patch device such as a device 100 hereof. An extremely clean signal is shown (no filtering or smoothing has been done on this data). Distinct p-waves are also shown (3 of which are shown as an example with arrows). P wave detection can be extremely important for ECG anomaly detection. Oxygen Saturation, as measured by Pulse Oxymetry, is shown on the bottom plot. This is data taken by a device on the chest and is taken in time concordance with the ECG data.

Figure 5B:
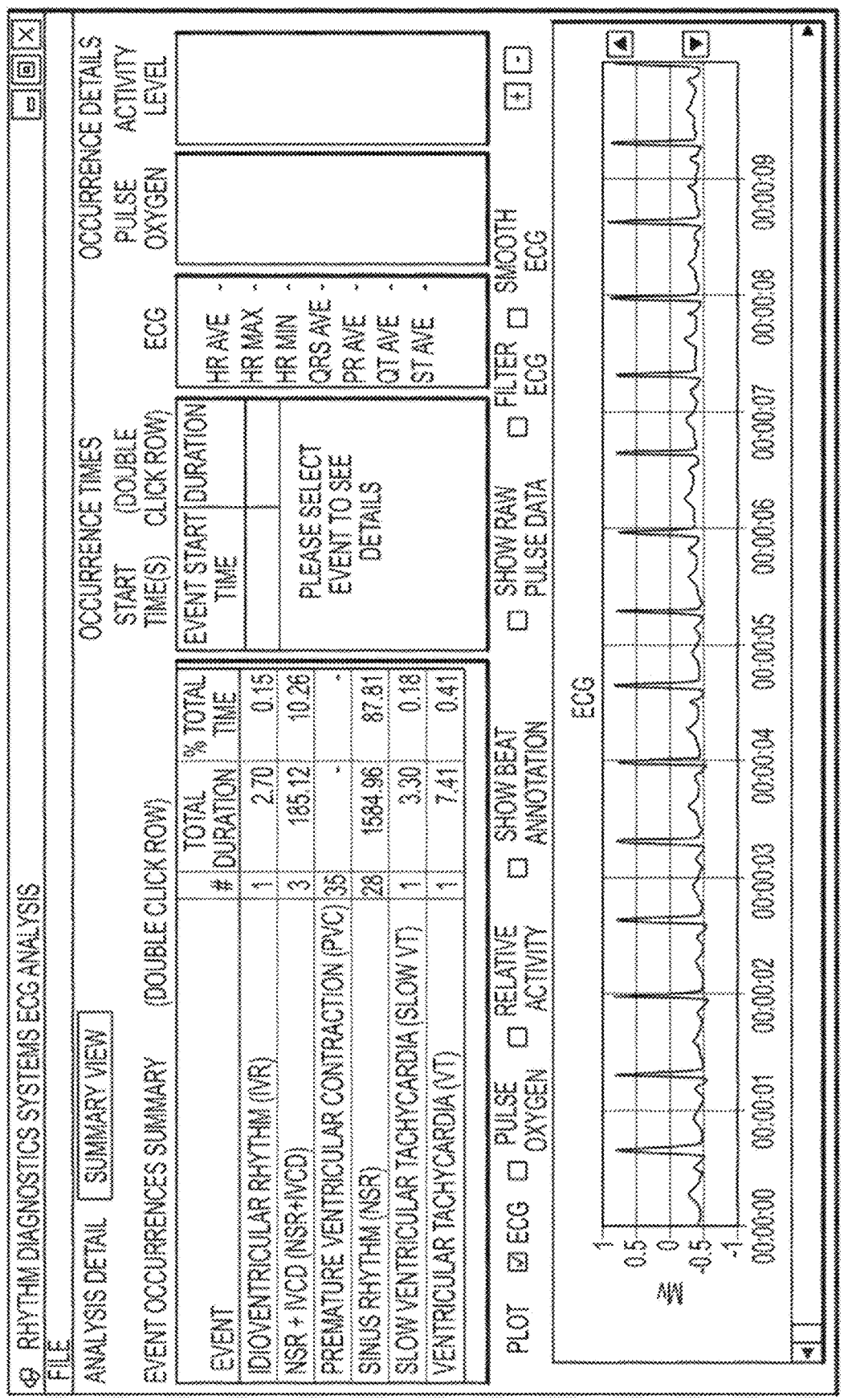

Another alternative is shown in FIG. 5B, which is an example screenshot of Analysis Software. This is a sample of ECG data taken from the MIT-BIH Arrhythmia Database, Record 205. As analyzed by the Analysis system hereof, we see in the Event Occurrences Summary list (top, left) five (5) anomaly types (plus normal sinus rhythm). This list also shows the number of occurrences of each anomaly, total duration of the anomaly in the complete ECG, and the percent time this anomaly occurs in the complete ECG. To view specific instances of each anomaly, the user double clicks the specific row in the Event Occurrences Summary list, as shown in FIG. 5C.

Figure 5C:
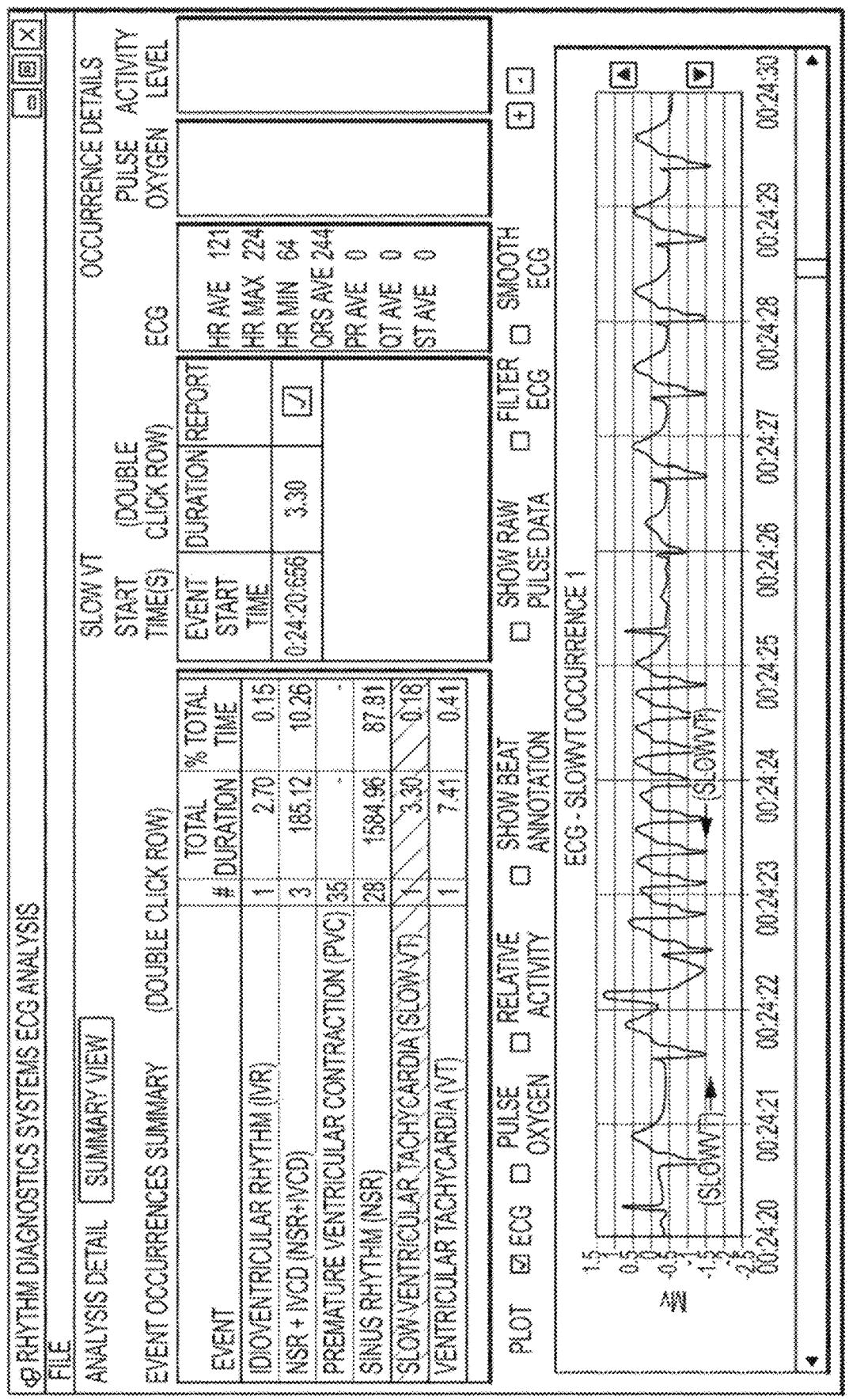

As introduced, FIG. 5C is an example screenshot showing specific instance of Ventricular Tachycardia. The ECG plot automatically navigates to the specific time in the ECG waveform and marks the beginning and end of the event. More detailed data about this specific event is now shown in the Occurrence Details: HR Average, HR Max, etc. for the duration of this event. To show the instances of another anomaly in this ECT, the user can click on the Premature Ventricular Contraction (PVC) row of the Event Occurrences Summary, as shown FIG. 5D.

Figure 5D:
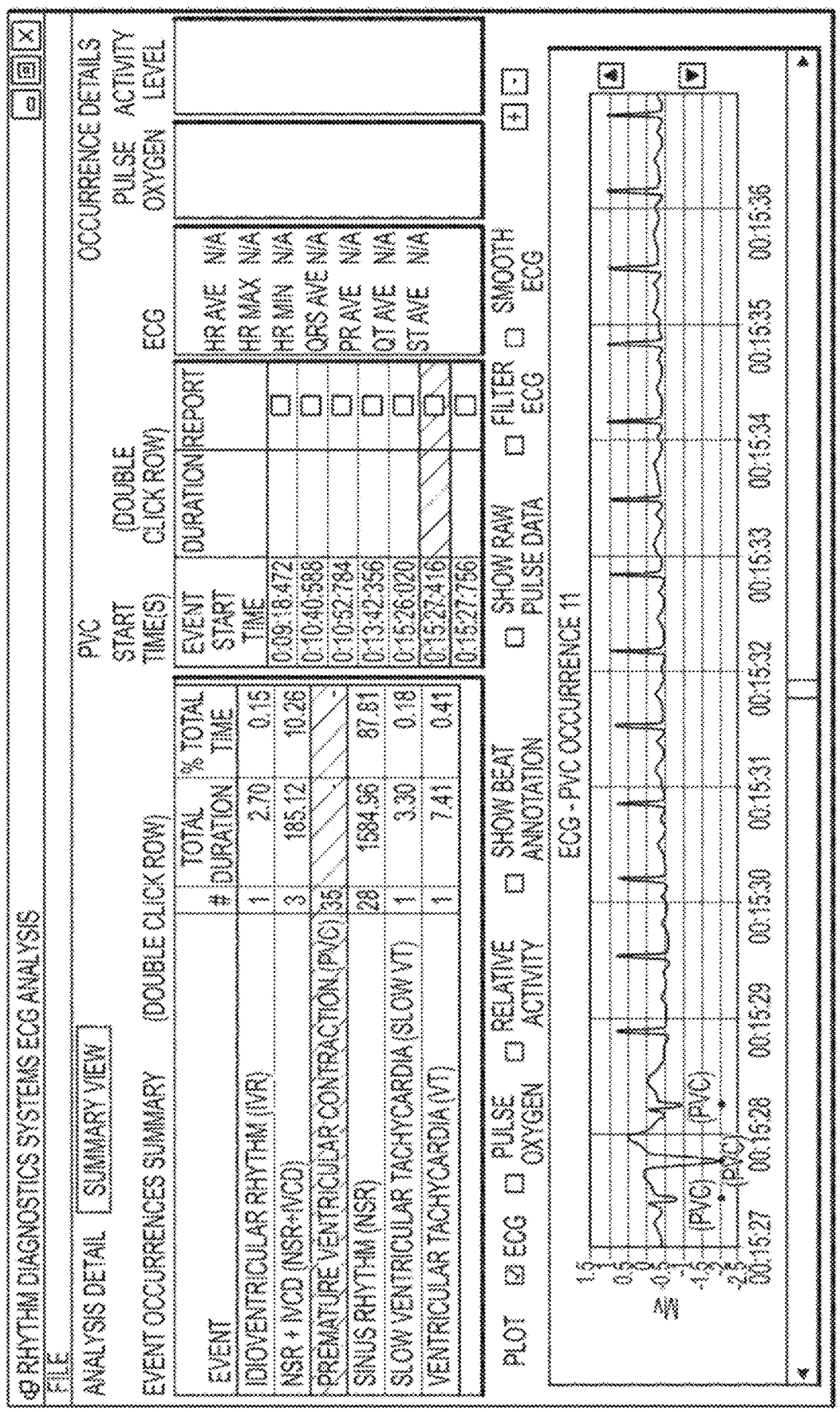

As introduced, FIG. 5D is an example screenshot showing specific instance of Premature Ventricular Contraction. This shows occurrences of the PVC. The Start Times list (middle top) shows all instances of PVC occurrences in this ECG and lists the start time for each occurrence. In this case, the user can click on the PVC that starts at 00:15:27 (the 11$^{th}$ occurrence). The ECG plot is automatically taken to this point in time to show and indicate the PVC instances in the waveform. Since there are 3 instances of a PVC in this timeslot, all 3 occurrences are marked. As mentioned above, in one aspect of the developments hereof, ECG signals collected in time concordance with pulse oximetry signals may be used to reduce the noise in the pulse oximetry signals and to permit the calculation of values for oxygen saturation, particularly in circumstances where sensors pulse oximetry data are placed on noise-prone locations of a patient, such as the chest. In some implementations, this aspect may be implemented by the following steps: (a) measuring an electrocardiogram signal over multiple heart beats; (b) measuring one or more pulse oximetry signals over multiple heart beats such that the electrocardiogram signal and the one or more pulse oximetry signals are in time concordance over one or more heart beats; (c) comparing a portion of the electrocardiogram signal and the one or more pulse oximetry signals in time concordance over one or more heart beats to determine a constant component and a primary periodic component of each of the one or more pulse oximetry signals; and (d) determining oxygen saturation from the constant components and primary periodic components of the one or more pulse oximetry signals. Measurement of the ECG signals and pulse oximetry signals may be implemented by implementations of devices hereof. In particular, pulse oximetry signals may be a reflective infrared signal and a reflective red light signal collected by a photodetector in a device hereof. Alternatives may include other colors, as for example green in addition to or in lieu of one or both of red and infrared. Such alternatives are described further below.

Intervals of pulse oximetry signals corresponding to heart beats may be determined by comparing such signals to the time concordant ECG signals. For example (not intended to be limiting), successive R-wave peaks of a time concordant ECG signal may be used to identify such intervals, although other features of the ECG signal may be used as well. Once such intervals are identified, values at corresponding times within the intervals may be averaged to reduce signal noise and to obtain more reliable values for the constant components (sometimes referred to as the "DC components") and the main periodic components (sometimes referred to as the "AC components") of the pulse oximetry signals, e.g. Warner et al, Anesthesiology, 108: 950-958 (2008). The number of signal values recorded in an interval depends on the signal sampling rate of the detectors and processing electronics employed. Also, as the intervals may vary in duration, the averaging may be applied to a subset of values in the intervals. As described below, oxygen saturation values may be computed from such DC and AC components using conventional algorithms. The number of heart beats or intervals over which such averages may be computed may vary widely, as noted below. In some implementations, signals from one or more heart beats or intervals may be analyzed; in other implementations, signals from a plurality of heart beats or intervals may be analyzed; and in some implementations, such plurality may be in the range of from 2 to 25, or in the range of from 5 to 20, or in the range of from 10 to 20.

As described, a method of pulse oximetry measures photoplethysmogram (PPG) signals at red and infrared wavelengths. The DC or mean value is estimated and subtracted, and the ratio of AC or pulsatile signal is estimated and/or averaged. Linear regression between the two signals can be used as described below. However, performance is limited because similar noise exists in both the red and infrared signals. Photoplethysmography taken using green light (~550 nm) is more resilient to motion noise because the light is absorbed much more by blood than by water or other tissue. However, the difference between oxygenated and deoxygenated blood in the green region of the spectrum is much less than red. In an alternative, a green PPG signal (or long time average of red/IR (see below)) may be used to determine the shape of the pulsatile signal. A weighted average of any number of different wavelengths (such as green, red and infrared) may be used to estimate the shape of the pulsatile waveform.

In further alternative implementations, a linear regression algorithm for Oxygen Saturation may be used. As such, either or both the patient's ECG signal and/or a green (or other color) LED PPG signal may be used. For a first example, an ECG signal may be used to determine when heart beats occur. The beat locations allow correlated time averaging of each of the two photoplethysmogram signals. A linear regression of the ensemble averages may then be used to determine the linear gain factor between the two signals. This gain factor can be used to determine the patient oxygen saturation.

If/when in the alternative and/or in addition, photoplethysmography (PPG) using green light (~550 nm) is implemented, the PPG signal may be used to determine the shape of the pulsatile signal. This lower-noise signal may then be used as the independent variable for linear regression with both the red and infrared signals. The ratio of these two regression results is an estimate of the correlation between the red and infrared signals. Noise can be reduced by ensemble averaging over multiple heart beats as disclosed herein (see e.g., description of frames below). In addition to or instead of using an ECG signal to determine beat timing, the green wavelength PPG signal may be used. Alternatively, a weighted average of any number of different wavelengths (such as green, red and infrared or long time average of red/IR (see below)) may be used. The ensemble averaging may be improved by detecting and removing outlier beats, possibly by discarding beats that have less correlation to the estimated ensemble average than others, or by estimating noise and weighting beats from areas of high noise less. Noise can also be improved through longer averaging periods.

As such, included may be a method for health monitoring comprising: (a) determining from either or both a user's ECG and/or a first photoplethysmogram PPG signal and/or a weighted combination of wavelengths when heart beats occur; (b) time averaging the first photoplethymogram PPG signal to generate a first pulse shape template or dataset; (c) time averaging each of two additional photoplethysmogram signals correlated to the beat locations; one of the additional signals being red, the other additional signal being IR; (d) generating ensemble averages for each of the red and IR signals; (e) comparing each of the red and IR ensemble averages to the first pulse shape template or dataset; (f) using a linear regression of each of the red and IR ensemble average comparisons to the first pulse template or dataset to determine the linear gain factor between the two signals; and, (g) determining from the gain factor the patient oxygen saturation.

In a similar view; included may be a method for determining pulse oxygenation; comprising: (a) detecting heart beats; using ECG, using green, or using a weighted combination of wavelengths; (b) generating one or more of a first pulse shape template or a dataset representing a first pulse shape, including using green wavelengths, an ensemble average of green over approximately the same amount of time as for either red or IR, an ensemble average of multiple wavelengths over approximately the same amount of time as for either red or IR, or an ensemble average of multiple wavelengths over significantly longer than the amount of time as for either red or IR; can use ensemble average gives beat shape; or a long time average of a single wavelength of any color; (c) obtaining a red pulse shape template or dataset representing same and an IR pulse shape template or dataset representing same, and compare each of these to the first pulse shape above; and, (d) correlating via linear regression between red ensemble average with the first pulse shape template or dataset to the IR ensemble average with the first pulse shape or dataset, where the ratio of these correlations is then used as the AC ratio for oxygen saturation.

The pulse shape template or dataset is in some implementations may be similar to the reference frame template described herein as well in that the pulse shape template represents a long-term ensemble average of the PPG signal. However, a difference is that the reference frame template described elsewhere herein was there designated for pulse transit time, while in the present description related to a first pulse shape or dataset or the like, is for oxygen saturation.

While a first method may be one where green light is used for the beat detection, other methods will be viable as well, as where ECG is used for heartbeat detection. Further, the alternatives include green or a long red and IR average used for the first pulse shape, and a shorter red and IR is used for the oxygen saturation comparisons to the first pulse shape. It may be helpful to understand that a long red and IR average used for the first pulse waveform shape (or dataset) is in relation to the relatively shorter red/IR signals used for the oxygen saturation measurement. Because the shape is expected to change slower than the oxygen saturation, a long average can be used for the shape, while still using a shorter average (and thus getting faster response times) for the oxygen saturation part.

Note, green has been found desirable because it has a high signal to noise ratio; the pulse signal is strong relative to other possible motion noise. However, other wavelengths could be used instead of green, i.e. green could be replaced by other colors in the spectrum of light, keeping in mind, some colors will behave better or other colors worse in the relationship of signal to noise. Note, other colors, even without a desirable signal to noise ratio can be used herein or herewith. Similarly, the preference for red and/or IR wavelengths has been that it has been found that red and/or IR have provided good relative reflectivity to the particular oxygenation of hemoglobin blood in a test subject. Each of: oxygenated blood reflects an effective amount comparatively of red light and de-oxygenated blood reflects an effective amount comparatively of infrared, IR, light. Other colors can be used instead of red and IR throughout, though the other colors may have less (or more) effectiveness in particular applications. It should also be noted that as understood in the art, whenever any particular color of light is described, a number of discrete wavelengths may be understood as falling within such definition, and that utility may fall within or outside the definition, though preferences may be identified by general color. Thus, colors other than green or red or IR are understood to be used and/or such color selection may be limited only by minimal effectiveness in either signal to noise ratio and/or reflectiveness related to oxygenation or other utility.

ECG or green PPG (or like) or long time average of red/IR (see below) data may be recorded in time-concordance with two or more photoplethysmographs of different light wavelengths. The heart beats are detected in the ECG or green PPG signal. These heart beats allow for definition of a 'frame' of photoplethysmogram data for the time between two adjacent heart beats. Two or more of these frames can then be averaged together at each point in time to create an average frame for the time interval. Because the photoplethysmogram is correlated with the heartbeat, the photoplethysmograph signal is reinforced by this averaging. However, any motion artifact or other noise source that is uncorrelated in time with the heartbeat is diminished. Thus, the signal-to-noise ratio of the average frame is typically higher than that of the individual frames.

Having constructed an average frame for at least two photoplethysmographs of different light wavelengths, linear regression can then be used to estimate the gain between the two average frame signals. This gain value may be used to estimate blood oxygen saturation information or other components present in the blood such as hemoglobin, carbon dioxide or others. The process may be repeated for additional and/or alternative light wavelengths in order to do so.

Exemplar/alternative methods hereof may include determining the gain between particular and/or discrete signals, as between the red and IR and/or green frame signals, if/when such may be used. These may be found by averaging the two frames together first. This may result in a signal with reduced noise. The gain is found by performing linear regression of the red versus combined and IR versus combined and then finding the ratio of these two results; or linear regression of the red versus combined with green and IR versus combined with green and then finding the ratio of these two results; or linear regression of red versus green and IR versus green and then finding the ratio of these two results; or by linear regression of combining green with each of red and IR and using the ratio of these results.

Another method involves selecting a possible gain value, multiplying the average frame signal by it, and determining the residual error with respect to an average frame of a different wavelength. This process may be repeated for a number of potential gain values. While simple linear regression finds the global minimum gain value, this method allows for finding local minima. Thus, if it is likely that the global minimum represents correlation caused by motion artifact, venous blood movement or another noise source, it may be ignored, and a local minimum may be selected instead.

Yet another method uses an ensemble average of the red and/or IR signals over a much longer time to determine the pulse waveform shape, then fitting shorter time averaged signals to that waveform shape. Basically, the green light signal or ECG signal described above may be replaced with a long time average of red/IR.

As mentioned above, patient wearable devices hereof for implementing the above aspects may be particularly useful for monitoring oxygen saturation in noisy regions for such measurements, for example, where there is significant local skin movement, such as the chest location.

Figure 6A:
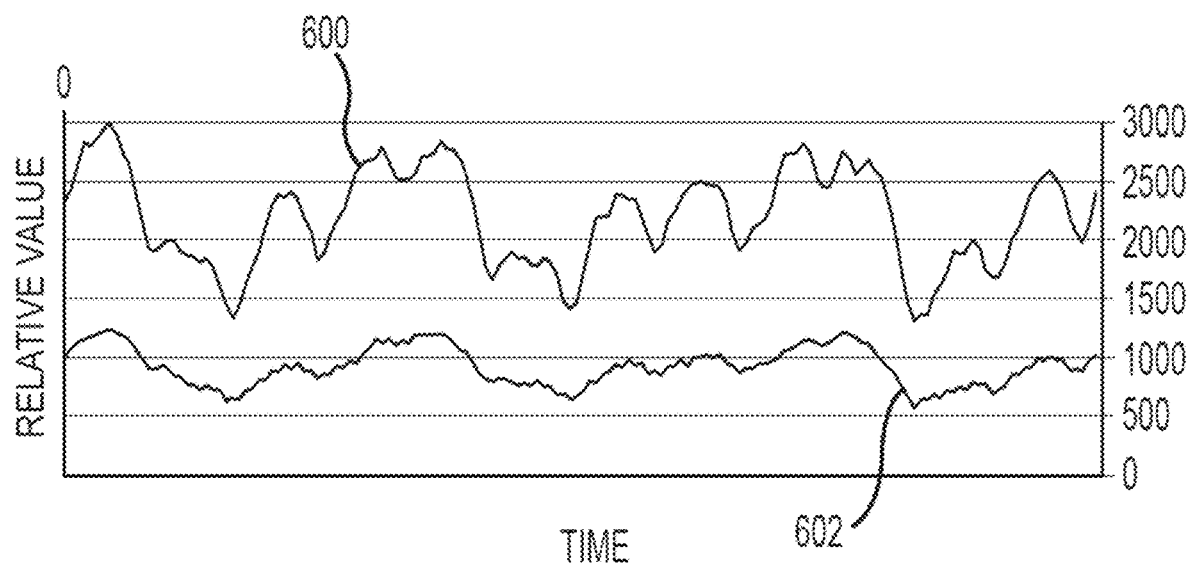
FIGS. 6A and 6B illustrate features of one embodiment for measuring oxygen saturation using pulse oximetry signals and electrocardiogram signals.
Figure 6B:
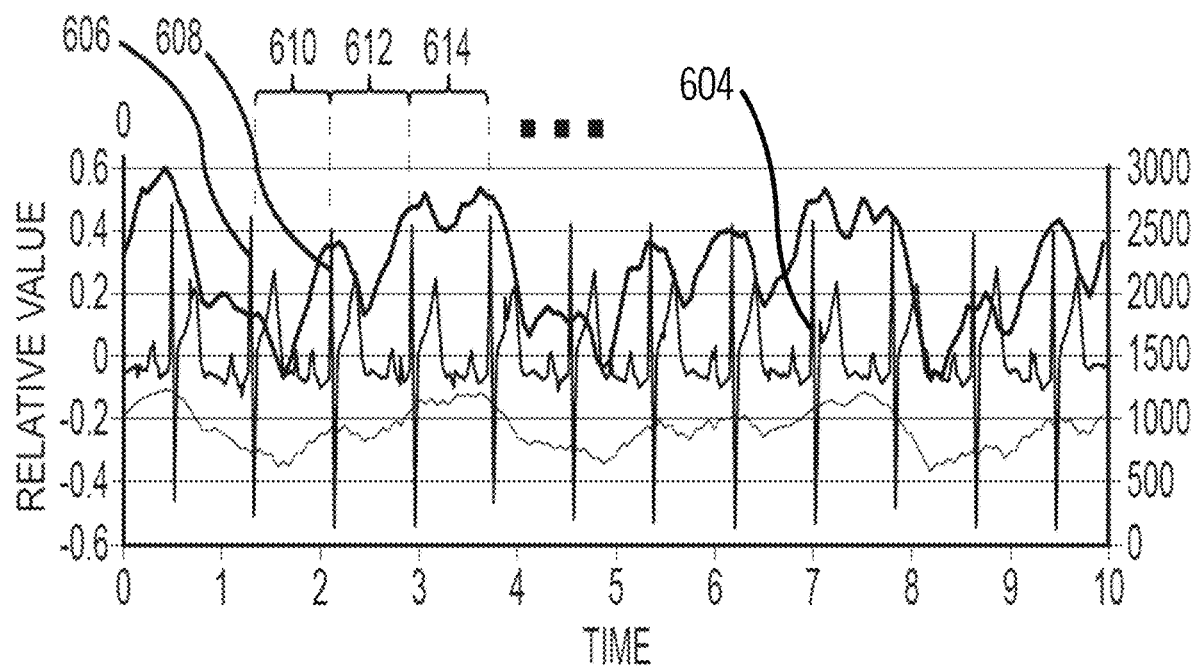
Figure 6C:
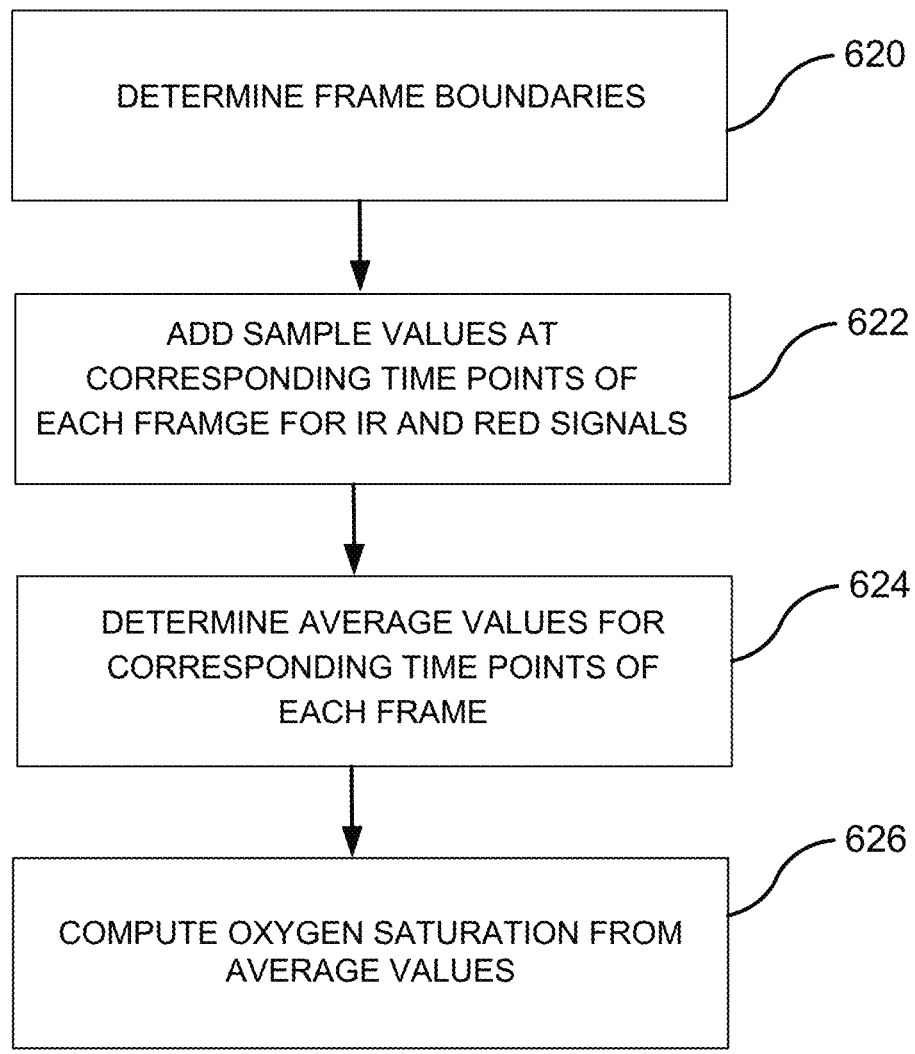
FIG. 6C is a flow chart showing steps of one embodiment for determining oxygen saturation values.

One implementation of the above aspect hereof is illustrated in FIGS. 6A-6C. In FIG. 6A, curve A (600) illustrates time varying output of the photodiode of a device hereof for infrared (IR) reflection and curve B (602) illustrates time varying output of the photodiode of the device for red light reflection. In some implementations, the skin is alternatively illuminated by the red and IR LEDs to generate the signals collected by the same photodiode. In FIG. 6B, time synchronized (i.e. time concordant) ECG data (or alternatively/additionally green PPG data or long time average of red/IR as introduced above), illustrated by curve C (604), is added to the plot of FIG. 6A. Peak values in the ECG data (e.g. peaks 606 and 608) (or green PPG or long time average of red/IR data, see above) may be used to define frames or intervals of pulse oximetry data. Additional consecutive frames or intervals are indicated by 612 and 614, and further frames may be similarly determined. In accordance with this aspect, pulse oximetry data from a plurality of frames is collected. The magnitude of the plurality may vary widely depending on particular applications. In some implementations, the plurality of frames collected is from 5 to 25; in one implementation, a plurality is between 8 and 10 frames. Typically, frames or intervals of pulse oximetry data contain different numbers of signal samples. That is, output from the sensors may be sampled at a predetermined rate, such a 32 samples per second. If the time between ECG (or green PPG or long time average of red/IR) peaks varies, then the number of samples per frame will vary. In one implementation, features in the ECG (or green PPG or long time average of red/IR) data serving as the starting points of a frame are selected so that an associated peak in the pulse oximetry data is approximately in the mid-point, or center, of the frame, after which a predetermined number of signal samples are recorded for each frame. Preferably in this implementation, the predetermined number is selected to be large enough to ensure that the pulse oximetry signal peak is roughly mid-frame. Sample values corresponding to time points above the predetermined value are not used. After a plurality of frames of data is collected, averages of the values at corresponding time points of the frames are computed. The values from such averages AC and DC components of the pulse oximetry data are determined and are then used to compute relative oxygen saturation by conventional methods, such as the ratio-of-ratios algorithm, e.g. Cypress Semiconductor document No. 001-26779 Rev A (Jan. 18, 2010). This basic procedure is summarized in the flow chart of FIG. 6C. First, frame size (in terms of number of samples) is determined (620). Next, values of samples at corresponding time points within each frame are summed (622), after which average values for each time point of each frame are computed (624) which, in turn, give the AC and DC components of IR and red and/or green light reflection with reduced noise. In some implementations, values for these components can be used to compute oxygen saturation using conventional algorithms (626). Relative values for oxygen saturation may be converted into absolute values by calibrating the measurements for particular implementations. Calibration may be carried out in controlled environments where individuals are exposed to varying atmospheric concentrations of oxygen and measured oxygen saturation values are related to corresponding oxygen levels.

In addition to the above implementation for comparing ECG and/or green PPG or long time average of red/IR signals with pulse oximetry signals, a range of other implementations for such comparing is within the comprehension of those of ordinary skill in the art. For example, in order to find peaks of the AC component of pulse oximetry signals in the presence of noise, features of the time concordant ECG signal that are located at characteristic times preceding and succeeding the pulse oximetry maximum and/or minimum values may be used to reliably determine the pulse oximetry peak and minimum values when averaged over a plurality of heart beats (without the need to average all values of the pulse oximetry signal over the heart beats). For example, if, within an interval, the R wave peak of an ECG signal characteristically preceded a pulse oximetry signal maximum by x milliseconds and trailed a pulse oximetry signal minimum by y milliseconds, then the essential information about the AC component of the pulse oximetry signal may be obtained by repeated measurements of just two values of pulse oximetry signals.

Figure 6D:
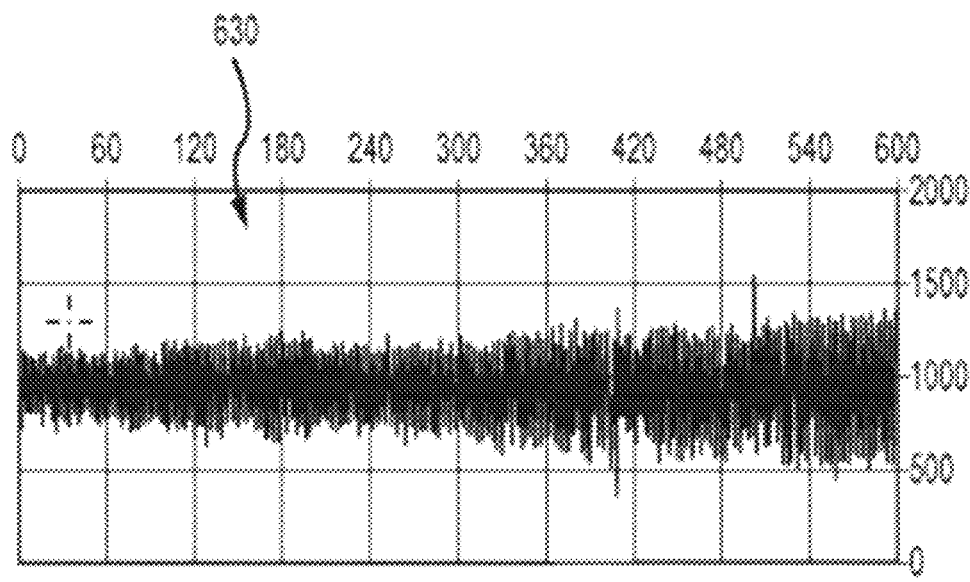
FIGS. 6D and 6E illustrate an embodiment for determining depth of respiration values.
Figure 6E:
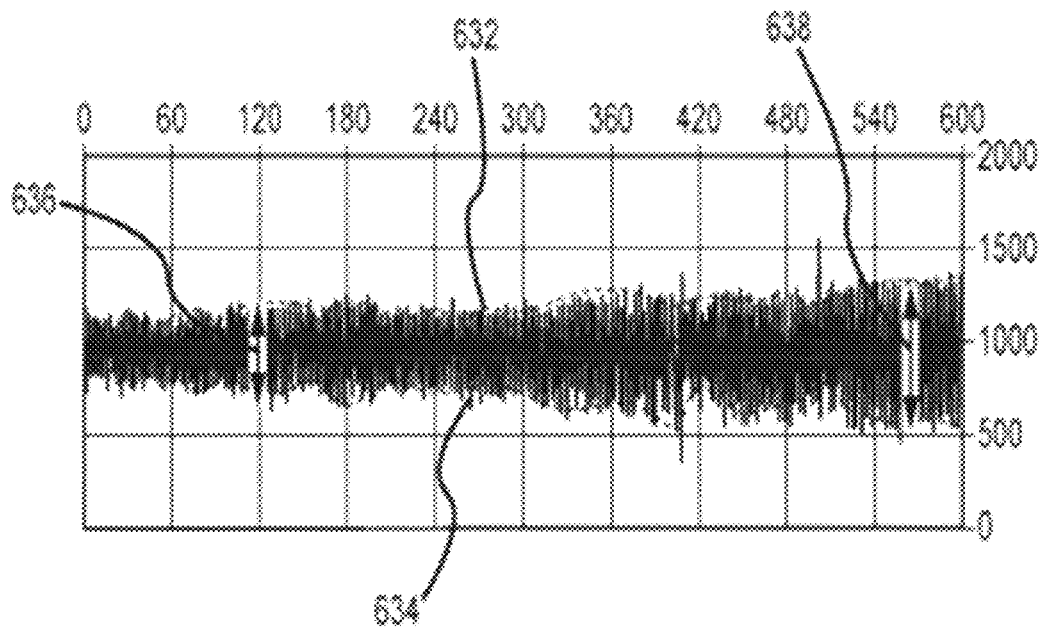

In some implementations, values for IR or red reflection measured by the photodiode may be used to estimate depth and/or rate of respiration. In FIG. 6D, a curve (630) of Red or IR or green values over time is illustrated. In FIG. 6E, maximum values and minimum values of curve (630) are shown by dashed curves (632) and (634), respectively. The difference between the maximum and minimum values at a time point is monotonically related to the depth of breath in an individual being monitored. Thus, as illustrated, breaths at time (636) are shallower than those at time (638). In some implementations, depth of breath versus time may be computed and monitored in an individual. Over time, the rate of respiration can be evaluated from the curve of maximum and minimum values over time.

Moreover, moving from an appreciation of a derivation of a respiration waveform from ECG R-S amplitude and/or R-R intervals, it has been found that a PPG and/or pulse oximeter as described herein can be used to relatively directly estimate a respiration waveform. As the chest expands and contracts during breathing, the motion hereof shows up as a wandering baseline artifact on the PPG signals. The respiration signal may be isolated by filtering out the PPG data to focus on the breathing/respiration signal. This may be particularly so with a chest-mounted PPG.

In addition, a chest mounted accelerometer may also or alternatively be used to measure the respiration waveform, especially when the user is lying on his/her back. As the chest expands and contracts, the chest accelerates up and down (or transversely, or otherwise depending upon orientation), which can be measured by the accelerometer.

Either of these, PPG and/or accelerometer, devices and/or methods may be used discretely or in combination with each other and/or with the above-described ECG-based respiration estimation technique. Using multiple methods may improve accuracy when compared to estimates based on a single method. Respiration rate and depth may then be estimated from the respiration signal using time-domain and/or frequency domain methods.

In some implementations, heart beat timing (e.g., from ECG) and PPG signals can be used to determine pulse transit time; i.e., the time for the pressure wave to travel from the heart to other locations in the body. Measurements of pulse transit time may then be used to determine or estimate blood pressure. Note, the heartbeat timing, ECG and/or PPG signals may be generated by conventional or other to-be-developed methods, systems or devices, or may be developed by wearable devices such as those otherwise described herein. I.e., the algorithms hereof may be separately usable, as well as being usable in the wearable cardiac device.

As disclosed herein elsewhere, the PPG signals of several heart beats may be averaged by correlating each with a respective heartbeat. The result is a PPG frame where the heart rate-correlated PPG signal is reinforced while uncorrelated noise is diminished. Moreover, because the PPG frame is already correlated to the timing of the heartbeat, pulse transit time may be estimated by determining the location of either the peak or minimum with respect to either the beginning or end of the frame itself. This may be done either by finding the minimum and/or maximum sample(s), or by interpolating the signal to find points between measured samples. For example, interpolation may be done with a quadratic fit, a cubic spline, digital filtering, or many other methods.

The pulse transit time may also be estimated by correlating the PPG frame with a sample signal. By shifting the two signals with respect to each other, the time shift resulting in the maximum correlation may be determined. If the sample signal is an approximation of the expected PPG frame, then the time shift with maximum correlation may be used to determine the pulse transit time.

Figure 7A:
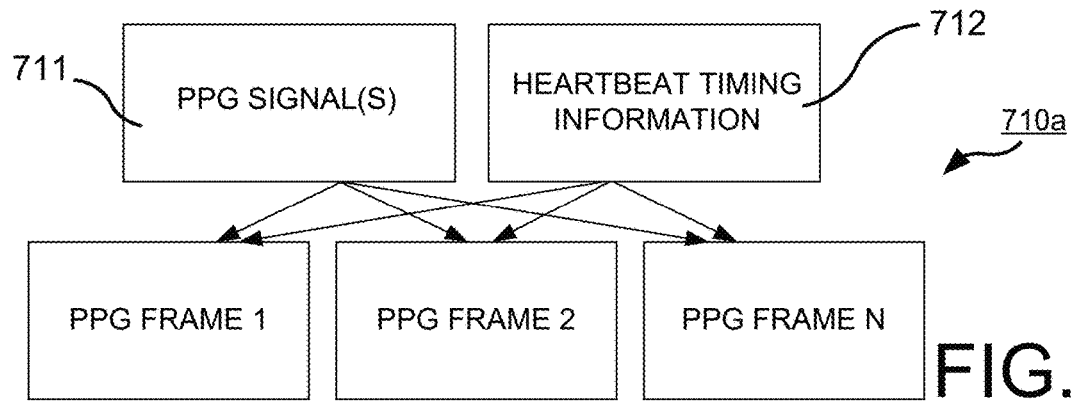
FIGS. 7A, 7B and 7C set forth flow diagrams for alternative methodologies hereof.
Figure 7B:
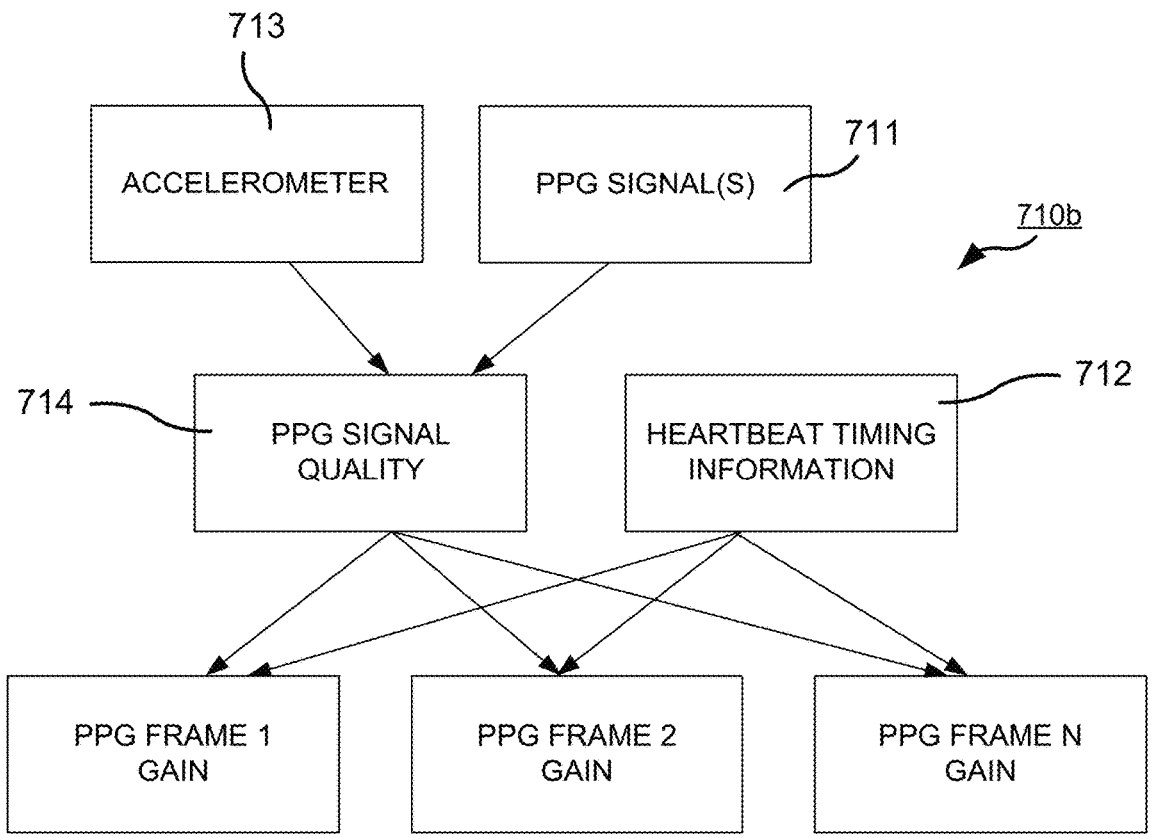
Figure 7C:
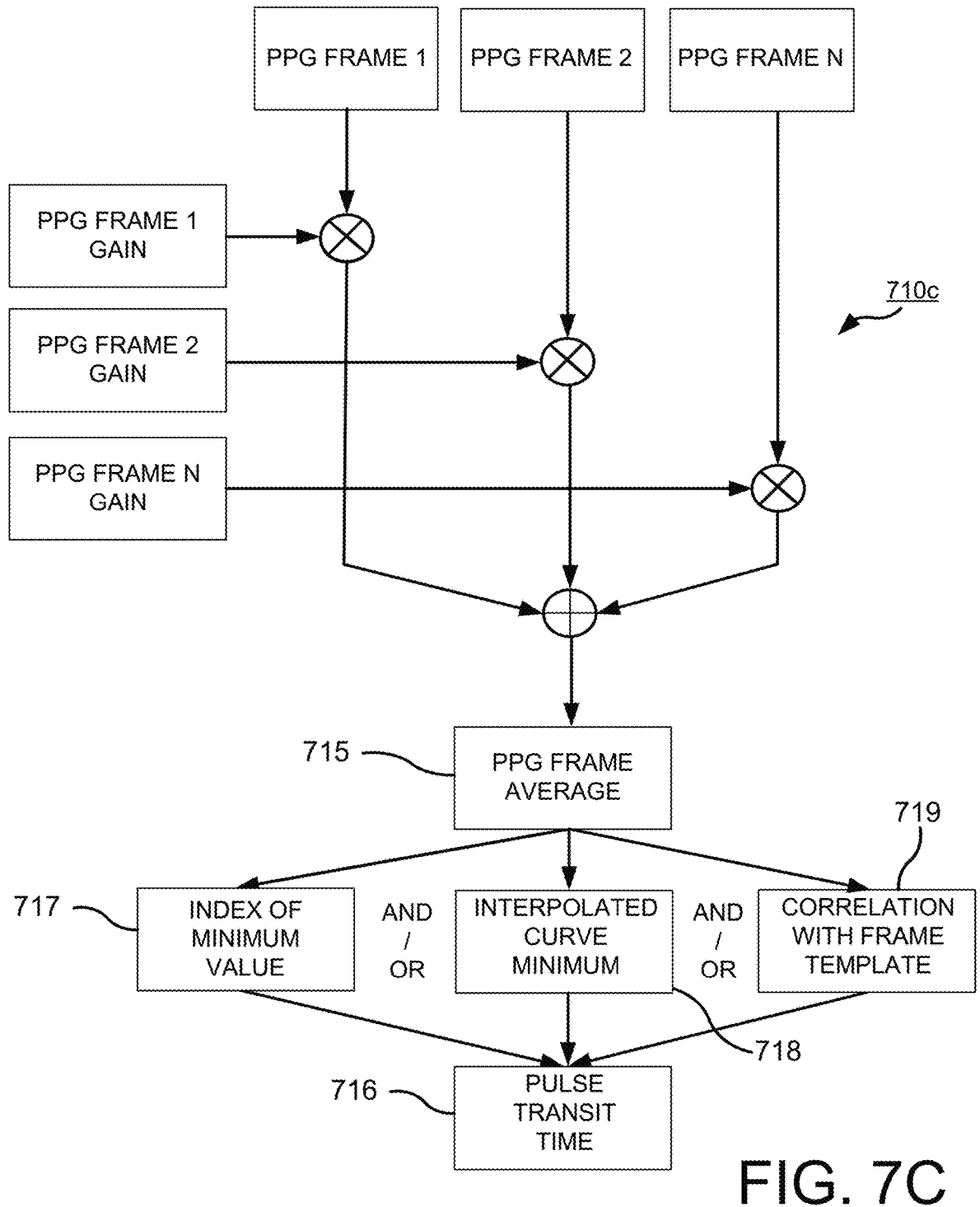

An exemplar methodology or algorithm herefor is described here and shown in the drawing FIGS. 7A, 7B and 7C. Initially, such a method 710 (which includes and/or is defined by parts 710a, 710b and/or 710c) takes at least one heartbeat (typical ECG) signal 712 and at least one PPG signal 711 as input as shown in FIG. 7A, e.g. The heartbeat timing information/signal 712 is used to generate heartbeat timing information by detecting the R-wave or other ECG feature from each beat; multiple ECG signals (i.e. different leads from locations on the body) may be used to obtain a better estimate of the heartbeat timing information. The PPG signal(s) 711 may use a single light wavelength or signals from multiple light wavelengths. Using the corresponding heartbeat timing information related to each PPG signal(s) 711, each PPG signal(s) 711 is segmented into "frames," see PPG Frame 1, PPG Frame 2 and PPG Frame N in FIG. 7A, where each frame contains the PPG signal of a single wavelength for the duration of one corresponding beat of the heart.

Optionally, but, typically, a PPG signal quality estimate may also be performed. An example of this is shown as method part 710b in FIG. 7B. This estimate may consider the variance of the PPG signal, the estimated signal-to-noise ratio of the PPG signal, PPG signal saturation, patient motion information from an accelerometer or gyroscope, an ECG or impedance measurement noise estimate, or other information about the PPG signal quality. Shown in FIG. 7B is an exemplar using accelerometer signal 713 in conjunction with PPG signal 711 to generate a PPG Signal Quality Value/Estimate 714. This signal quality estimate 714 may then be used in conjunction with the heartbeat timing information 712 to generate the gain for each frame, see PPG Frame 1 Gain, PPG Frame 2 Gain and PPG Frame N Gain in FIG. 7B, where lower signal quality results in a lower gain. To reduce computation time, the signal quality estimate 714 may be omitted and a constant may be used for the gain information.

As shown in FIG. 7C, the gain information (PPG Frame 1 Gain, PPG Frame 2 Gain and PPG Frame N Gain from FIG. 7B) may be used (here shown as combined/manipulated) with the frame information (PPG Frame 1, PPG Frame 2 and PPG Frame N from FIG. 7A) to create a weighted, n-sample moving-average frame 715, where the PPG signal that is correlated with the heartbeat timing is reinforced while the uncorrelated noise is reduced. The number of samples included in the frame (n) 715 may be adapted to reduce noise or decrease response time. The frames may be additionally weighted by time in order to increase the contribution of recent or near-future frames with respect to frames that are further away and potentially less-relevant. This additional weighting by time may be implemented using an IIR (Infinite Impulse Response) or FIR (Finite Impulse Response) filter.

Once the average frame 715 has been produced for a given instant in time, the pulse transit time 716 may be determined by finding the shift in the frame signal with respect to the heartbeat. This may be done simply by finding the sample index 717 where the signal is at a minimum or maximum and comparing it with the frame boundary (heartbeat timing) to determine the pulse transit time. For a more precise result, the signal may be interpolated 718 using a spline or polynomial fit around the minimum or maximum values, allowing the minimum or maximum to be determined with greater precision than the sample rate. Finally, the frame may be compared 719 to a reference frame template, where the average frame is shifted with respect to the template. The shift with the highest correlation between the average frame and the template indicates the transit time 716. This reference template may be a predetermined signal, or it may be allowed to adapt by using a long-term frame average with a known transit time.

Note, such methodologies may be used with PPG and heartbeat timing information obtained from a variety of sources, including but not limited to conventional and/or to-be-developed technologies; or, may be obtained one or the other alone or together and/or together with quality signal (PPG variance, estimated PPG signal-to-noise ratio, PPG signal saturation, patient motion accelerometer or gyroscope data, an ECG or impedance measurement noise estimate, or other information about the PPG signal quality) obtained from a wearable device and/or system as described further hereinbelow.

Some further alternatives may include data transmission and/or interpretation by local medical facilities, whether physician or doctor offices or e.g., ICU/CCU (Intensive Care Unit/Coronary Care Units), clinic, hospital or hospice, without limitation hereto. Accordingly, a device 100 hereof that will measure one or more of a variety of physiologic signals, possibly including electrocardiogram, photoplethysmogram, pulse oximetry and/or patient acceleration signals will be placed on the patient's chest and held with an adhesive as described herein. The device transmits the physiologic signals wirelessly or by wire (e.g., USB) to a nearby base station for interpretation and further transmission, if desired. The wireless transmission may use Bluetooth, Wi-Fi, Infrared, RFID (Radio Frequency IDentification), Near Field Communication (NFC) or another wireless protocol. The device may be powered by wireless induction, battery, or a combination of the two. The device 100 monitors physiological signals and/or collects data representative thereof. The collected data may then be transmitted wirelessly or by wire connection, in real time, to the nearby base station. The device may be wirelessly powered by the base station or by battery, removing the need for wires between the patient and the station.

Relatedly and/or alternatively, patients or wearers may be monitored wirelessly in a hospital, including an ICU (Intensive Care Unit) or hospice or other facility. As such, an ECG signal may be measured on a patient using a small, wireless patch device hereof. The signal is then digitized and transmitted wirelessly to a receiver. The receiver converts the signal back to analog, such that it approximates the original ECG signal in amplitude. This output is then presented to an existing hospital or hospice ECG monitor through the standard electrode leads. This allows the patient to be monitored using existing hospital infrastructure without any lead wires necessarily connecting the patient to the monitor. Patient chest impedance may be measured as well, allowing the reconstructed signal to approximate the ECG signal not only in amplitude, but in output impedance as well. This can be used to detect a disconnected patch. The output impedance may be continuously variable, or it may have discrete values that may be selected (e.g. one low value for a connected device and one high value to signify the patch has come loose). The impedance may also be used to signify problems with the wireless transmission.

Other alternative implementations may include coupling one or multiple sensors mounted to the forehead of an infant. Initially, a method of obtaining oxygen saturation data by mounting a device in the forehead of an infant might be used as introduced. However, an expansion or alternative may include coupling oxygen saturation sensors with relative position and temperature sensors on the same forehead-mounted device. The combined data can be utilized to ascertain if an infant is in any danger of suffocation due to a face-down position.

Thus, some of the alternative combinations hereof may include one or more of: 1) medical grade adhesives (from many possible sources) selected for their ability to maintain in intimate contact with the skin without damaging it, for several days (up to, say 10 days or two weeks in some examples), as well as operability with different types of sensors; 2) conductive electrodes or photo-sensitive detectors able to supply electrical signals from the skin or from the photo-response of cutaneous or subcutaneous tissues to photo-excitation; 3) amplifiers, microprocessors and memories, capable of treating these signals and storing them; 4) power supply for the electronics hereof with stored or with wirelessly accessible re-chargeability; 5) flex circuits capable of tying the above elements together within a flexible strip capable of conforming to a cutaneous region of interest.

Examples of physiological parameters that may be subject to monitoring, recordation/collection and/or analyzing may include one or more of: electrocardiograms, photo responses of photo-excited tissues for e.g., oxygen saturation of blood; pulse rates and associated fluctuations; indications of physical activity/acceleration. One or more of these may be used in monitoring ambulatory cardiac outpatients over several days and nights, which could thereby provide for recording, for post-test analysis, several days' worth of continuous ECG signals together with simultaneous recording of O2 saturation and an index of physical exertion. Similarly, one or more of these may be used in monitoring ambulatory pulmonary outpatients over several days and nights for recording, for post-test analysis, O2 saturation together with simultaneous recording of an index of physical activity. Alternatively and/or additionally, one or more of these could be used for monitoring in-patients or other patients of interest, as for example neonates, wirelessly (or in some cases wired), whether in clinics, emergency rooms, or ICUs, in some instances detecting the parameters of EKG, O2 and/or physical exertion, but instead of storing them would transmit them wirelessly to either a bedside monitor or a central station monitor, thus freeing the patient from attachment to physical wires. More particularly, devices hereof may be adhered to the forehead of a neonate for monitoring respiration and oxygen saturation. In further alternatives, devices hereof may be used to monitor respiration and ECG of patients suffering from sleep apnea. In yet further alternatives, devices hereof may be used to remotely monitor physiological parameters of athletes, first-responders (e.g. firefighters), soldiers, or other individuals that may be subjected to physical conditions that may warrant surveillance and monitoring of physiological parameters.

An exemplary computer system or computing resources which may be used herewith will now be described, though it should be noted that many alternatives in computing systems and resources may be available and operable within the reasonably foreseeable scope hereof so that the following is intended in no way to be limiting of the myriad possible computational alternatives properly intended within both the spirit and scope hereof.

Some of the implementations of the present developments include various steps. A variety of these steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 4 is an example of computing resources or a computer system 400 with which implementations hereof may be utilized. According to the present example, a sample such computer system 400 may include a bus 401, at least one processor 402, at least one communication port 403, a main memory 404, a removable storage media 405, a read only memory 406, and a mass storage 407. More or fewer of these elements may be used in particular implementations hereof.

Processor(s) 402 can be any known processor, such as, but not limited to, an Intel® Itanium® or Itanium 2® processor(s), or AMD® Opteron® or Athlon MP® processor(s), or Motorola® lines of processors or like newly developed lines. Communication port(s) 403 can be any of an RS-232 port for use with a modem based dialup connection, a 10/100 Ethernet port, a Universal Serial Bus (USB) port, or a Gigabit port using copper or fiber. Communication port(s) 403 may be chosen depending on a network such a Local Area Network (LAN), Wide Area Network (WAN), or any network to which the computer system 400 connects or may be adapted to connect.

Main memory 404 can be Random Access Memory (RAM), or any other dynamic storage device(s) commonly known in the art. Read only memory 406 can be any static storage device(s) such as Programmable Read Only Memory (PROM) chips for storing static information such as instructions for processor 402.

Mass storage 407 can be used to store information and instructions. For example, hard disks such as the Adaptec® family of SCSI drives, an optical disc, an array of disks such as RAID, such as the Adaptec family of RAID drives, or any other mass storage devices may be used.

Bus 401 communicatively couples processor(s) 402 with the other memory, storage and communication blocks. Bus 401 can be a PCI/PCI-X or SCSI based system bus depending on the storage devices used.

Removable storage media 405 can be any kind of external hard-drives, floppy drives, IOMEGA® Zip Drives, Compact Disc-Read Only Memory (CD-ROM), Compact Disc-Re-Writable (CD-RW), Digital Video Dis-Read Only Memory (DVD-ROM), and/or microSD cards.

The components described above are meant to exemplify some types of possibilities. In no way should the aforementioned examples limit the scope of the inventions hereof, as they are only exemplary implementations.

Implementations of the present inventions relate to devices, systems, methods, media, and arrangements for monitoring and processing cardiac parameters and data, inter alia. While detailed descriptions of one or more implementations of the inventions have been given above, various alternatives, modifications, and equivalents will be apparent to those skilled in the art without varying from the spirit of the inventions hereof. Therefore, the above description should not be taken as limiting the scope of the inventions, which is defined by the appended claims.

What is claimed is:

1. A device for health monitoring comprising:
   a photoplethysmography (PPG) unit comprising:
     a barrier wall frame;
     a light sensor;

a plurality of light sources providing at least two discrete wavelengths of light;
an encapsulant;
the barrier wall frame providing structure to support the light sensor and the plurality of light sources, and the encapsulant;
the barrier wall frame providing a barrier wall disposed between the light sensor and the plurality of light sources;
the plurality of light sources arrayed in at least two discrete concentric arrays relative to each other;
the at least two discrete concentric arrays defining at least one interior array and at least one exterior array;
the at least two discrete wavelengths of light being disposed each discretely on a discrete one of the at least two discrete concentric arrays;
the interior array having discretely red light wavelength light sources disposed thereon or therein; and,
the exterior array having discretely infrared wavelength light sources disposed thereon or therein.

2. A device according to claim 1 further comprising:
the interior array having a two to one ratio of light sources relative to the exterior array.

3. A device according to claim 1 further comprising:
the interior array having eight red light sources;
the exterior array having four infra-red light sources.

4. A device of claim 1 the light sensor or plurality of light sources of the photoplethysmography (PPG) unit providing one or more of:
a focused or controlled interrogation of a capillary bed in order to reduce local motion artifact effects; and,
interrogation of a wider area of capillary bed in order to reduce local motion artifact effects.

5. A method of measuring oxygen saturation in an individual, the method comprising the steps of:
measuring an electrocardiogram signal over multiple heart beats;
measuring with a device according to claim 1 one or more pulse oximetry signals over multiple heart beats such that the electrocardiogram signal and the one or more pulse oximetry signals are in time concordance over one or more heart beats;
comparing a portion of the electrocardiogram signal and the one or more pulse oximetry signals in time concordance over one or more heart beats to determine a constant component and a primary periodic component of each of the one or more pulse oximetry signals; and
determining oxygen saturation from the constant components and primary periodic components of the one or more pulse oximetry signals.

6. The method of claim 5 said pulse oximetry signals include a reflective infrared signal and a reflective red light signal.

7. The method of claim 5 said comparing includes defining intervals of said pulse oximetry signal based on characteristics of said electrocardiogram signal and averaging values of said pulse oximetry signal over a plurality of such intervals.

8. The method of claim 7 said constant components and said primary periodic components of said pulse oximetry signals are determined from said average values.

9. The method of claim 7 said electrocardiogram signal includes an R wave signal each with a peak value in each of said heart beats and said intervals are determined with respect to the peak values of the R wave signals.

10. A device for health monitoring comprising:
a photoplethysmography (PPG) unit comprising:
a barrier wall frame;
a light sensor;
a plurality of light sources providing at least two discrete wavelengths of light;
an encapsulant;
the barrier wall frame providing structure to support the light sensor and the plurality of light sources, and the encapsulant;
the barrier wall frame providing a barrier wall disposed between the light sensor and the plurality of light sources; and,
the plurality of light sources arrayed in at least two discrete concentric arrays relative to each other;
the at least two discrete concentric arrays defining at least one interior array and at least one exterior array;
the at least two discrete wavelengths of light being disposed each discretely on a discrete one of the at least two discrete concentric arrays;
the at least two discrete wavelengths of light being disposed each on a discrete one of the interior and exterior arrays;
the exterior array having a discrete wavelength of light from that of the interior array.

11. A device according to claim 10 further comprising:
the interior array having a two to one ratio of light sources relative to the exterior array.

12. A device according to claim 10 further comprising:
the interior array having eight red light sources;
the exterior array having four infra-red light sources.

13. A device for health monitoring comprising:
a photoplethysmography (PPG) unit comprising:
a barrier wall frame;
a light sensor;
a plurality of light sources providing at least two discrete wavelengths of light;
an encapsulant;
the barrier wall frame providing structure to support the light sensor and the plurality of light sources, and the encapsulant;
the barrier wall frame providing a barrier wall disposed between the light sensor and the plurality of light sources; and,
the plurality of light sources arrayed in at least two discrete concentric dispositions or arrays relative to each other;
the at least two discrete concentric arrays defining at least one interior array and at least one exterior array;
the interior array having red light wavelength light sources disposed thereon or therein;
the exterior array having infrared wavelength light sources disposed thereon or therein.

14. A device according to claim 13 further comprising:
the interior array having a two to one ratio of light sources relative to the exterior array.

15. A device according to claim 13 further comprising:
the interior array having eight red light sources;
the exterior array having four infra-red light sources.

* * * * *